US006437108B1

(12) United States Patent
Youngman et al.

(10) Patent No.: US 6,437,108 B1
(45) Date of Patent: Aug. 20, 2002

(54) ESSENTIAL BACTERIAL GENES AND THEIR USE

(75) Inventors: Philip Youngman, Boston; Christian Fritz, Natick; Christopher Murphy, Upton; Luz-Maria Guzman, Boston, all of MA (US)

(73) Assignee: Millennium Pharmaceuticals, Inc., Cambridge, MA (US)

(*) Notice: Subject to any disclaimer, the term of this patent is extended or adjusted under 35 U.S.C. 154(b) by 0 days.

(21) Appl. No.: 09/222,938

(22) Filed: Dec. 30, 1998

Related U.S. Application Data

(60) Provisional application No. 60/070,116, filed on Dec. 31, 1997.

(51) Int. Cl.[7] .................................................. C07H 21/02

(52) U.S. Cl. .......................... 536/23.1; 435/6; 435/233; 435/34; 435/69.1; 536/23.2; 514/44

(58) Field of Search ............................ 435/6, 69.1, 34, 435/233; 514/44; 536/23.2, 23.1

(56) References Cited

U.S. PATENT DOCUMENTS 5,756,305 A * 5/1998 Timberlake et al. .......... 435/34
5,821,076 A * 10/1998 Timberlake et al. .......... 435/34
5,910,414 A * 6/1999 Gwynn et al. ................. 435/6
5,962,303 A * 10/1999 Gwynn et al. .............. 435/233
5,976,828 A * 11/1999 Timberlake et al. .......... 435/34
6,001,631 A * 12/1999 Blanche et al. ............. 435/233

FOREIGN PATENT DOCUMENTS

| | | | |
|---|---|---|---|
| EP | 339783 A | * | 11/1989 |
| EP | 645460 A | * | 3/1995 |
| WO | WO 97/42210 | | 11/1997 |
| WO | WO 98/18931 | | 5/1998 |

OTHER PUBLICATIONS

Rose, Matthias et al, Microbiology, vol. 142, pp. 3097–3101, 1996.*

Pan, Xiao–Su et al, Journal of Bacteriology, vol. 178(14), pp. 4060–4069, Jul. 1996.*

(List continued on next page.)

*Primary Examiner*—Lynette R. F Smith
*Assistant Examiner*—Ginny Allen Portner
(74) *Attorney, Agent, or Firm*—Fish & Richardson P.C.

(57) ABSTRACT

Disclosed are 23 genes, termed "GEP" genes, found in *Streptococcus pneumonia*, which are located within operons that are essential for survival. Also disclosed is a related essential gene found in *Bacillus subtilis*. These genes and the polypeptides that they encode, as well as homologs thereof, can be used to identify antibacterial agents for treating bacterial infections such as streptococcal pneumonia.

19 Claims, 48 Drawing Sheets gep1493

```
1    TAAAGACACTGGAACGACCAACACCTTCCGCATTTTAGGTAAGAAAGCTGGTATGGCAACCTTTGTGATTGACTTTTTCAAAGGAACCCTAGCAACGCTG
     ATTTCTGTGACCTTGCTGGTTGTGGAAGGCGTAAAATCCATTCTTTCGACCATACCGTTGGAAACACTAACTGAAAAAGTTTCCTTGGGATCGTTGCGAC   100
1     K  D  T  G  T  T  N  T  F  R  I  L  G  K  K  A  G  M  A  T  F  V  I  D  F  F  K  G  T  L  A  T  L   33

101  CTTCCGATTATTTTTCATCTACAAGGCGTTTCTCCTCTCATCTTTGGACTTTTGGCTGTTATCGGCCATACCTTCCCTATCTTTGCAGGATTTAAAGGTG
     GAAGGCTAATAAAAAGTAGATGTTCCGCAAAGAGGAGAGTAGAAACCTGAAAACCGACAATAGCCGGTATGGAAGGGATAGAAACGTCCTAAATTTCCAC   200
34    L  P  I  I  F  H  L  Q  G  V  S  P  L  I  F  G  L  L  A  V  I  G  H  T  F  P  I  F  A  G  F  K  G  G   67

201  GTAAGGCTGTCGCAACCAGTGCTGGAGTGATTTTCGGATTTGCGCCTATCTTCTGTCTCTACCTTGCGATTATCTTCTTTGGACTCTCATATCTTGGCAG
     CATTCCGACAGCGTTGGTCACGACCTCACTAAAAGCCTAAACGCGGATAGAAGACAGAGATGGAACGCTAATAGAAGAAACCTGAGAGTATAGAACCGTC   300
68     K  A  V  A  T  S  A  G  V  I  F  G  F  A  P  I  F  C  L  Y  L  A  I  I  F  F  G  L  S  Y  L  G  S   100

301  TATGATTTCACTGTCTAGTGTCACAGCATCGATCGCGGCTGTTA   344   (SEQ ID NO: 14)
     ATACTAAAGTGACAGATCACAGTGTCGTAGCTAGCGCCGACAAT         (SEQ ID NO: 15)
101   M  I  S  L  S  S  V  T  A  S  I  A  A  V   114   (SEQ ID NO: 13)
```

OTHER PUBLICATIONS

Dujon et al.; "The nucleotide sequence of *Saccharomyces cerevisiae* chromosome XV"; *Nature*, vol. 387; Issue No. 6632s Supplement of Nature; pp. 98–102 (May 29, 1997).

Phillipsen et al.; "The nucleotide sequence of *Saccharomyces cerevisiae* chromosome XIV and its evolutionary implications"; *Nature* vol. 387; Issue No. 6632S Supplement to Natue; pp. 93–98 (May 29, 1997).

Bowman et al.; "The nucleotide sequence of *Saccharomyces cerevisiae* chromosome XIII"; *Nature*, vol. 387; Issue No. 6632S Supplement to Nature; pp. 90–93 (May 29, 1997).

Johnston et al.; "The nucleotide sequence of *Saccharomyces cerevisiae* chromosome XII"; *Nature*, vol. 387; Issue No. 6632S Supplement to Nature; pp. 87–90 (May 29, 1997).

Churcher et al.; "The nucleotide sequence of *Saccharomyces cerevisiae* chromosome IX"; *Nature*, vol. 387; Issue No. 6632S Supplement to Nature; pp. 84–87 (May 29, 1997).

Tettelin et al; "The nucleotide sequence of *Saccharomyces cerevisiae* chromosome VII"; *Nature*, vol. 387; Issue No. 6632S Supplement to Nature; pp. 81–84 (May 29, 1997).

Bussey et al.; "The nucleotide sequence of *Saccharomyces cerevisiae* chromosome XVI"; *Nature*, vol. 387; Issue No. 6632S Supplement to Nature; pp. 103–105 (May 29, 1997).

Payne et al.; "Yeast Protein Database (YPD): a database for the complete proteome of *Saccharomyces cerevisiae*"; *Nucleic Acids Research*, vol. 25, No. 1; pp. 57–62 (Oct. 21, 1996).

Blattner et al.; "The Complete Genome Sequence of *Escherichia coli* K–12"; *Science*, vol. 277; pp. 1453–1462; Sep. 5, 1997.

Kunst et al.; "The complete genome sequence of the Gram-positive bacterium *Bacillus subtilis"; Nature*, vol. 390; pp. 249–256; Nov. 20, 1997.

Zhang et al.; "Analysis of a *Streptococcus* pneumoniae gene encoding signal peptidase I and overproduction of the enzyme"; *Gene* vol. 194; pp. 249–255; 1997.

Daniel et al.; A Complex Four–Gene Operon Containing Essential Cell Division Gene pbpB in *Bacillus subtilis; Journal of Bacteriology* vol. 178, No. 8; pp. 2343–2350; Apr. 1996.

Guidolin et al.; "Nucleotide Sequence Analysis of Genes Essential for Capsular Polysaccharide Biosynthesis in *Streptococcus pneumonia* Type 19F"; *Infection and Immunology* vol. 62, No. 12; pp. 5384–5396; Dec. 1994.

International Search Report From PCT Application Dated Nov. 11, 1999.

* cited by examiner gep103

1 TGCTGATTTTTGGAGAAAGTTTATTAGAGATAAAAGAGTCTAAGGAAAAAAATTCCATTTGATATTTTTCTTCTATAAAATAGATAAAAATGGTACAATA 100
ACGACTAAAAACCTCTTTCAAATAATCTCTATTTTCTCAGATTCCTTTTTTTAAGGTAAACTATAAAAAGAAGATATTTTATCTATTTTTACCATGTTAT

101 ATAAATTGAGGTAATAAGGATGAGATTAGATAAATATTTAAAAGTATCGCGAATTATCAAGCGTCGTACAGTCGCAAAGGAAGTAGCAGATAAAGGTAGA 200
TATTTAACTCCATTATTCCTACTCTAATCTATTTATAAATTTTCATAGCGCTTAATAGTTCGCAGCATGTCAGCGTTTCCTTCATCGTCTATTTCCATCT
1 M R L D K Y L K V S R I I K R R T V A K E V A D K G R 27

201 ATCAAGGTTAATGGAATCTTGGCCAAAAGTTCAACGGACTTGAAAGTTAATGACCAAGTTGAAATTCGCTTTGGCAATAAGTTGCTGCTTGTAAAAGTAC 300
TAGTTCCAATTACCTTAGAACCGGTTTTCAAGTTGCCTGAACTTTCAATTACTGGTTCAACTTTAAGCGAAACCGTTATTCAACGACGAACATTTTCATG
28 I K V N G I L A K S S T D L K V N D Q V E I R F G N K L L L V K V L 61

301 TAGAGATGAAAGATAGTACAAAAAAAGAAGATGCAGCAGGAATGTATGAAATTATCAGTGAAACACGGGTAGAAGAAAATGTCTAAAAATATTGTACAAT 400
ATCTCTACTTTCTATCATGTTTTTTTCTTCTACGTCGTCCTTACATACTTTAATAGTCACTTTGTGCCCATCTTCTTTTACAGATTTTTATAACATGTTA
62 E M K D S T K K E D A A G M Y E I I S E T R V E E N V * 89

(SEQ ID NO: 2)
(SEQ ID NO: 3)
(SEQ ID NO: 1)

FIG. 1 gep1119

```
  1 GAAATCCGTTTCCAATGTGACTGTAGCCATGAACGCTTTATGAACGCTCTTGCCAGCCTTCCAAGCTCAGACTTACAGGAAATGAAAGAGGAAGACCACG 100
    CTTTAGGCAAAGGTTACACTGACATCGGTACTTGCGAAATACTTGCGAGAACGGTCGGAAGGTTCGAGTCTGAATGTCCTTTACTTTCTCCTTCTGGTGC

101 GGGCAGAAATCACTTGTCAATTCTGCCAAACTACTTACAACTTTGATGAAAAGGACCTGGAGGAACTCATTCGTGACAAATCTTAATACACCTTTTATGA 200
    CCCGTCTTTAGTGAACAGTTAAGACGGTTTGATGAATGTTGAAACTACTTTTCCTGGACCTCCTTGAGTAAGCACTGTTTAGAATTATGTGGAAAATACT
  1                                                     M  K  R  T  W  R  N  S  F  V  T  N  L  N  T  P  F  M  I  19

201 TTGGCAATATTGAGATTCCCAATCGTACCGTTTTAGCGCCTATGGCTGGCGTGACCAACTCAGCCTTTCGTACCATCGCAAAAGAGCTCGGAGCTGGACT 300
    AACCGTTATAACTCTAAGGGTTAGCATGGCAAAATCGCGGATACCGACCGCACTGGTTGAGTCGGAAAGCATGGTAGCGTTTTCTCGAGCCTCGACCTGA
 20  G  N  I  E  I  P  N  R  T  V  L  A  P  M  A  G  V  T  N  S  A  F  R  T  I  A  K  E  L  G  A  G  L  52

301 CGTTGTAATGGAAATGGTCTCTGACAAGGGAATCCAATACAACAACGAAAAAACCCTGCATATGCTTCATATCGATGAGGGCGAAAACCCTGTCTCTATC 400
    GCAACATTACCTTTACCAGAGACTGTTCCCTTAGGTTATGTTGTTGCTTTTTTGGGACGTATACGAAGTATAGCTACTCCCGCTTTTGGGACAGAGATAG
 53 V  V  M  E  M  V  S  D  K  G  I  Q  Y  N  N  E  K  T  L  H  M  L  H  I  D  E  G  E  N  P  V  S  I  85

401 CAACTTTTTGGTAGCGATGAAGACAGCCTAGCACGCGCAGCAGAATTCATCCAAGAAAACACCAAGACCGATATCGTCGATATCAACATGGGCTGCCCTG 500
    GTTGAAAAACCATCGCTACTTCTGTCGGATCGTGCGCGTCGTCTTAAGTAGGTTCTTTTGTGGTTCTGGCTATAGCAGCTATAGTTGTACCCGACGGGAC
 86 Q  L  F  G  S  D  E  D  S  L  A  R  A  A  E  F  I  Q  E  N  T  K  T  D  I  V  D  I  N  M  G  C  P  V  119

501 TCAACAAAATCGTGAAGAACGAAGCTGGAGCTATGTGGCTCAAGGATCCTGACAAGATCTACTCTATCATCAACAAGGTCCAGTCTGTCCTTGATATCCC 600
    AGTTGTTTTAGCACTTCTTGCTTCGACCTCGATACACCGAGTTCCTAGGACTGTTCTAGATGAGATAGTAGTTGTTCCAGGTCAGACAGGAACTATAGGG
120  N  K  I  V  K  N  E  A  G  A  M  W  L  K  D  P  D  K  I  Y  S  I  I  N  K  V  Q  S  V  L  D  I  P  152
```

```
601  ACTTACTGTCAAAATGCGTACCGGCTGGGCGGACCCATCTCTGGCAGTAGAAAATGCCCTCGCTGCTGAGGCTGCAGGTGTTTCTGCCCTCGCCATGCAT  700
     TGAATGACAGTTTTACGCATGGCCGACCCGCCTGGGTAGAGACCGTCATCTTTTACGGGAGCGACGACTCCGACGTCCACAAAGACGGGAGCGGTACGTA
153   L  T  V  K  M  R  T  G  W  A  D  P  S  L  A  V  E  N  A  L  A  A  E  A  A  G  V  S  A  L  A  M  H   185

701  GGCCGTACCCGTGAACAAATGTATACTGGCCACGCAGACCTTGAGACCCTTTACAAGGTTGCCCAAGCTCTAACCAAGATTCCATTCATCGCCAACGGTG  800
     CCGGCATGGGCACTTGTTTACATATGACCGGTGCGTCTGGAACTCTGGGAAATGTTCCAACGGGTTCGAGATTGGTTCTAAGGTAAGTAGCGGTTGCCAC
186  G  R  T  R  E  Q  M  Y  T  G  H  A  D  L  E  T  L  Y  K  V  A  Q  A  L  T  K  I  P  F  I  A  N  G  D   219

801  ATATCCGTACTGTCCAAGAAGCCAAGCAACGCATCGAAGAAGTTGGTGCTGACGCAGTCATGATTGGCCGAGCTGCCATGGGAAATCCTTACCTCTTCAA  900
     TATAGGCATGACAGGTTCTTCGGTTCGTTGCGTAGCTTCTTCAACCACGACTGCGTCAGTACTAACCGGCTCGACGGTACCCTTTAGGAATGGAGAAGTT
220   I  R  T  V  Q  E  A  K  Q  R  I  E  E  V  G  A  D  A  V  M  I  G  R  A  A  M  G  N  P  Y  L  F  N   252

901  CCAAATCAACCATTACTTTGAAACAGGAGAAATCCTACCTGATTTGACCTTTGAAGACAAGATGAAGATCGCCTACGAACACTTGAAACGATTGATTAAC  1000
     GGTTTAGTTGGTAATGAAACTTTGTCCTCTTTAGGATGGACTAAACTGGAAACTTCTGTTCTACTTCTAGCGGATGCTTGTGAACTTTGCTAACTAATTG
253   Q  I  N  H  Y  F  E  T  G  E  I  L  P  D  L  T  F  E  D  K  M  K  I  A  Y  E  H  L  K  R  L  I  N   285

1001 CTCAAAGGAGAAAACGTCGCAGTTCGTGAATTCCGCGGCCTCGCTCCTCACTATCTCCGTGGAACATCTGGCGCTGCCAAACTCCGTGGAGCCATTTCGC  1100
     GAGTTTCCTCTTTTGCAGCGTCAAGCACTTAAGGCGCCGGAGCGAGGAGTGATAGAGGCACCTTGTAGACCGCGACGGTTTGAGGCACCTCGGTAAAGCG
286  L  K  G  E  N  V  A  V  R  E  F  R  G  L  A  P  H  Y  L  R  G  T  S  G  A  A  K  L  R  G  A  I  S  Q   319

1101 AAGCTAGCACCCTAGCAGAGATTGAAGCCCTCTTGCAATTGGAGAAGGCTTAATAGTTTAAAACCCGTAACTCTCTTAAAGAGTCTCTTGAATGCCGCCA  1200
     TTCGATCGTGGGATCGTCTCTAACTTCGGGAGAACGTTAACCTCTTCCGAATTATCAAATTTTGGGCATTGAGAGAATTTCTCAGAGAACTTACGGCGGT
320   A  S  T  L  A  E  I  E  A  L  L  Q  L  E  K  A  *                                                  336
```

(SEQ ID NO: 5)
(SEQ ID NO: 6)
(SEQ ID NO: 4)

FIG. 2B gep1122

```
  1 AAGGCACGAGCTGGAAGTTTTCCCTCATATTTTTTCAATAGTTTATTAGCTACACGTTGAGCAACTTCAGAAAAATCAAATTCTTTCAAGTTCTCTTCTA 100
    TTCCGTGCTCGACCTTCAAAAGGGAGTATAAAAAAGTTATCAAATAATCGATGTGCAACTCGTTGAAGTCTTTTTAGTTTAAGAAAGTTCAAGAGAAGAT

101 TAGTAGATTTTGAAATCCCTTTTTGAGCTAGTTTCTGAGTCAGCACATAAGGACCCTTGTCTCCTGAAAGTTGATTGGTATTGATGATAGCATAAGCGTA 200
    ATCATCTAAAACTTTAGGGAAAAACTCGATCAAAGACTCAGTCGTGTATTCCTGGGAACAGAGGACTTTCAACTAACCATAACTACTATCGTATTCGCAT

201 CTGACCATCATTAATCCACTTATCTTCTTTAAGATTAGCAATAACTTGAGAAACGATGTTTTTATCAATATCGTATTTTTCAGATATTCTCTGACTTCT 300
    GACTGGTAGTAATTAGGTGAATAGAAGAAATTCTAATCGTTATTGAACTCTTTGCTACAAAAATAGTTATAGCATAAAAAGTCTATAAGAGACTGAAGA

301 TTTTCAGTGCGTGCTTTAAAGGATAAGTGGTAGAGGGCCAGATTCTTACCATAAGAAAATTGAGCAAAGTCTTGAATCTCTTTCAATTCCTCTTCGCTTA 400
    AAAAGTCACGCACGAAATTTCCTATTCACCATCTCCCGGTCTAAGAATGGTATTCTTTTAACTCGTTTCAGAACTTAGAGAAAGTTAAGGAGAAGCGAAT

401 TCACCTTATCTCTCGATAACATAAAACGAACAATTGTATCTTCGGTGATATAGCATTTGTCGCCATTATCAAGCTCCATCAGATAGAGTCTTTTTTTCTT 500
    AGTGGAATAGAGAGCTATTGTATTTTGCTTGTTAACATAGAAGCCACTATATCGTAAACAGCGGTAATAGTTCGAGGTAGTCTATCTCAGAAAAAAAGAA

501 TTCAAGTTTTGTGATTTTCATAGCTCTATTATAACTCAAAATGTGATAAGATAGGGGTATGAATCTGAAAGTGAAACAAAAAATACCATTAAAAATCAAG 600
    AAGTTCAAAACACTAAAAGTATCGAGATAATATTGAGTTTTACACTATTCTATCCCCATACTTAGACTTTCACTTTGTTTTTTATGGTAATTTTTAGTTC
  1                                                                   M N L K V K Q K I P L K I K 14
```

FIG. 3A

```
601  CGCATGGGAATTAACGGTGAGGGAATCGGCTTTTACCAAAAAACATTAGTCTTTGTACCAGGAGCTCTCAAAGGCGAAGATATCTATTGTCAGATTACTT  700
     GCGTACCCTTAATTGCCACTCCCTTAGCCGAAAATGGTTTTTTGTAATCAGAAACATGGTCCTCGAGAGTTTCCGCTTCTATAGATAACAGTCTAATGAA

15   R  M  G  I  N  G  E  G  I  G  F  Y  Q  K  T  L  V  F  V  P  G  A  L  K  G  E  D  I  Y  C  Q  I  T  S  48

701  CTATTAGACGCAACTTTGTTGAAGCAAAATTACTGAAGGTCAACAAGAAGTCTAAATTTCGAATTGTGCCATCTTGTACTATTTATAATGAATGCGGAGG  800
     GATAATCTGCGTTGAAACAACTTCGTTTTAATGACTTCCAGTTGTTCTTCAGATTTAAAGCTTAACACGGTAGAACATGATAAATATTACTTACGCCTCC

49    I  R  R  N  F  V  E  A  K  L  L  K  V  N  K  K  S  K  F  R  I  V  P  S  C  T  I  Y  N  E  C  G  G  81

801  CTGCCAAATCATGCACCTGCATTATGATAAGCAGCTGGAGTTCAAGACGGACTTACTTCATCAAGCGCTGAAAAAATTTGCTCCTGCAGGATATGAAAAT  900
     GACGGTTTAGTACGTGGACGTAATACTATTCGTCGACCTCAAGTTCTGCCTGAATGAAGTAGTTCGCGACTTTTTTAAACGAGGACGTCCTATACTTTTA

82    C  Q  I  M  H  L  H  Y  D  K  Q  L  E  F  K  T  D  L  L  H  Q  A  L  K  K  F  A  P  A  G  Y  E  N  114

901  TATGAAATTCGTCCAACTATTGGAATGCAGGAACCAAAATATTACAGAGCTAAGTTACAATTTCAGACTCGAAAATTTAAAAATCAGGTCAAGGCGGGCT  1000
     ATACTTTAAGCAGGTTGATAACCTTACGTCCTTGGTTTTATAATGTCTCGATTCAATGTTAAAGTCTGAGCTTTTAAATTTTTAGTCCAGTTCCGCCCGA

115  Y  E  I  R  P  T  I  G  M  Q  E  P  K  Y  Y  R  A  K  L  Q  F  Q  T  R  K  F  K  N  Q  V  K  A  G  L  148

1001 TATATGCACAAAACTCTCACTATTTAGTAGAGTTGAAAGACTGCCTGGTACAAGATAAGGAAACCCAAGTGATTGCTAATCGCTTAGCAGAATTACTTAC  1100
     ATATACGTGTTTTGAGAGTGATAAATCATCTCAACTTTCTGACGGACCATGTTCTATTCCTTTGGGTTCACTAACGATTAGCGAATCGTCTTAATGAATG

149   Y  A  Q  N  S  H  Y  L  V  E  L  K  D  C  L  V  Q  D  K  E  T  Q  V  I  A  N  R  L  A  E  L  L  T  181
```

```
1101 TTATCACCAGATTCCAATCACGGATGAGAGAAAAGTTCTAGGTGTCCGTACTATTATGGTCCGACGCGCGAGAAAGACCGGACAGGTTCAGATTATTATT
     AATAGTGGTCTAAGGTTAGTGCCTACTCTCTTTTCAAGATCCACAGGCATGATAATACCAGGCTGCGCGCTCTTTCTGGCCTGTCCAAGTCTAATAATAA 1200
182  Y  H  Q  I  P  I  T  D  E  R  K  V  L  G  V  R  T  I  M  V  R  R  A  R  K  T  G  Q  V  Q  I  I  I  214

1201 GTTACAAACCGCCAGCTTAATTTAACTCAATTGGTAAAAGAGTTGGTTAAAGATTTCCCAGAAGTTGTGACAGTAGCTGTTAATACAAATACAGCTAAAA
     CAATGTTTGGCGGTCGAATTAAATTGAGTTAACCATTTTCTCAACCAATTTCTAAAGGGTCTTCAACACTGTCATCGACAATTATGTTTATGTCGATTTT 1300
215  V  T  N  R  Q  L  N  L  T  Q  L  V  K  E  L  V  K  D  F  P  E  V  V  T  V  A  V  N  T  N  T  A  K  T  248

1301 CCAGTGAGATATATGGTGAAAAGACAGAGATTATCTGGGGGCAAGAGAGTATTCAAGAAGGTGTACTCAATTATGAATTTTCACTATCCCCTCGAGCTTT
     GGTCACTCTATATACCACTTTTCTGTCTCTAATAGACCCCCGTTCTCTCATAAGTTCTTCCACATGAGTTAATACTTAAAAGTGATAGGGGAGCTCGAAA 1400
249  S  E  I  Y  G  E  K  T  E  I  I  W  G  Q  E  S  I  Q  E  G  V  L  N  Y  E  F  S  L  S  P  R  A  F  281

1401 TTATCAACTAAATCCTGAGCAAACAGAAGTCCTCTATAGCGAAGCAGTAAAAGCGCTGGATGTTGATAAAGAAGACCATTTGATTGACGCTTATTGTGGA
     AATAGTTGATTTAGGACTCGTTTGTCTTCAGGAGATATCGCTTCGTCATTTTCGCGACCTACAACTATTTCTTCTGGTAAACTAACTGCGAATAACACCT 1500
282  Y  Q  L  N  P  E  Q  T  E  V  L  Y  S  E  A  V  K  A  L  D  V  D  K  E  D  H  L  I  D  A  Y  C  G  314

1501 GTTGGAACGATTGGATTTGCCTTTGCAAAGAAAGTAAAAACACTCAGAGGTATGGATATTATTCCAGAAGCTATTGAAGATGCCAAGCGAAATGCTAAAA
     CAACCTTGCTAACCTAAACGGAAACGTTTCTTTCATTTTTGTGAGTCTCCATACCTATAATAAGGTCTTCGATAACTTCTACGGTTCGCTTTACGATTTT 1600
315  V  G  T  I  G  F  A  F  A  K  K  V  K  T  L  R  G  M  D  I  I  P  E  A  I  E  D  A  K  R  N  A  K  R  348
```

FIG. 3C

```
1601 GAATGGATTTGACAATACTCATTATGAAGCTGGAACGGCAGAAGAGATTATTCCTCGTTGGTACAAGGAAGGCTACCGAGCAGATGCTTTGATTGTTGA 1700
     CTTACCCTAAACTGTTATGAGTAATACTTCGACCTTGCCGTCTTCTCTAATAAGGAGCAACCATGTTCCTTCCGATGGCTCGTCTACGAAACTAACAACT
 349   M  G  F  D  N  T  H  Y  E  A  G  T  A  E  E  I  I  P  R  W  Y  K  E  G  Y  R  A  D  A  L  I  V  D   381

1701 CCCACCACGTACAGGTCTGGATGATAAGTTATTAGATACTATTCTTACTTATGTACCAGAAAAAATGGTTTATATTTCTTGTAATGTTTCGACCTTGGCT 1800
     GGGTGGTGCATGTCCAGACCTACTATTCAATAATCTATGATAAGAATGAATACATGGTCTTTTTTACCAAATATAAAGAACATTACAAAGCTGGAACCGA
 382  P  P  R  T  G  L  D  D  K  L  L  D  T  I  L  T  Y  V  P  E  K  M  V  Y  I  S  C  N  V  S  T  L  A    414

1801 CGTGATTTGGTACGCTTAGTAGAAGTCTATGATCTTCATTATATCCAGTCGGTCGATATGTTCCCACATACAGCTCGAACTGAAGCTGTTGTAAAATTAA 1900
     GCACTAAACCATGCGAATCATCTTCAGATACTAGAAGTAATATAGGTCAGCCAGCTATACAAGGGTGTATGTCGAGCTTGACTTCGACAACATTTTAATT
 415 R  D  L  V  R  L  V  E  V  Y  D  L  H  Y  I  Q  S  V  D  M  F  P  H  T  A  R  T  E  A  V  V  K  L  I   448

1901 TAACAAAAGTTTAAAAAAGTAGTTGACAAAGTTTGAAAAGACTGTATAATAGTAAGAGTTGAAAATAACAACTCAGGTNCGTTGGTCAAGGGGTTAAGAC 2000
     ATTGTTTTCAAATTTTTTCATCAACTGTTTCAAACTTTTCTGACATATTATCATTCTCAACTTTTATTGTTGAGTCCANGCAACCAGTTCCCCAATTCTG
 449   T  K  V  *
                                                                                                           452

2001 ACGCCTTTTCACGGCGGTAACACGGGTTCGAATCCCGTACGGACTATGGTATGTTGCGGTTGGAACACTTGATGAAAAACTTTA 2084
     TGCGGAAAAGTGCCGCCATTGTGCCCAAGCTTAGGGCATGCCTGATACCATACAACGCCAACCTTGTGAACTACTTTTTGAAAT
```

(SEQ ID NO: 8)
(SEQ ID NO: 9)
(SEQ ID NO: 7)

FIG. 3D gep1315

```
  1  AAGAGCTCCTTTCTTTTTATTTATCTTAGCAAATTTCCCTCAAATTAGCTAGTAGCATAGCCTGTTTGTACTGGCTAAAAACAGGCTATTTCAAATTCAG  100
     TTCTCGAGGAAAGAAAAATAAATAGAATCGTTTAAAGGGAGTTTAATCGATCATCGTATCGGACAAACATGACCGATTTTTGTCCGATAAAGTTTAAGTC

101  TTTCAGACCATCTAGCATGGAAAAATCTGTTATAATAATGGAAAAGGAGAAGCGCATGCACAAGATTTTATTAATAGAAGATGATCAGGTCATTCGTCAA  200
     AAAGTCTGGTAGATCGTACCTTTTTAGACAATATTATTACCTTTTCCTCTTCGCGTACGTGTTCTAAAATAATTATCTTCTACTAGTCCAGTAAGCAGTT
  1                                                                M  H  K  I  L  L  I  E  D  D  Q  V  I  R  Q    15

201  CAGATTGGGAAAATGCTCTCTGAATGGGGATTTNAAGTGGTCCTGGTAGAAGACTTTATGGAAGTTTTGAGTCTATTTGTTCAGTCGGAACCTCATCTGG  300
     GTCTAACCCTTTTACGAGAGACTTACCCCTAAANTTCACCAGGACCATCTTCTGAAATACCTTCAAAACTCAGATAAACAAGTCAGCCTTGGAGTAGACC
 16  Q  I  G  K  M  L  S  E  W  G  F  X  V  V  L  V  E  D  F  M  E  V  L  S  L  F  V  Q  S  E  P  H  L  V   49

301  TCCTCATGGATATTGGTTTGCCCTTGTTTAATGGTTATCACTGGTGTCAGGAAATCCGCAAGATTTCCAAGGTACCTATCATGTTTCTTTCTTCGAGAGA  400
     AGGAGTACCTATAACCAAACGGGAACAAATTACCAATAGTGACCACAGTCCTTTAGGCGTTCTAAAGGTTCCATGGATAGTACAAAGAAAGAAGCTCTCT
 50   L  M  D  I  G  L  P  L  F  N  G  Y  H  W  C  Q  E  I  R  K  I  S  K  V  P  I  M  F  L  S  S  R  D   82

401  CCAGGCTATGGATATTGTCATGGCAATCAATATGGGGGCGGATGACTTTGTGACCAAGCCTTTTGACCAGCAGGTTCTTTTAGCTAAGGTTCAGGGCTTG  500
     GGTCCGATACCTATAACAGTACCGTTAGTTATACCCCCGCCTACTGAAACACTGGTTCGGAAAACTGGTCGTCCAAGAAAATCGATTCCAAGTCCCGAAC
 83   Q  A  M  D  I  V  M  A  I  N  M  G  A  D  D  F  V  T  K  P  F  D  Q  Q  V  L  L  A  K  V  Q  G  L  115
```

FIG. 4A

```
501  TTGCGTCGTTCCTATGAGTTTGGGCGTGATGAGAGTTTGCTGGAATATGCTGGTGTTATCCTCAATACCAAATCCATGGATTTACATTATCAAGGGCAAG  600
     AACGCAGCAAGGATACTCAAACCCGCACTACTCTCAAACGACCTTATACGACCACAATAGGAGTTATGGTTTAGGTACCTAAATGTAATAGTTCCCGTTC
116  L  R  R  S  Y  E  F  G  R  D  E  S  L  L  E  Y  A  G  V  I  L  N  T  K  S  M  D  L  H  Y  Q  G  Q  V  149

601  TCTTGAATTTGACCAAGAATGAATTCCAGATTTTACGCGTGTTATTTGAGCATGCAGGCAACATCGTAGCACGTGACGACCTGATGCGGGAACTTTGGAA  700
     AGAACTTAAACTGGTTCTTACTTAAGGTCTAAAATGCGCACAATAAACTCGTACGTCCGTTGTAGCATCGTGCACTGCTGGACTACGCCCTTGAAACCTT
150   L  N  L  T  K  N  E  F  Q  I  L  R  V  L  F  E  H  A  G  N  I  V  A  R  D  D  L  M  R  E  L  W  N  182

701  CAGTGACTTTTTCATTGATGATAATACCCTCTCTGTCAATGTGGCTCGTTTGCGTAAAAAGTTGGAGGAGCAGGGATTGGTAGGATTTATCGAGACCAAG  800
     GTCACTGAAAAAGTAACTACTATTATGGGAGAGACAGTTACACCGAGCAAACGCATTTTTCAACCTCCTCGTCCCTAACCATCCTAAATAGCTCTGGTTC
183   S  D  F  F  I  D  D  N  T  L  S  V  N  V  A  R  L  R  K  K  L  E  E  Q  G  L  V  G  F  I  E  T  K  215

801  AAAGGAATAGGGTACGGATTGAAGCATGCTTGATTGGAAACAATTTTTTCTAGCCTATCTGCGCTCCCGTAGTCGTCTTTTTATCTATCTGCTTTCTTTG  900
     TTTCCTTATCCCATGCCTAACTTCGTACGAACTAACCTTTGTTAAAAAAGATCGGATAGACGCGAGGGCATCAGCAGAAAAATAGATAGACGAAAGAAAC
216  K  G  I  G  Y  G  L  K  H  A  *
                                                                                                          226

901  GCATTTCTTGTCTTACTCTTTCAGTTTTTATTTGCCAGTCTAGGAATTTACTTCCTCTACTTTTTCTTCTTGTGTTGCTTTGTAACCATCTTATTTTTCA  1000
     CGTAAAGAACAGAATGAGAAAGTCAAAAATAAACGGTCAGATCCTTAAATGAAGGAGATGAAAAAGAAGAACACAACGAAACATTGGTAGAATAAAAAGT
```

(SEQ ID NO: 11)
(SEQ ID NO: 12)
(SEQ ID NO: 10)

FIG. 4B gep1493

```
1    TAAAGACACTGGAACGACCAACACCTTCCGCATTTTAGGTAAGAAAGCTGGTATGGCAACCTTTGTGATTGACTTTTTCAAAGGAACCCTAGCAACGCTG   100
     ATTTCTGTGACCTTGCTGGTTGTGGAAGGCGTAAAATCCATTCTTTCGACCATACCGTTGGAAACACTAACTGAAAAAGTTTCCTTGGGATCGTTGCGAC
1     K  D  T  G  T  T  N  T  F  R  I  L  G  K  K  A  G  M  A  T  F  V  I  D  F  F  K  G  T  L  A  T  L     33

101  CTTCCGATTATTTTTCATCTACAAGGCGTTTCTCCTCTCATCTTTGGACTTTTGGCTGTTATCGGCCATACCTTCCCTATCTTTGCAGGATTTAAAGGTG   200
     GAAGGCTAATAAAAAGTAGATGTTCCGCAAAGAGGAGAGTAGAAACCTGAAAACCGACAATAGCCGGTATGGAAGGGATAGAAACGTCCTAAATTTCCAC
34   L  P  I  I  F  H  L  Q  G  V  S  P  L  I  F  G  L  L  A  V  I  G  H  T  F  P  I  F  A  G  F  K  G  G   67

201  GTAAGGCTGTCGCAACCAGTGCTGGAGTGATTTTCGGATTTGCGCCTATCTTCTGTCTCTACCTTGCGATTATCTTCTTTGGACTCTCATATCTTGGCAG   300
     CATTCCGACAGCGTTGGTCACGACCTCACTAAAAGCCTAAACGCGGATAGAAGACAGAGATGGAACGCTAATAGAAGAAACCTGAGAGTATAGAACCGTC
68    K  A  V  A  T  S  A  G  V  I  F  G  F  A  P  I  F  C  L  Y  L  A  I  I  F  F  G  L  S  Y  L  G  S   100

301  TATGATTTCACTGTCTAGTGTCACAGCATCGATCGCGGCTGTTA   344   (SEQ ID NO: 14)
     ATACTAAAGTGACAGATCACAGTGTCGTAGCTAGCGCCGACAAT         (SEQ ID NO: 15)
101   M  I  S  L  S  S  V  T  A  S  I  A  A  V     114   (SEQ ID NO: 13)
```

FIG. 5 gep1507

```
  1 CTAAAGGTAAATTGAATGAAAAGTATAAAATTAAATGCTCTATCTTACATGGGAATTCGTGTCTTGAATATTATTTTTCCCATCCTAACTGGAACCTATG 100
    GATTTCCATTTAACTTACTTTTCATATTTTAATTTACGAGATAGAATGTACCCTTAAGCACAGAACTTATAATAAAAAGGGTAGGATTGACCTTGGATAC
  1              M  K  S  I  K  L  N  A  L  S  Y  M  G  I  R  V  L  N  I  I  F  P  I  L  T  G  T  Y  V  29

101 TCGCGCGTGTCTTGGACCGAACTGACTATGGTTACTTCAACTCAGTCGACACTATTTGTCATTTTTCTTGCCCTTTGCAACTTATGGTGTCTATAACTA 200
    AGCGCGCACAGAACCTGGCTTGACTGATACCAATGAAGTTGAGTCAGCTGTGATAAAACAGTAAAAAGAACGGGAAACGTTGAATACCACAGATATTGAT
 30  A  R  V  L  D  R  T  D  Y  G  Y  F  N  S  V  D  T  I  L  S  F  F  L  P  F  A  T  Y  G  V  Y  N  Y  62

201 CGGTTTAAGGGCTATCAGTAATGTCAAGGATAACAAAAAAGATCTTAACAGAACCTTTTCTAGTCTTTTTTATTTGTGCATCGCTTGTACGATTTTGACC 300
    GCCAAATTCCCGATAGTCATTACAGTTCCTATTGTTTTTTCTAGAATTGTCTTGGAAAAGATCAGAAAAAATAAACACGTAGCGAACATGCTAAAACTGG
 63  G  L  R  A  I  S  N  V  K  D  N  K  K  D  L  N  R  T  F  S  S  L  F  Y  L  C  I  A  C  T  I  L  T  95

301 ACTGCTGTCTATATCCTAGCCTATCCTCTCTTCTTTACTGATAATCCAATCGTCAAAAAGGTCTACCTTGTTATGGGGATTCAACTCATTGCCCAGATTT 400
    TGACGACAGATATAGGATCGGATAGGAGAGAAGAAATGACTATTAGGTTAGCAGTTTTTCCAGATGGAACAATACCCCTAAGTTGAGTAACGGGTCTAAA
 96 T  A  V  Y  I  L  A  Y  P  L  F  F  T  D  N  P  I  V  K  K  V  Y  L  V  M  G  I  Q  L  I  A  Q  I  F 129

401 TTTCAATCGAATGGGTCAATGAAGCTCTGGAAAATTACAGTTTCTCTTTTACAAAACTGC 460   (SEQ ID NO: 17)
    AAAGTTAGCTTACCCAGTTACTTCGAGACCTTTTAATGTCAAAGAGAAAATGTTTTGACG       (SEQ ID NO: 18)
130  S  I  E  W  V  N  E  A  L  E  N  Y  S  F  S  F  T  K  L     148   (SEQ ID NO: 16)
```

FIG. 6

```
    gep1511

1   CGTCGCATTTACCGTGATGGATTTCACGTATGTAATGATTTTTATGGACAACGTCGAGAGCAGGACGAGGAATGTATGTTTTGTGACGAGTTGCTATACA   100
    GCAGCGTAAATGGCACTACCTAAAGTGCATACATTACTAAAAATACCTGTTGCAGCTCTCGTCCTGCTCCTTACATACAAAACACTGCTCAACGATATGT

101 GGGAGTAGGCATGCAGATTCAAAAAAGTTTTAAGGGGCAGTCTCCCTATGGCAAGCTGTATCTAGTGGCAACGCCGATTGGCAATCTAGATGATATGACT   200
    CCCTCATCCGTACGTCTAAGTTTTTTCAAAATTCCCCGTCAGAGGGATACCGTTCGACATAGATCACCGTTGCGGCTAACCGTTAGATCTACTATACTGA
1              M  Q  I  Q  K  S  F  K  G  Q  S  P  Y  G  K  L  Y  L  V  A  T  P  I  G  N  L  D  D  M  T      30

201 TTTCGTGCTATCCAGACCTTGAAAGAAGTGGACTGGATTGCTGCTGAGGATACGCGCAATACAGGGCTTTTGCTCAAGCATTTTGACATTTCCACCAAGC   300
    AAAGCACGATAGGTCTGGAACTTTCTTCACCTGACCTAACGACGACTCCTATGCGCGTTATGTCCCGAAAACGAGTTCGTAAAACTGTAAAGGTGGTTCG
31  F  R  A  I  Q  T  L  K  E  V  D  W  I  A  A  E  D  T  R  N  T  G  L  L  L  K  H  F  D  I  S  T  K  Q   64

301 AGATCAGTTTTCATGAGCACAATGCAAAGGAAAAAATTCCTGATTTGATTGGTTTCTTGAAAGCAGGGCAAAGTATTGCTCAGGTCTCTGATGCCGGTTT   400
    TCTAGTCAAAAGTACTCGTGTTACGTTTCCTTTTTTAAGGACTAAACTAACCAAAGAACTTTCGTCCCGTTTCATAACGAGTCCAGAGACTACGGCCAAA
65    I  S  F  H  E  H  N  A  K  E  K  I  P  D  L  I  G  F  L  K  A  G  Q  S  I  A  Q  V  S  D  A  G  L   97

401 GCCTAGCATTTCAGACCCTGGTCATGATTTAGTTAAGGCAGCTATTGAGGAAGAAATTGCAGTTGTGACTGTTCCAGGTACCTCTGCAGGAATTTCTGCC   500
    CGGATCGTAAAGTCTGGGACCAGTACTAAATCAATTCCGTCGATAACTCCTTCTTTAACGTCAACACTGACAAGGTCCATGGAGACGTCCTTAAAGACGG
98    P  S  I  S  D  P  G  H  D  L  V  K  A  A  I  E  E  E  I  A  V  V  T  V  P  G  T  S  A  G  I  S  A   130
```

FIG. 7A

```
501  TTGATTGCCAGTGGTTTAGCGCCACAGCCACATATCTTTTACGGTTTTTACCGAGAAAATCAGGTCAACAGAAGCAATTTTTTGGCTCTAAAAAAGATT  600
     AACTAACGGTCACCAAATCGCGGTGTCGGTGTATAGAAAATGCCAAAAAATGGCTCTTTTAGTCCAGTTGTCTTCGTTAAAAAACCGAGATTTTTTCTAA
131  L  I  A  S  G  L  A  P  Q  P  H  I  F  Y  G  F  L  P  R  K  S  G  Q  Q  K  Q  F  F  G  S  K  K  D  Y  164

601  ATCCTGAAACACAGATTTTTTATGAATCACCTCATCGTGTAGCAGACACGTTGGAAAATATGTTAGAAGTCTACGGTGACCGCTCGGTTGTTTTGGTCAG  700
     TAGGACTTTGTGTCTAAAAAATACTTAGTGGAGTAGCACATCGTCTGTGCAACCTTTTATACAATCTTCAGATGCCACTGGCGAGCCAACAAAACCAGTC
165   P  E  T  Q  I  F  Y  E  S  P  H  R  V  A  D  T  L  E  N  M  L  E  V  Y  G  D  R  S  V  V  L  V  R  197

701  GGAATTGACCAAAATCTATGAAGAATACCAAAGAGGTACAATTTCTGAATTGCTGGAAAGCATCTCTGAAACGTCTCTCAAGGGTGAATGTCTTCTGATT  800
     CCTTAACTGGTTTTAGATACTTCTTATGGTTTCTCCATGTTAAAGACTTAACGACCTTTCGTAGAGACTTTGCAGAGAGTTCCCACTTACAGAAGACTAA
198   E  L  T  K  I  Y  E  E  Y  Q  R  G  T  I  S  E  L  L  E  S  I  S  E  T  S  L  K  G  E  C  L  L  I  230

801  GTTGAAGGTGCCAGCAAAGGTGTGGAGGAAAAGGATGAGGAAGACTTGTTCTTAGAAATCCAAGCCCGTATCCAGCAAGGCATGAAGAAAAATCAAGCTA  900
     CAACTTCCACGGTCGTTTCCACACCTCCTTTTCCTACTCCTTCTGAACAAGAATCTTTAGGTTCGGGCATAGGTCGTTCCGTACTTCTTTTTAGTTCGAT
231  V  E  G  A  S  K  G  V  E  E  K  D  E  E  D  L  F  L  E  I  Q  A  R  I  Q  Q  G  M  K  K  N  Q  A  I  264

901  TTAAGGAAATAGCTAAGATTTACCAGTGGAATAAGAGTCAACTCTACGCTGCCTACCACGACTGGGAAGAAAAACAATAAAGGGAGACAGGATGTAATAA  1000
     AATTCCTTTATCGATTCTAAATGGTCACCTTATTCTCAGTTGAGATGCGACGGATGGTGCTGACCCTTCTTTTTGTTATTTCCCTCTGTCCTACATTATT
265   K  E  I  A  K  I  Y  Q  W  N  K  S  Q  L  Y  A  A  Y  H  D  W  E  E  K  Q  *                      290
```

(SEQ ID NO: 20)
(SEQ ID NO: 21)
(SEQ ID NO: 19)

FIG. 7B gep1518

```
  1 ATGGCTTGGTTAAAAAAAGGTGGCAATGCTCTTTAAGTGCAAGTTATTGCGCTGTAGCATATAAATCTATTTCCTACATATTTTTAAACGTTCTACGAG   100
    TACCGAACCAATTTTTTTCCACCGTTACGAGAAATTCACGTTCAATAACGCGACATCGTATATTTAGATAAAGGATGTATAAAAAATTTGCAAGATGCTC

101 TTAATTTGAAACGTTTAGCTTGTGGTATAATAGATTTATGGATAAAAAATATGAAAAAATCTCTCAGGATTTGGGAGTGACGTTAAAGCAAATTGATACC   200
    AATTAAACTTTGCAAATCGAACACCATATTATCTAAATACCTATTTTTTATACTTTTTTAGAGAGTCCTAAACCCTCACTGCAATTTCGTTTAACTATGG
  1                                       M  D  K  K  Y  E  K  I  S  Q  D  L  G  V  T  L  K  Q  I  D  T    21

201 GTTCTAAGTTTGACAGCTGAAGGGGCGACTATTCCCTTTATCGCGCGTTATCGCAAGGACATGACTGGTAGTCTGGATGAGGTGGCGATTAAGGCTATTA   300
    CAAGATTCAAACTGTCGACTTCCCCGCTGATAAGGGAAATAGCGCGCAATAGCGTTCCTGTACTGACCATCAGACCTACTCCACCGCTAATTCCGATAAT
 22 V  L  S  L  T  A  E  G  A  T  I  P  F  I  A  R  Y  R  K  D  M  T  G  S  L  D  E  V  A  I  K  A  I  I    55

301 TTGATTTGGATAAAAGTCTGACAAATCTCAATGACCGTAAGGAAGCTGTCTTAGCTAAGATTCAAGAACAAGGTAAGTTGACCAAGGAATTGGAAGAAGC   400
    AACTAAACCTATTTTCAGACTGTTTAGAGTTACTGGCATTCCTTCGACAGAATCGATTCTAAGTTCTTGTTCCATTCAACTGGTTCCTTAACCTTCTTCG
 56  D  L  D  K  S  L  T  N  L  N  D  R  K  E  A  V  L  A  K  I  Q  E  Q  G  K  L  T  K  E  L  E  E  A    88

401 TATCTTAGTTGCCGAAAAATTAGCAGACGTTGAAGAACTCTATCTTCCTTATAAGGAAAAGCGTCGTACCAAGGCAACCATTGCCCGTGAAGCTGGACTC   500
    ATAGAATCAACGGCTTTTTAATCGTCTGCAACTTCTTGAGATAGAAGGAATATTCCTTTTCGCAGCATGGTTCCGTTGGTAACGGGCACTTCGACCTGAG
 89  I  L  V  A  E  K  L  A  D  V  E  E  L  Y  L  P  Y  K  E  K  R  R  T  K  A  T  I  A  R  E  A  G  L    121

501 TTTCCTCTTGCTCGTTTGATTTTGCAGAATATAGTTGACTTAGAGAAAGAAGCTGAAAAGTTCGTCTGTGAAGGATTTGCGACTGGCAAGGAAGCCTTGA   600
    AAAGGAGAACGAGCAAACTAAAACGTCTTATATCAACTGAATCTCTTTCTTCGACTTTTCAAGCAGACACTTCCTAAACGCTGACCGTTCCTTCGGAACT
122 F  P  L  A  R  L  I  L  Q  N  I  V  D  L  E  K  E  A  E  K  F  V  C  E  G  F  A  T  G  K  E  A  L  T   155
```

FIG. 8A

```
 601 CCGGTGCAGTTGATATTTTGGTCGAAGCCTTATCGGAAGATGTGACCTTGCGTTCTATGACTTATCAGGAAGTGCTGAGACACTCTAAACTCACTTCTCA  700
     GGCCACGTCAACTATAAAACCAGCTTCGGAATAGCCTTCTACACTGGAACGCAAGATACTGAATAGTCCTTCACGACTCTGTGAGATTTGAGTGAAGAGT
 156   G  A  V  D  I  L  V  E  A  L  S  E  D  V  T  L  R  S  M  T  Y  Q  E  V  L  R  H  S  K  L  T  S  Q   188

 701 AGCCAAGGATGAAAGTCTTGATGAAAAGCAGGTTTTTCAGATTTATTATGATTTTTCAGAGACAGTTGGAACTATGCAAGGCTATCGTACCTTGGCTCTC  800
     TCGGTTCCTACTTTCAGAACTACTTTTCGTCCAAAAAGTCTAAATAATACTAAAAAGTCTCTGTCAACCTTGATACGTTCCGATAGCATGGAACCGAGAG
 189  A  K  D  E  S  L  D  E  K  Q  V  F  Q  I  Y  Y  D  F  S  E  T  V  G  T  M  Q  G  Y  R  T  L  A  L    221

 801 AATCGTGGGGAGAAACTTGGTGTCTTGAAGATCGGTTTTGAACATGCGACGGACCGTATTCTTGCCTTCTTTGCTACTCGTTTCAAGGTGAAAAATGCTT  900
     TTAGCACCCCTCTTTGAACCACAGAACTTCTAGCCAAAACTTGTACGCTGCCTGGCATAAGAACGGAAGAAACGATGAGCAAAGTTCCACTTTTTACGAA
 222 N  R  G  E  K  L  G  V  L  K  I  G  F  E  H  A  T  D  R  I  L  A  F  F  A  T  R  F  K  V  K  N  A  Y   255

 901 ATATTGATGAAGTTGTTCAGCAATCCGTTAAGAAAAAGGTCTTGCCTGCTATTGAGCGTCGTATTCGGACAGAATTAACTGAGAAAGCTGAAGAGGGAGC  1000
     TATAACTACTTCAACAAGTCGTTAGGCAATTCTTTTTCCAGAACGGACGATAACTCGCAGCATAAGCCTGTCTTAATTGACTCTTTCGACTTCTCCCTCG
 256   I  D  E  V  V  Q  Q  S  V  K  K  K  V  L  P  A  I  E  R  R  I  R  T  E  L  T  E  K  A  E  E  G  A   288

1001 TATCCAACTTTTTTCTGACAATCTGCGCAATCTCCTCTTGGTTGCTCCACTGAAAGGGCGCGTGGTTCTTGGATTTGACCCAGCCTTTCGTACAGGTGCC  1100
     ATAGGTTGAAAAAAGACTGTTAGACGCGTTAGAGGAGAACCAACGAGGTGACTTTCCCGCGCACCAAGAACCTAAACTGGGTCGGAAAGCATGTCCACGG
 289  I  Q  L  F  S  D  N  L  R  N  L  L  L  V  A  P  L  K  G  R  V  V  L  G  F  D  P  A  F  R  T  G  A    321

1101 AAGTTAGCTGTCGTGGATGCAACAGGAAAAATGCTGACAACTCAGGTTATTTATCCTGTTAAACCAGCATCAGCTCGTCAAATCGAAGAAGCCAAGAAAG  1200
     TTCAATCGACAGCACCTACGTTGTCCTTTTTACGACTGTTGAGTCCAATAAATAGGACAATTTGGTCGTAGTCGAGCAGTTTAGCTTCTTCGGTTCTTTC
 322 K  L  A  V  V  D  A  T  G  K  M  L  T  T  Q  V  I  Y  P  V  K  P  A  S  A  R  Q  I  E  E  A  K  K  D   355

1201 ATTTAGCAGATTTAATTGGTCAATACGGTGTAGAGATTATTGCCATTGGAAATGGAACGGCCAGTCGTGAAAGTGAAGCTTTTGTAGCGGAAGTTCTGAA  1300
     TAAATCGTCTAAATTAACCAGTTATGCCACATCTCTAATAACGGTAACCTTTACCTTGCCGGTCAGCACTTTCACTTCGAAAACATCGCCTTCAAGACTT
 356   L  A  D  L  I  G  Q  Y  G  V  E  I  I  A  I  G  N  G  T  A  S  R  E  S  E  A  F  V  A  E  V  L  K   388
```

FIG. 8B

```
1301 AGATTTCCCTGAAGTCAGCTATGTTATCGTTAATGAAAGTGGTGCTTCTGTCTATTCTGCCAGCGAACTTGCTCGTCAGGAGTTTCCAGACTTGACCGTT 1400
     TCTAAAGGGACTTCAGTCGATACAATAGCAATTACTTTCACCACGAAGACAGATAAGACGGTCGCTTGAACGAGCAGTCCTCAAAGGTCTGAACTGGCAA

389   D  F  P  E  V  S  Y  V  I  V  N  E  S  G  A  S  V  Y  S  A  S  E  L  A  R  Q  E  F  P  D  L  T  V   421

1401 GAAAAACGCTCTGCCATTTCTATCGCCCGTCGTTTGCAAGATCCTCTTGCGGAATTGGTCAAAATCGATCCTAAGTCAATTGGTGTCGGTCAATACCAAC 1500
     CTTTTTGCGAGACGGTAAAGATAGCGGGCAGCAAACGTTCTAGGAGAACGCCTTAACCAGTTTTAGCTAGGATTCAGTTAACCACAGCCAGTTATGGTTG

422  E  K  R  S  A  I  S  I  A  R  R  L  Q  D  P  L  A  E  L  V  K  I  D  P  K  S  I  G  V  G  Q  Y  Q  H  455

1501 ACGATGTCAGTCAGAAGAAACTATCTGAGAGTCTGGACTTTGTTGTCGATACAGTGGTTAACCAAGTTGGTGTCAATGTCAATACAGCTAGCCCAGCTCT 1600
     TGCTACAGTCAGTCTTCTTTGATAGACTCTCAGACCTGAAACAACAGCTATGTCACCAATTGGTTCAACCACAGTTACAGTTATGTCGATCGGGTCGAGA

456   D  V  S  Q  K  K  L  S  E  S  L  D  F  V  V  D  T  V  V  N  Q  V  G  V  N  V  N  T  A  S  P  A  L   488

1601 TCTTTCACACGTAGCTGGACTCAACAAAACTATCTCTGAAAATATTGTCAAATACCGCGAGGAAGAAGGAAAAATCACTTCACGCGCCCAAATCAAGAAA 1700
     AGAAAGTGTGCATCGACCTGAGTTGTTTTGATAGAGACTTTTATAACAGTTTATGGCGCTCCTTCTTCCTTTTTAGTGAAGTGCGCGGGTTTAGTTCTTT

489   L  S  H  V  A  G  L  N  K  T  I  S  E  N  I  V  K  Y  R  E  E  E  G  K  I  T  S  R  A  Q  I  K  K   521

1701 GTTCCTCGTCTGGGAGCCAAGGCCTTTGAGCAGGCTGCTGGTTTCCTTCGTATCCCTGAAAGTAGCAATATCCTTGATAATACAGGAGTTCACCCAGAG 1799
     CAAGGAGCAGACCCTCGGTTCCGGAAACTCGTCCGACGACCAAAGGAAGCATAGGGACTTTCATCGTTATAGGAACTATTATGTCCTCAAGTGGGTCTC

522  V  P  R  L  G  A  K  A  F  E  Q  A  A  G  F  L  R  I  P  E  S  S  N  I  L  D  N  T  G  V  H  P  E  554
```

(SEQ ID NO: 23)
(SEQ ID NO: 24)
(SEQ ID NO: 22)

FIG. 8C

```
gep1546
  1  TACTGGGGCAAGGGTTTCTTACCCTGTTCTGAATGTGAAGGTCTTTCTTGAAAATGGTGAAGTTAAGATTTTCAGAGCACTCAACGAAGCCAGNATCCGC  100
     ATGACCCCGTTCCCAAAGAATGGGACAAGACTTACACTTCCAGAAAGAACTTTTACCACTTCAATTCTAAAAGTCTCGTGAGTTGCTTCGGTCNTAGGCG
  1   T  G  A  R  V  S  Y  P  V  L  N  V  K  V  F  L  E  N  G  E  V  K  I  F  R  A  L  N  E  A  X  I  R   33

101  AGGTCTGATCGAACCATGGTGGCAGATATTGTAATAAATGGTGTTCCCTTTGAACGTTTTCGTGGAGACGGGCTAACAGTTTCGACACCGACTGGTAGTA  200
     TCCAGACTAGCTTGGTACCACCGTCTATAACATTATTTACCACAAGGGAAACTTGCAAAAGCACCTCTGCCCGATTGTCAAAGCTGTGGCTGACCATCAT
 34  R  S  D  R  T  M  V  A  D  I  V  I  N  G  V  P  F  E  R  F  R  G  D  G  L  T  V  S  T  P  T  G  S  T   67

201  CTGCCTATAACAAGTCTCTTGGCGGTGCTGTTTTACACCCTACCATTGAAGCTTTGCAATTAACGGAGATTGCCAGCCTTAATAATCGTGTCTATCGAAC  300
     GACGGATATTGTTCAGAGAACCGCCACGACAAAATGTGGGATGGTAACTTCGAAACGTTAATTGCCTCTAACGGTCGGAATTATTAGCACAGATAGCTTG
 68   A  Y  N  K  S  L  G  G  A  V  L  H  P  T  I  E  A  L  Q  L  T  E  I  A  S  L  N  N  R  V  Y  R  T  100

301  ATTGGGCTCTTCCATTATTGTGCCTAAGAAGGATAAGATTGAACTTATTCCAACAAGAAACGATTATCATACTATTTCGGTTGACAATAGCGTTTATTCT  400
     TAACCCGAGAAGGTAATAACACGGATTCTTCCTATTCTAACTTGAATAAGGTTGTTCTTTGCTAATAGTATGATAAAGCCAACTGTTATCGCAAATAAGA
101   L  G  S  S  I  I  V  P  K  K  D  K  I  E  L  I  P  T  R  N  D  Y  H  T  I  S  V  D  N  S  V  Y  S  133

401  TTCCGTAATATTGAGCGTATTGAGTATCAAATCGACCATCATAAGATTCACTTTGTCGCGACTCCTAGCCATACCAGTTTCTGGAACCGTGTTAAGGATG  500
     AAGGCATTATAACTCGCATAACTCATAGTTTAGCTGGTAGTATTCTAAGTGAAACAGCGCTGAGGATCGGTATGGTCAAAGACCTTGGCACAATTCCTAC
134  F  R  N  I  E  R  I  E  Y  Q  I  D  H  H  K  I  H  F  V  A  T  P  S  H  T  S  F  W  N  R  V  K  D  A  167

501  CCTTTATCGGTGAGGTGGATGAATGAGGTTTGAATTTATCGCAGATGAACATGTCAAGGTTAAGACCTTTTTAAAAAA  578  (SEQ ID NO: 26)
     GGAAATAGCCACTCCACCTACTTACTCCAAACTTAAATAGCGTCTACTTGTACAGTTCCAATTCTGGAAAAATTTTTT       (SEQ ID NO: 27)
168   F  I  G  E  V  D  E  *                                                        175  (SEQ ID NO: 25)
```

FIG. 9 gep1551

```
  1  GGCTCTAAAAGAAACCTACTGGAGAGTGATAGATGGGAAGTACTATTATTTTGATCCTTTATCCGGAGAGATGGTTGTCGGCTGGCAATATATACCTGCT  100
     CCGAGATTTTCTTTGGATGACCTCTCACTATCTACCCTTCATGATAATAAAACTAGGAAATAGGCCTCTCTACCAACAGCCGACCGTTATATATGGACGA
  1                                                                    M  V  V  G  W  Q  Y  I  P  A        10

101  CCACACAAGGGGGTTACGATTGGTCCTTCTCCAAGAATAGAGATTGCTCTTAGACCAGATTGGTTTTATTTTGGTCAAGATGGTGTCTTACAAGAATTTG  200
     GGTGTGTTCCCCCAATGCTAACCAGGAAGAGGTTCTTATCTCTAACGAGAATCTGGTCTAACCAAAATAAAACCAGTTCTACCACAGAATGTTCTTAAAC
 11  P  H  K  G  V  T  I  G  P  S  P  R  I  E  I  A  L  R  P  D  W  F  Y  F  G  Q  D  G  V  L  Q  E  F  V  44

201  TTGGCAAGCAAGTTTTAGAAGCAAAAACTGCTACGAATACCAACAAACATCATGGGGAAGAATATGATAGCCAAGCAGAGAAACGAGTCTATTATTTTGA  300
     AACCGTTCGTTCAAAATCTTCGTTTTTGACGATGCTTATGGTTGTTTGTAGTACCCCTTCTTATACTATCGGTTCGTCTCTTTGCTCAGATAATAAAACT
 45   G  K  Q  V  L  E  A  K  T  A  T  N  T  N  K  H  H  G  E  E  Y  D  S  Q  A  E  K  R  V  Y  Y  F  E    77

301  AGATCAGCGTAGTTATCATACTTTAAAAACTGGTTGGATTTATGAAGAGGGTTATTGGTATTATTTACAGAAGGATGGTGGCTTTGATTCTCGCATCAAC  400
     TCTAGTCGCATCAATAGTATGAAATTTTTGACCAACCTAAATACTTCTCCCAATAACCATAATAAATGTCTTCCTACCACCGAAACTAAGAGCGTAGTTG
 78   D  Q  R  S  Y  H  T  L  K  T  G  W  I  Y  E  E  G  Y  W  Y  Y  L  Q  K  D  G  G  F  D  S  R  I  N    110
```

FIG. 10A

```
401 AGATTGACGGTTGGAGAGCTAGCACGTGGTTGGGTTAAGGATTACCCTCTTACGTATGATGAAGAGAAGCTAAAAGCAGCTCCATGGTACTATCTAGATC 500
    TCTAACTGCCAACCTCTCGATCGTGCACCAACCCAATTCCTAATGGGAGAATGCATACTACTTCTCTTCGATTTTCGTCGAGGTACCATGATAGATCTAG
111 R  L  T  V  G  E  L  A  R  G  W  V  K  D  Y  P  L  T  Y  D  E  E  K  L  K  A  A  P  W  Y  Y  L  D  P 144

501 CAGCAACTGGCTGGCAAAACCTTGGGAACAAATGGTACTACCTCCGTTCATCAGGAGCTATGGTAACTGGCTGGTATCAAGATGGTTTAACTTGGTACTA 600
    GTCGTTGACCGACCGTTTTGGAACCCTTGTTTACCATGATGGAGGCAAGTAGTCCTCGATACCATTGACCGACCATAGTTCTACCAAATTGAACCATGAT
145  A  T  G  W  Q  N  L  G  N  K  W  Y  Y  L  R  S  S  G  A  M  V  T  G  W  Y  Q  D  G  L  T  W  Y  Y 177

601 CCTAAATGCAGGTAATGGAGACATGAAGACAGGTTGGTTCCAAGTCAATGGTAACTGGTACTATGCCTATGATTCAGGTGCTTTAGCTGTTAATACCACA 700
    GGATTTACGTCCATTACCTCTGTACTTCTGTCCAACCAAGGTTCAGTTACCATTGACCATGATACGGATACTAAGTCCACGAAATCGACAATTATGGTGT
178  L  N  A  G  N  G  D  M  K  T  G  W  F  Q  V  N  G  N  W  Y  Y  A  Y  D  S  G  A  L  A  V  N  T  T 210

701 GTAGGTGGTTACTACTTAAACTATAATGGTGAATGGGTTAAGTAATGAAGGCTAATTGTAAACTGTGATGGATACTTAACTTTGTATAATAGGTGGATAA 800
    CATCCACCAATGATGAATTTGATATTACCACTTACCCAATTCATTACTTCCGATTAACATTTGACACTACCTATGAATTGAAACATATTATCCACCTATT
211 V  G  G  Y  Y  L  N  Y  N  G  E  W  V  K  *                                                          225
```

(SEQ ID NO: 29)
(SEQ ID NO: 30)
(SEQ ID NO: 28)

FIG. 10B

```
gep1561

  1  TTTTATGGATATTTATATTAAGAAAGCCATTATTCACCAGTTCAGTCCGGATGATACCGAGCTGTTCTTAGCAGATAAGTTTCTCAATATTACTCCAAAA  100
     AAAATACCTATAAATATAATTCTTTCGGTAATAAGTGGTCAAGTCAGGCCTACTATGGCTCGACAAGAATCGTCTATTCAAAGAGTTATAATGAGGTTTT
  1    M  D  I  Y  I  K  K  A  I  I  H  Q  F  S  P  D  D  T  E  L  F  L  A  D  K  F  L  N  I  T  P  K   32

101  ATCGAAGAATACCTACGTAAAAAAATTGAACATGTGTATTCAGATGAAGCCAAGACTGGGATTTTCGAAGAAGAAAATCCCTTCTTCAATCATATTACAG  200
     TAGCTTCTTATGGATGCATTTTTTTAACTTGTACACATAAGTCTACTTCGGTTCTGACCCTAAAAGCTTCTTCTTTTAGGGAAGAAGTTAGTATAATGTC
 33  I  E  E  Y  L  R  K  K  I  E  H  V  Y  S  D  E  A  K  T  G  I  F  E  E  E  N  P  F  F  N  H  I  T  D   66

201  ACGATTTGTTGGAGACATCAGTAACGCTGGCTAATCTCTGGAAAGAGGAGTTTAGCATTTCTGAAAATCTCAAGACCAATGACTTGATTTTTGTTCAATT  300
     TGCTAAACAACCTCTGTAGTCATTGCGACCGATTAGAGACCTTTCTCCTCAAATCGTAAAGACTTTTAGAGTTCTGGTTACTGAACTAAAAACAAGTTAA
 67   D  L  L  E  T  S  V  T  L  A  N  L  W  K  E  E  F  S  I  S  E  N  L  K  T  N  D  L  I  F  V  Q  F   99

301  TTCTAAAGAAGGTGTAGAACATTTCGCTTTCTTGCGAATTGCCCTGCGGGAGACCTTGACCCACCTCGGAGGAGAAGTTGATAATCCAATCAAGCTGACT  400
     AAGATTTCTTCCACATCTTGTAAAGCGAAAGAACGCTTAACGGGACGCCCTCTGGAACTGGGTGGAGCCTCCTCTTCAACTATTAGGTTAGTTCGACTGA
100   S  K  E  G  V  E  H  F  A  F  L  R  I  A  L  R  E  T  L  T  H  L  G  G  E  V  D  N  P  I  K  L  T   132

401  CAGAATAACCTGCCTGGATTTGGAACGGGTGCTGACGAGGCCTTGGTGGTCAATCTTCAGAGTCGCAAGTATCACCTGATTGAAAAACGAATCAAGTACA  500
     GTCTTATTGGACGGACCTAAACCTTGCCCACGACTGCTCCGGAACCACCAGTTAGAAGTCTCAGCGTTCATAGTGGACTAACTTTTTGCTTAGTTCATGT
133  Q  N  N  L  P  G  F  G  T  G  A  D  E  A  L  V  V  N  L  Q  S  R  K  Y  H  L  I  E  K  R  I  K  Y  N   166
```

FIG. 11A

```
501  ACGGGACTTTTTTGAACTATTTTTCAGATAATCTTCTTGCTGTCGCTCCTAAGATTTCTCCTAAAAAATCTATCAAGGAACTGGAAAAAACAGCCCAGAG  600
     TGCCCTGAAAAAACTTGATAAAAAGTCTATTAGAAGAACGACAGCGAGGATTCTAAAGAGGATTTTTTAGATAGTTCCTTGACCTTTTTTGTCGGGTCTC
167   G  T  F  L  N  Y  F  S  D  N  L  L  A  V  A  P  K  I  S  P  K  K  S  I  K  E  L  E  K  T  A  Q  R   199

601  AATTGCTGAATCTTTTAACACAGATGATTTTCAATTTCAATCCAAGGTCAAATCAGCTATTTTCAACAACCTAGAAGAAAGCAATGAATTGTCACCTGAG  700
     TTAACGACTTAGAAAATTGTGTCTACTAAAAGTTAAAGTTAGGTTCCAGTTTAGTCGATAAAAGTTGTTGGATCTTCTTTCGTTACTTAACAGTGGACTC
200   I  A  E  S  F  N  T  D  D  F  Q  F  Q  S  K  V  K  S  A  I  F  N  N  L  E  E  S  N  E  L  S  P  E   232

701  AAATTGGCTAATGACCTTTTTGACAACAATCTGACGGCTCGTTTGAGCTTTATTGACCAAGTCAGAGAAGCCGTACCAGAACCTGTTCAATTTGATGAAA  800
     TTTAACCGATTACTGGAAAAACTGTTGTTAGACTGCCGAGCAAACTCGAAATAACTGGTTCAGTCTCTTCGGCATGGTCTTGGACAAGTTAAACTACTTT
233  K  L  A  N  D  L  F  D  N  N  L  T  A  R  L  S  F  I  D  Q  V  R  E  A  V  P  E  P  V  Q  F  D  E  I   266

801  TTGATGCCAGTCGCCAATTAAAGAAATTTGAAAACCAAAAACTCTCCTTATCAAATGGAATTGAGCTCATCGTTCCCAATAACGTCTATCAAGACGCCGA  900
     AACTACGGTCAGCGGTTAATTTCTTTAAACTTTTGGTTTTTGAGAGGAATAGTTTACCTTAACTCGAGTAGCAAGGGTTATTGCAGATAGTTCTGCGGCT
267   D  A  S  R  Q  L  K  K  F  E  N  Q  K  L  S  L  S  N  G  I  E  L  I  V  P  N  N  V  Y  Q  D  A  E   299

901  GTCTGTTGAGTTTATCCAAAACGAAAATGGAACCTACTCTATCTTAATCAAAAATATCGAGGATATCCAAAGTAAATAATGTTTAAACGAATTCGAAGAG  1000
     CAGACAACTCAAATAGGTTTTGCTTTTACCTTGGATGAGATAGAATTAGTTTTTATAGCTCCTATAGGTTTCATTTATTACAAATTTGCTTAAGCTTCTC
300   S  V  E  F  I  Q  N  E  N  G  T  Y  S  I  L  I  K  N  I  E  D  I  Q  S  K  *                        325

1001 TGCTTGTACTAGCAGTCTTCCTTTTTGCTGGCTATAAAGCTTACCGCGTTCATCAAGATGTCAAACAAGTCATGACCTATCAACCCATGGTGCGAGAAAT  1100
     ACGAACATGATCGTCAGAAGGAAAAACGACCGATATTTCGAATGGCGCAAGTAGTTCTACAGTTTGTTCAGTACTGGATAGTTGGGTACCACGCTCTTTA
```

(SEQ ID NO: 32)
(SEQ ID NO: 33)
(SEQ ID NO: 31)

FIG. 11B

```
gep1580

  1  AAATGTGCTATAATACTAGAAAAATACTTGTGGAGGTTCCATTATGGCAATATTTTTCATGATTTTTCTGATTGTTTGTGTGCTCCTATTGGTGATAGTC  100
     TTTACACGATATTATGATCTTTTTATGAACACCTCCAAGGTAATACCGTTATAAAAAGTACTAAAAAGACTAACAAACACACGAGGATAACCACTATCAG
  1                                                      M  A  I  F  F  M  I  F  L  I  V  C  V  L  L  L  V  I  V   19

101  ACACTGAGTACAGTTTATGTGGTTCGTCAGCAGTCGGTGGCGATTATTGAACGCTTTGGGAAATACCAAAAGGTTGCTAATAGCGGTATTCATATTCGCT  200
     TGTGACTCATGTCAAATACACCAAGCAGTCGTCAGCCACCGCTAATAACTTGCGAAACCCTTTATGGTTTTCCAACGATTATCGCCATAAGTATAAGCGA
 20  T  L  S  T  V  Y  V  V  R  Q  Q  S  V  A  I  I  E  R  F  G  K  Y  Q  K  V  A  N  S  G  I  H  I  R  L   53

201  TGCCTTTTGGGATTGACTCGATTGCAGCACGGATTCAGTTGCGCTTGTTGCAAAGTGATATTGTGGTTGAGACTAAGACCAAGGACAATGTGTTCGTTAT  300
     ACGGAAAACCCTAACTGAGCTAACGTCGTGCCTAAGTCAACGCGAACAACGTTTCACTATAACACCAACTCTGATTCTGGTTCCTGTTACACAAGCAATA
 54   P  F  G  I  D  S  I  A  A  R  I  Q  L  R  L  L  Q  S  D  I  V  V  E  T  K  T  K  D  N  V  F  V  M   86

301  GATGAATGTAGCGACTCAGTACCGTGTCAACGAGCAGAGCGTGACAGATGCTTACTATAAACTCATACGTCCAGAATCTCAGATTAAATCTTATATCGAA  400
     CTACTTACATCGCTGAGTCATGGCACAGTTGCTCGTCTCGCACTGTCTACGAATGATATTTGAGTATGCAGGTCTTAGAGTCTAATTTAGAATATAGCTT
 87   M  N  V  A  T  Q  Y  R  V  N  E  Q  S  V  T  D  A  Y  Y  K  L  I  R  P  E  S  Q  I  K  S  Y  I  E   119

401  GATGCTCTTCGCTCTTCTGTTCCAAAATTAACCTTGGATGAATTGTTTGAGAAAAAAGATGAGATTGCCCTTGAGGTTCAACACCAAGTAGCAGAAGAAA  500
     CTACGAGAAGCGAGAAGACAAGGTTTTAATTGGAACCTACTTAACAAACTCTTTTTTCTACTCTAACGGGAACTCCAAGTTGTGGTTCATCGTCTTCTTT
120  D  A  L  R  S  S  V  P  K  L  T  L  D  E  L  F  E  K  K  D  E  I  A  L  E  V  Q  H  Q  V  A  E  E  M  153
```

FIG. 12A

```
501 TGACCACTTACGGCTACATTATCGTGAAAACCTTGATTACCAAGGTCGAACCAGATGCAGAAGTTAAGCAATCTATGAATGAAATCAATGCGGCGCAACG 600
    ACTGGTGAATGCCGATGTAATAGCACTTTTGGAACTAATGGTTCCAGCTTGGTCTACGTCTTCAATTCGTTAGATACTTACTTTAGTTACGCCGCGTTGC
154  T  T  Y  G  Y  I  I  V  K  T  L  I  T  K  V  E  P  D  A  E  V  K  Q  S  M  N  E  I  N  A  A  Q  R   186

601 TAAGCGGGTCGCAGCACAAGAATTGGCGGAAGCTGACAAGATTAAAATTGTCACTGCAGCTGAAGCCGAAGCAGAAAAAGACCGCCTTCATGGTGTGGGG 700
    ATTCGCCCAGCGTCGTGTTCTTAACCGCCTTCGACTGTTCTAATTTTAACAGTGACGTCGACTTCGGCTTCGTCTTTTTCTGGCGGAAGTACCACACCCC
187  K  R  V  A  A  Q  E  L  A  E  A  D  K  I  K  I  V  T  A  A  E  A  E  A  E  K  D  R  L  H  G  V  G   219

701 ATTGCCCAACAACGTAAGGCGATTGTGGATGGATTGGCAGAGTCTATCACCGAACTCAAGGAAGCCAATGTTGGCATGACAGAAGAACAAATCATGTCTA 800
    TAACGGGTTGTTGCATTCCGCTAACACCTACCTAACCGTCTCAGATAGTGGCTTGAGTTCCTTCGGTTACAACCGTACTGTCTTCTTGTTTAGTACAGAT
220 I  A  Q  Q  R  K  A  I  V  D  G  L  A  E  S  I  T  E  L  K  E  A  N  V  G  M  T  E  E  Q  I  M  S  I  253

801 TCCTCTTGACCAACCAGTATTTGGATACCTTGAATACCTTTGCCTCTAAAGGAAATCAAACCATCTTTTTACCAAATACTCCAAATGGTGTGGATGATAT 900
    AGGAGAACTGGTTGGTCATAAACCTATGGAACTTATGGAAACGGAGATTTCCTTTAGTTTGGTAGAAAAATGGTTTATGAGGTTTACCACACCTACTATA
254  L  L  T  N  Q  Y  L  D  T  L  N  T  F  A  S  K  G  N  Q  T  I  F  L  P  N  T  P  N  G  V  D  D  I   286

901 CCGTACACAAATCTTGTCAGCCCTTCGCGCTGAGAAGAAATAATAGACTAATACTCTTCGAAAATCTCTTCAAACTACGTCAGCGTCGTCTTGCCGTATA 1000
    GGCATGTGTTTAGAACAGTCGGGAAGCGCGACTCTTCTTTATTATCTGATTATGAGAAGCTTTTAGAGAAGTTTGATGCAGTCGCAGCAGAACGGCATAT
287  R  T  Q  I  L  S  A  L  R  A  E  K  K  *                                                             300
```

(SEQ ID NO: 35)
(SEQ ID NO: 36)
(SEQ ID NO: 34)

FIG. 12B gep1713

```
  1  CCTTGATATGGTGGATAAAATAGGGTTTTNATTTTGGAAAACGTTTCCTTTGTNTTCAAATTGCTAAAAAANTGGTACAATANAGGAAAGCTTACTATTA  100
     GGAACTATACCACCTATTTTATCCCAAAANTAAAACCTTTTGCAAAGGAAACANAAGTTTAACGATTTTTTNACCATGTTATNTCCTTTCGAATGATAAT

101  TCTGAATCAGCAGATTTGGAGAGAAAGGATTCATTTTGAAATCAATAGGCTTTATTGAAAAGCTGAAGGGGTTGTCTAGTAAAGAGCTGATTTTATTGGG  200
     AGACTTAGTCGTCTAAACCTCTCTTTCCTAAGTAAAACTTTAGTTATCCGAAATAACTTTTCGACTTCCCCAACAGATCATTTCTCGACTAAAATAACCC
  1                                                    L  K  S  I  G  F  I  E  K  L  K  G  L  S  S  K  E  L  I  L  L  G   22

201  AATTATCCTAAGTATCTTTTTACCCTTTTATCTTTTTGTAGTTGTACTCTGTTTATATATTATCAGTTTGATTTTTACAGGAGACATGAAAAGTATTCTT  300
     TTAATAGGATTCATAGAAAAATGGGAAAATAGAAAAACATCAACATGAGACAAATATATAATAGTCAAACTAAAAATGTCCTCTGTACTTTTCATAAGAA
 23   I  I  L  S  I  F  L  P  F  Y  L  F  V  V  V  L  C  L  Y  I  I  S  L  I  F  T  G  D  M  K  S  I  L   55

301  CAGAAAATGGGGGAGCATCCGATGCTGCTTCTTTTTCTTAGCTATAGTACTGTTATATCCATTCTTGCACAAAATTGGATGGGTCTTGTGGCTTCAGTAG  400
     GTCTTTTACCCCCTCGTAGGCTACGACGAAGAAAAAGAATCGATATCATGACAATATAGGTAAGAACGTGTTTTAACCTACCCAGAACACCGAAGTCATC
 56  Q  K  M  G  E  H  P  M  L  L  L  F  L  S  Y  S  T  V  I  S  I  L  A  Q  N  W  M  G  L  V  A  S  V  G   89

401  GAATGTTTCTATTTACTATTTTCTTTTTGCACTATCAGTCGATTTTATCCCATAAATTCTTTCGATTGATTTTGCAGTTCGTCTTGTTTGGTAGTGTCTT  500
     CTTACAAAGATAAATGATAAAAGAAAAACGTGATAGTCAGCTAAAATAGGGTATTTAAGAAAGCTAACTAAAACGTCAAGCAGAACAAACCATCACAGAA
 90   M  F  L  F  T  I  F  F  L  H  Y  Q  S  I  L  S  H  K  F  F  R  L  I  L  Q  F  V  L  F  G  S  V  L   122

501  GTCAGCTGCTTTTGCCAGTTTAGAACATTTCCAAATTGTGAAGAAATTTAACTATGCTTTTCTTTCACCCAATATGCAGGTGTGGCATCAGAACCGGGCA  600
     CAGTCGACGAAAACGGTCAAATCTTGTAAAGGTTTAACACTTCTTTAAATTGATACGAAAAGAAAGTGGGTTATACGTCCACACCGTAGTCTTGGCCCGT
123   S  A  A  F  A  S  L  E  H  F  Q  I  V  K  K  F  N  Y  A  F  L  S  P  N  M  Q  V  W  H  Q  N  R  A   155
```

FIG. 13A

```
601  GAAGTGACCTTCTTTAATCCTAATTATTATGGAATTATTTGTTGTTTCTGTATTATGATTGCTTTCTATCTGTTTACAACGACCAAGTTGAATTGGTTGA  700
     CTTCACTGGAAGAAATTAGGATTAATAATACCTTAATAAACAACAAAGACATAATACTAACGAAAGATAGACAAATGTTGCTGGTTCAACTTAACCAACT
156  E V T F F N P N Y Y G I I C C F C I M I A F Y L F T T T K L N W L K  189

701  AAGTATTCTGTGTGATTGCAGGCTTTGTTAATCTCTTTGGTTTGAACTTTACTCAAAATCGAACTGCCTTTCCTGCTATTATCGCTGGAGCAATTATCTA  800
     TTCATAAGACACACTAACGTCCGAAACAATTAGAGAAACCAAACTTGAAATGAGTTTTAGCTTGACGGAAAGGACGATAATAGCGACCTCGTTAATAGAT
190   V F C V I A G F V N L F G L N F T Q N R T A F P A I I A G A I I Y  222

801  TCTCTTTACGACTATTAAAAACTGGAAGGCCTTTTGGCTTAGTATTGGGGTCTTCGCGATTGGTTTGAGTTTCCTCTTTTCTAGTGATTTGGGAGTTCGA  900
     AGAGAAATGCTGATAATTTTTGACCTTCCGGAAAACCGAATCATAACCCCAGAAGCGCTAACCAAACTCAAAGGAGAAAAGATCACTAAACCCTCAAGCT
223   L F T T I K N W K A F W L S I G V F A I G L S F L F S S D L G V R  255

901  ATGGGTACTTTAGACTCTTCTATGGAAGAACGCATTTCTATCTGGGATGCTGGGATGGCCTTGTTTAAGCAAAATCCTTTTTGGGGTGAAGGGCCATTGA  1000
     TACCCATGAAATCTGAGAAGATACCTTCTTGCGTAAAGATAGACCCTACGACCCTACCGGAACAAATTCGTTTTAGGAAAAACCCCACTTCCCGGTAACT
256  M G T L D S S M E E R I S I W D A G M A L F K Q N P F W G E G P L T  289

1001 CCTATATGCACTCTTATCCTCGGATACATGCTCCTTATCATGAACATGCCCACAGTCTTTATATTGATACGATTCTGAGTTACGGAATTGTGGGTACCAT  1100
     GGATATACGTGAGAATAGGAGCCTATGTACGAGGAATAGTACTTGTACGGGTGTCAGAAATATAACTATGCTAAGACTCAATGCCTTAACACCCATGGTA
290   Y M H S Y P R I H A P Y H E H A H S L Y I D T I L S Y G I V G T I  322

1101 TTTATTAGTTTTGTCTTCTGTTGCTCCTGTTCGCTTGATGATGGATATGAGTCAGGAGTCGGGGAAACGTCCGATTATCGGCCTTTATCTATCTTTCCTT  1200
     AAATAATCAAAACAGAAGACAACGAGGACAAGCGAACTACTACCTATACTCAGTCCTCAGCCCCTTTGCAGGCTAATAGCCGGAAATAGATAGAAAGGAA
323   L L V L S S V A P V R L M M D M S Q E S G K R P I I G L Y L S F L  355

1201 ACAGTGGTTGCTGTGCACGGAATTTTTGACTTGGCTCTCTTCTGGATTCAGTCAGGCTTTATTTTCTTGCTAGTTATGTGCAGTATTCCATTGGCTTTA 1299
     TGTCACCAACGACACGTGCCTTAAAAACTGAACCGAGAGAAGACCTAAGTCAGTCCGAAATAAAAGAACGATCAATACACGTCATAAGGTAACCGAAAT
356  T V V A V H G I F D L A L F W I Q S G F I F L L V M C S I P L A L  388
```

(SEQ ID NO: 38)
(SEQ ID NO: 39)
(SEQ ID NO: 37)

FIG. 13B

```
gep222

  1 AAGGAGTGAACATCTGGCTCGGTACTTCAATTGATGAAAGTATGCGTGATGAAATTCGTGTAACAGTTGTCGCAACGGGTGTTCGTCAAGACCGCGTAGA 100
    TTCCTCACTTGTAGACCGAGCCATGAAGTTAACTACTTTCATACGCACTACTTTAAGCACATTGTCAACAGCGTTGCCCACAAGCAGTTCTGGCGCATCT

101 AAAGGTTGTGGCTCCACAAGCTAGATCTGCTACTAACTACCGTGAGACAGTGAAACCAGCTCATTCACATGGCTTTGATCGTCATTTTGATATGGCAGAA 200
    TTTCCAACACCGAGGTGTTCGATCTAGACGATGATTGATGGCACTCTGTCACTTTGGTCGAGTAAGTGTACCGAAACTAGCAGTAAAACTATACCGTCTT

201 ACAGTTGAATTGCCAAAACAAAATCCACGTCGTTTGGAACCAACTCAGGCATCTGCTTTTGGTGATTGGGATCTTCGCCGTGAATCGATTGTTCGTACAA 300
    TGTCAACTTAACGGTTTTGTTTTAGGTGCAGCAAACCTTGGTTGAGTCCGTAGACGAAAACCACTAACCCTAGAAGCGGCACTTAGCTAACAAGCATGTT

301 CAGATTCAGTCGTTTCTCCAGTCGAGCGCTTTGAAGCCCCAATTTCACAAGATGAAGATGAATTGGATACACCTCCATTTTTCAAAAATCGTTAAGTAAA 400
    GTCTAAGTCAGCAAAGAGGTCAGCTCGCGAAACTTCGGGGTTAAAGTGTTCTACTTCTACTTAACCTATGTGGAGGTAAAAAGTTTTTAGCAATTCATTT
  1                                                                                                    M 1

401 TGAATGTAAAAGAAAATACAGAACTTGTTTTTCGAGAAGTTGCAGAGGCTAGTCTGAGTGCTCATCGAGAGAGTGGTTCGGTCTCTGTCATTGCAGTTAT 500
    ACTTACATTTTCTTTTATGTCTTGAACAAAAAGCTCTTCAACGTCTCCGATCAGACTCACGAGTAGCTCTCTCACCAAGCCAGAGACAGTAACGTCAATA
  2   N  V  K  E  N  T  E  L  V  F  R  E  V  A  E  A  S  L  S  A  H  R  E  S  G  S  V  S  V  I  A  V  I  34
```

FIG. 14A

```
501  CAAGTATGTAGATGTACCGACAGCGGAAGCCTTGCTTCCGCTAGGTGTTCATCATATCGGTGAAAATCGTGTAGATAAGTTTCTGGAAAAATATGAAGCT  600
     GTTCATACATCTACATGGCTGTCGCCTTCGGAACGAAGGCGATCCACAAGTAGTATAGCCACTTTTAGCACATCTATTCAAAGACCTTTTTATACTTCGA

35    K  Y  V  D  V  P  T  A  E  A  L  L  P  L  G  V  H  H  I  G  E  N  R  V  D  K  F  L  E  K  Y  E  A   67

601  TTAAAAGATCGAGATGTGACTTGGCATTTGATTGGTACCTTGCAAAGACGTAAGGTGAAAGATGTCATTCAATACGTTGATTATTTCCATGCATTGGACT  700
     AATTTTCTAGCTCTACACTGAACCGTAAACTAACCATGGAACGTTTCTGCATTCCACTTTCTACAGTAAGTTATGCAACTAATAAAGGTACGTAACCTGA

68   L  K  D  R  D  V  T  W  H  L  I  G  T  L  Q  R  R  K  V  K  D  V  I  Q  Y  V  D  Y  F  H  A  L  D  S  101

701  CAGTAAAGCTAGCAGGGGAAATTCAAAAAAGAAGTGACCGAGTCATCAAGTGTTTCCTTCAAGTAAATATTTCTAAAGAAGAAAGCAAACACGGTTTTTC  800
     GTCATTTCGATCGTCCCCTTTAAGTTTTTTCTTCACTGGCTCAGTAGTTCACAAAGGAAGTTCATTTATAAAGATTTCTTCTTTCGTTTGTGCCAAAAAG

102    V  K  L  A  G  E  I  Q  K  R  S  D  R  V  I  K  C  F  L  Q  V  N  I  S  K  E  E  S  K  H  G  F  S   134

801  GAGAGAGGAACTGCTGGAAATCTTGCCAGAGTTAGCCAGACTAGATAAGATTGAATATGTTGGTTTAATGACGATGGCACCTTTTGAGGCTAGCAGTGAG  900
     CTCTCTCCTTGACGACCTTTAGAACGGTCTCAATCGGTCTGATCTATTCTAACTTATACAACCAAATTACTGCTACCGTGGAAAACTCCGATCGTCACTC

135   R  E  E  L  L  E  I  L  P  E  L  A  R  L  D  K  I  E  Y  V  G  L  M  T  M  A  P  F  E  A  S  S  E   167

901  CAGTTGAAAGAGATTTTCAAGGCGGCCCAAGATTTACAAAGAGAAATTCAAGAGAAACAAATTCCAAATATGCCTTTAGAGCACACTGGCGGCCGTTAC 999
     GTCAACTTTCTCTAAAAGTTCCGCCGGGTTCTAAATGTTTCTCTTTAAGTTCTCTTTGTTTAAGGTTTATACGGAAATCTCGTGTGACCGCCGGCAATG

168  Q  L  K  E  I  F  K  A  A  Q  D  L  Q  R  E  I  Q  E  K  Q  I  P  N  M  P  L  E  H  T  G  G  R  Y  200
```

(SEQ ID NO: 41)
(SEQ ID NO: 42)
(SEQ ID NO: 40)

FIG. 14B gep2283

```
  1  GTACTCCCAGTCCACTTTTAGCAGTAAGTTTATTATTTACTTTTAATCAGCCACAATTTCTTGTCTTGAATCAGATTTTGGTAGGTAGTTTGGTAATTCT   100
     CATGAGGGTCAGGTGAAAATCGTCATTCAAATAATAAATGAAAATTAGTCGGTGTTAAAGAACAGAACTTAGTCTAAAACCATCCATCAAACCATTAAGA
  1    T  P  S  P  L  L  A  V  S  L  L  F  T  F  N  Q  P  Q  F  L  V  L  N  Q  I  L  V  G  S  L  V  I  L    33

101  ACTTATTGCATATATAGTTGTAAAAATCCCATTTTCTTATAGAATGGTACGTGCTATTTTATTTAGTGTTGATGATGAGATGGAAGATGCAGCAAGAAGT   200
     TGAATAACGTATATATCAACATTTTTAGGGTAAAAGAATATCTTACCATGCACGATAAAATAAATCACAACTACTACTCTACCTTCTACGTCGTTCTTCA
 34   L  I  A  Y  I  V  V  K  I  P  F  S  Y  R  M  V  R  A  I  L  F  S  V  D  D  E  M  E  D  A  A  R  S    66

201  ATGGGTGCTTCACCTTTTTATACTATGATGAAGGTTATCATTCCATTTATTTTACCGGTTGTTCTCTCTGTTATTGCTTTAAACTTTAACTCTTTATTAA   300
     TACCCACGAAGTGGAAAAATATGATACTACTTCCAATAGTAAGGTAAATAAAATGGCCAACAAGAGAGACAATAACGAAATTTGAAATTGAGAAATAATT
 67  M  G  A  S  P  F  Y  T  M  M  K  V  I  I  P  F  I  L  P  V  V  L  S  V  I  A  L  N  F  N  S  L  L  T   100

301  CTGACTTCGACTTATCTGTATTCCTTTACCATCCCCTAGCTCAACCATTAGGTATTACGATTCGATCTGCAGGTGATGAAACAGCAACATCTAATGCACA   400
     GACTGAAGCTGAATAGACATAAGGAAATGGTAGGGGATCGAGTTGGTAATCCATAATGCTAAGCTAGACGTCCACTACTTTGTCGTTGTAGATTACGTGT
101    D  F  D  L  S  V  F  L  Y  H  P  L  A  Q  P  L  G  I  T  I  R  S  A  G  D  E  T  A  T  S  N  A  Q   133

401  AGCTCTGGTATTTGTTTATACAATTGTTCTGATGATTATTTCTGGAACGGTATTATACTTCACACAAAGACCGGGGCGTAAAGTAAGGAAATAATCATGA   500
     TCGAGACCATAAACAAATATGTTAACAAGACTACTAATAAAGACCTTGCCATAATATGAAGTGTGTTTCTGGCCCCGCATTTCATTCCTTTATTAGTACT
134   A  L  V  F  V  Y  T  I  V  L  M  I  I  S  G  T  V  L  Y  F  T  Q  R  P  G  R  K  V  R  K  *         164
```

FIG. 15A

```
501  CAGCCACTAGTCTTGGGTTATCAAATATTGAAATAGTTGTCAGGATTGTTTTATCAGTAGTCATTGGTAGTATAATTGGTTTAGAGAGAGGGAGCAAATC  600
     GTCGGTGATCAGAACCCAATAGTTTATAACTTTATCAACAGTCCTAACAAAATAGTCATCAGTAACCATCATATTAACCAAATCTCTCTCCCTCGTTTAG

601  CCAGCCTGCAGGCATCCGAACTTATAGTATTGTTTGTCTAGCTGCATGTTTGATTATGATGACGAATGAATACGTATCTTATAAATTTGGGACAGGAGAT  700
     GGTCGGACGTCCGTAGGCTTGAATATCATAACAAACAGATCGACGTACAAACTAATACTACTGCTTACTTATGCATAGAATATTTAAACCCTGTCCTCTA

701  CCTACACGATTAGGAGCTCAAGTTATATCAGGTGTGGGTTTTCTAGGCGCTGGAACGATTCTTATTACAGATAAAAAGAAAATTACAGGTCTGACAACTG  800
     GGATGTGCTAATCCTCGAGTTCAATATAGTCCACACCCAAAAGATCCGCGACCTTGCTAAGAATAATGTCTATTTTTCTTTTAATGTCCAGACTGTTGAC

801  CAGCAGGCATTTGGGCTTCGGCAGGAATTGGATTAGCTATTGGAGTAGGTTTTTATGAGGGAGCTCTTTTAGTAGCCATTTCTGTTTGGGGTGTGATATC  900
     GTCGTCCGTAAACCCGAAGCCGTCCTTAACCTAATCGATAACCTCATCCAAAAATACTCCCTCGAGAAAATCATCGGTAAAGACAAACCCCACACTATAG

901  CATGTTCCAACCACTAAAAAAATATCTGCAAAATCGTTCTAAAATGATTGAATTGTATATAGTAGTTAAATCCTTTAG  978
     GTACAAGGTTGGTGATTTTTTTATAGACGTTTTAGCAAGATTTTACTAACTTAACATATATCATCAATTTAGGAAATC
```

(SEQ ID NO: 44)
(SEQ ID NO: 45)
(SEQ ID NO: 43)

FIG. 15B gep273

```
1   CAATGTGTTCCCGAACTTTTTAGAAAACATCTTCCTGAAAAAAGAGTTCGAACACTCAAAGACCAATTTGGTCAAAATAGGATGGTTGTGGTTGATGATG   100
    GTTACACAAGGGCTTGAAAAATCTTTTGTAGAAGGACTTTTTTCTCAAGCTTGTGAGTTTCTGGTTAAACCAGTTTTATCCTACCAACACCAACTACTAC
1                                                                                                         M  M    2

101 GACAGGATTAGACAAGAGTTGGAAAAGGGTGGAGCTGTCGTTCTACCTACAGAGACTGTTTATGGTCTTTTTTCCAAGGCCTTAGATGAAAAAGCAGTTG   200
    CTGTCCTAATCTGTTCTCAACCTTTTCCCACCTCGACAGCAAGATGGATGTCTCTGACAAATACCAGAAAAAAGGTTCCGGAATCTACTTTTTCGTCAAC
3   D  R  I  R  Q  E  L  E  K  G  G  A  V  V  L  P  T  E  T  V  Y  G  L  F  S  K  A  L  D  E  K  A  V  D    36

201 ACCATGTTTACCAACTCAAACGTCGTCCTAGAGATAAGGCACTCAATCTCAATATCGCCTCTTTCGAGGACATCTTGCACTTTTCAAAGAATCAGCCAGC   300
    TGGTACAAATGGTTGAGTTTGCAGCAGGATCTCTATTCCGTGAGTTAGAGTTATAGCGGAGAAAGCTCCTGTAGAACGTGAAAAGTTTCTTAGTCGGTCG
37   H  V  Y  Q  L  K  R  R  P  R  D  K  A  L  N  L  N  I  A  S  F  E  D  I  L  H  F  S  K  N  Q  P  A    69

301 TTATCTACAAAAACTTGTAGAGACCTTTTTGCCAGGTCCCTTGACCATTATTCTCGAAGCCAATGACCGAGTTCCCTATTGGGTAAATTCTGACCTTGCA   400
    AATAGATGTTTTTGAACATCTCTGGAAAAACGGTCCAGGGAACTGGTAATAAGAGCTTCGGTTACTGGCTCAAGGGATAACCCATTTAAGACTGGAACGT
70   Y  L  Q  K  L  V  E  T  F  L  P  G  P  L  T  I  I  L  E  A  N  D  R  V  P  Y  W  V  N  S  D  L  A    102

401 ACTATTGGATTTCGGATGCCCAGTCACCCTATCACACTGGATTTAATTCGAGAGACAGGTCCCTTGATTGGGCCGTCTGCCAATATCTCAGGTCAGGCAA   500
    TGATAACCTAAAGCCTACGGGTCAGTGGGATAGTGTGACCTAAATTAAGCTCTCTGTCCAGGGAACTAACCCGGCAGACGGTTATAGAGTCCAGTCCGTT
103 T  I  G  F  R  M  P  S  H  P  I  T  L  D  L  I  R  E  T  G  P  L  I  G  P  S  A  N  I  S  G  Q  A  S    136

501 GTGGTGTAACCTTTGAACAAATTCTGAAGGATTTTGACCAAGAGGTTCTGGGTCTGGAAGACGATGCTTTTCTAACTGGACAGGATTCAACTATTGTGGA   600
    CACCACATTGGAAACTTGTTTAAGACTTCCTAAAACTGGTTCTCCAAGACCCAGACCTTCTGCTACGAAAAGATTGACCTGTCCTAAGTTGATAACACCT
137  G  V  T  F  E  Q  I  L  K  D  F  D  Q  E  V  L  G  L  E  D  D  A  F  L  T  G  Q  D  S  T  I  V  D    169
```

FIG. 16A

```
601  TTTGTCTGGAGACAAGGTGAAAATCTTACCCAAGGCGCAATTAAACGAGAAGATATTCTTGCTCGGTTGCCAGAGATTTCTTTTGAGGAGGCTTGAAATG  700
     AAACAGACCTCTGTTCCACTTTTAGAATGGGTTCCGCGTTAATTTGCTCTTCTATAAGAACGAGCCAACGGTCTCTAAAGAAAACTCCTCCGAACTTTAC
170   L  S  G  D  K  V  K  I  L  P  K  A  Q  L  N  E  K  I  F  L  L  G  C  Q  R  F  L  L  R  R  L  E  M   202

701  CTAAGAGATTTGCAAGAAACAGATGTGAAAGCGATATGTGACATCAACCAAGAGGCTTTGGGTTATACTTTTAGTCCAGAGGAAACGGCTAGCCAACTAG  800
     GATTCTCTAAACGTTCTTTGTCTACACTTTCGCTATACACTGTAGTTGGTTCTCCGAAACCCAATATGAAAATCAGGTCTCCTTTGCCGATCGGTTGATC
203  L  R  D  L  Q  E  T  D  V  K  A  I  C  D  I  N  Q  E  A  L  G  Y  T  F  S  P  E  E  T  A  S  Q  L  A  236

801  CTAGACTGTCTCAGGATTCCCATCATTTCCTACTTGGCTATGAGGATGCAGCTAATCATGTCTTACTTGGATATGTCCACGCTGAAGTTTACGAATCACT  900
     GATCTGACAGAGTCCTAAGGGTAGTAAAGGATGAACCGATACTCCTACGTCGATTAGTACAGAATGAACCTATACAGGTGCGACTTCAAATGCTTAGTGA
237   R  L  S  Q  D  S  H  H  F  L  L  G  Y  E  D  A  A  N  H  V  L  L  G  Y  V  H  A  E  V  Y  E  S  L   269

901  CTATTCCAAAGCAGGATTTAATATCTTAGCTTTAGCAGTTTCACCTCAAGCGCAAGGTCAAGGTATCGGTAAAAGTTTACTACAAGGGTTGGAACAAGAA  1000
     GATAAGGTTTCGTCCTAAATTATAGAATCGAAATCGTCAAAGTGGAGTTCGCGTTCCAGTTCCATAGCCATTTTCAAATGATGTTCCCAACCTTGTTCTT
270   Y  S  K  A  G  F  N  I  L  A  L  A  V  S  P  Q  A  Q  G  Q  G  I  G  K  S  L  L  Q  G  L  E  Q  E   302

1001 GCCAAAAGATGTGGTTATGGGTTTATCCGCTTAAATTCTGCCAATCATCGTCTGGGTGCTCATGCATTTTATGAAAAAGTTGGCTATACTTGTGATAAAA  1100
     CGGTTTTCTACACCAATACCCAAATAGGCGAATTTAAGACGGTTAGTAGCAGACCCACGAGTACGTAAAATACTTTTTCAACCGATATGAACACTATTTT
303  A  K  R  C  G  Y  G  F  I  R  L  N  S  A  N  H  R  L  G  A  H  A  F  Y  E  K  V  G  Y  T  C  D  K  M  336

1101 TGCAGAAACGGTTTATTCGCATCTTTTAGTTTGATTTTCTTATTGTAAAATCAAACTAATGGACTAGTCACACAATAAAGGAGAAGACCTATGATTTTTG  1200
     ACGTCTTTGCCAAATAAGCGTAGAAAATCAAACTAAAAGAATAACATTTTAGTTTGATTACCTGATCAGTGTGTTATTTCCTCTTCTGGATACTAAAAAC
337   Q  K  R  F  I  R  I  F  *                                                                            345
```

(SEQ ID NO: 47)
(SEQ ID NO: 48)
(SEQ ID NO: 46)

FIG. 16B

```
gep286

  1 AAGATAATAGAAAATAGAATGTAACGAATGAGAGAAAAATGGCATTTGGAGATAATGGAAATCGTAAAAAAACTATGTTTGAGAAAATAACCTTGTTTAT 100
    TTCTATTATCTTTTATCTTACATTGCTTACTCTCTTTTTACCGTAAACCTCTATTACCTTTAGCATTTTTTTGATACAAACTCTTTTATTGGAACAAATA

101 CGTGATTATCATGCTAGTAGCAAGTTTATTGGGAATTTTTGCAACTGCAATTGGTGCCTTCAGTAATCTATAAAATTGATTCAAGAAAATTTAGTGACTG 200
    GCACTAATAGTACGATCATCGTTCAAATAACCCTTAAAAACGTTGACGTTAACCACGGAAGTCATTAGATATTTTAACTAAGTTCTTTTAAATCACTGAC

201 GGATTTCCCAGCCCTTTTTTAAAGTGAGAAGAAATAATGAGTATGTTTTTAGATACAGCTAAGATTAAGGTCAAGGCTGGTAATGGTGGCGATGGTATGG 300
    CCTAAAGGGTCGGGAAAAAATTTCACTCTTCTTTATTACTCATACAAAAATCTATGTCGATTCTAATTCCAGTTCCGACCATTACCACCGCTACCATACC
  1                                        M  F  L  D  T  A  K  I  K  V  K  A  G  N  G  G  D  G  M  V  20

301 TTGCCTTTCGTCGTGAAAAATATGTCCCTAATGGAGGCCCTTGGGGTGGTGATGGTGGTCGTGGAGGCAATGTGGTCTTCGTTGTAGACGAAGGACTACG 400
    AACGGAAAGCAGCACTTTTTATACAGGGATTACCTCCGGGAACCCCACCACTACCACCAGCACCTCCGTTACACCAGAAGCAACATCTGCTTCCTGATGC
 21  A  F  R  R  E  K  Y  V  P  N  G  G  P  W  G  G  D  G  G  R  G  G  N  V  V  F  V  V  D  E  G  L  R  53

401 TACCTTGATGGATTTCCGCTACAATCGTCATTTCAAGGCTGATTCTGGTGAAAAAGGGATGACCAAAGGGATGCATGGTCGTGGTGCTGAGGACCTTAGA 500
    ATGGAACTACCTAAAGGCGATGTTAGCAGTAAAGTTCCGACTAAGACCACTTTTTCCCTACTGGTTTCCCTACGTACCAGCACCACGACTCCTGGAATCT
 54  T  L  M  D  F  R  Y  N  R  H  F  K  A  D  S  G  E  K  G  M  T  K  G  M  H  G  R  G  A  E  D  L  R  86

501 GTTCGAGTACCACAAGGTACGACTGTTCGTGATGCGGAGACTGGCAAGGTTTTAACAGATTTGATTGAACATGGGCAAGAATTTATCGTTGCCCACGGTG 600
    CAAGCTCATGGTGTTCCATGCTGACAAGCACTACGCCTCTGACCGTTCCAAAATTGTCTAAACTAACTTGTACCCGTTCTTAAATAGCAACGGGTGCCAC
 87 V  R  V  P  Q  G  T  T  V  R  D  A  E  T  G  K  V  L  T  D  L  I  E  H  G  Q  E  F  I  V  A  H  G  G 120

601 GTCGTGGTGGACGTGGAAATATTCGTTTCGCGACACCAAAAAATCCTGCACCGGAAATCTCTGAAAATGGAGAACCAGGTCAGGAACGTGAGTTACAATT 700
    CAGCACCACCTGCACCTTTATAAGCAAAGCGCTGTGGTTTTTTAGGACGTGGCCTTTAGAGACTTTTACCTCTTGGTCCAGTCCTTGCACTCAATGTTAA
121  R  G  G  R  G  N  I  R  F  A  T  P  K  N  P  A  P  E  I  S  E  N  G  E  P  G  Q  E  R  E  L  Q  L 153
```

FIG. 17A

```
701  GGAACTAAAAATCTTGGCAGATGTCGGTTTAGTAGGATTCCCATCTGTAGGGAAGTCAACACTTTTAAGTGTTATTACCTCAGCTAAGCCTAAAATTGGT  800
     CCTTGATTTTTAGAACCGTCTACAGCCAAATCATCCTAAGGGTAGACATCCCTTCAGTTGTGAAAATTCACAATAATGGAGTCGATTCGGATTTTAACCA
154  E L K I L A D V G L V G F P S V G K S T L L S V I T S A K P K I G  186

801  GCCTACCACTTTACCACTATTGTACCAAATTTAGGTATGGTTCGCACCCAATCAGGTGAATCCTTTGCAGTAGCCGACTTGCCAGGTTTGATTGAAGGGG  900
     CGGATGGTGAAATGGTGATAACATGGTTTAAATCCATACCAAGCGTGGGTTAGTCCACTTAGGAAACGTCATCGGCTGAACGGTCCAAACTAACTTCCCC
187  A Y H F T T I V P N L G M V R T Q S G E S F A V A D L P G L I E G A  220

901  CTAGTCAAGGTGTTGGTTTGGGAACTCAGTTCCTCCGTCACATCGAGCGTACACGTGTTATCCTTCACATCATTGATATGTCAGCTAGCGAAGGCCGTGA  1000
     GATCAGTTCCACAACCAAACCCTTGAGTCAAGGAGGCAGTGTAGCTCGCATGTGCACAATAGGAAGTGTAGTAACTATACAGTCGATCGCTTCCGGCACT
221  S Q G V G L G T Q F L R H I E R T R V I L H I I D M S A S E G R D  253

1001 TCCATATGAGGATTACCTAGCTATCAATAAAGAGCTGGAGTCTTACAATCTTCGCCTCATGGAGCGTCCACAGATTATTGTAACTAATAAGATGGACATG  1100
     AGGTATACTCCTAATGGATCGATAGTTATTTCTCGACCTCAGAATGTTAGAAGCGGAGTACCTCGCAGGTGTCTAATAACATTGATTATTCTACCTGTAC
254  P Y E D Y L A I N K E L E S Y N L R L M E R P Q I I V T N K M D M  286

1101 CCTGAGAGTCAGGAAAATCTTGAAGAATTTAAGAAAAAATTGGCTGAAAATTATGATGAATTTGAAGAGTTACCAGCTATCTTCCCAATTTCTGGATTGA  1200
     GGACTCTCAGTCCTTTTAGAACTTCTTAAATTCTTTTTTAACCGACTTTTAATACTACTTAAACTTCTCAATGGTCGATAGAAGGGTTAAAGACCTAACT
287  P E S Q E N L E E F K K K L A E N Y D E F E E L P A I F P I S G L T  320

1201 CCAAGCAAGGTCTGGCAACACTTTTAGATGCTACAGCTGAATTGTTAGACAAGACACCAGAATTTTTGCTCTACGACGAGTCCGATATGGAAGAAGAAGT  1300
     GGTTCGTTCCAGACCGTTGTGAAAATCTACGATGTCGACTTAACAATCTGTTCTGTGGTCTTAAAAACGAGATGCTGCTCAGGCTATACCTTCTTCTTCA
321  K Q G L A T L L D A T A E L L D K T P E F L L Y D E S D M E E E V  353

1301 TTACTATGGATTTGACGAAGAAGAAAAAGCCTTTGAAATTAGTCGTGATGACGATGCGACATGGGTACTTTCTGGTGAAAAACTCATGAAACTCTTTAAT  1400
     AATGATACCTAAACTGCTTCTTCTTTTTCGGAAACTTTAATCAGCACTACTGCTACGCTGTACCCATGAAAGACCACTTTTTGAGTACTTTGAGAAATTA
354  Y Y G F D E E E K A F E I S R D D D A T W V L S G E K L M K L F N  386

1401 ATGACCAACTTTGATCGTGATGAATCTGTCATGAAACTTTA  1441   (SEQ ID NO: 50)
     TACTGGTTGAAACTAGCACTACTTAGACAGTACTTTGAAAT         (SEQ ID NO: 51)
387  M T N F D R D E S V M K L  399                    (SEQ ID NO: 49)
```

FIG. 17B gep311

```
  1 TGGAATGCCCTTAAGAAAACAATTGAAAATCAAGAAAAACAGTAAGACAAGTTTCTTTTGTCTTATGAATTATTAGAAATGAAGAAAGAAAGGATATTAT 100
    ACCTTACGGGAATTCTTTTGTTAACTTTTAGTTCTTTTTGTCATTCTGTTCAAAGAAAACAGAATACTTAATAATCTTTACTTCTTTCTTTCCTATAATA

  1                                                                                                  M   1

101 GGCTGAAGAAAGAGTAGAACCAAAACCAATTGACCTTGGTGAATATAAATTTGGTTTCCATGACGATGTAGAGCCTGTCTTATCGACAGGAAAAGGACTC 200
    CCGACTTCTTTCTCATCTTGGTTTTGGTTAACTGGAACCACTTATATTTAAACCAAAGGTACTGCTACATCTCGGACAGAATAGCTGTCCTTTTCCTGAG

  2  A  E  E  R  V  E  P  K  P  I  D  L  G  E  Y  K  F  G  F  H  D  D  V  E  P  V  L  S  T  G  K  G  L  34

201 AACGAAGGTGTTATTCGTGAATTATCTGCTGCTAAGGGTGAGCCTGAGTGGATGTTGGAGTTCCGTTTGAAGTCTTATGAAACCTTCAAAAAAATGCCCA 300
    TTGCTTCCACAATAAGCACTTAATAGACGACGATTCCCACTCGGACTCACCTACAACCTCAAGGCAAACTTCAGAATACTTTGGAAGTTTTTTTACGGGT

 35 N  E  G  V  I  R  E  L  S  A  A  K  G  E  P  E  W  M  L  E  F  R  L  K  S  Y  E  T  F  K  K  M  P  M  68

301 TGCAAACTTGGGGAGCAGACTTGTCAGAGATTGACTTTGATGACTTAATCTACTACCAAAAACCATCTGACAAACCAGCCCGTTCTTGGGATGATGTACC 400
    ACGTTTGAACCCCTCGTCTGAACAGTCTCTAACTGAAACTACTGAATTAGATGATGGTTTTTGGTAGACTGTTTGGTCGGGCAAGAACCCTACTACATGG

 69   Q  T  W  G  A  D  L  S  E  I  D  F  D  D  L  I  Y  Y  Q  K  P  S  D  K  P  A  R  S  W  D  D  V  P  101

401 TGAAAAGATTAAAGAAACCTTTGAACGTATCGGGATTCCAGAAGCTGAACGTGCTTATTTAGCAGGGGCTTCTGCCCAGTACGAGTCAGAAGTGGTTTAC 500
    ACTTTTCTAATTTCTTTGGAAACTTGCATAGCCCTAAGGTCTTCGACTTGCACGAATAAATCGTCCCCGAAGACGGGTCATGCTCAGTCTTCACCAAATG

102  E  K  I  K  E  T  F  E  R  I  G  I  P  E  A  E  R  A  Y  L  A  G  A  S  A  Q  Y  E  S  E  V  V  Y  134

501 CACAACATGAAGGAAGAGTTCCAAAAATTAGGTATTATCTTTACAGATACAGATTCCGCACTCAAGGAATACCCAGACTTATTTAAACAATACTTTGCGA 600
    GTGTTGTACTTCCTTCTCAAGGTTTTTAATCCATAATAGAAATGTCTATGTCTAAGGCGTGAGTTCCTTATGGGTCTGAATAAATTTGTTATGAAACGCT

135 H  N  M  K  E  E  F  Q  K  L  G  I  I  F  T  D  T  D  S  A  L  K  E  Y  P  D  L  F  K  Q  Y  F  A  K  168
```

```
601  AGTTGGTACCGCCGACAGATAACAAGTTGGCAGCCCTCAACTCAGCAGTATGGTCGGGTGGAACTTTTATCTACGTGCCAAAAGGTGTCAAGGTAGATAT  700
     TCAACCATGGCGGCTGTCTATTGTTCAACCGTCGGGAGTTGAGTCGTCATACCAGCCCACCTTGAAAATAGATGCACGGTTTTCCACAGTTCCATCTATA

169   L  V  P  P  T  D  N  K  L  A  A  L  N  S  A  V  W  S  G  G  T  F  I  Y  V  P  K  G  V  K  V  D  I   201

701  TCCACTTCAAACTTATTTCCGTATCAATAACGAAAATATAGGTCAGTTCGAACGTACCTTGATTATCGTTGATGAGGGAGCAAGCGTCCACTACGTAGAA  800
     AGGTGAAGTTTGAATAAAGGCATAGTTATTGCTTTTATATCCAGTCAAGCTTGCATGGAACTAATAGCAACTACTCCCTCGTTCGCAGGTGATGCATCTT

202   P  L  Q  T  Y  F  R  I  N  N  E  N  I  G  Q  F  E  R  T  L  I  I  V  D  E  G  A  S  V  H  Y  V  E   234

801  GGATGTACAGCACCAACATATTCAAGCAATAGCTTACACGCTGCCATTGTAGAAATTTTTGCTTTGGACGGAGCTTATATGCGTTATACAACTATCCAAA  900
     CCTACATGTCGTGGTTGTATAAGTTCGTTATCGAATGTGCGACGGTAACATCTTTAAAAACGAAACCTGCCTCGAATATACGCAATATGTTGATAGGTTT

235  G  C  T  A  P  T  Y  S  S  N  S  L  H  A  A  I  V  E  I  F  A  L  D  G  A  Y  M  R  Y  T  T  I  Q  N  268

901  ACTGGTCTGATAACGTCTATAACTTGGTAACAAAGCGTGCTAAGGCTCAAAAGGATGCCACTGTTGAGTGGATTGATGGAAACTTGGGTGCCAAAACGAC  1000
     TGACCAGACTATTGCAGATATTGAACCATTGTTTCGCACGATTCCGAGTTTTCCTACGGTGACAACTCACCTAACTACCTTTGAACCCACGGTTTTGCTG

269   W  S  D  N  V  Y  N  L  V  T  K  R  A  K  A  Q  K  D  A  T  V  E  W  I  D  G  N  L  G  A  K  T  T   301

1001 TATGAAATATCCATCTGTTTACCTTGATGGAGAAGGAGCGCGTGGTACCATGCTCTCTATCGCCTTTGCTAATGCAGGGCAACACCAAGACACGGGTGCT  1100
     ATACTTTATAGGTAGACAAATGGAACTACCTCTTCCTCGCGCACCATGGTACGAGAGATAGCGGAAACGATTACGTCCCGTTGTGGTTCTGTGCCCACGA

302   M  K  Y  P  S  V  Y  L  D  G  E  G  A  R  G  T  M  L  S  I  A  F  A  N  A  G  Q  H  Q  D  T  G  A   334

1101 AAGATGATTCACAATGCTCCACATACCAGCTCGTCTATTGTGTCTAAATCCATCGCTAAAGGTGGAGGAAAGGTTGACTACCGTGGACAAGTCACCTTTA  1200
     TTCTACTAAGTGTTACGAGGTGTATGGTCGAGCAGATAACACAGATTTAGGTAGCGATTTCCACCTCCTTTCCAACTGATGGCACCTGTTCAGTGGAAAT

335  K  M  I  H  N  A  P  H  T  S  S  S  I  V  S  K  S  I  A  K  G  G  G  K  V  D  Y  R  G  Q  V  T  F  N  368

1201 ACAAGAACTCTAAGAAATCTGTTTCCCACATTGAATGTGATACCATTATCATGGATGACCTTT  1263   (SEQ ID NO: 53)
     TGTTCTTGAGATTCTTTAGACAAAGGGTGTAACTTACACTATGGTAATAGTACCTACTGGAAA         (SEQ ID NO: 54)

369   K  N  S  K  K  S  V  S  H  I  E  C  D  T  I  I  M  D  D  L   388       (SEQ ID NO: 52)
```

FIG. 18B gep3262

```
1    AGCTGGAATTTATGAGCAAGTATCCTATCTTAAAGAAGGAAGAAGTGTTTATCTAACTCGTTATAATGAAGTTCAAACTGAAACAGCAACTTTAATCTTA  100
     TCGACCTTAAATACTCGTTCATAGGATAGAATTTCTTCCTTCTTCACAAATAGATTGAGCAATATTACTTCAAGTTTGACTTTGTCGTTGAAATTAGAAT
1     A  G  I  Y  E  Q  V  S  Y  L  K  E  G  R  S  V  Y  L  T  R  Y  N  E  V  Q  T  E  T  A  T  L  I  L  33

101  GGAGCTATTGTGGGGATAGCTAGTTCCTTGTTACTCTTTTATTCTGTCAATCTTCTATATTTCGAGCAATTCCGCCGAGATATCTTGATTAAACGAATTT  200
     CCTCGATAACACCCCTATCGATCAAGGAACAATGAGAAAATAAGACAGTTAGAAGATATAAAGCTCGTTAAGGCGGCTCTATAGAACTAATTTGCTTAAA
34   G  A  I  V  G  I  A  S  S  L  L  L  F  Y  S  V  N  L  L  Y  F  E  Q  F  R  R  D  I  L  I  K  R  I  S  67

201  CAGGTTTACGATTTTTTGAAACACATGCTCAGTATATGGTTAGTCAATTTGCCAGTTTTGTATTTGGTGCTAGTCTCTTTATTTTAAGCAGTCGAGACTT  300
     GTCCAAATGCTAAAAAACTTTGTGTACGAGTCATATACCAATCAGTTAAACGGTCAAAACATAAACCACGATCAGAGAAATAAAATTCGTCAGCTCTGAA
68     G  L  R  F  F  E  T  H  A  Q  Y  M  V  S  Q  F  A  S  F  V  F  G  A  S  L  F  I  L  S  S  R  D  L  100

301  GGTGATTGGCTTGCTCACTTTATTAGTCTTTCTAGCTAGTGCAGTTTTGACGCTTTACCGTCAAGCGCAGAAAGAATCTCGTGTTTCTATGACAATTATG  400
     CCACTAACCGAACGAGTGAAATAATCAGAAAGATCGATCACGTCAAAACTGCGAAATGGCAGTTCGCGTCTTTCTTAGAGCACAAAGATACTGTTAATAC
101   V  I  G  L  L  T  L  L  V  F  L  A  S  A  V  L  T  L  Y  R  Q  A  Q  K  E  S  R  V  S  M  T  I  M  133

401  AAAGGAAAATAGGATGATTGAACTAAAGAATATATCTAAAAAATTTGGAAGCCGTCAGCTATTTTCAGATACGAATCTTTA  481  (SEQ ID NO: 56)
     TTTCCTTTTATCCTACTAACTTGATTTCTTATATAGATTTTTTAAACCTTCGGCAGTCGATAAAAGTCTATGCTTAGAAAT       (SEQ ID NO: 57)
134  K  G  K  *                                                                           137  (SEQ ID NO: 55)
```

FIG. 19

```
gep3387

  1 TTTTATCTAGTACAGTATATTTATTGCGCTGTCGCCAATATTCAATCCATCCAAATGTATTAGAATGGATCTTAGTTTTACTTCAAGATATGACGACTGG 100
    AAAATAGATCATGTCATATAAATAACGCGACAGCGGTTATAAGTTAGGTAGGTTTACATAATCTTACCTAGAATCAAAATGAAGTTCTATACTGCTGACC

  1                                                                                        M  T  T  G   4

101 AGTATATTGCTTTCCGTTCACATATATATTGTTCTTTTTTTATTTGATGAATAACTATTTTAATAGGTTGGAGTGTCGCATTCGTCTGAAATCAATTAAG 200
    TCATATAACGAAAGGCAAGTGTATATATAACAAGAAAAAAATAAACTACTTATTGATAAAATTATCCAACCTCACAGCGTAAGCAGACTTTAGTTAATTC

  5  V  Y  C  F  P  F  T  Y  I  L  F  F  F  Y  L  M  N  N  Y  F  N  R  L  E  C  R  I  R  L  K  S  I  K   37

201 CACTTTACCAGTTTTAGTTTCAAATTAGCAGCTCTTAGTACGGGGATTTGGACGGCGACTTTATTTTTATTGATTTTTCTAATTGCATTTAGTAATGGTT 300
    GTGAAATGGTCAAAATCAAAGTTTAATCGTCGAGAATCATGCCCCTAAACCTGCCGCTGAAATAAAAATAACTAAAAAGATTAACGTAAATCATTACCAA

 38 H  F  T  S  F  S  F  K  L  A  A  L  S  T  G  I  W  T  A  T  L  F  L  L  I  F  L  I  A  F  S  N  G  F  71

301 TTAGCTTCTCTTTGGAGATAAAGGAGGTTGATTTTTTAAGAGAATTTTATGGTATAAGTATTGCAAACAATGCTAGTTTCTTTATAGGATTTTTTTTCTC 400
    AATCGAAGAGAAACCTCTATTTCCTCCAACTAAAAAATTCTCTTAAAATACCATATTCATAACGTTTGTTACGATCAAAGAAATATCCTAAAAAAAAGAG

 72  S  F  S  L  E  I  K  E  V  D  F  L  R  E  F  Y  G  I  S  I  A  N  N  A  S  F  F  I  G  F  F  F  S  104

401 TTATATAGCATACTATTTCTTTTTATCCTTACTTACTATTAGCAGTTTTTCTTGGTTTAAAAAATCAAACATGAGCTTAGTATTTCTGTTTACTTTTTTA 500
    AATATATCGTATGATAAAGAAAAATAGGAATGAATGATAATCGTCAAAAAGAACCAAATTTTTTAGTTTGTACTCGAATCATAAAGACAAATGAAAAAAT

105  Y  I  A  Y  Y  F  F  L  S  L  L  T  I  S  S  F  S  W  F  K  K  S  N  M  S  L  V  F  L  F  T  F  L   137

501 TTTGTAGAATCCTTATTCTGGATTTATCAGTTGGACAATGGGATAATTGGATTATTGCCAATTTTTCAGTATATGGTAAATTCCAATCCGTATGCATTGA 600
    AAACATCTTAGGAATAAGACCTAAATAGTCAACCTGTTACCCTATTAACCTAATAACGGTTAAAAAGTCATATACCATTTAAGGTTAGGCATACGTAACT

138 F  V  E  S  L  F  W  I  Y  Q  L  D  N  G  I  I  G  L  L  P  I  F  Q  Y  M  V  N  S  N  P  Y  A  L  I  171

601 TTTATTGGCTTACATTACTATCTATCATAATTCCATTGACTGTATTTTCTGTTCATAGAAACTGGAGGAGAGTGTAAAAGTTGGAAATGGGAAAGTTAAG 700
    AAATAACCGAATGTAATGATAGATAGTATTAAGGTAACTGACATAAAAGACAAGTATCTTTGACCTCCTCTCACATTTTCAACCTTTACCCTTTCAATTC

172  Y  W  L  T  L  L  S  I  I  I  P  L  T  V  F  S  V  H  R  N  W  R  R  V  *                         196
```

(SEQ ID NO: 59)
(SEQ ID NO: 60)
(SEQ ID NO: 58)

FIG. 20 gep47

```
  1 AGGGAACAAGAAAATTTCAGGTTTTCGTGATATAATAGAAGTCTGTATATAAGGAGGTAAATCATGGAGTTAGTGCATGGAATTTCAACACATTTTATCC 100
    TCCCTTGTTCTTTTAAAGTCCAAAAGCACTATATTATCTTCAGACATATATTCCTCCATTTAGTACCTCAATCACGTACCTTAAAGTTGTGTAAAATAGG

  1                                                      M  E  L  V  H  G  I  S  T  H  F  I  Q   13

101 AATCAAAAAAGTTTAAAACAAACAAAATTACCGTGCGTTTTACCGCTCCATTATCCCTTGATACGATTGCAGGTCACATGTTGAGTGCAAGTATGCTAGA 200
    TTAGTTTTTTCAAATTTTGTTTGTTTTAATGGCACGCAAAATGGCGAGGTAATAGGGAACTATGCTAACGTCCAGTGTACAACTCACGTTCATACGATCT

 14  S  K  K  F  K  T  N  K  I  T  V  R  F  T  A  P  L  S  L  D  T  I  A  G  H  M  L  S  A  S  M  L  E   46

201 GACTGCTAATCAGATGTACCCCACTTCTCAAGATTTGAGGAGACACTTGGCCAGTCTATACGGTACAGATATGTCAACCAATTGTTTCAGAAGAGGGCAA 300
    CTGACGATTAGTCTACATGGGGTGAAGAGTTCTAAACTCCTCTGTGAACCGGTCAGATATGCCATGTCTATACAGTTGGTTAACAAAGTCTTCTCCCGTT

 47  T  A  N  Q  M  Y  P  T  S  Q  D  L  R  R  H  L  A  S  L  Y  G  T  D  M  S  T  N  C  F  R  R  G  Q   79

301 AGCCACATTATAGAATTGACATTTACCTATGTTCGTGATGAGTTTTTAAGTAGGAAAAACGTGCTAACCTCTCAGATTTTGGAACTTGTAAAAGAAACTC 400
    TCGGTGTAATATCTTAACTGTAAATGGATACAAGCACTACTCAAAAATTCATCCTTTTTGCACGATTGGAGAGTCTAAAACCTTGAACATTTTCTTTGAG

 80  S  H  I  I  E  L  T  F  T  Y  V  R  D  E  F  L  S  R  K  N  V  L  T  S  Q  I  L  E  L  V  K  E  T  L  113

401 TTTTTCACCCGCAGTAGTTGATAATGGGTTTGATCCGGCCTTATTTGAAATTGAGAAAAAACAATTGCTAGCAAGTTTAGCAGCTGATATGGATGATTC 500
    AAAAAGTGGGCGTCATCAACTATTACCCAAACTAGGCCGGAATAAACTTTAACTCTTTTTTGTTAACGATCGTTCAAATCGTCGACTATACCTACTAAG

114  F  S  P  A  V  V  D  N  G  F  D  P  A  L  F  E  I  E  K  K  Q  L  L  A  S  L  A  A  D  M  D  D  S   146

501 TTTTTATTTTGCACATAAAGAATTGGATAAATTGTTTTTTCATGATGAACGTCTTCAATTGGAATATAGTGATTTACGAAATCGTATTTTAGCTGAAACT 600
    AAAAATAAAACGTGTATTTCTTAACCTATTTAACAAAAAAGTACTACTTGCAGAAGTTAACCTTATATCACTAAATGCTTTAGCATAAAATCGACTTTGA

147  F  Y  F  A  H  K  E  L  D  K  L  F  F  H  D  E  R  L  Q  L  E  Y  S  D  L  R  N  R  I  L  A  E  T   179
```

```
601  CCACAAAGTTCTTATTCTTGTTTCCAAGAATTTTTAGCCAATGATCGAATAGATTTCTTTTTCCTAGGTGATTTTAATGAGGTTGAAATTCAAAATGTAT  700
     GGTGTTTCAAGAATAAGAACAAAGGTTCTTAAAAATCGGTTACTAGCTTATCTAAAGAAAAAGGATCCACTAAAATTACTCCAACTTTAAGTTTTACATA
180  P  Q  S  S  Y  S  C  F  Q  E  F  L  A  N  D  R  I  D  F  F  F  L  G  D  F  N  E  V  E  I  Q  N  V  L  213

701  TAGAATCATTTGGCTTTAAAGGTCGAAAAGGAGATGTGAAGGTTCAGTATTGTCAACCTTATTCTAATATCCTTCAGGAAGGTATGGTTCGGAAAAATGT  800
     ATCTTAGTAAACCGAAATTTCCAGCTTTTCCTCTACACTTCCAAGTCATAACAGTTGGAATAAGATTATAGGAAGTCCTTCCATACCAAGCCTTTTTACA
214   E  S  F  G  F  K  G  R  K  G  D  V  K  V  Q  Y  C  Q  P  Y  S  N  I  L  Q  E  G  M  V  R  K  N  V  246

801  GGGACAATCCATTTTGGAATTAGGTTATCATTACCGTTCTAAATATGGTGATGAGCAACATTTACCCATGATTGTAATGAATGGTTTACTTGGTGGATTT  900
     CCCTGTTAGGTAAAACCTTAATCCAATAGTAATGGCAAGATTTATACCACTACTCGTTGTAAATGGGTACTAACATTACTTACCAAATGAACCACCTAAA
247   G  Q  S  I  L  E  L  G  Y  H  Y  R  S  K  Y  G  D  E  Q  H  L  P  M  I  V  M  N  G  L  L  G  G  F  279

901  GCTCACTCTAAGCTCTTTACAAATGTCCGTGAAAATGCTGGATTAGCTTATACCATTTCAAGTGAGCTTGATTTATTTAGTGGATTCTTGAGGATGTATG  1000
     CGAGTGAGATTCGAGAAATGTTTACAGGCACTTTTACGACCTAATCGAATATGGTAAAGTTCACTCGAACTAAATAAATCACCTAAGAACTCCTACATAC
280  A  H  S  K  L  F  T  N  V  R  E  N  A  G  L  A  Y  T  I  S  S  E  L  D  L  F  S  G  F  L  R  M  Y  A  313

1001 CTGGTATCAATCGAGAAAATCGTAACCAGGCTCGTAAAATGATGAATAATCAACTGCTTGATTTAAAAAAAGGTTATTTTACAGAGTTTGAGTTAAATCA  1100
     GACCATAGTTAGCTCTTTTAGCATTGGTCCGAGCATTTTACTACTTATTAGTTGACGAACTAAATTTTTTTCCAATAAAATGTCTCAAACTCAATTTAGT
314   G  I  N  R  E  N  R  N  Q  A  R  K  M  M  N  N  Q  L  L  D  L  K  K  G  Y  F  T  E  F  E  L  N  Q  346
```

FIG. 21B

```
1101 GACCAAGGAAATGATTCGTTGGTCGTTGTTACTTTCTCAAGATAATCAATCTTCATTGATTGAACGTGCTTATCAAAATGCCTTATTTGGAAAATCTTCA 1200
     CTGGTTCCTTTACTAAGCAACCAGCAACAATGAAAGAGTTCTATTAGTTAGAAGTAACTAACTTGCACGAATAGTTTTACGGAATAAACCTTTTAGAAGT

347   T  K  E  M  I  R  W  S  L  L  L  S  Q  D  N  Q  S  S  L  I  E  R  A  Y  Q  N  A  L  F  G  K  S  S  379

1201 GCAGACTTTAAAAGTTGGATTGCAAAGCTTGAACAAATTGACAAAGATGCTATTTGTAGAGTAGCTAATAATGTGAAACTACAAGCGATTTACTTTATGG 1300
     CGTCTGAAATTTTCAACCTAACGTTTCGAACTTGTTTAACTGTTTCTACGATAAACATCTCATCGATTATTACACTTTGATGTTCGCTAAATGAAATACC

380  A  D  F  K  S  W  I  A  K  L  E  Q  I  D  K  D  A  I  C  R  V  A  N  N  V  K  L  Q  A  I  Y  F  M  E  413

1301 AAGGAATAGAATGACAAAGGTTGTTTTTGAAGAAAAATACTATCCAGCTGTAAAAGAAAAGGTTTATCGAACTCGTTTGGCCAACGGATTGACAGTTGCT 1400
     TTCCTTATCTTACTGTTTCCAACAAAAACTTCTTTTTATGATAGGTCGACATTTTCTTTTCCAAATAGCTTGAGCAAACCGGTTGCCTAACTGTCAACGA

414   G  I  E  *                                                                                          417
```

(SEQ ID NO: 62)
(SEQ ID NO: 63)
(SEQ ID NO: 61)

FIG. 21C gep61

```
  1 GTTTTTTGACCATTTCAAAAGTCGTTAGCACAGAAAAAGAAGTCGTCTATACTTCGAAAGAAATTTATTACCTTTCACAATCTGACTTTGGTATTTATTT 100
    CAAAAAACTGGTAAAGTTTTCAGCAATCGTGTCTTTTTCTTCAGCAGATATGAAGCTTTCTTTAAATAATGGAAAGTGTTAGACTGAAACCATAAATAAA

101 TAGAGAAAAATTAAGTTCTCCCATGGTTTATGGAGAGGTTCCTGTTTATGCGAATGAAGATTTAGTAGTGGAATCTGGGAAATTGACTCCCAAAACAAGT 200
    ATCTCTTTTTAATTCAAGAGGGTACCAAATACCTCTCCAAGGACAAATACGCTTACTTCTAAATCATCACCTTAGACCCTTTAACTGAGGGTTTTGTTCA
  1                       M  V  Y  G  E  V  P  V  Y  A  N  E  D  L  V  V  E  S  G  K  L  T  P  K  T  S   26

201 TTTCAAATAACCGAGTGGCGCTTAAATAAACAAGGAATTCCAGTATTTAAGCTATCAAATCATCAATTTATAGCTGCGGACAAACGATTTTTATATGATC 300
    AAAGTTTATTGGCTCACCGCGAATTTATTTGTTCCTTAAGGTCATAAATTCGATAGTTTAGTAGTTAAATATCGACGCCTGTTTGCTAAAAATATACTAG
 27 F  Q  I  T  E  W  R  L  N  K  Q  G  I  P  V  F  K  L  S  N  H  Q  F  I  A  A  D  K  R  F  L  Y  D  Q   60

301 AATCAGAGGTAACTCCAACAATAAAAAAAGTATGGTTAGAATCTGACTTTAAACTGTACAATAGTCCTTATGATTTAAAAGAAGTGAAATCATCCTTATC 400
    TTAGTCTCCATTGAGGTTGTTATTTTTTTCATACCAATCTTAGACTGAAATTTGACATGTTATCAGGAATACTAAATTTTCTTCACTTTAGTAGGAATAG
 61  S  E  V  T  P  T  I  K  K  V  W  L  E  S  D  F  K  L  Y  N  S  P  Y  D  L  K  E  V  K  S  S  L  S   93

401 AGCTTATTCGCAAGTATCAATCGACAAGACCATGTTTGTAGAAGGAAGAGAATTTCTACATATTGATCAGGCTGGATGGGTAGCTAAAGAATCAACTTCT 500
    TCGAATAAGCGTTCATAGTTAGCTGTTCTGGTACAAACATCTTCCTTCTCTTAAAGATGTATAACTAGTCCGACCTACCCATCGATTTCTTAGTTGAAGA
 94  A  Y  S  Q  V  S  I  D  K  T  M  F  V  E  G  R  E  F  L  H  I  D  Q  A  G  W  V  A  K  E  S  T  S   126

501 GAAGAAGATAATCGGATGAGTAAAGTTCAAGAAATGTTATCTGAAAAAATATCAGAAAGATTCTTTCTCTATTTATGTTAAGCAACTGACTACTGGAAAAG 600
    CTTCTTCTATTAGCCTACTCATTTCAAGTTCTTTACAATAGACTTTTTTATAGTCTTTCTAAGAAAGAGATAAATACAATTCGTTGACTGATGACCTTTTC
127 E  E  D  N  R  M  S  K  V  Q  E  M  L  S  E  K  Y  Q  K  D  S  F  S  I  Y  V  K  Q  L  T  T  G  K  E   160
```

FIG. 22A

```
 601 AAGCTGGTATCAATCAAGATGAAAAGATGTATGCAGCCAGCGTTTTGAAACTCTCTTATCTCTATTATACGCAAGAAAAAATAAATGAGGGTCTTTATCA  700
     TTCGACCATAGTTAGTTCTACTTTTCTACATACGTCGGTCGCAAAACTTTGAGAGAATAGAGATAATATGCGTTCTTTTTTATTTACTCCCAGAAATAGT
 161  A  G  I  N  Q  D  E  K  M  Y  A  A  S  V  L  K  L  S  Y  L  Y  Y  T  Q  E  K  I  N  E  G  L  Y  Q   193

 701 GTTAGATACGACTGTAAAATACGTATCTGCAGTCAATGATTTTCCAGGTTCTTATAAACCAGAGGGAAGTGGTAGTCTTCCTAAAAAAGAAGATAATAAA  800
     CAATCTATGCTGACATTTTATGCATAGACGTCAGTTACTAAAAGGTCCAAGAATATTTGGTCTCCCTTCACCATCAGAAGGATTTTTTCTTCTATTATTT
 194  L  D  T  T  V  K  Y  V  S  A  V  N  D  F  P  G  S  Y  K  P  E  G  S  G  S  L  P  K  K  E  D  N  K   226

 801 GAATATTCTTTAAAGGATTTAATTACGAAAGTATCAAAAGAATCTGATAATGTAGCTCATAATCTATTGGGATATTACATTTCAAACCAATCTGATGCCA  900
     CTTATAAGAAATTTCCTAAATTAATGCTTTCATAGTTTTCTTAGACTATTACATCGAGTATTAGATAACCCTATAATGTAAAGTTTGGTTAGACTACGGT
 227 E  Y  S  L  K  D  L  I  T  K  V  S  K  E  S  D  N  V  A  H  N  L  L  G  Y  Y  I  S  N  Q  S  D  A  T  260

 901 CATTCAAATCCAAGATGTCTGCCATTATGGGAGATGATTGGGATCCAAAAGAAAAATTGATTTCTTCTAAGATGGCCGGGAAGTTTATGGAAGCTATTTA  1000
     GTAAGTTTAGGTTCTACAGACGGTAATACCCTCTACTAACCCTAGGTTTTCTTTTTAACTAAAGAAGATTCTACCGGCCCTTCAAATACCTTCGATAAAT
 261  F  K  S  K  M  S  A  I  M  G  D  D  W  D  P  K  E  K  L  I  S  S  K  M  A  G  K  F  M  E  A  I  Y   293

1001 TAATCAAAATGGATTTGTGCTAGAGTCTTTGACTAAAACAGATTTTGATAGTCAGCGAATTGCCAAAGGTGTTTCTGTTAAAGTAGCTCATAAAATTGGA  1100
     ATTAGTTTTACCTAAACACGATCTCAGAAACTGATTTTGTCTAAAACTATCAGTCGCTTAACGGTTTCCACAAAGACAATTTCATCGAGTATTTTAACCT
 294  N  Q  N  G  F  V  L  E  S  L  T  K  T  D  F  D  S  Q  R  I  A  K  G  V  S  V  K  V  A  H  K  I  G   326

1101 GATGCGGATGAATTTAAGCATGATACGGGTGTTGTCTATGCAGATTCTCCATTTATTCTTTCTATTTTCACTAAGAATTCTGATTATGATACGATTTCTA  1200
     CTACGCCTACTTAAATTCGTACTATGCCCACAACAGATACGTCTAAGAGGTAAATAAGAAAGATAAAAGTGATTCTTAAGACTAATACTATGCTAAAGAT
 327 D  A  D  E  F  K  H  D  T  G  V  V  Y  A  D  S  P  F  I  L  S  I  F  T  K  N  S  D  Y  D  T  I  S  K  360

1201 AGATAGCCAAGGATGTTTATGAGGTTCTAAAATGAGGGAACCAGATTTTTTAAATCATTTTCTCAAGAAGGGATATTTCAAAAAGCATGCTAAGGCGGTT  1300
     TCTATCGGTTCCTACAAATACTCCAAGATTTTACTCCCTTGGTCTAAAAAATTTAGTAAAAGAGTTCTTCCCTATAAAGTTTTTCGTACGATTCCGCCAA
 361  I  A  K  D  V  Y  E  V  L  K  *                                                                      371
```

(SEQ ID NO: 65)
(SEQ ID NO: 66)
(SEQ ID NO: 64)

FIG. 22B gep76

```
  1  TTGAAAAATATTATCTATAAGAACGACATATAAATGTAACAAAGGCGTAATATTTATTAGGCCTTTTTTGGTATACTAGTATTGTCTTTAAAAGAAGGA  100
     AACTTTTTATAATAGATATTCTTGCTGTATATTTACATTGTTTCCGCATTATAAATAATCCGGAAAAAAACCATATGATCATAACAGAAATTTTCTTCCT

101  GTATCTACGTAATATGAAGAAAAAAATCTTAGCGTCACTTTTATTAAGTACAGTAATGGTTTCTCAAGTAGCTGTTTTAACAACTGCGCATGCAGAAACG  200
     CATAGATGCATTATACTTCTTTTTTTAGAATCGCAGTGAAAATAATTCATGTCATTACCAAAGAGTTCATCGACAAAATTGTTGACGCGTACGTCTTTGC
  1            M  K  K  K  I  L  A  S  L  L  L  S  T  V  M  V  S  Q  V  A  V  L  T  T  A  H  A  E  T   29

201  ACTGATGACAAAATTGCTGCTCAAGATAATAAAATTAGTAACTTAACAGCACAACAACAAGAAGCCCAAAAACAAGTTGACCAAATTCAGGAGCAAGTAT  300
     TGACTACTGTTTTAACGACGAGTTCTATTATTTTAATCATTGAATTGTCGTGTTGTTGTTCTTCGGGTTTTTGTTCAACTGGTTTAAGTCCTCGTTCATA
 30  T  D  D  K  I  A  A  Q  D  N  K  I  S  N  L  T  A  Q  Q  Q  E  A  Q  K  Q  V  D  Q  I  Q  E  Q  V  S   63

301  CAGCTATTCAAGCTGAGCAGTCTAACTTGCAAGCTGAAAATGATAGATTACAAGCAGAATCTAAGAAACTCGAGGGTGAGATTACAGAACTTTCTAAAAA  400
     GTCGATAAGTTCGACTCGTCAGATTGAACGTTCGACTTTTACTATCTAATGTTCGTCTTAGATTCTTTGAGCTCCCACTCTAATGTCTTGAAAGATTTTT
 64   A  I  Q  A  E  Q  S  N  L  Q  A  E  N  D  R  L  Q  A  E  S  K  K  L  E  G  E  I  T  E  L  S  K  N   96

401  CATTGTTTCTCGTAACCAATCGTTGGAAAAACAAGCTCGTAGTGCTCAAACAAATGGAGCCGTAACTAGCTATATCAATACCATTGTAAACTCAAAATCA  500
     GTAACAAAGAGCATTGGTTAGCAACCTTTTTGTTCGAGCATCACGAGTTTGTTTACCTCGGCATTGATCGATATAGTTATGGTAACATTTGAGTTTTAGT
 97   I  V  S  R  N  Q  S  L  E  K  Q  A  R  S  A  Q  T  N  G  A  V  T  S  Y  I  N  T  I  V  N  S  K  S  129
```

FIG. 23A

```
501  ATTACAGAAGCTATTTCACGTGTTGCTGCAATGAGTGAAATCGTATCTGCAAACAACAAAATGTTAGAACAACAAAAGGCAGATAAAAAAGCTATTTCTG
     TAATGTCTTCGATAAAGTGCACAACGACGTTACTCACTTTAGCATAGACGTTTGTTGTTTTACAATCTTGTTGTTTTCCGTCTATTTTTTCGATAAAGAC  600
130  I  T  E  A  I  S  R  V  A  A  M  S  E  I  V  S  A  N  N  K  M  L  E  Q  Q  K  A  D  K  K  A  I  S  E  163

601  AAAAACAAGTAGCAAATAATGATGCTATCAATACTGTAATTGCTAATCAACAAAAATTGGCTGATGATGCTCAAGCATTGACTACGAAACAGGCAGAACT
     TTTTTGTTCATCGTTTATTACTACGATAGTTATGACATTAACGATTAGTTGTTTTTAACCGACTACTACGAGTTCGTAACTGATGCTTTGTCCGTCTTGA  700
164   K  Q  V  A  N  N  D  A  I  N  T  V  I  A  N  Q  Q  K  L  A  D  D  A  Q  A  L  T  T  K  Q  A  E  L  196

701  AAAAGCTGCTGAATTAAGTCTTGCTGCTGAGAAAGCGACTAGCTGAAGGGGAAAAAGCAAGGCTATTAGAGCAAGAAGCAGCAGCTGAGGCAGAGGCTCG
     TTTTCGACGACTTAATTCAGAACGACGACTCTTTCGCTGATCGACTTCCCCTTTTTCGTTCCGATAATCTCGTTCTTCGTCGTCGACTCCGTCTCCGAGC  800
197  K  A  A  E  L  S  L  A  A  E  K  A  T  S  *                                                         211
```

(SEQ ID NO: 68)
(SEQ ID NO: 69)
(SEQ ID NO: 67)

FIG. 23B

YNES_BACSU

```
  1  ATGTTAATTGCTTTATTGATTATTTTGGCCTACTTGATAGGCAGCATTCCATCTGGCTTAATTGTGGGCAAGCTTGCCAAAGGAATTGATATTCGGGAGC  100
     TACAATTAACGAAATAACTAATAAAACCGGATGAACTATCCGTCGTAAGGTAGACCGAATTAACACCCGTTCGAACGGTTTCCTTAACTATAAGCCCTCG

  1  M L I A L L I I L A Y L I G S I P S G L I V G K L A K G I D I R E H  34

101  ACGGAAGCGGCAACTTAGGCGCTACCAATGCATTCCGTACATTGGGTGTAAAAGCTGGTTCGGTCGTCATAGCCGGAGATATTTTGAAAGGGACACTGGC  200
     TGCCTTCGCCGTTGAATCCGCGATGGTTACGTAAGGCATGTAACCCACATTTTCGACCAAGCCAGCAGTATCGGCCTCTATAAAACTTTCCCTGTGACCG

 35   G S G N L G A T N A F R T L G V K A G S V V I A G D I L K G T L A  67

201  AACTGCATTGCCTTTTCTCATGCATGTTGATATTCACCCGCTTCTTGCAGGAGTCTTTGCGGTTTTAGGCCACGTGTTTCCCATCTTCGCCAAATTTAAA  300
     TTGACGTAACGGAAAAGAGTACGTACAACTATAAGTGGGCGAAGAACGTCCTCAGAAACGCCAAAATCCGGTGCACAAAGGGTAGAAGCGGTTTAAATTT

 68  T A L P F L M H V D I H P L L A G V F A V L G H V F P I F A K F K  100

301  GGCGGTAAAGCCGTGGCGACATCAGGAGGCGTTTTGCTATTTTACGCACCCCTGTTATTTATCACGATGGTTGCGGTATTCTTCATCTTTTTATACTTGA  400
     CCGCCATTTCGGCACCGCTGTAGTCCTCCGCAAAACGATAAAATGCGTGGGGACAATAAATAGTGCTACCAACGCCATAAGAAGTAGAAAAATATGAACT

101  G G K A V A T S G G V L L F Y A P L L F I T M V A V F F I F L Y L T  134
```

```
401  CTAAATTTGTTTCTCTCTCATCGATGTTAACAGGGATCTATACTGTTATATATAGTTTCTTTGTCCATGATACGTATTTATTGATTGTCGTTACCCTGCT  500
     GATTTAAACAAAGAGAGAGTAGCTACAATTGTCCCTAGATATGACAATATATATCAAAGAAACAGGTACTATGCATAAATAACTAACAGCAATGGGACGA

135   K  F  V  S  L  S  S  M  L  T  G  I  Y  T  V  I  Y  S  F  F  V  H  D  T  Y  L  L  I  V  V  T  L  L   167

501  CACTATTTTTGTGATATACAGACACCGAGCGAACATTAAACGAATTATCAATAAAACAGAACCTAAAGTAAAATGGTTATAA  582  (SEQ ID NO: 71)
     GTGATAAAAACACTATATGTCTGTGGCTCGCTTGTAATTTGCTTAATAGTTATTTTGTCTTGGATTTCATTTTACCAATATT       (SEQ ID NO: 72)
168   T  I  F  V  I  Y  R  H  R  A  N  I  K  R  I  I  N  K  T  E  P  K  V  K  W  L  *   193  (SEQ ID NO: 70)
```

FIG. 24B

NON-POLAR GENE KNOCKOUTS IN S. PNEUMONIAE

ESSENTIAL BACTERIAL GENES AND THEIR USE

CROSS-REFERENCE TO RELATED APPLICATION

This application claims priority under 35 U.S.C. §119 from provisional application U.S. Ser. No. 60/070,116, filed Dec. 31, 1997, which is incorporated herein by reference in its entirety.

BACKGROUND OF THE INVENTION

The invention relates to essential bacterial genes and their use in identifying antibacterial agents.

Bacterial infections may be cutaneous, subcutaneous, or systemic. Opportunistic bacterial infections proliferate, especially in patients afflicted with AIDS or other diseases that compromise the immune system. The bacterium *Streptococcus pneumonia* typically infects the respiratory tract and can cause lobar pneumonia, as well as meningitis, sinusitis, and other infections.

SUMMARY OF THE INVENTION

The invention is based on the discovery of 23 genes in the bacterium *Streptococcus pneumoniae*, and a related gene in the bacterium *Bacillus subtilis*, that are located within operons that are essential for survival. These 23 Streptococcus genes are referred to herein as "GEP genes" (which stands for general essential protein); for convenience, the polypeptides encoded by these genes are referred to herein as "GEP polypeptides." Each GEP gene is located within an operon that contains a gene that is essential for survival of *Streptococcus pneumoniae*; the essential gene can be the GEP gene or another gene located within the same operon. Bacterial operons contain several genes that are related, e.g., with respect to function or biochemical pathway. Transcription of an operon leads to the production of a single transcript in which multiple coding regions are linked. Thus, an operon containing one or more essential genes can be considered an "essential operon," since disruption of expression of one gene located within the operon will interfere with expression of the other genes in the operon. Each coding region of the transcript is separately translated into an individual polypeptide by ribosomes that initiate translation at multiple points along the transcript. Having identified one gene in the operon, one can readily identify and sequence the other genes located within the operon.

The genes encoding the GEP polypeptides are useful molecular tools for identifying similar genes in pathogenic microorganisms, such as pathogenic strains of Bacillus. In addition, the operons containing genes encoding GEP polypeptides, and the polypeptides encoded by such operons, are useful targets for identifying compounds that are inhibitors of the pathogens in which the GEP polypeptides are expressed. Such inhibitors inhibit bacterial growth by being bacteriostatic (e.g., inhibiting reproduction or cell division) or by being bacteriocidal (i.e., by causing cell death).

The invention, therefore, features an isolated polypeptide encoded by a nucleic acid located within an operon encoding a GEP polypeptide, termed gep103, having the amino acid sequence set forth in SEQ ID NO:1, or conservative variations thereof. An isolated operon comprising a nucleic acid encoding gep103 also is included within the invention. In addition, the invention includes an isolated nucleic acid of (a) an operon comprising the sequence of SEQ ID NO:2, as depicted in FIG. 1, or degenerate variants thereof; (b) an operon comprising the sequence of SEQ ID NO:2, or degenerate variants thereof, wherein T is replaced by U; (c) nucleic acids complementary to (a) and (b); and (d) fragments of (a), (b), and (c) that are at least 15 base pairs in length and that hybridize under stringent conditions to genomic DNA encoding the polypeptide of SEQ ID NO:1. As described above for gep103, other nucleic acids and polypeptides encoded by nucleic acids located within operons encoding GEP polypeptides are included within the invention, including: (a) operons comprising the nucleic acids represented by the SEQ ID NOs. listed below, as depicted in the Figures listed below, or degenerate variants thereof; (b) operons comprising the nucleic acids represented by the SEQ ID NOs. listed below, wherein T is replaced by U; (c) nucleic acids complementary to (a) and (b); and (d) fragments of (a), (b), and (c) that are at least 15 base pairs in length and that hybridize under stringent conditions to genomic DNA 5 encoding the polypeptides represented by the SEQ ID NOs. listed below.

TABLE 1

GEP nucleic acids and polypeptides

| GEP NUCLEIC ACID OR POLY-PEPTIDE | FIG. NO. | SEQ ID NO. OF AMINO ACID SEQUENCE | SEQ ID NO. OF THE CODING STRAND OF THE NUCLEIC ACID SEQUENCE | SEQ ID NO. OF THE NON-CODING STRAND OF THE NUCLEIC ACID SEQUENCE |
|---|---|---|---|---|
| gep103 | 1 | 1 | 2 | 3 |
| gep1119 | 2A–B | 4 | 5 | 6 |
| gep1122 | 3A–D | 7 | 8 | 9 |
| gep1315 | 4A–B | 10 | 11 | 12 |
| gep1493 | 5 | 13 | 14 | 15 |
| gep1507 | 6 | 16 | 17 | 18 |
| gep1511 | 7A–B | 19 | 20 | 21 |
| gep1518 | 8A–C | 22 | 23 | 24 |
| gep1546 | 9 | 25 | 26 | 27 |
| gep1551 | 10A–B | 28 | 29 | 30 |
| gep1561 | 11A–B | 31 | 32 | 33 |
| gep1580 | 12A–B | 34 | 35 | 36 |
| gep1713 | 13A–B | 37 | 38 | 39 |
| gep222 | 14A–B | 40 | 41 | 42 |
| gep2283 | 15A–B | 43 | 44 | 45 |
| gep273 | 16A–B | 46 | 47 | 48 |
| gep286 | 17A–B | 49 | 50 | 51 |
| gep311 | 18A–B | 52 | 53 | 54 |
| gep3262 | 19 | 55 | 56 | 57 |
| gep3387 | 20 | 58 | 59 | 60 |
| gep47 | 21A–C | 61 | 62 | 63 |
| gep61 | 22A–B | 64 | 65 | 66 |
| gep76 | 23A–B | 67 | 68 | 69 |

The invention also includes allelic variants (i.e., genes encoding isozymes) of the genes located within operons encoding the GEP polypeptides listed above. For example, the invention includes a gene that encodes a GEP polypeptide but which gene includes one or more point mutations, deletions, promotor variants, or splice site variants, provided that the resulting GEP polypeptide functions as a GEP polypeptide (e.g., as determined in a conventional complementation assay).

Identification of these GEP genes and the determination that they are located within operons containing an essential gene allows homologs of the GEP genes to be found in other organisms strains of Streptococcus. Also, orthologs of these genes can be identified in other species (e.g., Bacillus sp.). While "homologs" are structurally similar genes contained within a species, "orthologs" are functionally equivalent genes from other species (within or outside of a given genus, e.g., from *Bacillus subtilis* or *E. coli*). Such homologs and orthologs are expected to be located within operons that are essential for survival. Such homologous and orthologous genes and polypeptides can be used to identify compounds that inhibit the growth of the host organism (e.g., compounds that are bacteriocidal or bacteriostatic against pathogenic strains of the organism). Homologous and orthologous genes and polypeptides that are essential for survival can serve as targets for identifying a broad spectrum of antibacterial agents.

An ortholog of gep1493, termed B-yneS, has been identified in *B. subtilis* and is essential for survival of *B. subtilis*. The amino acid sequence (SEQ ID NO: 70), coding sequence (SEQ ID NO:71), and non-coding sequence (SEQ ID NO:72) of B-yneS is set forth in FIGS. 24A–B. As with the other polypeptides and genes disclosed herein, the B-yneS polypeptide and gene can be used in the methods described herein to identify antibacterial agents.

The term gep103 polypeptide or gene as used herein is intended to include the polypeptide and gene set forth in FIG. 1 herein, as well as homologs of the sequences set forth in FIG. 1. Also encompassed by the term gep103 gene are degenerate variants of the nucleic acid sequence set forth in FIG. 1 (SEQ ID NO:2). Degenerate variants of a nucleic acid sequence exist because of the degeneracy of the amino acid code; thus, those sequences that vary from the sequence represented by SEQ ID NO:2, but which nonetheless encode a gep103 polypeptide are included within the invention. Likewise, because of the similarity in the structures of amino acids, conservative variations (as described herein) can be made in the amino acid sequence of the gep103 polypeptide while retaining the function of the polypeptide (e.g., as determined in a conventional complementation assay). Other gep103 polypeptides and genes identified in additional Streptococcus strains may be such conservative variations or degenerate variants of the particular gep103 polypeptide and nucleic acid set forth in FIG. 1 (SEQ ID NOs:1 and 2, respectively). The gep103 polypeptide and gene share at least 80%, e.g., 90%, sequence identity with SEQ ID NOs:1 and 2, respectively. Regardless of the percent sequence identity between the gep103 sequence and the sequence represented by SEQ ID NOs:1 and 2, the gep103 genes and polypeptides encompassed by the invention are able to complement for the lack of gep103 function (e.g., in a temperature-sensitive mutant) in a standard 35 complementation assay. Additional gep103 genes that are identified and cloned from additional Streptococcus strains, and pathogenic strains in particular, can be used to produce gep103 polypeptides for use in the various methods described herein, e.g., for identifying antibacterial agents. Likewise, the terms gep1119, gep1122, gep1315, gep1493, gep1507, gep1511, gep1518, gep1546, gep1551, gep1561, gep1580, gep1713, gep222, gep2283, gep273, gep286, gep311, gep3262, gep3387, gep47, gep61, and gep76 encompass homologs, conservative variations, and degenerate variants of the sequences depicted in FIGS. 2A–23B, respectively. Such homologs, conservative variations, and degenerate variants also are included within the invention.

Since the various GEP genes described herein have been identified and shown to be located within operons that are essential for survival, the GEP genes and polypeptides encoded by nucleic acid sequences located within operons containing GEP genes and their homologs and orthologs can be used to identify antibacterial agents. More specifically, the polypeptides encoded by nucleic acid sequences located within operons containing GEP genes can be used, separately or together, in assays to identify test compounds that bind to these polypeptides. Such test compounds are expected to be antibacterial agents, in contrast to compounds that do not bind to these GEP polypeptides. As described herein, any of a variety of art-known methods can be used to assay for binding of test compounds to the polypeptides. The invention includes, for example, a method for identifying an antibacterial agent where the method entails: (a) contacting a polypeptide encoded by a nucleic acid sequence located within an operon containing a GEP gene, or homolog or ortholog thereof, with a test compound; (b) detecting binding of the test compound to the polypeptide or homolog or ortholog; and (c) determining whether a test compound that binds to the polypeptide or homolog or ortholog inhibits growth of bacteria, relative to growth of bacteria cultured in the absence of the test compound that binds to the polypeptide or homolog or ortholog, as an indication that the test compound is an antibacterial agent.

In various embodiments, the GEP polypeptide is derived from a non-pathogenic or pathogenic Streptococcus strain, such as *Streptococcus pneumoniae, Streptococcus pyogenes, Streptococcus agalactiae, Streptococcus endocarditis, Streptococcus faecium, Streptococcus sangus, Streptococcus viridans*, and *Streptococcus hemolyticus*. Suitable orthologs of the Streptococcus GEP genes can be derived from the bacterium *Bacillus subtilis*. The test compound can be immobilized on a substrate, and binding of the test compound to the polypeptide or homolog or ortholog can be detected as immobilization of the polypeptide or homolog or ortholog on the immobilized test compound, e.g., in an immunoassay with an antibody that specifically binds to the polypeptide.

If desired, the test compound can be a test polypeptide (e.g., a polypeptide having a random or predetermined amino acid sequence; or a naturally-occurring or synthetic polypeptide). Alternatively, the test compound can be a nucleic acid, such as a DNA or RNA molecule. In addition, small organic molecules can be tested. The test compound can be a naturally-occurring compound or it can be synthetically produced, if desired. Synthetic libraries, chemical libraries, and the like can be screened to identify compounds that bind to the polypeptides. More generally, binding of test compounds to the polypeptide or homolog or ortholog can be detected either in vitro or in vivo. Regardless of the source of the test compound, the polypeptides described herein can be used to identify compounds that are bactericidal or bacteriostatic to a variety of pathogenic or non-pathogenic strains.

In an exemplary method, binding of a test compound to a polypeptide encoded by a nucleic acid located within an operon containing a GEP gene can be detected in a conventional two-hybrid system for detecting protein/protein interactions (e.g., in yeast or mammalian cells). Generally, in such a method, (a) the polypeptide encoded by a nucleic acid located within an operon containing a GEP gene is provided as a fusion protein that includes the polypeptide fused to (i) a transcription activation domain of a transcription factor or (ii) a DNA-binding domain of a transcription factor; (b) the test polypeptide is provided as a fusion protein that includes the test polypeptide fused to (i) a transcription activation domain of a transcription factor or (ii) a DNA-binding domain of a transcription factor; and (c) binding of the test polypeptide to the polypeptide is detected as reconstitution of a transcription factor. Homologs and orthologs of the GEP polypeptides can be used in similar methods. Reconstitution of the transcription factor can be detected, for example, by detecting transcription of a gene that is operably linked to a DNA sequence bound by the DNA-binding domain of the reconstituted transcription factor (See, for example, White, 1996, Proc. Natl. Acad. Sci. 93:10001–10003 and references cited therein and Vidal et al., 1996, Proc. Natl. Acad. Sci. 93:10315–10320).

In an alternative method, an isolated operon containing a nucleic acid molecule encoding a GEP polypeptide is used to identify a compound that decreases the expression of a GEP polypeptide in vivo. Such compounds can be used as antibacterial agents. To discover such compounds, cells that express a GEP polypeptide are cultured, exposed to a test compound (or a mixture of test compounds), and the level of expression or activity is compared with the level of GEP polypeptide expression or activity in cells that are otherwise identical but that have not been exposed to the test compound(s). Many standard quantitative assays of gene expression can be utilized in this aspect of the invention.

To identify compounds that modulate expression of a GEP polypeptide (or homologous or orthologous sequence), the test compound(s) can be added at varying concentrations to the culture medium of cells that express a GEP polypeptide (or homolog or ortholog), as described herein. Such test compounds can include small molecules (typically, non-protein, non-polysaccharide chemical entities), polypeptides, and nucleic acids. The expression of the GEP polypeptide is then measured, for example, by Northern blot PCR analysis or RNAse protection analyses using a nucleic acid molecule of the invention as a probe. The level of expression in the presence of the test molecule, compared with the level of expression in its absence, will indicate whether or not the test molecule alters the expression of the GEP polypeptide. Because the GEP polypeptides are expressed from operons that are essential for survival, test compounds that inhibit the expression and/or function of the GEP polypeptide will inhibit growth of the cells or kill the cells.

Compounds that modulate the expression of the polypeptides of the invention can be identified by carrying out the assays described herein and then measuring the levels of the GEP polypeptides expressed in the cells, e.g., by performing a Western blot analysis using antibodies that bind to a GEP polypeptide.

The invention further features methods of identifying from a large group of mutants those strains that have conditional lethal mutations. In general, the gene and corresponding gene product are subsequently identified, although the strains themselves can be used in screening or diagnostic assays. The mechanism(s) of action for the identified genes and gene products provide a rational basis for the design of antibacterial therapeutic agents. These antibacterial agents reduce the action of the gene product in a wild type strain, and therefore are useful in treating a subject with that type, or a similarly susceptible type of infection by administering the agent to the subject in a pharmaceutically effective amount. Reduction in the action of the gene product includes competitive inhibition of the gene product for the active site of an enzyme or receptor; non-competitive inhibition; disrupting an intracellular cascade path which requires the gene product; binding to the gene product itself, before or after post-translational processing; and acting as a gene product mimetic, thereby down-regulating the activity. Therapeutic agents include monoclonal antibodies raised against the gene product.

Furthermore, the presence of the gene sequence in certain cells (e.g., a pathogenic bacterium of the same genus or similar species), and the absence or divergence of the sequence in host cells can be determined, if desired. Therapeutic agents directed toward genes or gene products that are not present in the host have several advantages, including fewer side effects, and lower overall dosage.

The invention includes pharmaceutical formulations that include a pharmaceutically acceptable excipient and an antibacterial agent identified using the methods described herein. In particular, the invention includes pharmaceutical formulations that contain antibacterial agents that inhibit the growth of, or kill, pathogenic Streptococcus strains. Such pharmaceutical formulations can be used for treating a Streptococcus infection in an organism. Such a method entails administering to the organism a therapeutically effective amount of the pharmaceutical formulation. In particular, such pharmaceutical formulations can be used to treat streptococcal pneumonia in mammals such as humans and domesticated mammals (e.g., cows, pigs, dogs, and cats), and in plants. The efficacy of such antibacterial agents in humans can be estimated in an animal model system well known to those of skill in the art (e.g., mouse and rabbit model systems).

Also included within the invention are polyclonal and monoclonal antibodies that specifically bind to the various GEP polypeptides described herein (e.g., gep103). Such antibodies can facilitate detection of GEP polypeptides in various Streptococcus strains. These antibodies also are useful for detecting binding of a test compound to GEP polypeptides (e.g., using the assays described herein). In addition, monoclonal antibodies that bind to GEP polypeptides are themselves adequate antibacterial agents when administered to a mammal, as such monoclonal antibodies are expected to impede one or more functions of GEP polypeptides.

As used herein, "nucleic acids" encompass both RNA and DNA, including genomic DNA and synthetic (e.g., chemically synthesized) DNA. The nucleic acid can be double-stranded or single-stranded. Where single-stranded, the nucleic acid may be a sense strand or an antisense strand. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

An "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a genomic DNA fragment produced by PCR or restriction endonuclease treatment) independent of other sequences. It also includes a recombinant DNA that is part of a hybrid gene encoding an additional polypeptide sequence. The term "isolated" can refer to a nucleic acid or polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state. As used herein, the term "isolated nucleic acid molecule" includes an operon containing a contiguous cluster of linked sequences. "Isolated operons" are those operons that are not naturally occurring and which are not associated with the sequences by which they are normally surrounded in a bacterial genome.

A nucleic acid sequence that is "substantially identical" to a GEP nucleotide sequence is at least 80% (e.g., 85%) identical to the nucleotide sequence of the nucleic acid sequences represented by the SEQ ID NOs listed in Table 1, as depicted in FIGS. 1–23B. For purposes of comparison of nucleic acids, the length of the reference nucleic acid sequence will generally be at least 40 nucleotides, e.g., at least 60 nucleotides or more nucleotides. Sequence identity can be measured using sequence analysis software (e.g., Sequence Analysis Software Package of the Genetics Computer Group, University of Wisconsin Biotechnology Center, 1710 University Avenue, Madison, Wis. 53705).

The GEP polypeptides useful in practicing the invention include, but are not limited to, recombinant polypeptides and natural polypeptides. Also useful in the invention are nucleic acid sequences that encode forms of GEP polypeptides in which naturally occurring amino acid sequences are altered or deleted. Preferred nucleic acids encode polypeptides that are soluble under normal physiological conditions. Also within the invention are nucleic acids encoding fusion proteins in which a portion of a GEP polypeptide is fused to an unrelated polypeptide (e.g., a marker polypeptide or a fusion partner) to create a fusion protein. For example, the polypeptide can be fused to a hexa-histidine tag to facilitate purification of bacterially expressed polypeptides, or to a hemagglutinin tag to facilitate purification of polypeptides expressed in eukaryotic cells. The invention also includes, for example, isolated polypeptides (and the nucleic acids that encode these polypeptides) that include a first portion and a second portion; the first portion includes, e.g., a GEP polypeptide, and the second portion includes an immunoglobulin constant (Fc) region or a detectable marker.

The fusion partner can be, for example, a polypeptide which facilitates secretion, e.g., a secretory sequence. Such a fused polypeptide is typically referred to as a preprotein. The secretory sequence can be cleaved by the host cell to form the mature protein. Also within the invention are nucleic acids that encode a GEP polypeptide fused to a polypeptide sequence to produce an inactive preprotein. Preproteins can be converted into the active form of the protein by removal of the inactivating sequence.

The invention also includes nucleic acids that hybridize, e.g., under stringent hybridization conditions (as defined herein) to all or a portion of the nucleotide sequences represented by the SEQ ID NOs. listed in Table 1, or their complements. The hybridizing portion of the hybridizing nucleic acids is typically at least 15 (e.g., 20, 30, or 50) nucleotides in length. The hybridizing portion of the hybridizing nucleic acid is at least 80%, e.g., at least 95%, or at least 98%, identical to the sequence of a portion or all of a nucleic acid encoding a GEP polypeptide or its complement. Hybridizing nucleic acids of the type described herein can be used as a cloning probe, a primer (e.g., a PCR primer), or a diagnostic probe. Nucleic acids that hybridize to the nucleotide sequences represented by the SEQ ID NOs. listed in Table 1 are considered "antisense oligonucleotides." Also included within the invention are ribozymes that inhibit the function of operons containing the GEP genes of the invention, as determined, for example, in a complementation assay.

Also useful in the invention are various cells, e.g., transformed host cells, that contain a GEP nucleic acid described herein. A "transformed cell" is a cell into which (or into an ancestor of which) has been introduced, by means of recombinant DNA techniques, a nucleic acid encoding a GEP polypeptide. Both prokaryotic and eukaryotic cells are included, e.g., bacteria, Streptococcus, Bacillus, and the like.

Also useful in the invention are genetic constructs (e.g., vectors and plasmids) that include a nucleic acid of the invention which is operably linked to a transcription and/or translation sequence to enable expression, e.g., expression vectors. By "operably linked" is meant that a selected nucleic acid, e.g., a DNA molecule encoding a GEP polypeptide, is positioned adjacent to one or more sequence elements, e.g., a promoter, which directs transcription and/or translation of the sequence such that the sequence elements can control transcription and/or translation of the selected nucleic acid.

The invention also features purified or isolated polypeptides encoded by nucleic acids located within operons containing GEP genes, as listed in Table 1. As used herein, both "protein" and "polypeptide" mean any chain of amino acids, regardless of length or post-translational modification (e.g., glycosylation or phosphorylation). Thus, the terms gep103 polypeptide, gep1119 polypeptide, gep1122 polypeptide, gep1315 polypeptide, gep1493 polypeptide, gep1507 polypeptide, gep1511 polypeptide, gep1518 polypeptide, gep1546 polypeptide, gep1551 polypeptide, gep1561 polypeptide, gep1580 polypeptide, gep1713 polypeptide, gep222 polypeptide, gep2283 polypeptide, gep273 polypeptide, gep286 polypeptide, gep311 polypeptide, gep3262 polypeptide, gep3387 polypeptide, gep47 polypeptide, gep61 polypeptide, and gep76 polypeptide include full-length, naturally occurring gep103, gep1119, gep1122, gep1315, gep1493, gep1507, gep1511, gep1518, gep1546, gep1551, gep1561, gep1580, gep1713, gep222, gep2283, gep273, gep286, gep311, gep3262, gep3387, gep47, gep61, and gep76 proteins, respectively, as well as recombinantly or synthetically produced polypeptides that correspond to the full-length, naturally occurring proteins, or to a portion of the naturally occurring or synthetic polypeptide.

A "purified" or "isolated" compound is a composition that is at least 60% by weight the compound of interest, e.g., a GEP polypeptide or antibody. Preferably the preparation is at least 75% (e.g., at least 90% or 99%) by weight the compound of interest. Purity can be measured by any appropriate standard method, e.g., column chromatography, polyacrylamide gel electrophoresis, or HPLC analysis.

Preferred GEP polypeptides include a sequence substantially identical to all or a portion of a naturally occurring GEP polypeptide, e.g., including all or a portion of the sequences shown in FIGS. 1–23B. Polypeptides "substantially identical" to the GEP polypeptide sequences described herein have an amino acid sequence that is at least 80% (e.g., 85%, 90%, 95%, or 99%) identical to the amino acid sequence of the GEP polypeptides represented by the SEQ ID NOs. listed in Table 1. For purposes of comparison, the length of the reference GEP polypeptide sequence will generally be at least 16 amino acids, e.g., at least 20 or 25 amino acids.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference polypeptide. Thus, a polypeptide that is 50% identical to a reference polypeptide that is 100 amino acids long can be a 50 amino acid polypeptide that is completely identical to a 50 amino acid long portion of the reference polypeptide. It also might be a 100 amino acid long polypeptide which is 50% identical to the reference polypeptide over its entire length. Of course, other polypeptides also will meet the same criteria.

The invention also features purified or isolated antibodies that specifically bind to a GEP polypeptide. By "specifically binds" is meant that an antibody recognizes and binds to a particular antigen, e.g., a GEP polypeptide, but does not substantially recognize and bind to other molecules in a sample, e.g., a biological sample that naturally includes a GEP polypeptide.

In another aspect, the invention features a method for detecting a GEP polypeptide in a sample. This method includes: obtaining a sample suspected of containing a GEP polypeptide; contacting the sample with an antibody that specifically binds to a GEP polypeptide under conditions that allow the formation of complexes of an antibody and the GEP polypeptide; and detecting the complexes, if any, as an indication of the presence of a GEP polypeptide in the sample.

Also encompassed by the invention is a method of obtaining a gene related to (i.e., a functional homolog or ortholog of) a GEP gene. Such a method entails obtaining a labeled probe that includes an isolated nucleic acid which encodes all or a portion of a GEP nucleic acid, or a homolog or ortholog thereof; screening a nucleic acid fragment library with the labeled probe under conditions that allow hybridization of the probe to nucleic acid fragments in the library, thereby forming nucleic acid duplexes; isolating labeled duplexes, if any; and preparing a full-length gene sequence from the nucleic acid fragments in any labeled duplex to obtain a gene related to the GEP gene.

The invention offers several advantages. For example, the methods for identifying antibacterial agents can be configured for high throughput screening of numerous candidate antibacterial agents.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated herein by reference in their entirety. In the case of a conflict, the present specification, including definitions, will control. In addition, the materials, methods, and examples are illustrative and are not intended to limit the scope of the invention, which is defined by the claims.

Other features and advantages of the invention will be apparent from the following detailed description, and from the claims.

BRIEF DESCRIPTION OF THE DRAWINGS

FIG. 1 is a representation of the amino acid and coding strand and non-coding strand nucleic acid sequences of the gep103 polypeptide and gene from a *Streptococcus pneumonia* strain (SEQ ID NOs:1, 2, and 3 respectively).

FIGS. 2A–B are a representation of the amino acid and coding strand and non-coding strand nucleic acid sequences of the gep1119 polypeptide and gene from a *Streptococcus pneumonia* strain (SEQ ID NOs:4, 5 and 6, respectively).

FIGS. 3A–D are a representation of the amino acid and coding strand and non-coding strand nucleic acid sequences of the gep1122 polypeptide and gene from a *Streptococcus pneumonia* strain (SEQ ID NOs:7, 8, and 9, respectively).

FIGS. 4A–B are a representation of the amino acid and coding strand and non-coding strand nucleic acid sequences of the gep1315 polypeptide and gene from a *Streptococcus pneumonia* strain (SEQ ID NOs:10, 11, and 12, respectively).

FIG. 5 is a representation of the amino acid and coding strand and non-coding strand nucleic acid sequences of the gep1493 polypeptide and gene from a *Streptococcus pneumonia* strain (SEQ ID NOs:13, 14, and 15, respectively).

FIG. 6 is a representation of the amino acid and coding strand and non-coding strand nucleic acid sequences of the gep1507 polypeptide and gene from a *Streptococcus pneumonia* (SEQ ID NOs:16, 17, and 18, respectively).

FIGS. 7A–B are a representation of the amino acid and coding strand and non-coding strand nucleic acid sequences of the gep1511 polypeptide and gene from a *Streptococcus pneumonia* (SEQ ID NOs:19, 20, and 21, respectively).

FIGS. 8A–C are a representation of the amino acid and coding strand and non-coding strand nucleic acid sequences of the gep1518 polypeptide and gene from a *Streptococcus pneumonia* (SEQ ID NOs:22, 23, and 24, respectively).

FIG. 9 is a representation of the amino acid and coding strand and non-coding strand nucleic acid sequences of the gep1546 polypeptide and gene from a *Streptococcus pneumonia* strain (SEQ ID NOs:25, 26, and 27, respectively).

FIGS. 10A–B are a representation of the amino acid and coding strand and non-coding strand nucleic acid sequences of the gep1551 polypeptide and gene from a *Streptococcus pneumonia* strain (SEQ ID NOs:28, 29, and 30, respectively).

FIGS. 11A–B are a representation of the amino acid and coding strand and non-coding strand nucleic acid sequences of the gep1561 polypeptide and gene from a *Streptococcus pneumonia* strain (SEQ ID NOs:31, 32, and 33, respectively).

FIGS. 12A–B are a representation of the amino acid and coding strand and non-coding strand nucleic acid sequences of the gep1580 polypeptide and gene from a *Streptococcus pneumonia* strain (SEQ ID NOs:34, 35, and 36, respectively).

FIGS. 13A–B are a representation of the amino acid and coding strand and non-coding strand nucleic acid sequences of the gep1713 polypeptide and gene from a *Streptococcus pneumonia* (SEQ ID NOs:37, 38, and 39, respectively).

FIGS. 14A–B are a representation of the amino acid and coding strand and non-coding strand nucleic acid sequences of the gep222 polypeptide and gene from a *Streptococcus pneumonia* (SEQ ID NOs:40, 41, and 42, respectively).

FIGS. 15A–B are a representation of the amino acid and coding strand and non-coding strand nucleic acid sequences of the gep2283 polypeptide and gene from a *Streptococcus pneumonia* (SEQ ID NOs:43, 44, and 45, respectively).

FIGS. 16A–B are a representation of the amino acid and coding strand and non-coding strand nucleic acid sequences of the gep273 polypeptide and gene from a *Streptococcus pneumonia* strain (SEQ ID NOs:46, 47, and 48, respectively).

FIGS. 17A–B are a representation of the amino acid and coding strand and non-coding strand nucleic acid sequences of the gep286 polypeptide and gene from a *Streptococcus pneumonia* strain (SEQ ID NOs:49, 50, and 51, respectively).

FIGS. 18A–B are a representation of the amino acid and coding strand and non-coding strand nucleic acid sequences of the gep311 polypeptide and gene from a *Streptococcus pneumonia* (SEQ ID NOs:52, 53, and 54, respectively).

FIG. 19 is a representation of the amino acid and coding strand and non-coding strand nucleic acid sequences of the gep3262 polypeptide and gene from a *Streptococcus pneumonia* (SEQ ID NOs:55, 56, and 57, respectively).

FIG. 20 is a representation of the amino acid and coding strand and non-coding strand nucleic acid sequences of the gep3387 polypeptide and gene from a *Streptococcus pneumonia* (SEQ ID NOs:58, 59, and 60, respectively).

FIGS. 21A–C are a representation of the amino acid and coding strand and non-coding strand nucleic acid sequences of the gep47 polypeptide and gene from a *Streptococcus pneumonia* strain (SEQ ID NOs:61, 62, and 63, respectively).

FIGS. 22A–B are a representation of the amino acid and coding 10 strand and non-coding strand nucleic acid sequences of the gep61 polypeptide and gene from a *Streptococcus pneumonia* strain (SEQ ID NOs:64, 65, and 66, respectively).

FIGS. 23A–B are a representation of the amino acid and coding strand and non-coding strand nucleic acid sequences of the gep76 polypeptide and gene from a *Streptococcus pneumonia* strain (SEQ ID NOs:67, 68, and 69, respectively).

FIGS. 24A–B are a representation of the amino acid and coding strand and non-coding strand nucleic acid sequences of the B-yneS polypeptide and gene from a *Bacillus subtilis* strain (SEQ ID NOs:70, 71, and 72, respectively).

DETAILED DESCRIPTION OF THE INVENTION

Identifying Streptococcus Genes in Essential Operons

Figure 25:
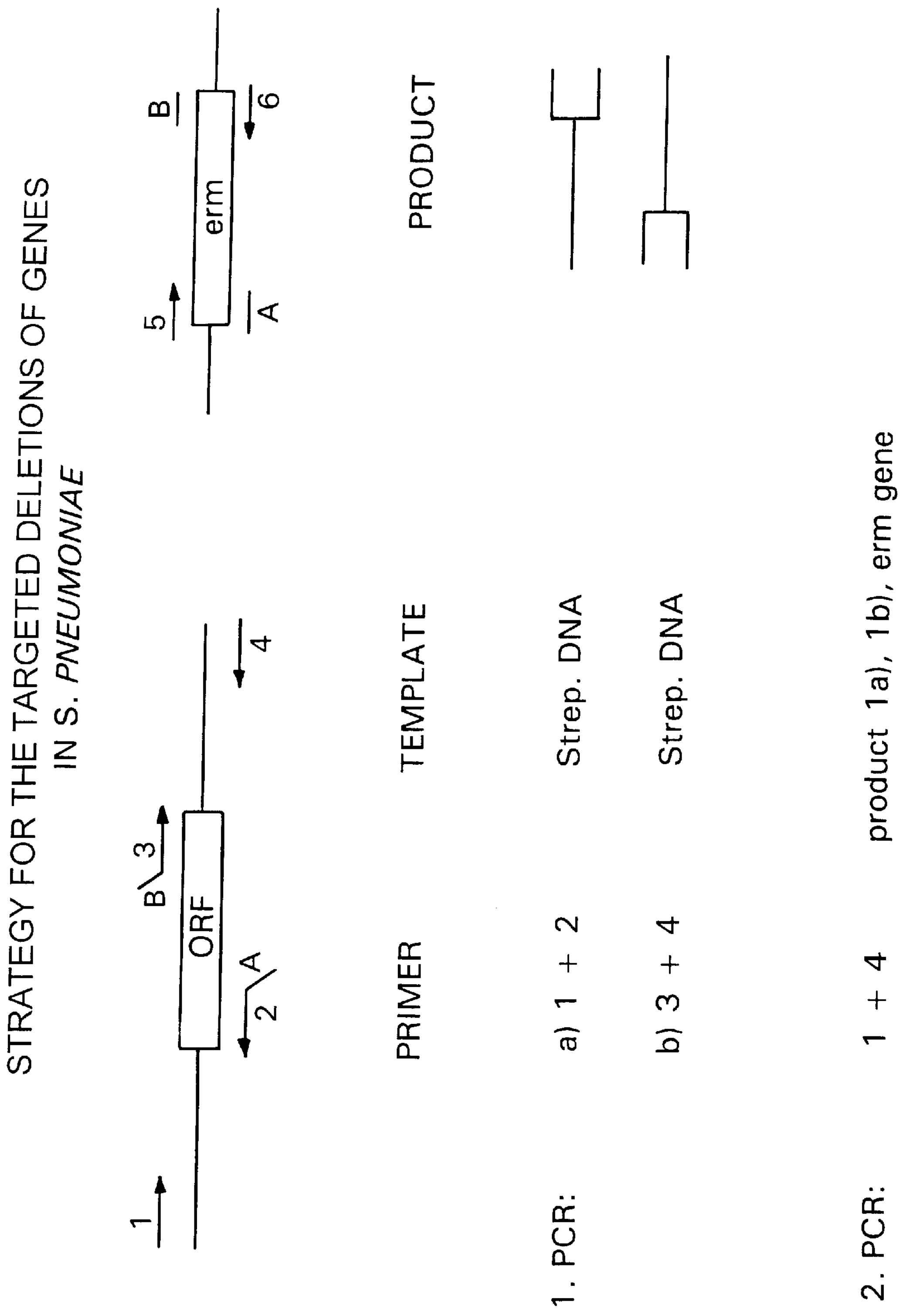
FIG. 25 is a schematic representation of the PCR strategy used to produce DNA molecules used for targeted deletions of essential genes in *Streptococcus pneumoniae.*

As shown by the experiments described below, each of the GEP genes is located within an operon that is essential for survival of *Streptococcus pneumonia. Streptococcus pneumonia* is available from the ATCC. To identify genes located within essential operons, mutants of *Streptococcus pneumonia* were produced. In general, mutagenesis of *Streptococcus pneumonia* can be accomplished using any of various art-known methods.

In general, and for the examples set forth below, genes located within essential *Streptococcus pneumonia* operons can be identified using genes from a *Streptococcus pneumonia* RX1 genomic library, which was produced using standard methods (see Kim et al., Nucl. Acids. Res. 20: 1083–1085 (1992) and Ausubel et al. (eds.), 1995, Current Protocols in Molecular Biology, (John Wiley & Sons, N.Y.)). Genes in this Streptococcus library were disrupted using a shuttle mutagenesis approach with the transposon TnPho-A. Each disrupted gene then was tested to determine whether it was located within an operon that is essential for survival of *Streptococcus pneumonia*. In this method, 2 ml of LB broth supplemented with chloramphenicol (10 μg/ml), $MgSO_4$ (10 mM) and maltose (0.2%) were inoculated with 50 μl of the *Streptococcus pneumonia* RX-1 plasmid library. The culture was grown at 37° C. while shaking until the $OD_{650}$ of the culture reached 0.8 (approximately 2 hours). A 1 ml aliquot of TnPho-A-containing phage ($10^9$ pfu/ml) was added to 1 ml of the Streptococcus culture, producing a ratio of approximately 10 phage to 1 cell. The phage and cells were incubated at 37° C. for 30 minutes. A 4 ml aliquot of LB broth, warmed to 370° C., then was added to the phage/cell mixture, and the mixture was incubated at 37° C., while shaking, for 1 hour. The cells then were pelleted by centrifuging them at 3500 rpm in a Beckman tabletop centrifuge for 5 minutes.

The pelleted cells then were resuspended in 800 μl of LB broth, and a 200 μl aliquot of cells was plated onto each of four petri plates containing LB agar supplemented with chloramphenicol (10 μg/ml), kanamycin (50 μg/ml), and erythromycin (300 μg/ml). The plates then were incubated overnight at 37° C., and the number of colonies appearing on the plates was counted. Approximately 18,000 colonies then were pooled and used to inoculate 50 ml of LB broth, which was incubated overnight at 37° C. Plasmid DNA from the culture then was extracted using a Qiagen MIDI Prep Kit; other art-known extraction methods can be substituted.

The concentration of the extracted DNA was measured, and 100 ng of the DNA was transformed, by electroporation, into *E. coli* DH1OB cells (Gibco BRL). A 1 ml aliquot of SOC broth then was added the transformed cells, and the cells were incubated at 37° C. for 1 hour before being pelleted by centrifugation at 3500 RPM for 5 minutes. The cells then were resuspended in 200 μl of LB broth, and aliquots of 2, 20, and 50 μl were plated onto petri plates containing LB agar and antibiotics as described above. After incubating the plates overnight at 37° C., 93 colonies were picked and used, individually, to inoculate 1.25 ml of Terrific broth supplemented with chloramphenicol (10 μg/ml), kanamycin (50μg/ml), and erythromycin (300 μg/ml). The cultures were incubated at 37° C. G for approximately 20 hours, while shaking. The DNA from each culture then was extracted, using a conventional alkaline lysis miniprep method.

The extracted DNA samples then were used, individually, to transform *Streptococcus pneumonia* cells in a 96-well microtitre format. The transposon promotes insertion of the mutagenized gene into the bacterial chromosome. Non-transforming clones indicate that the mutation was within an operon containing an essential gene.

The non-transforming clones then were grown in 50 ml of Terrific broth supplemented with chloramphenicol (10 μg/ml), kanamycin (50 μg/ml), and erythromycin (300 μg/ml). DNA from these clones was extracted and retransformed into *Streptococcus pneumonia* and plated on petri dishes to confirm that they were non-transforming. The genes located within essential operons then were sequenced, using primers that hybridize to sequences of the transposon. The sequences of the primers were:

5' GCAGCCCGGTTTTCCAGAACAGG3' (SEQ ID NO: 73) and

5' GATTTAGCCCAGTCGGCCGCACG3' (SEQ ID NO: 74).

In an alternative method, which also was used, the transposon Tn 10 was used to disrupt genes in a *Streptococcus*

*pneumonia* fosmid library, which was produced using standard methods. A 50 ml aliquot of TBMM broth supplemented with chloramphenicol (10 μg/ml), $MgSO_4$ (10 mM), and maltose (0.2%) were inoculated with a single fosmid colony from the fosmid library, and the cultures were grown overnight at 37° C. The cells then were pelleted and resuspended in 5 ml of LB broth supplemented with chloramphenicol (10 μg/ml), $MgSO_4$ (10 mM), and maltose (0.2%). A 100 μl aliquot of the cells then was mixed with 100 μl of Tn10 phage lysate ($10^{10}$ pfu/ml), and the mixture was incubated at room temperature for 15 minutes and then incubated at 37° C. for 15 minutes.

A 5 ml aliquot of LB broth supplemented with IPTG (1 mM) and sodium citrate (50 mM) and warmed to 37° C. then was added to the cell/phage mixture. After incubating the cell/phage mixture at 37° C., while shaking, the cells were pelleted and resuspended in 800 μl of LB broth. The cells then were plated onto 4 plates of LB agar supplemented with chloramphenicol (10 μg/ml) and erythromycin (300 μg/ml). After incubating the cells overnight at 37° C., at least 10,000 of the resulting colonies were used to inoculate 50 ml of LB broth. DNA then was extracted and quantified using standard methods, and 100 ng of DNA were used to transform *E. coli* DH10B cells (Gibco BRL) via electroporation. After adding 1 ml of SOC broth to the cells, the cells were incubated at 37° C. for 1 hour. The cells then were pelleted and suspended in 200 μl LB broth, and aliquots of 2, 20, and 50 μl were plated onto LB agar supplemented with chloramphenicol (10 μg/ml), kanamycin (50 μg/ml), and erythromycin (300 μg/ml). The plates then were incubated overnight at 37° C., and 93 colonies were picked and used to inoculate 1.25 ml of Terrific broth supplemented with chloramphenicol (10 μg/ml), kanamycin (50 μg/ml) and erythromycin (300 μg/ml). These cultures were incubated for approximately 20 hours, while shaking, and the DNA was isolated using a standard miniprep method. The extracted DNA then was used to transform *Streptococcus pneumonia*, and the genes located within essential operons were sequenced as described above. The sequences of the primers used for sequencing were:

5' CCGCCATTCTTTGCTGTTTCG3' (SEQ ID NO: 75) and

5' TTACACGTTACTAAAGGGAATG3' (SEQ ID NO: 76).

Identification of the gep1493, gep1507, gep1546, gep273, gep286, and gep76 Genes as Essential Genes As shown by the experiments described below, the gep1493, gep1507, gep1546, gep273, gep286, and gep76 genes each have been shown to be essential for survival of *Streptococcus pneumoniae.*

Each of the gep1493, gep1507, gep1546, gep273, gep286, and gep76 genes has been identified as essential by creating a targeted deletion of each gene, separately, in *Streptococcus pneumoniae. Each of the gep*1493, gep1507, gep1546, gep273, gep286, and gep76 genes was, separately, replaced with a nucleic acid sequence conferring resistance to the antibiotic erythromycin (an "erm" gene). Other genetic markers can be used in lieu of this particular antibiotic resistance marker. Polymerase chain reaction (PCR) amplification was used to make a targeted deletion in the Streptococcus genomic DNA, as shown in FIG. 25. Several PCR reactions were used to produce the DNA molecules needed to carry out target deletion of the genes of interest. First, using primers 5 and 6, an erm gene was amplified from pIL252 from *B. subtilis* (available from the Bacillus Genetic Stock Center, Columbus, Ohio). Primer 5 consists of 21 nucleotides that are identical to the promoter region of the erm gene and complementary to Sequence A. Primer 5 has the sequence 5' GTG TTC GTG CTG ACT TGC ACC3' (SEQ ID NO: 77). Primer 6 consists of 21 nucleotides that are complementary to the 3' end of the erm gene. Primer 6 has the sequence 5' GAA TTA TTT CCT CCC GTT AAA3' (SEQ ID NO: 78). PCR amplification of the erm gene was carried out under the following conditions: 30 cycles of 94° C. for 1 minute, 55° C. for 1 minute, and 72° C. for 1.5 minutes, followed by one cycle of 72° C. for 10 minutes.

In the second and third PCR reactions, sequences flanking the gene of interest were amplified and produced as hybrid DNA molecules that also contained a portion of the erm gene. The second reaction produced a double-stranded DNA molecule (termed "Left Flanking Molecule") that includes sequences upstream of the 5' end of the gene of interest and the first 21 nucleotides of the erm gene. As shown in FIG. 25, this reaction utilized primer 1, which is 21 nucleotides in length and identical to a sequence that is located approximately 500 bp upstream of the translation start site of the gene of interest. Primers 1 and 2 are gene-specific and include the sequences 5' CTC CGT GAA GTC CAC CTG AT3' (SEQ ID NO:79) and 5' GGT GCA AGT CAG CAC GAA CAC GCG ACA TAG GTT CCA GTT AGG3' (SEQ ID NO:80), respectively, for gep1493. Primer 2 is 42 nucleotides in length, with 21 of the nucleotides at the 3' end of the primer being complementary to the 5' end of the sense strand of the gene of interest. The 21 nucleotides at the 5' end of the primer were identical to Sequence A and are therefore complementary to the 5' end of the erm gene. Thus, PCR amplification using primers 1 and 2 produced the left flanking DNA molecule, which is a hybrid DNA molecule containing a sequence located upstream of the gene of interest and 21 base pairs of the erm gene, as shown in FIG. 25.

The third PCR reaction was similar to the second reaction, but produced the right flanking DNA molecule, shown in FIG. 25. The right flanking DNA molecule contains 21 base pairs of the 3' end of the erm gene, a 21 base pair portion of the 3' end of the gene of interest, and sequences downstream of the gene of interest. This right flanking DNA molecule was produced with gene-specific primers 3 and 4. For gep 1493, primers 3 and 4 included the sequences 5' TTT AAC GGG AGG AAA TAA TTC CCA TAT CGT GGC TCC TGA AT 3' (SEQ ID NO:81) and 5' TAA AGC CCT CAT GTC GAA CC3' (SEQ ID NO:82), respectively. Primer 3 is 42 nucleotides; the 21 nucleotides at the 5' end of Primer 3 are identical to Sequence B and therefore are identical to the 3' end of the erm gene. The 21 nucleotides at the 3' end of Primer 3 are identical to the 3' end of the gene of interest. Primer 4 is 21 nucleotides in length and is complementary to a sequence located approximately 500 bp downstream of the gene of interest. As discussed above, primers 1–4 are gene-specific, and the sequences disclosed above were used for gep1493. Gene-specific primers were used to identify the other essential genes described herein, as shown in Table 2.

TABLE 2

Primers Used in Identifying Essential Genes

| Gene | Primer 1 | Primer 2 | Primer 3 | Primer 4 |
|---|---|---|---|---|
| gep1493 | 5'CTCCGTGAAGTC CACCTGAT3' (SEQ ID NO:79) | 5'GGTGCAAGTCAGCA CGAACACTGCTCGCGT AGATTGATTTG3' (SEQ ID NO:80) | 5'TTTAACGGGAGG AAATAATTCGGGGA TTGAACCTAACCCA T3' (SEQ ID NO:81) | 5'TTGGCAAGAAGG CAGAGAAT3' (SEQ ID NO:82) |
| gep1507 | 5'GCATGAGAAACC CAGTCTCC3' (SEQ ID NO:83) | 5'GGTGCAAGTCAGCA CGAACACGCGACATAG GTTCCAGTTAGG3' (SEQ ID NO:84) | 5'TTTAACGGGAGG<br>5'TAAAGCCCTCAT<br>AAATAATTCCCATA TCGTGGCTCCTGAA T3' (SEQ ID NO:85) | GTCGAACC3' (SEQ ID NO:86) |
| gep1546 | 5'CAGTGACGATAC AGATGAAGAA3' (SEQ ID NO:87) | 5'GGTGCAAGTCAGCA CGAACACGATGCTGGC TTCGTTGAGTG3' (SEQ ID NO:88) | 5'TTTAACGGGAGG<br>5'CCAGCAAAGGAA<br>AAATAATTCGTCGC GACTCCTAGCCATA C3' (SEQ ID NO:89) | AACCGATA3' (SEQ ID NO:90) |
| gep273 | 5'GGTCAGTGACAG CAGCAGAT3' (SEQ ID NO:91) | 5'GGTGCAAGTCAGCA CGAACACGGCCTTGGA AAAAAGACCAT3' (SEQ ID NO:92) | 5'TTTAACGGGAGG<br>5'CCCATAACCGTA<br>AAATAATTCCCGCT TAAATTCTGCCAAT C3' (SEQ ID NO:93) | TCACCTGG3' (SEQ ID NO:94) |
| gep286 | 5'CGGAACGGCTAT GAAAA3' (SEQ ID NO:95) | 5'GGTGCAAGTCAGCA CGAACACACGACGAAA GGCAACCATAC3' (SEQ ID NO:96) | 5'TTTAACGGGAGG<br>5'TCGCCCTACTTT<br>AAATAATTCTGGTA TGGGGGTTGATGAA G3' (SEQ ID NO:97) | TCGTATGC3' (SEQ ID NO:98) |
| gep76 | 5'AGCGATATTAGT GCGGGAGA3' (SEQ ID NO:99) | 5'GGTGCAAGTCAGCA CGAACACCAGCAATTT TGTCATCAGTCG3' (SEQ ID NO:100) | 5'TTTAACGGGAGG AAATAATTCCTGGG GTAATGGAGCACAG T3' (SEQ ID NO:101) | 5'GGGATTGTCACG GTAAAACC3' (SEQ ID NO:102) |

PCR amplification of the left and right flanking DNA molecules was carried out, separately, in 50 μl reaction mixtures containing: 1 μl *Streptococcus pneumoniae* (RX1) DNA (0.25 μg), 2.5 μl Primer 1 or Primer 4 (10 pmol/pl), 2.5 μl Primer 2 or Primer 3 (20 pmol/μl), 1.2 μl a mixture dNTPS (10 mM each), 37 1 μl $H_2O$, 0.7 μl Taq polymerase (5 U/μl), and 5 μl 10×Taq polymerase buffer (10 mM Tris, 50 mM KCl, 2.5 mM $MgCl_2$). The left and right flanking DNA molecules were amplified using the following PCR cycling program: 95° C. for 2 minutes; 72° C. for 1 minute; 94° C. for 30 seconds; 49° C. for 30 seconds; 72° C. for 1 minute; repeating the 94° C., 49° C., and 72° C. incubations 30 times; 72° C. for 10 minutes and then stopping the reactions. A 15 μl aliquot of each reaction mixture then was electrophoresed through a 1.2% low melting point agarose gel in TAE buffer and then stained with ethidium bromide. Fragments containing the amplified left and right flanking DNA molecules were excised from the gel and purified using the QIAQUICK™ gel extraction kit (Qiagen, Inc.) Other art-known methods for amplifying and isolating DNA can be substituted. The flanking left and right DNA fragments were eluted into 30 μl TE buffer at pH 8.0.

The amplified erm gene and left and right flanking DNA molecules were then fused together to produce the fusion product, as shown in FIG. 25. The fusion PCR reaction was carried out in a volume of 50 μl containing: 2 μl of each of the left and right flanking DNA molecules and the erm gene PCR product; 5 μl of 10×buffer; 2.5 μl of Primer 1 (10 pmol/μl); 2.5 μl of Primer 4 (10 pmol/μl), 1.2 μl dNTP mix (10 mM each) 32 μl $H_2O$, and 0.7 μl Taq polymerase. The PCR reaction was carried out using the following cycling program: 95° C. for 2 minutes; 72° C. for 1 minute; 94° C. for 30 seconds, 48° C. for 30 seconds; 72° C. for 3 minutes; repeat the 94° C., 48° C. and 72° C. incubations 25 times; 72° C. for 10 minutes. After the reaction was stopped, a 12 μl aliquot of the reaction mixture was electrophoresed through an agarose gel to confirm the presence of a final product of approximately 2 kb.

Figure 26:
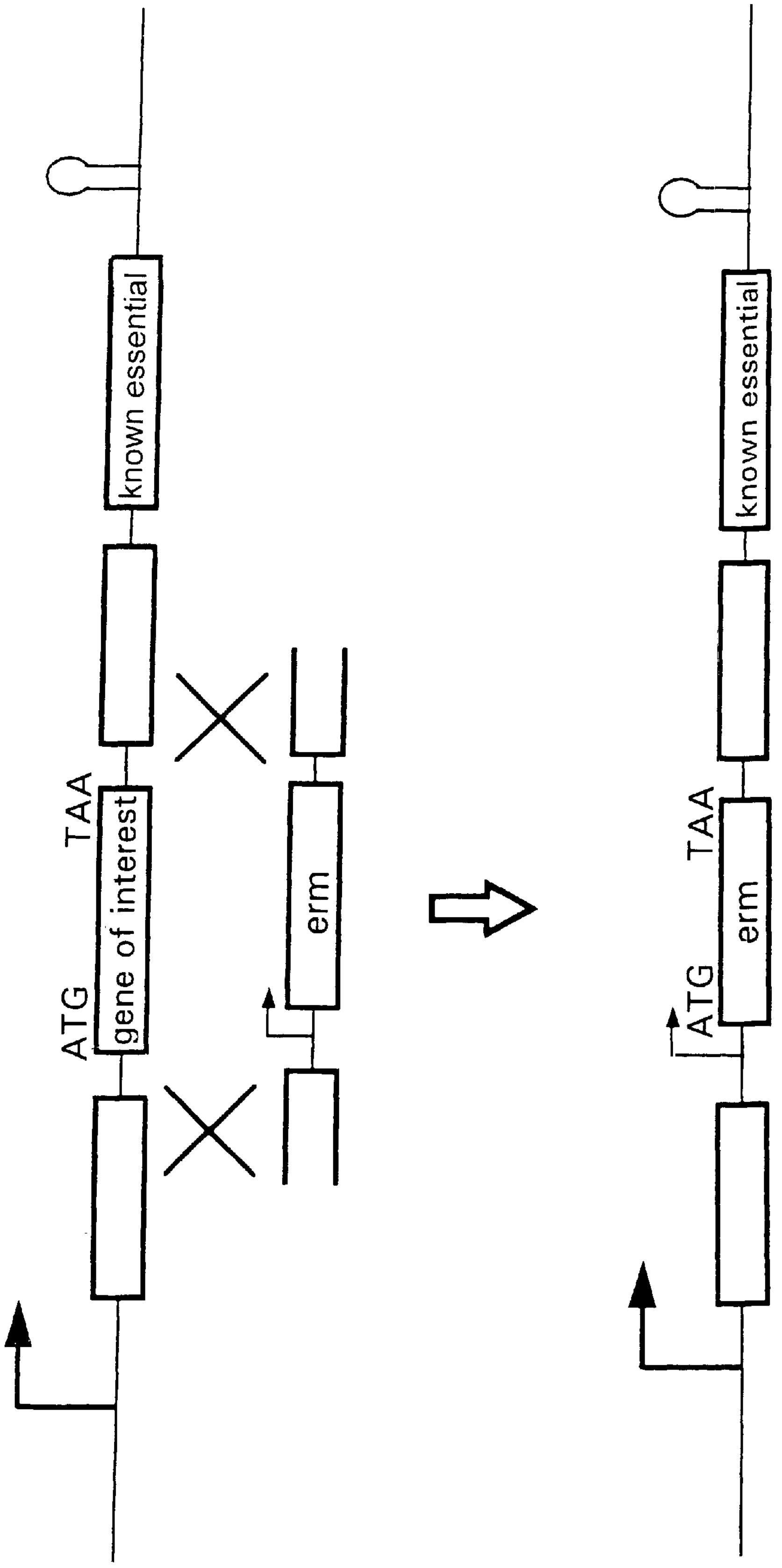
FIG. 26 is a schematic representation of the strategy used to produce targeted deletions of essential genes in *Streptococcus pneumoniae.*

A 5 μl aliquot of the fusion product was used to transform *S. pneumoniae* grown on a medium containing erythromycin in accordance with standard techniques. As shown in FIG. 26, the fusion product and the *S. pneumoniae* genome undergo a homologous recombination event so that the erm gene replaces the chromosomal copy of the gene of interest, thereby creating a gene knockout. Disruption of an essential gene results in no growth on a medium containing erythromycin. Using this gene knockout method, the gep1493, gep1507, gep1546, gep273, gep286, and gep76 genes were each identified as being essential for survival.

Identification of Homologs and Orthologs of GEP Polypeptides

Having shown that the various GEP genes are essential or located within operons that are essential for survival of Streptococcus, it can be expected that homologs and orthologs of the polypeptides encoded by these genes, when present in other organisms, for example *B. subtilis*, are essential or located within operons that are essential for survival of that organism as well, and therefore are useful targets for identifying antibacterial agents. Using the sequences of the GEP polypeptides identified in Streptococcus, homologs and orthologs of these polypeptides can be identified in other organisms. For example, the coding sequences of the GEP nucleic acids can be used to search the GenBank database of nucleotide sequences to identify homologs or orthologs that are expressed from essential operons in other organisms. Sequence comparisons can be performed using the Basic Local Alignment Search Tool (BLAST) (Altschul et al., J. Mol. Biol., 215:403–410 1990). The percent sequence identity shared by the GEP polypeptides and their homologs or orthologs can be determined using the GAP program from the Genetics Computer Group (GCG) Wisconsin Sequence Analysis Package (Wisconsin Package Version 9.0, GCG; Madison, Wis.). The following parameters are suitable: gap creation penalty, 12

(protein) 50 (DNA); gap extension penalty, 4 (protein) 3 (DNA). Typically, the GEP polypeptides and their homologs share at least 25% (e.g., at least 40%) sequence identity. Typically, the DNA sequences encoding GEP polypeptides and their homologs share at least 35% (e.g., at least 45%) sequence identity. To confirm that the homologs or orthologs of the GEP polypeptides are expressed from operons that are essential for survival of bacteria, the operon encoding each of the homologs or orthologs can be, separately, deleted from the genome of the host organism.

Identification of Essential Operons in Additional Streptococcus Strains

Now that the various GEP genes have been identified as being located within operons that are essential for survival, these genes, or fragments thereof, can be used to detect homologous or orthologous genes in other organisms. In particular, these genes can be used to analyze various pathogenic and non-pathogenic strains of bacteria. Fragments of a nucleic acid (DNA or RNA) encoding a GEP polypeptide or homolog or ortholog (or sequences complementary thereto) can be used as probes in conventional nucleic acid hybridization assays of pathogenic bacteria. For example, nucleic acid probes (which typically are 8–30, or usually 15–20, nucleotides in length) can be used to detect GEP genes or homologs or orthologs thereof in art-known molecular biology methods, such as Southern blotting, Northern blotting, dot or slot blotting, PCR amplification methods, colony hybridization methods, and the like. Typically, an oligonucleotide probe based on the nucleic acid sequences described herein, or fragments thereof, is labeled and used to screen a genomic library constructed from mRNA obtained from a Streptococcus or bacterial strain of interest. A suitable method of labeling involves using polynucleotide kinase to add $^{32}$P-labeled ATP to the oligonucleotide used as the probe. This method is well known in the art, as are several other suitable methods (e.g., biotinylation and enzyme labeling).

Hybridization of the oligonucleotide probe to the library, or other nucleic acid sample, typically is performed under stringent to highly stringent conditions. Nucleic acid duplex or hybrid stability is expressed as the melting temperature or $T_m$, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE). Then, assuming that 1% mismatching results in a 1° C. decrease in the $T_m$, the temperature of the final wash in the hybridization reaction is reduced accordingly (for example, if sequences having ≧95% identity with the probe are sought, the final wash temperature is decreased by 5° C.). In practice, the change in $T_m$ can be between 0.5° and 1.5° C. per 1% mismatch.

As used herein, highly stringent conditions refer to hybridization at 68° C. in 5×SSC/5×Denhardt's solution/1.0% SDS, and washing in 0.2×SSC/0.1% SDS at 42° C. Stringent conditions refer to washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

In one approach, libraries constructed from pathogenic or non-pathogenic Streptococcus or bacterial strains can be screened. For example, such strains can be screened for expression of GEP genes by Northern blot analysis. Upon detection of transcripts of the GEP genes or homologs or orthologs thereof, libraries can be constructed from RNA isolated from the appropriate strain, utilizing standard techniques well known to those of skill in the art. Alternatively, a total genomic DNA library can be screened using an GEP gene probe (or a probe directed to a homolog or ortholog thereof).

New gene sequences can be isolated, for example, by performing PCR using two degenerate oligonucleotide primer pools designed on the basis of nucleotide sequences within the GEP genes, or their homologs or orthologs, as depicted herein. The template for the reaction can be DNA obtained from strains known or suspected to express a GEP allele or an allele of a homolog or ortholog thereof. The PCR product can be subcloned and sequenced to ensure that the amplified sequences represent the sequences of a new GEP nucleic acid sequence, or a sequence of a homolog or ortholog thereof.

Synthesis of the various GEP polypeptides or their homologs or orthologs (or an antigenic fragment thereof) for use as antigens, or for other purposes, can readily be accomplished using any of the various art-known techniques. For example, a polypeptide or homolog or ortholog thereof, or an antigenic fragment(s), can be synthesized chemically in vitro, or enzymatically (e.g., by in vitro transcription and translation). Alternatively, the gene can be expressed in, and the polypeptide purified from, a cell (e.g., a cultured cell) by using any of the numerous, available gene expression systems. For example, the polypeptide antigen can be produced in a prokaryotic host (e.g., *E. coli* or *B. subtilis*) or in eukaryotic cells, such as yeast cells or insect cells (e.g., by using a baculovirus-based expression vector).

Proteins and polypeptides can also be produced in plant cells, if desired. For plant cells viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The optimal methods of transformation or transfection and the choice of expression vehicle will depend on the host system selected. Transformation and transfection methods are described, e.g., in Ausubel et al., supra; expression vehicles may be chosen from those provided, e.g., in *Cloning Vectors: A Laboratory Manual* (P. H. Pouwels et al., 1985, Supp. 1987). The host cells harboring the expression vehicle can be cultured in conventional nutrient media, adapted as needed for activation of a chosen gene, repression of a chosen gene, selection of transformants, or amplification of a chosen gene.

If desired, GEP polypeptides or their homologs or orthologs can be produced as fusion proteins. For example, the expression vector pUR278 (Ruther et al., *EMBO J.*, 2:1791, 1983) can be used to create lacZ fusion proteins. The art-known pGEX vectors can be used to express foreign polypeptides as fusion proteins with glutathione S-transferase (GST). In general, such fusion proteins are soluble and can be easily purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an exemplary insect cell expression system, a baculovirus such as *Autographa californica* nuclear polyhedrosis virus (AcNPV), which grows in *Spodoptera frugiperda* cells, can be used as a vector to express foreign genes. A coding sequence encoding a GEP polypeptide or homolog or ortholog can be cloned into a non-essential region (for example the polyhedrin gene) of the viral genome and placed under control of a promoter, e.g., the polyhedrin promoter or an exogenous promoter. Successful insertion of a gene encoding a GEP polypeptide or homolog or ortholog can result in inactivation of the polyhedrin gene and production of non-occluded recombinant virus (i.e., virus lacking the proteinaceous coat encoded by the polyhedrin gene). These recombinant viruses are then used to infect insect cells (e.g., *Spodoptera frugiperda* cells) in which the inserted gene is expressed (see, e.g., Smith et al., *J. Virol.*, 46:584, 1983; Smith, U.S. Pat. No. 4,215,051).

In mammalian host cells, a number of viral-based expression systems can be utilized. When an adenovirus is used as an expression vector, the nucleic acid sequence encoding the GEP polypeptide or homolog or ortholog can be ligated to an adenovirus transcription/translation control complex, e.g., the late promoter and tripartite leader sequence. This chimeric gene can then be inserted into the adenovirus genome by in vitro or in vivo recombination. Insertion into a non-essential region of the viral genome (e.g., region E1 or E3) will result in a recombinant virus that is viable and capable of expressing a essential gene product in infected hosts (see, e.g., Logan, Proc. Natl. Acad. Sci. USA, 81:3655, 1984).

Specific initiation signals may be required for efficient translation of inserted nucleic acid sequences. These signals include the ATG initiation codon and adjacent sequences. In general, exogenous translational control signals, including, perhaps, the ATG initiation codon, should be provided. Furthermore, the initiation codon must be in phase with the reading frame of the desired coding sequence to ensure translation of the entire sequence. These exogenous translational control signals and initiation codons can be of a variety of origins, both natural and synthetic. The efficiency of expression may be enhanced by the inclusion of appropriate transcription enhancer elements, or transcription terminators (Bittner et al., Methods in Enzymol., 153:516, 1987).

The GEP polypeptides and homologs and orthologs can be expressed individually or as fusions with a heterologous polypeptide, such as a signal sequence or other polypeptide having a specific cleavage site at the N-and/or C-terminus of the protein or polypeptide. The heterologous signal sequence selected should be one that is recognized and processed, i.e., cleaved by a signal peptidase, by the host cell in which the fusion protein is expressed.

A host cell can be chosen that modulates the expression of the inserted sequences, or modifies and processes the gene product in a specific, desired fashion. Such modifications and processing (e.g., cleavage) of protein products may facilitate optimal functioning of the protein. Various host cells have characteristic and specific mechanisms for post-translational processing and modification of proteins and gene products. Appropriate cell lines or host systems familiar to those of skill in the art of molecular biology can be chosen to ensure the correct modification and processing of the foreign protein expressed. To this end, eukaryotic host cells that possess the cellular machinery for proper processing of the primary transcript, and phosphorylation of the gene product can be used. Such mammalian host cells include, but are not limited to, CHO, VERO, BHK, HeLa, COS, MDCK, 293, 3T3, WI38, and choroid plexus cell lines.

If desired, the GEP polypeptide or homolog or ortholog thereof can be produced by a stably-transfected mammalian cell line. A number of vectors suitable for stable transection of mammalian cells are available to the public, see, e.g., Pouwels et al. (supra); methods for constructing such cell lines are also publicly known, e.g., in Ausubel et al. (supra). In one example, DNA encoding the protein is cloned into an expression vector that includes the dihydrofolate reductase (DHFR) gene. Integration of the plasmid and, therefore, the GEP polypeptide-encoding gene into the host cell chromosome is selected for by including 0.01–300 $\mu$M methotrexate in the cell culture medium (as described in Ausubel et al., supra). This dominant selection can be accomplished in most cell types.

Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include PCVSEII-DHFR and pAdD26SV(A) (described in Ausubel et al., supra).

A number of other selection systems can be used, including but not limited to, herpes simplex virus thymidine kinase genes, hypoxanthine-guanine phosphoribosyltransferase genes, and adenine phosphoribosyltransferase genes, which can be employed in tk, hgprt, or aprt cells, respectively. In addition, gpt, which confers resistance to mycophenolic acid (Mulligan et al., *Proc. Natl. Acad. Sci. USA*, 78:2072, 1981); neo, which confers resistance to the aminoglycoside G-418 (Colberre-Garapin et al., *J. Mol. Biol.*, 150:1, 1981); and hygro, which confers resistance to hygromycin (Santerre et al., *Gene*, 30:147, 1981), can be used.

Alternatively, any fusion protein can be readily purified by utilizing an antibody or other molecule that specifically binds to the fusion protein being expressed. For example, a system described in Janknecht et al., *Proc. Natl. Acad. Sci. USA*, 88:8972 (1981), allows for the ready purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers.

Alternatively, a GEP polypeptide or homolog or ortholog, or a portion thereof, can be fused to an immunoglobulin Fc domain. Such a fusion protein can be readily purified using a protein A column, for example. Moreover, such fusion proteins permit the production of a chimeric form of a GEP polypeptide or homolog or ortholog having increased stability in vivo.

Once the recombinant GEP polypeptide (or homolog or ortholog) is expressed, it can be isolated (i.e., purified). Secreted forms of the polypeptides can be isolated from cell culture media, while non-secreted forms must be isolated from the host cells. Polypeptides can be isolated by affinity chromatography. For example, an anti-gep103 antibody (e.g., produced as described herein) can be attached to a column and used to isolate the protein. Lysis and fractionation of cells harboring the protein prior to affinity chromatography can be performed by standard methods (see, e.g., Ausubel et al., supra). Alternatively, a fusion protein can be constructed and used to isolate a GEP polypeptide (e.g., a gep103-maltose binding fusion protein, a gep-103-β-galactosidase fusion protein, or a gep103-trpE fusion protein; see, e.g., Ausubel et al., supra; New England Biolabs Catalog, Beverly, Mass.). The recombinant protein can, if desired, be further purified, e.g., by high performance liquid chromatography using standard techniques (see, e.g., Fisher, *Laboratory Techniques In Biochemistry And Molecular Biology*, eds., Work and Burdon, Elsevier, 1980).

Given the amino acid sequences described herein, polypeptides useful in practicing the invention, particularly fragments of GEP polypeptides can be produced by standard chemical synthesis (e.g., by the methods described in *Solid Phase Peptide Synthesis*, 2nd ed., The Pierce Chemical Co., Rockford, Ill., 1984) and used as antigens, for example.

Antibodies

The GEP polypeptides (or antigenic fragments or analogs of such polypeptides) can be used to raise antibodies useful in the invention, and such polypeptides can be produced by recombinant or peptide synthetic techniques (see, e.g., *Solid Phase Peptide Synthesis*, supra; Ausubel et al., supra). Likewise, antibodies can be raised against the GEP homologs and orthologs. In general, the polypeptides can be coupled to a carrier protein, such as KLH, as described in Ausubel et al., supra, mixed with an adjuvant, and injected into a host mammal. Antibodies can be purified, for example, by affinity chromatography methods in which the polypeptide antigen is immobilized on a resin.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete adjuvant), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Antibodies useful in the invention include monoclonal antibodies, polyclonal antibodies, humanized or chimeric antibodies, single chain antibodies, Fab fragments, $F(ab')_2$ fragments, and molecules produced using a Fab expression library.

Monoclonal antibodies (mAbs), which are homogeneous populations of antibodies to a particular antigen, can be prepared using the GEP polypeptides or homologs or orthologs thereof and standard hybridoma technology (see, e.g., Kohler et al., *Nature*, 256:495, 1975; Kohler et al., *Eur. J. Immunol.*, 6:511, 1976; Kohler et al., *Eur. J. Immunol.*, 6:292, 1976; Hammerling et al., In *Monoclonal Antibodies and T Cell Hybridomas*, Elsevier, N.Y., 1981; Ausubel et al., supra).

In particular, monoclonal antibodies can be obtained by any technique that provides for the production of antibody 30 molecules by continuous cell lines in culture, such as those described in Kohler et al., *Nature*, 256:495, 1975, and U.S. Pat. No. 4,376,110; the human B-cell hybridoma technique (Kosbor et al., *Immunology Today*, 4:72, 1983; Cole et al., *Proc. Natl. Acad. Sci. USA*, 80:2026, 1983); and the EBV-hybridoma technique (Cole et al., *Monoclonal Antibodies and Cancer Therapy*, Alan R. Liss, Inc., pp. 77–96, 1983). Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of a GEP polypeptide or homolog or ortholog thereof in an immunoassay, such as a Western blot or immunoprecipitation analysis using standard techniques, e.g., as described in Ausubel et al., supra. Antibodies that specifically bind to the GEP polypeptides, or conservative variants and homologs or orthologs thereof, are useful in the invention. For example, such antibodies can be used in an immunoassay to detect a GEP polypeptide in is pathogenic or non-pathogenic strains of bacteria.

Preferably, antibodies of the invention are produced using fragments of the GEP polypeptides that appear likely to be antigenic, by criteria such as high frequency of charged residues. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

If desired, several (e.g., two or three) fusions can be generated for each protein, and each fusion can be injected into at least two rabbits. Antisera can be raised by injections in a series, typically including at least three booster injections. Typically, the antisera is checked for its ability to immunoprecipitate a recombinant GEP polypeptide or homolog or ortholog, or unrelated control proteins, such as glucocorticoid receptor, chloramphenicol acetyltransferase, or luciferase.

Techniques developed for the production of "chimeric antibodies" (Morrison et al., *Proc. Natl. Acad. Sci.*, 81:6851, 1984; Neuberger et al., *Nature*, 312:604, 1984; Takeda et al., *Nature*, 314:452, 1984) can be used to splice the genes from a mouse antibody molecule of appropriate antigen specificity together with genes from a human antibody molecule of appropriate biological activity. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; and U.S. Pat. Nos. 4,946,778 and 4,704,692) can be adapted to produce single chain antibodies against a GEP polypeptide or homolog or ortholog. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments can include but are not limited to $F(ab')_2$ fragments, which can be produced by pepsin digestion of the antibody molecule, and Fab fragments, which can be generated by reducing the disulfide bridges of $F(ab')_2$ fragments. Alternatively, Fab expression libraries can be constructed (Huse et al., *Science*, 246:1275, 1989) to allow rapid and easy identification of monoclonal Fab fragments with the desired specificity.

Polyclonal and monoclonal antibodies that specifically bind to GEP polypeptides or homologs or orthologs can be used, for example, to detect expression of a GEP gene or homolog or ortholog in another strain of bacteria. For example, a GEP polypeptide can be readily detected in conventional immunoassays of bacteria cells or extracts.

Examples of suitable assays include, without limitation, Western blotting, ELISAs, radioimmune assays, and the like.

Assay for Antibacterial Agents

The invention provides a method for identifying an antibacterial agent(s). Although the inventors are not bound by any particular theory as to the biological mechanism involved, the new antibacterial agents are thought to inhibit specifically (1) the function of a polypeptide(s) encoded by a nucleic acid located within an operon containing a GEP gene, or (2) expression of the a gene located within an operon containing a GEP gene, or homologs or orthologs thereof. Screening for antibacterial agents can be rapidly accomplished by identifying those compounds (e.g., polypeptides or small molecules) that specifically bind to a polypeptide encoded by a nucleic acid located within an operon containing a GEP gene. A homolog or ortholog of a GEP polypeptide can be substituted for the GEP polypeptide in the methods summarized herein. Specific binding of a test compound to a polypeptide can be detected, for example, in vitro by reversibly or irreversibly immobilizing the test compound(s) on a substrate, e.g., the surface of a well of a 96-well polystyrene microtitre plate. Methods for immobilizing polypeptides and other small molecules are well known in the art. For example, the microtitre plates can be coated with a polypeptide encoded by a nucleic acid located within an operon containing a GEP gene (e.g., a GEP polypeptide or a combination of GEP polypeptides and/or homologs and/or orthologs) by adding the polypeptide(s) in a solution (typically, at a concentration of 0.05 to 1 mg/ml in a volume of 1–100 $\mu$l) to each well, and incubating the plates at room temperature to 37° C. for 0.1 to 36 hours. Polypeptides that are not bound to the plate can be removed by shaking the excess solution from the plate, and then washing the plate (once or repeatedly) with water or a buffer. Typically, the polypeptide, homolog, or ortholog is contained in water or a buffer. The plate is then washed with a buffer that lacks the bound polypeptide. To block the free protein-binding sites on the plates, the plates are blocked with a protein that is unrelated to the bound polypeptide. For example, 300 $\mu$l of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to the new polypeptides (or homologs or orthologs thereof) can be detected by any of a variety of art-known methods. For example, an antibody that specifically binds to a GEP polypeptide can be used in an immunoassay. If desired, the antibody can be labeled (e.g., fluorescently or with a radioisotope) and detected directly (see, e.g., West and McMahon, *J. Cell Biol.* 74:264, 1977). Alternatively, a second antibody can be used for detection (e.g., a labeled antibody that binds to the Fc portion of an anti-GEP103 antibody). In an alternative detection method, the GEP polypeptide is labeled, and the label is detected (e.g., by labeling a GEP polypeptide with a radioisotope, fluorophore, chromophore, or the like). In still another method, the GEP polypeptide is produced as a fusion protein with a protein that can be detected optically, e.g., green fluorescent protein (which can be detected under UV light). In an alternative method, the polypeptide (e.g., gep103) can be produced as a fusion protein with an enzyme having a detectable enzymatic activity, such as horse radish peroxidase, alkaline phosphatase, β-galactosidase, or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and β-galactosidase) and non-enzymatic polypeptides (e.g., serum proteins, such as BSA and globulins, and milk proteins, such as caseins).

In various in vivo methods for identifying polypeptides that bind to GEP polypeptides, the conventional two-hybrid assays of protein/protein interactions can be used (see e.g., Chien et al., *Proc. Natl. Acad. Sci. USA*, 88:9578, 1991; Fields et al., U.S. Pat. No. 5,283,173; Fields and Song, *Nature*, 340:245, 1989; Le Douarin et al., *Nucleic Acids Research*, 23:876, 1995; Vidal et al., *Proc. Natl. Acad. Sci. USA*, 93:10315–10320, 1996; and White, *Proc. Natl. Acad. Sci. USA*, 93:10001–10003, 1996). Kits for practicing various two-hybrid methods are commercially available (e.g., from Clontech; Palo Alto, Calif.).

Generally, the two-hybrid methods involve in vivo reconstitution of two separable domains of a transcription factor. The DNA binding domain (DB) of the transcription factor is required for recognition of a chosen promoter. The activation domain (AD) is required for contacting other components of the host cell's transcriptional machinery. The transcription factor is reconstituted through the use of hybrid proteins. One hybrid is composed of the AD and a first protein of interest. The second hybrid is composed of the DB and a second protein of interest.

Useful reporter genes are those that are operably linked to a promoter which is specifically recognized by the DB. Typically, the two-hybrid system employs the yeast *Saccharomyces cerevisiae* and reporter genes, the expression of which can be selected under appropriate conditions. Other eukaryotic cells, including mammalian and insect cells, can be used, if desired. The two-hybrid system provides a convenient method for cloning a gene encoding a polypeptide (i.e., a candidate antibacterial agent) that binds to a second, preselected polypeptide (e.g., gep103). Typically, though not necessarily, a DNA library is constructed such that randomly generated sequences are fused to the AD, and the protein of interest (e.g., gep103) is fused to the DB.

In such two-hybrid methods, two fusion proteins are produced. One fusion protein contains the GEP polypeptide (or homolog or ortholog thereof) fused to either a transactivator domain or DNA binding domain of a transcription factor (e.g., of Gal4). The other fusion protein contains a test polypeptide fused to either the DNA binding domain or a transactivator domain of a transcription factor. Once brought together in a single cell (e.g., a yeast cell or mammalian cell), one of the fusion proteins contains the transactivator domain and the other fusion protein contains the DNA binding domain. Therefore, binding of the GEP polypeptide to the test polypeptide (i.e., candidate antibacterial agent) reconstitutes the transcription factor. Reconstitution of the transcription factor can be detected by detecting expression of a gene (i.e., a reporter gene) that is operably linked to a DNA sequence that is bound by the DNA binding domain of the transcription factor.

The methods described above can be used for high throughput screening of numerous test compounds to identify candidate antibacterial (or anti-bacterial) agents. Having identified a test compound as a candidate antibacterial agent, the candidate antibacterial agent can be further tested for inhibition of bacterial growth in vitro or in vivo (e.g., using an animal, e.g., rodent, model system) if desired. Using other, art-known variations of such methods, one can test the ability of a nucleic acid (e.g., DNA or RNA) used as the test compound to bind to a polypeptide encoded by a nucleic acid sequence located within an operon containing a GEP gene or homolog or ortholog thereof.

In vitro, further testing can be accomplished by means known to those in the art such as an enzyme inhibition assay or a whole-cell bacterial growth inhibition assay. For example, an agar dilution assay identifies a substance that inhibits bacterial growth. Microtiter plates are prepared with serial dilutions of the test compound; adding to the preparation a given amount of growth substrate; and providing a preparation of Streptococcus cells. Inhibition of growth is determined, for example, by observing changes in optical densities of the bacterial cultures.

Inhibition of bacterial growth is demonstrated, for example, by comparing (in the presence and absence of a test compound) the rate of growth or the absolute growth of bacterial cells. Inhibition includes a reduction of one of the above measurements by at least 20% (e.g., at least 25%, 30%, 40%, 50%, 75%, 80%, or 90%).

Rodent (e.g., murine) and rabbit animal models of streptococcal infections are known to those of skill in the art, and such animal model systems are accepted for screening antibacterial agents as an indication of their therapeutic efficacy in human patients. In a typical in vivo assay, an animal is infected with a pathogenic Streptococcus strain, e.g., by inhalation of *Streptococcus pneumoniae*, and conventional methods and criteria are used to diagnose the mammal as being afflicted with streptococcal pneumonia. The candidate antibacterial agent then is administered to the mammal at a dosage of 1–100 mg/kg of body weight, and the mammal is monitored for signs of amelioration of disease. Alternatively, the test compound can be administered to the mammal prior to infecting the mammal with Streptococcus, and the ability of the treated mammal to resist infection is measured. Of course, the results obtained in the presence of the test compound should be compared with results in control animals, which are not treated with the test compound. Administration of candidate antibacterial agent to the mammal can be carried out as described below, for example.

Pharmaceutical Formulations

Treatment includes administering a pharmaceutically effective amount of a composition containing an antibacterial agent to a subject in need of such treatment, thereby inhibiting bacterial growth in the subject. Such a composition typically contains from about 0.1 to 90% by weight (such as 1 to 20% or 1 to 10%) of an antibacterial agent of the invention in a pharmaceutically acceptable carrier.

Solid formulations of the compositions for oral administration may contain suitable carriers or excipients, such as corn starch, gelatin, lactose, acacia, sucrose, microcrystalline cellulose, kaolin, mannitol, dicalcium phosphate, calcium carbonate, sodium chloride, or alginic acid. Disintegrators that can be used include, without limitation, microcrystalline cellulose, corn starch, sodium starch glycolate and alginic acid. Tablet binders that may be used include acacia, methylcellulose, sodium carboxymethylcellulose, polyvinylpyrrolidone (Povidone), hydroxypropyl methylcellulose, sucrose, starch, and ethylcellulose. Lubricants that may be used include magnesium stearates, stearic acid, silicone fluid, talc, waxes, oils, and colloidal silica.

Liquid formulations of the compositions for oral administration prepared in water or other aqueous vehicles may contain various suspending agents such as methylcellulose, alginates, tragacanth, pectin, kelgin, carrageenan, acacia, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

Injectable formulations of the compositions may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds may be administered by the drip method, whereby a pharmaceutical formulation containing the antibacterial agent and a physiologically acceptable excipient is infused. Physiologically acceptable excipients may include, for example, 5% dextrose, 0.9% saline, Ringer's solution or other suitable excipients. Intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound may be prepared and administered as a suspension in an aqueous base or a pharmaceutically acceptable oil base, such as an ester of a long chain fatty acid, (e.g., ethyl oleate).

A topical semi-solid ointment formulation typically contains a concentration of the active ingredient from about 1 to 20%, e.g., 5 to 10% in a carrier such as a pharmaceutical cream base. Various formulations for topical use include drops, tinctures, lotions, creams, solutions, and ointments containing the active ingredient and various supports and vehicles.

The optimal percentage of the antibacterial agent in each pharmaceutical formulation varies according to the formulation itself and the therapeutic effect desired in the specific pathologies and correlated therapeutic regimens. Appropriate dosages of the antibacterial agents can readily be determined by those of ordinary skill in the art of medicine by monitoring the mammal for signs of disease amelioration or inhibition, and increasing or decreasing the dosage and/or frequency of treatment as desired. The optimal amount of the antibacterial compound used for treatment of conditions caused by or contributed to by bacterial infection may depend upon the manner of administration, the age and the body weight of the subject and the condition of the subject to be treated. Generally, the antibacterial compound is administered at a dosage of 1 to 100 mg/kg of body weight, and typically at a dosage of 1 to 10 mg/kg of body weight.

EXAMPLE

Using the transposon-based mutagenesis methods described above, the *Streptococcus pneumonia* genome was mutagenized, and 23 genes were identified as being located within operons that are essential for survival of *Streptococcus pneumonia*. These genes are listed in Table 1, above, and their nucleic acid and amino acid sequences are represented by SEQ ID NOs:1–69, as shown in FIGS. 1–23B.

Now that each of these genes is known to be located within an operon that is essential for survival of Streptococcus, the polypeptides encoded by nucleic acids located within those operons can be used to identify antibacterial agents by using the assays described herein. Other art-known assays to detect interactions of test compounds with proteins, or to detect inhibition of bacterial growth also can be used with the nucleic acids located within operons containing the GEP genes, and gene products and homologs or orthologs thereof.

Other Embodiments

The invention also features fragments, variants, analogs, and derivatives of the GEP polypeptides described above that retain one or more of the biological activities of the GEP polypeptides, e.g., as determined in a complementation assay. Also included within the invention are naturally-occurring and non-naturally-occurring allelic variants. Compared with the naturally-occurring GEP gene, sequences depicted in FIGS. 1–23B, the nucleic acid sequence encoding allelic variants may have a substitution, deletion, or addition of one or more nucleotides. The preferred allelic variants are functionally equivalent to a GEP polypeptide, e.g., as determined in a complementation assay.

It is to be understood that, while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. An isolated nucleotide sequence encoding a gep1493 polypeptide comprising the amino acid sequence of SEQ ID NO:13, as depicted in FIG. 5, or a gep1493 polypeptide comprising the amino acid sequence of SEQ ID NO:13 with conservative amino acid substitutions within the following groups: glycine and alanine; valine, isoleucine, and leucine; aspartic acid and glutamic acid; asparagine and glutamine; serine and threonine; lysine and arginine; and phenylalanine and tyrosine, and is an essential polypeptide.

2. An isolated nucleic acid molecule comprising a nucleic acid sequence selected from the group consisting of:

a nucleotide sequence comprising the sequence of SEQ D NO:14, as depicted in FIG. 5, degenerate variants of SEQ ID NO:14 that encode the amino acid sequence of SEQ ID NO:13, a nucleotide sequence comprising the sequence of SEQ ID NO:14, wherein T is replaced by U, and degenerate variants of SEQ ID NO:14, wherein T is replaced by U, and that encode the amino acid sequence of SEQ ID NO:13.

3. An expression vector comprising one of the nucleotide sequences of claim 1 operably linked to a nucleotide sequence regulatory element that controls expression of said nucleotide sequence.

4. An expression vector comprising one of the nucleic acid molecules of claim 1, wherein said nucleic acid molecule is operably linked to a nucleotide sequence regulatory element that controls expression of said nucleic acid molecule.

5. A host cell comprising one of the nucleotide sequences of claim 1 exogenously introduced into said cell.

6. The host cell of claim 5, wherein the cell is a yeast or bacterium.

7. A genetically engineered host cell comprising one of the nucleotide sequences of claim 1 operably linked to a heterologous nucleotide sequence regulatory element that controls expression of the nucleotide sequence in the host cell.

8. The host cell of claim 7, wherein the cell is a yeast or bacterium.

9. A vector comprising one of the nucleotide sequences of claim 1.

10. A vector comprising one of the nucleic acid molecules of claim 9.

11. A host cell comprising one of the nucleic acid molecules of claim 2 exogenously introduced into said cell.

12. The host cell of claim 11, wherein the cell is a yeast or bacterium.

13. A genetically engineered host cell comprising one of die nucleic acid molecules of claim 9 operably linked to a nucleotide sequence regulatory element that controls expression of the nucleic acid molecule in the host cell.

14. The host cell of claim 13, wherein the cell is a yeast or bacterium.

15. An isolated nucleic acid molecule from Streptococcus comprising a nucleotide sequence having the sequence of SEQ ID NO:14.

16. A vector comprising the nucleotide sequence of claim 15.

17. An expression vector comprising the nucleotide sequence of claim 15 operably linked to a nucleotide sequence regulatory element that controls expression of said nucleotide sequence.

18. A host cell comprising the exogenously introduced nucleotide sequence of claim 15.

19. A genetically engineered host cell comprising the nucleotide sequence of claim 15 operably linked to a heterologous nucleotide sequence regulatory element that controls expression of the nucleotide sequence in the host cell.

* * * * *

```
                         SEQUENCE LISTING


<160> NUMBER OF SEQ ID NOS:  102

<210> SEQ ID NO 1
<211> LENGTH: 88
<212> TYPE: PRT
<213> ORGANISM: Streptococcus pneumoniae

<400> SEQUENCE: 1

Met Arg Leu Asp Lys Tyr Leu Lys Val Ser Arg Ile Ile Lys Arg Arg
  1               5                  10                  15

Thr Val Ala Lys Glu Val Ala Asp Lys Gly Arg Ile Lys Val Asn Gly
             20                  25                  30

Ile Leu Ala Lys Ser Ser Thr Asp Leu Lys Val Asn Asp Gln Val Glu
         35                  40                  45

Ile Arg Phe Gly Asn Lys Leu Leu Leu Val Lys Val Leu Glu Met Lys
     50                  55                  60

Asp Ser Thr Lys Lys Glu Asp Ala Ala Gly Met Tyr Glu Ile Ile Ser
 65                  70                  75                  80

Glu Thr Arg Val Glu Glu Asn Val
                 85


<210> SEQ ID NO 2
<211> LENGTH: 400
<212> TYPE: DNA
<213> ORGANISM: Streptococcus pneumoniae
<220> FEATURE:
<221> NAME/KEY: CDS
<222> LOCATION: (120)...(383)

<400> SEQUENCE: 2

tgctgatttt tggagaaagt ttattagaga taaaagagtc taaggaaaaa aattccattt     60

gatatttttc ttctataaaa tagataaaaa tggtacaata ataaattgag gtaataagg     119

atg aga tta gat aaa tat tta aaa gta tcg cga att atc aag cgt cgt      167
Met Arg Leu Asp Lys Tyr Leu Lys Val Ser Arg Ile Ile Lys Arg Arg
  1               5                  10                  15

aca gtc gca aag gaa gta gca gat aaa ggt aga atc aag gtt aat gga      215
Thr Val Ala Lys Glu Val Ala Asp Lys Gly Arg Ile Lys Val Asn Gly
             20                  25                  30

atc ttg gcc aaa agt tca acg gac ttg aaa gtt aat gac caa gtt gaa      263
Ile Leu Ala Lys Ser Ser Thr Asp Leu Lys Val Asn Asp Gln Val Glu
         35                  40                  45

att cgc ttt ggc aat aag ttg ctg ctt gta aaa gta cta gag atg aaa      311
Ile Arg Phe Gly Asn Lys Leu Leu Leu Val Lys Val Leu Glu Met Lys
     50                  55                  60
```

-continued

```
gat agt aca aaa aaa gaa gat gca gca gga atg tat gaa att atc agt      359
Asp Ser Thr Lys Lys Glu Asp Ala Ala Gly Met Tyr Glu Ile Ile Ser
 65                  70                  75                  80

gaa aca cgg gta gaa gaa aat gtc taaaaatatt gtacaat                   400
Glu Thr Arg Val Glu Glu Asn Val
                 85
```

<210> SEQ ID NO 3
<211> LENGTH: 400
<212> TYPE: DNA
<213> ORGANISM: Streptococcus pneumoniae

<400> SEQUENCE: 3

```
acgactaaaa acctctttca aataatctct attttctcag attccttttt ttaaggtaaa     60

ctataaaaag aagatatttt atctattttt accatgttat tatttaactc cattattcct    120

actctaatct atttataaat tttcatagcg cttaatagtt cgcagcatgt cagcgtttcc    180

ttcatcgtct atttccatct tagttccaat taccttagaa ccggttttca agttgcctga    240

actttcaatt actggttcaa ctttaagcga aaccgttatt caacgacgaa cattttcatg    300

atctctactt tctatcatgt ttttttcttc tacgtcgtcc ttacatactt taatagtcac    360

tttgtgccca tcttctttta cagattttta taacatgtta                          400
```

<210> SEQ ID NO 4
<211> LENGTH: 335
<212> TYPE: PRT
<213> ORGANISM: Streptococcus pneumoniae

<400> SEQUENCE: 4

```
Met Lys Arg Thr Trp Arg Asn Ser Phe Val Thr Asn Leu Asn Thr Pro
  1               5                  10                  15

Phe Met Ile Gly Asn Ile Glu Ile Pro Asn Arg Thr Val Leu Ala Pro
             20                  25                  30

Met Ala Gly Val Thr Asn Ser Ala Phe Arg Thr Ile Ala Lys Glu Leu
         35                  40                  45

Gly Ala Gly Leu Val Val Met Glu Met Val Ser Asp Lys Gly Ile Gln
     50                  55                  60

Tyr Asn Asn Glu Lys Thr Leu His Met Leu His Ile Asp Glu Gly Glu
 65                  70                  75                  80

Asn Pro Val Ser Ile Gln Leu Phe Gly Ser Asp Glu Asp Ser Leu Ala
                 85                  90                  95

Arg Ala Ala Glu Phe Ile Gln Glu Asn Thr Lys Thr Asp Ile Val Asp
            100                 105                 110

Ile Asn Met Gly Cys Pro Val Asn Lys Ile Val Lys Asn Glu Ala Gly
        115                 120                 125

Ala Met Trp Leu Lys Asp Pro Asp Lys Ile Tyr Ser Ile Ile Asn Lys
    130                 135                 140

Val Gln Ser Val Leu Asp Ile Pro Leu Thr Val Lys Met Arg Thr Gly
145                 150                 155                 160

Trp Ala Asp Pro Ser Leu Ala Val Glu Asn Ala Leu Ala Ala Glu Ala
                165                 170                 175

Ala Gly Val Ser Ala Leu Ala Met His Gly Arg Thr Arg Glu Gln Met
            180                 185                 190

Tyr Thr Gly His Ala Asp Leu Glu Thr Leu Tyr Lys Val Ala Gln Ala
        195                 200                 205

Leu Thr Lys Ile Pro Phe Ile Ala Asn Gly Asp Ile Arg Thr Val Gln
```

-continued

```
    210                 215                 220

Glu Ala Lys Gln Arg Ile Glu Glu Val Gly Ala Asp Ala Val Met Ile
225                 230                 235                 240

Gly Arg Ala Ala Met Gly Asn Pro Tyr Leu Phe Asn Gln Ile Asn His
                245                 250                 255

Tyr Phe Glu Thr Gly Glu Ile Leu Pro Asp Leu Thr Phe Glu Asp Lys
            260                 265                 270

Met Lys Ile Ala Tyr Glu His Leu Lys Arg Leu Ile Asn Leu Lys Gly
        275                 280                 285

Glu Asn Val Ala Val Arg Glu Phe Arg Gly Leu Ala Pro His Tyr Leu
    290                 295                 300

Arg Gly Thr Ser Gly Ala Ala Lys Leu Arg Gly Ala Ile Ser Gln Ala
305                 310                 315                 320

Ser Thr Leu Ala Glu Ile Glu Ala Leu Leu Gln Leu Glu Lys Ala
                325                 330                 335


<210> SEQ ID NO 5
<211> LENGTH: 1200
<212> TYPE: DNA
<213> ORGANISM: Streptococcus pneumoniae
<220> FEATURE:
<221> NAME/KEY: CDS
<222> LOCATION: (146)...(1150)

<400> SEQUENCE: 5

gaaatccgtt tccaatgtga ctgtagccat gaacgcttta tgaacgctct tgccagcctt      60

ccaagctcag acttacagga aatgaaagag gaagaccacg gggcagaaat cacttgtcaa     120

ttctgccaaa ctacttacaa ctttg atg aaa agg acc tgg agg aac tca ttc       172
                            Met Lys Arg Thr Trp Arg Asn Ser Phe
                              1               5

gtg aca aat ctt aat aca cct ttt atg att ggc aat att gag att ccc       220
Val Thr Asn Leu Asn Thr Pro Phe Met Ile Gly Asn Ile Glu Ile Pro
 10                  15                  20                  25

aat cgt acc gtt tta gcg cct atg gct ggc gtg acc aac tca gcc ttt       268
Asn Arg Thr Val Leu Ala Pro Met Ala Gly Val Thr Asn Ser Ala Phe
                 30                  35                  40

cgt acc atc gca aaa gag ctc gga gct gga ctc gtt gta atg gaa atg       316
Arg Thr Ile Ala Lys Glu Leu Gly Ala Gly Leu Val Val Met Glu Met
             45                  50                  55

gtc tct gac aag gga atc caa tac aac aac gaa aaa acc ctg cat atg       364
Val Ser Asp Lys Gly Ile Gln Tyr Asn Asn Glu Lys Thr Leu His Met
         60                  65                  70

ctt cat atc gat gag ggc gaa aac cct gtc tct atc caa ctt ttt ggt       412
Leu His Ile Asp Glu Gly Glu Asn Pro Val Ser Ile Gln Leu Phe Gly
     75                  80                  85

agc gat gaa gac agc cta gca cgc gca gca gaa ttc atc caa gaa aac       460
Ser Asp Glu Asp Ser Leu Ala Arg Ala Ala Glu Phe Ile Gln Glu Asn
 90                  95                 100                 105

acc aag acc gat atc gtc gat atc aac atg ggc tgc cct gtc aac aaa       508
Thr Lys Thr Asp Ile Val Asp Ile Asn Met Gly Cys Pro Val Asn Lys
                110                 115                 120

atc gtg aag aac gaa gct gga gct atg tgg ctc aag gat cct gac aag       556
Ile Val Lys Asn Glu Ala Gly Ala Met Trp Leu Lys Asp Pro Asp Lys
            125                 130                 135

atc tac tct atc atc aac aag gtc cag tct gtc ctt gat atc cca ctt       604
Ile Tyr Ser Ile Ile Asn Lys Val Gln Ser Val Leu Asp Ile Pro Leu
        140                 145                 150

act gtc aaa atg cgt acc ggc tgg gcg gac cca tct ctg gca gta gaa       652
```

-continued

```
Thr Val Lys Met Arg Thr Gly Trp Ala Asp Pro Ser Leu Ala Val Glu
    155                 160                 165

aat gcc ctc gct gct gag gct gca ggt gtt tct gcc ctc gcc atg cat      700
Asn Ala Leu Ala Ala Glu Ala Ala Gly Val Ser Ala Leu Ala Met His
170                 175                 180                 185

ggc cgt acc cgt gaa caa atg tat act ggc cac gca gac ctt gag acc      748
Gly Arg Thr Arg Glu Gln Met Tyr Thr Gly His Ala Asp Leu Glu Thr
                190                 195                 200

ctt tac aag gtt gcc caa gct cta acc aag att cca ttc atc gcc aac      796
Leu Tyr Lys Val Ala Gln Ala Leu Thr Lys Ile Pro Phe Ile Ala Asn
            205                 210                 215

ggt gat atc cgt act gtc caa gaa gcc aag caa cgc atc gaa gaa gtt      844
Gly Asp Ile Arg Thr Val Gln Glu Ala Lys Gln Arg Ile Glu Glu Val
        220                 225                 230

ggt gct gac gca gtc atg att ggc cga gct gcc atg gga aat cct tac      892
Gly Ala Asp Ala Val Met Ile Gly Arg Ala Ala Met Gly Asn Pro Tyr
    235                 240                 245

ctc ttc aac caa atc aac cat tac ttt gaa aca gga gaa atc cta cct      940
Leu Phe Asn Gln Ile Asn His Tyr Phe Glu Thr Gly Glu Ile Leu Pro
250                 255                 260                 265

gat ttg acc ttt gaa gac aag atg aag atc gcc tac gaa cac ttg aaa      988
Asp Leu Thr Phe Glu Asp Lys Met Lys Ile Ala Tyr Glu His Leu Lys
                270                 275                 280

cga ttg att aac ctc aaa gga gaa aac gtc gca gtt cgt gaa ttc cgc     1036
Arg Leu Ile Asn Leu Lys Gly Glu Asn Val Ala Val Arg Glu Phe Arg
            285                 290                 295

ggc ctc gct cct cac tat ctc cgt gga aca tct ggc gct gcc aaa ctc     1084
Gly Leu Ala Pro His Tyr Leu Arg Gly Thr Ser Gly Ala Ala Lys Leu
        300                 305                 310

cgt gga gcc att tcg caa gct agc acc cta gca gag att gaa gcc ctc     1132
Arg Gly Ala Ile Ser Gln Ala Ser Thr Leu Ala Glu Ile Glu Ala Leu
    315                 320                 325

ttg caa ttg gag aag gct taatagttta aaacccgtaa ctctcttaaa            1180
Leu Gln Leu Glu Lys Ala
330                 335

gagtctcttg aatgccgcca                                               1200


<210> SEQ ID NO 6
<211> LENGTH: 1200
<212> TYPE: DNA
<213> ORGANISM: Streptococcus pneumoniae

<400> SEQUENCE: 6

ctttaggcaa aggttacact gacatcggta cttgcgaaat acttgcgaga acggtcggaa     60

ggttcgagtc tgaatgtcct ttactttctc cttctggtgc cccgtcttta gtgaacagtt    120

aagacggttt gatgaatgtt gaaactactt ttcctggacc tccttgagta agcactgttt    180

agaattatgt ggaaaatact aaccgttata actctaaggg ttagcatggc aaaatcgcgg    240

ataccgaccg cactggttga gtcggaaagc atggtagcgt tttctcgagc ctcgacctga    300

gcaacattac ctttaccaga gactgttccc ttaggttatg ttgttgcttt tttgggacgt    360

atacgaagta tagctactcc cgcttttggg acagagatag gttgaaaaac catcgctact    420

tctgtcggat cgtgcgcgtc gtcttaagta ggttcttttg tggttctggc tatagcagct    480

atagttgtac ccgacgggac agttgtttta gcacttcttg cttcgacctc gatacaccga    540

gttcctagga ctgttctaga tgagatagta gttgttccag gtcagacagg aactataggg    600

tgaatgacag ttttacgcat ggccgacccg cctgggtaga gaccgtcatc ttttacggga    660
```

-continued

```
gcgacgactc cgacgtccac aaagacggga gcggtacgta ccggcatggg cacttgttta    720

catatgaccg gtgcgtctgg aactctggga aatgttccaa cgggttcgag attggttcta    780

aggtaagtag cggttgccac tataggcatg acaggttctt cggttcgttg cgtagcttct    840

tcaaccacga ctgcgtcagt actaaccggc tcgacggtac cctttaggaa tggagaagtt    900

ggtttagttg gtaatgaaac tttgtcctct ttaggatgga ctaaactgga aacttctgtt    960

ctacttctag cggatgcttg tgaactttgc taactaattg gagtttcctc ttttgcagcg   1020

tcaagcactt aaggcgccgg agcgaggagt gatagaggca ccttgtagac cgcgacggtt   1080

tgaggcacct cggtaaagcg ttcgatcgtg ggatcgtctc taacttcggg agaacgttaa   1140

cctcttccga attatcaaat tttgggcatt gagagaattt ctcagagaac ttacggcggt   1200


<210> SEQ ID NO 7
<211> LENGTH: 451
<212> TYPE: PRT
<213> ORGANISM: Streptococcus pneumoniae

<400> SEQUENCE: 7

Met Asn Leu Lys Val Lys Gln Lys Ile Pro Leu Lys Ile Lys Arg Met
  1               5                  10                  15

Gly Ile Asn Gly Glu Gly Ile Gly Phe Tyr Gln Lys Thr Leu Val Phe
             20                  25                  30

Val Pro Gly Ala Leu Lys Gly Glu Asp Ile Tyr Cys Gln Ile Thr Ser
         35                  40                  45

Ile Arg Arg Asn Phe Val Glu Ala Lys Leu Leu Lys Val Asn Lys Lys
     50                  55                  60

Ser Lys Phe Arg Ile Val Pro Ser Cys Thr Ile Tyr Asn Glu Cys Gly
 65                  70                  75                  80

Gly Cys Gln Ile Met His Leu His Tyr Asp Lys Gln Leu Glu Phe Lys
                 85                  90                  95

Thr Asp Leu Leu His Gln Ala Leu Lys Lys Phe Ala Pro Ala Gly Tyr
            100                 105                 110

Glu Asn Tyr Glu Ile Arg Pro Thr Ile Gly Met Gln Glu Pro Lys Tyr
        115                 120                 125

Tyr Arg Ala Lys Leu Gln Phe Gln Thr Arg Lys Phe Lys Asn Gln Val
    130                 135                 140

Lys Ala Gly Leu Tyr Ala Gln Asn Ser His Tyr Leu Val Glu Leu Lys
145                 150                 155                 160

Asp Cys Leu Val Gln Asp Lys Glu Thr Gln Val Ile Ala Asn Arg Leu
                165                 170                 175

Ala Glu Leu Leu Thr Tyr His Gln Ile Pro Ile Thr Asp Glu Arg Lys
            180                 185                 190

Val Leu Gly Val Arg Thr Ile Met Val Arg Arg Ala Arg Lys Thr Gly
        195                 200                 205

Gln Val Gln Ile Ile Ile Val Thr Asn Arg Gln Leu Asn Leu Thr Gln
    210                 215                 220

Leu Val Lys Glu Leu Val Lys Asp Phe Pro Glu Val Val Thr Val Ala
225                 230                 235                 240

Val Asn Thr Asn Thr Ala Lys Thr Ser Glu Ile Tyr Gly Glu Lys Thr
                245                 250                 255

Glu Ile Ile Trp Gly Gln Glu Ser Ile Gln Glu Gly Val Leu Asn Tyr
            260                 265                 270

Glu Phe Ser Leu Ser Pro Arg Ala Phe Tyr Gln Leu Asn Pro Glu Gln
        275                 280                 285
```

-continued

```
Thr Glu Val Leu Tyr Ser Glu Ala Val Lys Ala Leu Asp Val Asp Lys
    290                 295                 300

Glu Asp His Leu Ile Asp Ala Tyr Cys Gly Val Gly Thr Ile Gly Phe
305                 310                 315                 320

Ala Phe Ala Lys Lys Val Lys Thr Leu Arg Gly Met Asp Ile Ile Pro
                325                 330                 335

Glu Ala Ile Glu Asp Ala Lys Arg Asn Ala Lys Arg Met Gly Phe Asp
            340                 345                 350

Asn Thr His Tyr Glu Ala Gly Thr Ala Glu Glu Ile Ile Pro Arg Trp
        355                 360                 365

Tyr Lys Glu Gly Tyr Arg Ala Asp Ala Leu Ile Val Asp Pro Pro Arg
    370                 375                 380

Thr Gly Leu Asp Asp Lys Leu Leu Asp Thr Ile Leu Thr Tyr Val Pro
385                 390                 395                 400

Glu Lys Met Val Tyr Ile Ser Cys Asn Val Ser Thr Leu Ala Arg Asp
                405                 410                 415

Leu Val Arg Leu Val Glu Val Tyr Asp Leu His Tyr Ile Gln Ser Val
            420                 425                 430

Asp Met Phe Pro His Thr Ala Arg Thr Glu Ala Val Val Lys Leu Ile
        435                 440                 445

Thr Lys Val
    450


<210> SEQ ID NO 8
<211> LENGTH: 2084
<212> TYPE: DNA
<213> ORGANISM: Streptococcus pneumoniae
<220> FEATURE:
<221> NAME/KEY: CDS
<222> LOCATION: (559)...(1911)
<221> NAME/KEY: misc_feature
<222> LOCATION: (1)...(2084)
<223> OTHER INFORMATION: n = A,T,C or G

<400> SEQUENCE: 8

aaggcacgag ctggaagttt tccctcatat tttttcaata gtttattagc tacacgttga      60

gcaacttcag aaaaatcaaa ttctttcaag ttctcttcta tagtagattt tgaaatccct     120

ttttgagcta gtttctgagt cagcacataa ggacccttgt ctcctgaaag ttgattggta     180

ttgatgatag cataagcgta ctgaccatca ttaatccact tatcttcttt aagattagca     240

ataacttgag aaacgatgtt tttatcaata tcgtattttt tcagatattc tctgacttct     300

ttttcagtgc gtgctttaaa ggataagtgg tagagggcca gattcttacc ataagaaaat     360

tgagcaaagt cttgaatctc tttcaattcc tcttcgctta tcaccttatc tctcgataac     420

ataaaacgaa caattgtatc ttcggtgata tagcatttgt cgccattatc aagctccatc     480

agatagagtc tttttttctt ttcaagtttt gtgattttca tagctctatt ataactcaaa     540

atgtgataag atagggggt atg aat ctg aaa gtg aaa caa aaa ata cca tta      591
                     Met Asn Leu Lys Val Lys Gln Lys Ile Pro Leu
                       1               5                  10

aaa atc aag cgc atg gga att aac ggt gag gga atc ggc ttt tac caa      639
Lys Ile Lys Arg Met Gly Ile Asn Gly Glu Gly Ile Gly Phe Tyr Gln
            15                  20                  25

aaa aca tta gtc ttt gta cca gga gct ctc aaa ggc gaa gat atc tat      687
Lys Thr Leu Val Phe Val Pro Gly Ala Leu Lys Gly Glu Asp Ile Tyr
        30                  35                  40

tgt cag att act tct att aga cgc aac ttt gtt gaa gca aaa tta ctg      735
```

-continued

```
Cys Gln Ile Thr Ser Ile Arg Arg Asn Phe Val Glu Ala Lys Leu Leu
     45                  50                  55

aag gtc aac aag aag tct aaa ttt cga att gtg cca tct tgt act att      783
Lys Val Asn Lys Lys Ser Lys Phe Arg Ile Val Pro Ser Cys Thr Ile
 60                  65                  70                  75

tat aat gaa tgc gga ggc tgc caa atc atg cac ctg cat tat gat aag      831
Tyr Asn Glu Cys Gly Gly Cys Gln Ile Met His Leu His Tyr Asp Lys
                 80                  85                  90

cag ctg gag ttc aag acg gac tta ctt cat caa gcg ctg aaa aaa ttt      879
Gln Leu Glu Phe Lys Thr Asp Leu Leu His Gln Ala Leu Lys Lys Phe
             95                 100                 105

gct cct gca gga tat gaa aat tat gaa att cgt cca act att gga atg      927
Ala Pro Ala Gly Tyr Glu Asn Tyr Glu Ile Arg Pro Thr Ile Gly Met
        110                 115                 120

cag gaa cca aaa tat tac aga gct aag tta caa ttt cag act cga aaa      975
Gln Glu Pro Lys Tyr Tyr Arg Ala Lys Leu Gln Phe Gln Thr Arg Lys
    125                 130                 135

ttt aaa aat cag gtc aag gcg ggc tta tat gca caa aac tct cac tat     1023
Phe Lys Asn Gln Val Lys Ala Gly Leu Tyr Ala Gln Asn Ser His Tyr
140                 145                 150                 155

tta gta gag ttg aaa gac tgc ctg gta caa gat aag gaa acc caa gtg     1071
Leu Val Glu Leu Lys Asp Cys Leu Val Gln Asp Lys Glu Thr Gln Val
                160                 165                 170

att gct aat cgc tta gca gaa tta ctt act tat cac cag att cca atc     1119
Ile Ala Asn Arg Leu Ala Glu Leu Leu Thr Tyr His Gln Ile Pro Ile
            175                 180                 185

acg gat gag aga aaa gtt cta ggt gtc cgt act att atg gtc cga cgc     1167
Thr Asp Glu Arg Lys Val Leu Gly Val Arg Thr Ile Met Val Arg Arg
        190                 195                 200

gcg aga aag acc gga cag gtt cag att att att gtt aca aac cgc cag     1215
Ala Arg Lys Thr Gly Gln Val Gln Ile Ile Ile Val Thr Asn Arg Gln
    205                 210                 215

ctt aat tta act caa ttg gta aaa gag ttg gtt aaa gat ttc cca gaa     1263
Leu Asn Leu Thr Gln Leu Val Lys Glu Leu Val Lys Asp Phe Pro Glu
220                 225                 230                 235

gtt gtg aca gta gct gtt aat aca aat aca gct aaa acc agt gag ata     1311
Val Val Thr Val Ala Val Asn Thr Asn Thr Ala Lys Thr Ser Glu Ile
                240                 245                 250

tat ggt gaa aag aca gag att atc tgg ggg caa gag agt att caa gaa     1359
Tyr Gly Glu Lys Thr Glu Ile Ile Trp Gly Gln Glu Ser Ile Gln Glu
            255                 260                 265

ggt gta ctc aat tat gaa ttt tca cta tcc cct cga gct ttt tat caa     1407
Gly Val Leu Asn Tyr Glu Phe Ser Leu Ser Pro Arg Ala Phe Tyr Gln
        270                 275                 280

cta aat cct gag caa aca gaa gtc ctc tat agc gaa gca gta aaa gcg     1455
Leu Asn Pro Glu Gln Thr Glu Val Leu Tyr Ser Glu Ala Val Lys Ala
    285                 290                 295

ctg gat gtt gat aaa gaa gac cat ttg att gac gct tat tgt gga gtt     1503
Leu Asp Val Asp Lys Glu Asp His Leu Ile Asp Ala Tyr Cys Gly Val
300                 305                 310                 315

gga acg att gga ttt gcc ttt gca aag aaa gta aaa aca ctc aga ggt     1551
Gly Thr Ile Gly Phe Ala Phe Ala Lys Lys Val Lys Thr Leu Arg Gly
                320                 325                 330

atg gat att att cca gaa gct att gaa gat gcc aag cga aat gct aaa     1599
Met Asp Ile Ile Pro Glu Ala Ile Glu Asp Ala Lys Arg Asn Ala Lys
            335                 340                 345

aga atg gga ttt gac aat act cat tat gaa gct gga acg gca gaa gag     1647
Arg Met Gly Phe Asp Asn Thr His Tyr Glu Ala Gly Thr Ala Glu Glu
        350                 355                 360
```

-continued

```
att att cct cgt tgg tac aag gaa ggc tac cga gca gat gct ttg att     1695
Ile Ile Pro Arg Trp Tyr Lys Glu Gly Tyr Arg Ala Asp Ala Leu Ile
    365                 370                 375

gtt gac cca cca cgt aca ggt ctg gat gat aag tta tta gat act att     1743
Val Asp Pro Pro Arg Thr Gly Leu Asp Asp Lys Leu Leu Asp Thr Ile
380                 385                 390                 395

ctt act tat gta cca gaa aaa atg gtt tat att tct tgt aat gtt tcg     1791
Leu Thr Tyr Val Pro Glu Lys Met Val Tyr Ile Ser Cys Asn Val Ser
                400                 405                 410

acc ttg gct cgt gat ttg gta cgc tta gta gaa gtc tat gat ctt cat     1839
Thr Leu Ala Arg Asp Leu Val Arg Leu Val Glu Val Tyr Asp Leu His
            415                 420                 425

tat atc cag tcg gtc gat atg ttc cca cat aca gct cga act gaa gct     1887
Tyr Ile Gln Ser Val Asp Met Phe Pro His Thr Ala Arg Thr Glu Ala
        430                 435                 440

gtt gta aaa tta ata aca aaa gtt taaaaaagta gttgacaaag tttgaaaaga    1941
Val Val Lys Leu Ile Thr Lys Val
    445                 450

ctgtataata gtaagagttg aaaataacaa ctcaggtncg ttggtcaagg ggttaagaca   2001

cgccttttca cggcggtaac acgggttcga atcccgtacg gactatggta tgttgcggtt   2061

ggaacacttg atgaaaaact tta                                           2084


<210> SEQ ID NO 9
<211> LENGTH: 2084
<212> TYPE: DNA
<213> ORGANISM: Streptococcus pneumoniae
<220> FEATURE:
<221> NAME/KEY: misc_feature
<222> LOCATION: (1)...(2084)
<223> OTHER INFORMATION: n = A,T,C or G

<400> SEQUENCE: 9

ttccgtgctc gaccttcaaa agggagtata aaaaagttat caaataatcg atgtgcaact     60

cgttgaagtc tttttagttt aagaaagttc aagagaagat atcatctaaa actttaggga    120

aaaactcgat caaagactca gtcgtgtatt cctgggaaca gaggactttc aactaaccat    180

aactactatc gtattcgcat gactggtagt aattaggtga atagaagaaa ttctaatcgt    240

tattgaactc tttgctacaa aaatagttat agcataaaaa agtctataag agactgaaga    300

aaaagtcacg cacgaaattt cctattcacc atctcccggt ctaagaatgg tattctttta    360

actcgtttca gaacttagag aaagttaagg agaagcgaat agtggaatag agagctattg    420

tattttgctt gttaacatag aagccactat atcgtaaaca gcggtaatag ttcgaggtag    480

tctatctcag aaaaaaagaa aagttcaaaa cactaaaagt atcgagataa tattgagttt    540

tacactattc tatccccata cttagacttt cactttgttt tttatggtaa tttttagttc    600

gcgtaccctt aattgccact cccttagccg aaaatggttt tttgtaatca gaaacatggt    660

cctcgagagt ttccgcttct atagataaca gtctaatgaa gataatctgc gttgaaacaa    720

cttcgtttta atgacttcca gttgttcttc agatttaaag cttaacacgg tagaacatga    780

taaatattac ttacgcctcc gacggtttag tacgtggacg taatactatt cgtcgacctc    840

aagttctgcc tgaatgaagt agttcgcgac ttttttaaac gaggacgtcc tatactttta    900

atactttaag caggttgata accttacgtc cttggtttta taatgtctcg attcaatgtt    960

aaagtctgag cttttaaatt tttagtccag ttccgcccga atatacgtgt tttgagagtg   1020

ataaatcatc tcaactttct gacggaccat gttctattcc tttgggttca ctaacgatta   1080

gcgaatcgtc ttaatgaatg aatagtggtc taaggttagt gcctactctc ttttcaagat   1140
```

-continued

```
ccacaggcat gataatacca ggctgcgcgc tctttctggc ctgtccaagt ctaataataa   1200

caatgtttgg cggtcgaatt aaattgagtt aaccattttc tcaaccaatt tctaaagggt   1260

cttcaacact gtcatcgaca attatgttta tgtcgatttt ggtcactcta tataccactt   1320

ttctgtctct aatagacccc cgttctctca taagttcttc cacatgagtt aatacttaaa   1380

agtgataggg gagctcgaaa aatagttgat ttaggactcg tttgtcttca ggagatatcg   1440

cttcgtcatt ttcgcgacct acaactattt cttctggtaa actaactgcg aataacacct   1500

caaccttgct aacctaaacg gaaacgtttc tttcattttt gtgagtctcc atacctataa   1560

taaggtcttc gataacttct acggttcgct ttacgatttt cttaccctaa actgttatga   1620

gtaatacttc gaccttgccg tcttctctaa taaggagcaa ccatgttcct tccgatggct   1680

cgtctacgaa actaacaact gggtggtgca tgtccagacc tactattcaa taatctatga   1740

taagaatgaa tacatggtct tttttaccaa atataaagaa cattacaaag ctggaaccga   1800

gcactaaacc atgcgaatca tcttcagata ctagaagtaa tataggtcag ccagctatac   1860

aagggtgtat gtcgagcttg acttcgacaa cattttaatt attgttttca aattttttca   1920

tcaactgttt caaacttttc tgacatatta tcattctcaa cttttattgt tgagtccang   1980

caaccagttc cccaattctg tgcggaaaag tgccgccatt gtgcccaagc ttagggcatg   2040

cctgatacca tacaacgcca accttgtgaa ctactttttg aaat                    2084
```

<210> SEQ ID NO 10
<211> LENGTH: 225
<212> TYPE: PRT
<213> ORGANISM: Streptococcus pneumoniae
<220> FEATURE:
<221> NAME/KEY: VARIANT
<222> LOCATION: (1)...(225)
<223> OTHER INFORMATION: Xaa = Any Amino Acid

<400> SEQUENCE: 10

```
Met His Lys Ile Leu Leu Ile Glu Asp Asp Gln Val Ile Arg Gln Gln
  1               5                  10                  15

Ile Gly Lys Met Leu Ser Glu Trp Gly Phe Xaa Val Val Leu Val Glu
             20                  25                  30

Asp Phe Met Glu Val Leu Ser Leu Phe Val Gln Ser Glu Pro His Leu
         35                  40                  45

Val Leu Met Asp Ile Gly Leu Pro Leu Phe Asn Gly Tyr His Trp Cys
     50                  55                  60

Gln Glu Ile Arg Lys Ile Ser Lys Val Pro Ile Met Phe Leu Ser Ser
 65                  70                  75                  80

Arg Asp Gln Ala Met Asp Ile Val Met Ala Ile Asn Met Gly Ala Asp
                 85                  90                  95

Asp Phe Val Thr Lys Pro Phe Asp Gln Gln Val Leu Leu Ala Lys Val
            100                 105                 110

Gln Gly Leu Leu Arg Arg Ser Tyr Glu Phe Gly Arg Asp Glu Ser Leu
        115                 120                 125

Leu Glu Tyr Ala Gly Val Ile Leu Asn Thr Lys Ser Met Asp Leu His
    130                 135                 140

Tyr Gln Gly Gln Val Leu Asn Leu Thr Lys Asn Glu Phe Gln Ile Leu
145                 150                 155                 160

Arg Val Leu Phe Glu His Ala Gly Asn Ile Val Ala Arg Asp Asp Leu
                165                 170                 175

Met Arg Glu Leu Trp Asn Ser Asp Phe Phe Ile Asp Asp Asn Thr Leu
```

-continued

```
            180                 185                 190

Ser Val Asn Val Ala Arg Leu Arg Lys Lys Leu Glu Glu Gln Gly Leu
        195                 200                 205

Val Gly Phe Ile Glu Thr Lys Lys Gly Ile Gly Tyr Gly Leu Lys His
    210                 215                 220

Ala
225


<210> SEQ ID NO 11
<211> LENGTH: 1000
<212> TYPE: DNA
<213> ORGANISM: Streptococcus pneumoniae
<220> FEATURE:
<221> NAME/KEY: CDS
<222> LOCATION: (156)...(830)
<221> NAME/KEY: misc_feature
<222> LOCATION: (1)...(1000)
<223> OTHER INFORMATION: n = A,T,C or G

<400> SEQUENCE: 11

aagagctcct ttctttttat ttatcttagc aaatttccct caaattagct agtagcatag     60

cctgtttgta ctggctaaaa acaggctatt tcaaattcag tttcagacca tctagcatgg    120

aaaaatctgt tataataatg gaaaaggaga agcgc atg cac aag att tta tta       173
                                       Met His Lys Ile Leu Leu
                                         1               5

ata gaa gat gat cag gtc att cgt caa cag att ggg aaa atg ctc tct      221
Ile Glu Asp Asp Gln Val Ile Arg Gln Gln Ile Gly Lys Met Leu Ser
             10                  15                  20

gaa tgg gga ttt naa gtg gtc ctg gta gaa gac ttt atg gaa gtt ttg      269
Glu Trp Gly Phe Xaa Val Val Leu Val Glu Asp Phe Met Glu Val Leu
         25                  30                  35

agt cta ttt gtt cag tcg gaa cct cat ctg gtc ctc atg gat att ggt      317
Ser Leu Phe Val Gln Ser Glu Pro His Leu Val Leu Met Asp Ile Gly
     40                  45                  50

ttg ccc ttg ttt aat ggt tat cac tgg tgt cag gaa atc cgc aag att      365
Leu Pro Leu Phe Asn Gly Tyr His Trp Cys Gln Glu Ile Arg Lys Ile
 55                  60                  65                  70

tcc aag gta cct atc atg ttt ctt tct tcg aga gac cag gct atg gat      413
Ser Lys Val Pro Ile Met Phe Leu Ser Ser Arg Asp Gln Ala Met Asp
                 75                  80                  85

att gtc atg gca atc aat atg ggg gcg gat gac ttt gtg acc aag cct      461
Ile Val Met Ala Ile Asn Met Gly Ala Asp Asp Phe Val Thr Lys Pro
             90                  95                 100

ttt gac cag cag gtt ctt tta gct aag gtt cag ggc ttg ttg cgt cgt      509
Phe Asp Gln Gln Val Leu Leu Ala Lys Val Gln Gly Leu Leu Arg Arg
        105                 110                 115

tcc tat gag ttt ggg cgt gat gag agt ttg ctg gaa tat gct ggt gtt      557
Ser Tyr Glu Phe Gly Arg Asp Glu Ser Leu Leu Glu Tyr Ala Gly Val
    120                 125                 130

atc ctc aat acc aaa tcc atg gat tta cat tat caa ggg caa gtc ttg      605
Ile Leu Asn Thr Lys Ser Met Asp Leu His Tyr Gln Gly Gln Val Leu
135                 140                 145                 150

aat ttg acc aag aat gaa ttc cag att tta cgc gtg tta ttt gag cat      653
Asn Leu Thr Lys Asn Glu Phe Gln Ile Leu Arg Val Leu Phe Glu His
                155                 160                 165

gca ggc aac atc gta gca cgt gac gac ctg atg cgg gaa ctt tgg aac      701
Ala Gly Asn Ile Val Ala Arg Asp Asp Leu Met Arg Glu Leu Trp Asn
            170                 175                 180

agt gac ttt ttc att gat gat aat acc ctc tct gtc aat gtg gct cgt      749
Ser Asp Phe Phe Ile Asp Asp Asn Thr Leu Ser Val Asn Val Ala Arg
```

-continued 185 190 195 ttg cgt aaa aag ttg gag gag cag gga ttg gta gga ttt atc gag acc 797
Leu Arg Lys Lys Leu Glu Glu Gln Gly Leu Val Gly Phe Ile Glu Thr
200 205 210 aag aaa gga ata ggg tac gga ttg aag cat gct tgattggaaa caatttttc 850
Lys Lys Gly Ile Gly Tyr Gly Leu Lys His Ala
215 220 225 tagcctatct gcgctcccgt agtcgtcttt ttatctatct gctttctttg gcatttcttg 910
tcttactctt tcagttttta tttgccagtc taggaattta cttcctctac tttttcttct 970
tgtgttgctt tgtaaccatc ttatttttca 1000

<210> SEQ ID NO 12
<211> LENGTH: 1000
<212> TYPE: DNA
<213> ORGANISM: Streptococcus pneumoniae
<220> FEATURE:
<221> NAME/KEY: misc_feature
<222> LOCATION: (1)...(1000)
<223> OTHER INFORMATION: n = A,T,C or G

<400> SEQUENCE: 12
ttctcgagga aagaaaaata aatagaatcg tttaaaggga gtttaatcga tcatcgtatc 60
ggacaaacat gaccgatttt tgtccgataa agtttaagtc aaagtctggt agatcgtacc 120
tttttagaca atattattac cttttcctct tcgcgtacgt gttctaaaat aattatcttc 180
tactagtcca gtaagcagtt gtctaaccct tttacgagag acttacccct aaanttcacc 240
aggaccatct tctgaaatac cttcaaaact cagataaaca agtcagcctt ggagtagacc 300
aggagtacct ataaccaaac gggaacaaat taccaatagt gaccacagtc ctttaggcgt 360
tctaaaggtt ccatggatag tacaaagaaa gaagctctct ggtccgatac ctataacagt 420
accgttagtt ataccccgc ctactgaaac actggttcgg aaaactggtc gtccaagaaa 480
atcgattcca agtcccgaac aacgcagcaa ggatactcaa acccgcacta ctctcaaacg 540
accttatacg accacaatag gagttatggt ttaggtacct aaatgtaata gttcccgttc 600
agaacttaaa ctggttctta cttaaggtct aaaatgcgca caataaactc gtacgtccgt 660
tgtagcatcg tgcactgctg gactacgccc ttgaaacctt gtcactgaaa aagtaactac 720
tattatggga gagacagtta caccgagcaa acgcattttt caacctcctc gtccctaacc 780
atcctaaata gctctggttc tttccttatc ccatgcctaa cttcgtacga actaaccttt 840
gttaaaaaag atcggataga cgcgagggca tcagcagaaa aatagataga cgaaagaaac 900
cgtaaagaac agaatgagaa agtcaaaaat aaacggtcag atccttaaat gaaggagatg 960
aaaaagaaga acacaacgaa acattggtag aataaaaagt 1000

<210> SEQ ID NO 13
<211> LENGTH: 114
<212> TYPE: PRT
<213> ORGANISM: Streptococcus pneumoniae

<400> SEQUENCE: 13

Lys Asp Thr Gly Thr Thr Asn Thr Phe Arg Ile Leu Gly Lys Lys Ala
1 5 10 15

Gly Met Ala Thr Phe Val Ile Asp Phe Phe Lys Gly Thr Leu Ala Thr
20 25 30

Leu Leu Pro Ile Ile Phe His Leu Gln Gly Val Ser Pro Leu Ile Phe
35 40 45

-continued

```
Gly Leu Leu Ala Val Ile Gly His Thr Phe Pro Ile Phe Ala Gly Phe
     50                  55                  60

Lys Gly Gly Lys Ala Val Ala Thr Ser Ala Gly Val Ile Phe Gly Phe
 65                  70                  75                  80

Ala Pro Ile Phe Cys Leu Tyr Leu Ala Ile Ile Phe Phe Gly Leu Ser
                 85                  90                  95

Tyr Leu Gly Ser Met Ile Ser Leu Ser Ser Val Thr Ala Ser Ile Ala
            100                 105                 110

Ala Val


<210> SEQ ID NO 14
<211> LENGTH: 344
<212> TYPE: DNA
<213> ORGANISM: Streptococcus pneumoniae
<220> FEATURE:
<221> NAME/KEY: CDS
<222> LOCATION: (2)...(343)

<400> SEQUENCE: 14

t aaa gac act gga acg acc aac acc ttc cgc att tta ggt aag aaa gct      49
  Lys Asp Thr Gly Thr Thr Asn Thr Phe Arg Ile Leu Gly Lys Lys Ala
    1               5                  10                  15

ggt atg gca acc ttt gtg att gac ttt ttc aaa gga acc cta gca acg        97
Gly Met Ala Thr Phe Val Ile Asp Phe Phe Lys Gly Thr Leu Ala Thr
            20                  25                  30

ctg ctt ccg att att ttt cat cta caa ggc gtt tct cct ctc atc ttt       145
Leu Leu Pro Ile Ile Phe His Leu Gln Gly Val Ser Pro Leu Ile Phe
        35                  40                  45

gga ctt ttg gct gtt atc ggc cat acc ttc cct atc ttt gca gga ttt       193
Gly Leu Leu Ala Val Ile Gly His Thr Phe Pro Ile Phe Ala Gly Phe
     50                  55                  60

aaa ggt ggt aag gct gtc gca acc agt gct gga gtg att ttc gga ttt       241
Lys Gly Gly Lys Ala Val Ala Thr Ser Ala Gly Val Ile Phe Gly Phe
 65                  70                  75                  80

gcg cct atc ttc tgt ctc tac ctt gcg att atc ttc ttt gga ctc tca       289
Ala Pro Ile Phe Cys Leu Tyr Leu Ala Ile Ile Phe Phe Gly Leu Ser
                 85                  90                  95

tat ctt ggc agt atg att tca ctg tct agt gtc aca gca tcg atc gcg       337
Tyr Leu Gly Ser Met Ile Ser Leu Ser Ser Val Thr Ala Ser Ile Ala
            100                 105                 110

gct gtt a                                                             344
Ala Val


<210> SEQ ID NO 15
<211> LENGTH: 344
<212> TYPE: DNA
<213> ORGANISM: Streptococcus pneumoniae

<400> SEQUENCE: 15

atttctgtga ccttgctggt tgtggaaggc gtaaaatcca ttctttcgac cataccgttg      60

gaaacactaa ctgaaaaagt ttccttggga tcgttgcgac gaaggctaat aaaaagtaga     120

tgttccgcaa agaggagagt agaaacctga aaaccgacaa tagccggtat ggaagggata     180

gaaacgtcct aaatttccac cattccgaca gcgttggtca cgacctcact aaaagcctaa     240

acgcggatag aagacagaga tggaacgcta atagaagaaa cctgagagta tagaaccgtc     300

atactaaagt gacagatcac agtgtcgtag ctagcgccga caat                      344


<210> SEQ ID NO 16
<211> LENGTH: 148
```

-continued

```
<212> TYPE: PRT
<213> ORGANISM: Streptococcus pneumoniae

<400> SEQUENCE: 16

Met Lys Ser Ile Lys Leu Asn Ala Leu Ser Tyr Met Gly Ile Arg Val
  1               5                  10                  15

Leu Asn Ile Ile Phe Pro Ile Leu Thr Gly Thr Tyr Val Ala Arg Val
            20                  25                  30

Leu Asp Arg Thr Asp Tyr Gly Tyr Phe Asn Ser Val Asp Thr Ile Leu
        35                  40                  45

Ser Phe Phe Leu Pro Phe Ala Thr Tyr Gly Val Tyr Asn Tyr Gly Leu
    50                  55                  60

Arg Ala Ile Ser Asn Val Lys Asp Asn Lys Lys Asp Leu Asn Arg Thr
 65                  70                  75                  80

Phe Ser Ser Leu Phe Tyr Leu Cys Ile Ala Cys Thr Ile Leu Thr Thr
                 85                  90                  95

Ala Val Tyr Ile Leu Ala Tyr Pro Leu Phe Phe Thr Asp Asn Pro Ile
            100                 105                 110

Val Lys Lys Val Tyr Leu Val Met Gly Ile Gln Leu Ile Ala Gln Ile
        115                 120                 125

Phe Ser Ile Glu Trp Val Asn Glu Ala Leu Glu Asn Tyr Ser Phe Ser
    130                 135                 140

Phe Thr Lys Leu
145


<210> SEQ ID NO 17
<211> LENGTH: 460
<212> TYPE: DNA
<213> ORGANISM: Streptococcus pneumoniae
<220> FEATURE:
<221> NAME/KEY: CDS
<222> LOCATION: (16)...(459)

<400> SEQUENCE: 17

ctaaaggtaa attga atg aaa agt ata aaa tta aat gct cta tct tac atg      51
                 Met Lys Ser Ile Lys Leu Asn Ala Leu Ser Tyr Met
                   1               5                  10

gga att cgt gtc ttg aat att att ttt ccc atc cta act gga acc tat       99
Gly Ile Arg Val Leu Asn Ile Ile Phe Pro Ile Leu Thr Gly Thr Tyr
        15                  20                  25

gtc gcg cgt gtc ttg gac cga act gac tat ggt tac ttc aac tca gtc      147
Val Ala Arg Val Leu Asp Arg Thr Asp Tyr Gly Tyr Phe Asn Ser Val
    30                  35                  40

gac act att ttg tca ttt ttc ttg ccc ttt gca act tat ggt gtc tat      195
Asp Thr Ile Leu Ser Phe Phe Leu Pro Phe Ala Thr Tyr Gly Val Tyr
 45                  50                  55                  60

aac tac ggt tta agg gct atc agt aat gtc aag gat aac aaa aaa gat      243
Asn Tyr Gly Leu Arg Ala Ile Ser Asn Val Lys Asp Asn Lys Lys Asp
                 65                  70                  75

ctt aac aga acc ttt tct agt ctt ttt tat ttg tgc atc gct tgt acg      291
Leu Asn Arg Thr Phe Ser Ser Leu Phe Tyr Leu Cys Ile Ala Cys Thr
            80                  85                  90

att ttg acc act gct gtc tat atc cta gcc tat cct ctc ttc ttt act      339
Ile Leu Thr Thr Ala Val Tyr Ile Leu Ala Tyr Pro Leu Phe Phe Thr
        95                  100                 105

gat aat cca atc gtc aaa aag gtc tac ctt gtt atg ggg att caa ctc      387
Asp Asn Pro Ile Val Lys Lys Val Tyr Leu Val Met Gly Ile Gln Leu
    110                 115                 120

att gcc cag att ttt tca atc gaa tgg gtc aat gaa gct ctg gaa aat      435
```

-continued

```
Ile Ala Gln Ile Phe Ser Ile Glu Trp Val Asn Glu Ala Leu Glu Asn
125                 130                 135                 140

tac agt ttc tct ttt aca aaa ctg c                                460
Tyr Ser Phe Ser Phe Thr Lys Leu
                145


<210> SEQ ID NO 18
<211> LENGTH: 460
<212> TYPE: DNA
<213> ORGANISM: Streptococcus pneumoniae

<400> SEQUENCE: 18

gatttccatt taacttactt ttcatatttt aatttacgag atagaatgta cccttaagca     60

cagaacttat aataaaaagg gtaggattga ccttggatac agcgcgcaca gaacctggct    120

tgactgatac caatgaagtt gagtcagctg tgataaaaca gtaaaaagaa cgggaaacgt    180

tgaataccac agatattgat gccaaattcc cgatagtcat tacagttcct attgtttttt    240

ctagaattgt cttggaaaag atcagaaaaa ataaacacgt agcgaacatg ctaaaactgg    300

tgacgacaga tataggatcg gataggagag aagaaatgac tattaggtta gcagtttttc    360

cagatggaac aatacccccta agttgagtaa cgggtctaaa aaagttagct tacccagtta    420

cttcgagacc ttttaatgtc aaagagaaaa tgttttgacg                          460


<210> SEQ ID NO 19
<211> LENGTH: 289
<212> TYPE: PRT
<213> ORGANISM: Streptococcus pneumoniae

<400> SEQUENCE: 19

Met Gln Ile Gln Lys Ser Phe Lys Gly Gln Ser Pro Tyr Gly Lys Leu
  1               5                  10                  15

Tyr Leu Val Ala Thr Pro Ile Gly Asn Leu Asp Asp Met Thr Phe Arg
             20                  25                  30

Ala Ile Gln Thr Leu Lys Glu Val Asp Trp Ile Ala Ala Glu Asp Thr
         35                  40                  45

Arg Asn Thr Gly Leu Leu Leu Lys His Phe Asp Ile Ser Thr Lys Gln
     50                  55                  60

Ile Ser Phe His Glu His Asn Ala Lys Glu Lys Ile Pro Asp Leu Ile
 65                  70                  75                  80

Gly Phe Leu Lys Ala Gly Gln Ser Ile Ala Gln Val Ser Asp Ala Gly
                 85                  90                  95

Leu Pro Ser Ile Ser Asp Pro Gly His Asp Leu Val Lys Ala Ala Ile
            100                 105                 110

Glu Glu Glu Ile Ala Val Val Thr Val Pro Gly Thr Ser Ala Gly Ile
        115                 120                 125

Ser Ala Leu Ile Ala Ser Gly Leu Ala Pro Gln Pro His Ile Phe Tyr
    130                 135                 140

Gly Phe Leu Pro Arg Lys Ser Gly Gln Gln Lys Gln Phe Phe Gly Ser
145                 150                 155                 160

Lys Lys Asp Tyr Pro Glu Thr Gln Ile Phe Tyr Glu Ser Pro His Arg
                165                 170                 175

Val Ala Asp Thr Leu Glu Asn Met Leu Glu Val Tyr Gly Asp Arg Ser
            180                 185                 190

Val Val Leu Val Arg Glu Leu Thr Lys Ile Tyr Glu Glu Tyr Gln Arg
        195                 200                 205

Gly Thr Ile Ser Glu Leu Leu Glu Ser Ile Ser Glu Thr Ser Leu Lys
```

-continued

```
    210                 215                 220

Gly Glu Cys Leu Leu Ile Val Glu Gly Ala Ser Lys Gly Val Glu Glu
225                 230                 235                 240

Lys Asp Glu Glu Asp Leu Phe Leu Glu Ile Gln Ala Arg Ile Gln Gln
                245                 250                 255

Gly Met Lys Lys Asn Gln Ala Ile Lys Glu Ile Ala Lys Ile Tyr Gln
            260                 265                 270

Trp Asn Lys Ser Gln Leu Tyr Ala Ala Tyr His Asp Trp Glu Glu Lys
        275                 280                 285

Gln


<210> SEQ ID NO 20
<211> LENGTH: 1000
<212> TYPE: DNA
<213> ORGANISM: Streptococcus pneumoniae
<220> FEATURE:
<221> NAME/KEY: CDS
<222> LOCATION: (111)...(977)

<400> SEQUENCE: 20

cgtcgcattt accgtgatgg atttcacgta tgtaatgatt tttatggaca acgtcgagag     60

caggacgagg aatgtatgtt ttgtgacgag ttgctataca gggagtaggc atg cag       116
                                                       Met Gln
                                                         1

att caa aaa agt ttt aag ggg cag tct ccc tat ggc aag ctg tat cta      164
Ile Gln Lys Ser Phe Lys Gly Gln Ser Pro Tyr Gly Lys Leu Tyr Leu
          5                  10                  15

gtg gca acg ccg att ggc aat cta gat gat atg act ttt cgt gct atc      212
Val Ala Thr Pro Ile Gly Asn Leu Asp Asp Met Thr Phe Arg Ala Ile
     20                  25                  30

cag acc ttg aaa gaa gtg gac tgg att gct gct gag gat acg cgc aat      260
Gln Thr Leu Lys Glu Val Asp Trp Ile Ala Ala Glu Asp Thr Arg Asn
 35                  40                  45                  50

aca ggg ctt ttg ctc aag cat ttt gac att tcc acc aag cag atc agt      308
Thr Gly Leu Leu Leu Lys His Phe Asp Ile Ser Thr Lys Gln Ile Ser
                 55                  60                  65

ttt cat gag cac aat gca aag gaa aaa att cct gat ttg att ggt ttc      356
Phe His Glu His Asn Ala Lys Glu Lys Ile Pro Asp Leu Ile Gly Phe
             70                  75                  80

ttg aaa gca ggg caa agt att gct cag gtc tct gat gcc ggt ttg cct      404
Leu Lys Ala Gly Gln Ser Ile Ala Gln Val Ser Asp Ala Gly Leu Pro
         85                  90                  95

agc att tca gac cct ggt cat gat tta gtt aag gca gct att gag gaa      452
Ser Ile Ser Asp Pro Gly His Asp Leu Val Lys Ala Ala Ile Glu Glu
    100                 105                 110

gaa att gca gtt gtg act gtt cca ggt acc tct gca gga att tct gcc      500
Glu Ile Ala Val Val Thr Val Pro Gly Thr Ser Ala Gly Ile Ser Ala
115                 120                 125                 130

ttg att gcc agt ggt tta gcg cca cag cca cat atc ttt tac ggt ttt      548
Leu Ile Ala Ser Gly Leu Ala Pro Gln Pro His Ile Phe Tyr Gly Phe
                135                 140                 145

tta ccg aga aaa tca ggt caa cag aag caa ttt ttt ggc tct aaa aaa      596
Leu Pro Arg Lys Ser Gly Gln Gln Lys Gln Phe Phe Gly Ser Lys Lys
            150                 155                 160

gat tat cct gaa aca cag att ttt tat gaa tca cct cat cgt gta gca      644
Asp Tyr Pro Glu Thr Gln Ile Phe Tyr Glu Ser Pro His Arg Val Ala
        165                 170                 175

gac acg ttg gaa aat atg tta gaa gtc tac ggt gac cgc tcg gtt gtt      692
Asp Thr Leu Glu Asn Met Leu Glu Val Tyr Gly Asp Arg Ser Val Val
```

-continued

```
    180                 185                 190

ttg gtc agg gaa ttg acc aaa atc tat gaa gaa tac caa aga ggt aca      740
Leu Val Arg Glu Leu Thr Lys Ile Tyr Glu Glu Tyr Gln Arg Gly Thr
195                 200                 205                 210

att tct gaa ttg ctg gaa agc atc tct gaa acg tct ctc aag ggt gaa      788
Ile Ser Glu Leu Leu Glu Ser Ile Ser Glu Thr Ser Leu Lys Gly Glu
                215                 220                 225

tgt ctt ctg att gtt gaa ggt gcc agc aaa ggt gtg gag gaa aag gat      836
Cys Leu Leu Ile Val Glu Gly Ala Ser Lys Gly Val Glu Glu Lys Asp
            230                 235                 240

gag gaa gac ttg ttc tta gaa atc caa gcc cgt atc cag caa ggc atg      884
Glu Glu Asp Leu Phe Leu Glu Ile Gln Ala Arg Ile Gln Gln Gly Met
        245                 250                 255

aag aaa aat caa gct att aag gaa ata gct aag att tac cag tgg aat      932
Lys Lys Asn Gln Ala Ile Lys Glu Ile Ala Lys Ile Tyr Gln Trp Asn
    260                 265                 270

aag agt caa ctc tac gct gcc tac cac gac tgg gaa gaa aaa caa          977
Lys Ser Gln Leu Tyr Ala Ala Tyr His Asp Trp Glu Glu Lys Gln
275                 280                 285

taaagggaga caggatgtaa taa                                           1000


<210> SEQ ID NO 21
<211> LENGTH: 1000
<212> TYPE: DNA
<213> ORGANISM: Streptococcus pneumoniae

<400> SEQUENCE: 21

gcagcgtaaa tggcactacc taaagtgcat acattactaa aaatacctgt tgcagctctc     60

gtcctgctcc ttacatacaa aacactgctc aacgatatgt ccctcatccg tacgtctaag    120

ttttttcaaa attccccgtc agagggatac cgttcgacat agatcaccgt tgcggctaac    180

cgttagatct actatactga aaagcacgat aggtctggaa ctttcttcac ctgacctaac    240

gacgactcct atgcgcgtta tgtcccgaaa acgagttcgt aaaactgtaa aggtggttcg    300

tctagtcaaa agtactcgtg ttacgtttcc ttttttaagg actaaactaa ccaaagaact    360

ttcgtcccgt ttcataacga gtccagagac tacggccaaa cggatcgtaa agtctgggac    420

cagtactaaa tcaattccgt cgataactcc ttctttaacg tcaacactga caaggtccat    480

ggagacgtcc ttaaagacgg aactaacggt caccaaatcg cggtgtcggt gtatagaaaa    540

tgccaaaaaa tggctctttt agtccagttg tcttcgttaa aaaaccgaga ttttttctaa    600

taggactttg tgtctaaaaa atacttagtg gagtagcaca tcgtctgtgc aaccttttat    660

acaatcttca gatgccactg gcgagccaac aaaaccagtc ccttaactgg ttttagatac    720

ttcttatggt ttctccatgt taaagactta acgacctttc gtagagactt tgcagagagt    780

tcccacttac agaagactaa caacttccac ggtcgtttcc acacctcctt ttcctactcc    840

ttctgaacaa gaatctttag gttcgggcat aggtcgttcc gtacttcttt ttagttcgat    900

aattccttta tcgattctaa atggtcacct tattctcagt tgagatgcga cggatggtgc    960

tgacccttct ttttgttatt tccctctgtc ctacattatt                         1000


<210> SEQ ID NO 22
<211> LENGTH: 554
<212> TYPE: PRT
<213> ORGANISM: Streptococcus pneumoniae

<400> SEQUENCE: 22

Met Asp Lys Lys Tyr Glu Lys Ile Ser Gln Asp Leu Gly Val Thr Leu
```

-continued

```
1               5                   10                  15

Lys Gln Ile Asp Thr Val Leu Ser Leu Thr Ala Glu Gly Ala Thr Ile
            20                  25                  30

Pro Phe Ile Ala Arg Tyr Arg Lys Asp Met Thr Gly Ser Leu Asp Glu
        35                  40                  45

Val Ala Ile Lys Ala Ile Ile Asp Leu Asp Lys Ser Leu Thr Asn Leu
    50                  55                  60

Asn Asp Arg Lys Glu Ala Val Leu Ala Lys Ile Gln Glu Gln Gly Lys
65                  70                  75                  80

Leu Thr Lys Glu Leu Glu Glu Ala Ile Leu Val Ala Glu Lys Leu Ala
                85                  90                  95

Asp Val Glu Glu Leu Tyr Leu Pro Tyr Lys Glu Lys Arg Arg Thr Lys
            100                 105                 110

Ala Thr Ile Ala Arg Glu Ala Gly Leu Phe Pro Leu Ala Arg Leu Ile
        115                 120                 125

Leu Gln Asn Ile Val Asp Leu Glu Lys Glu Ala Glu Lys Phe Val Cys
    130                 135                 140

Glu Gly Phe Ala Thr Gly Lys Glu Ala Leu Thr Gly Ala Val Asp Ile
145                 150                 155                 160

Leu Val Glu Ala Leu Ser Glu Asp Val Thr Leu Arg Ser Met Thr Tyr
                165                 170                 175

Gln Glu Val Leu Arg His Ser Lys Leu Thr Ser Gln Ala Lys Asp Glu
            180                 185                 190

Ser Leu Asp Glu Lys Gln Val Phe Gln Ile Tyr Tyr Asp Phe Ser Glu
        195                 200                 205

Thr Val Gly Thr Met Gln Gly Tyr Arg Thr Leu Ala Leu Asn Arg Gly
    210                 215                 220

Glu Lys Leu Gly Val Leu Lys Ile Gly Phe Glu His Ala Thr Asp Arg
225                 230                 235                 240

Ile Leu Ala Phe Phe Ala Thr Arg Phe Lys Val Lys Asn Ala Tyr Ile
                245                 250                 255

Asp Glu Val Val Gln Gln Ser Val Lys Lys Lys Val Leu Pro Ala Ile
            260                 265                 270

Glu Arg Arg Ile Arg Thr Glu Leu Thr Glu Lys Ala Glu Glu Gly Ala
        275                 280                 285

Ile Gln Leu Phe Ser Asp Asn Leu Arg Asn Leu Leu Leu Val Ala Pro
    290                 295                 300

Leu Lys Gly Arg Val Val Leu Gly Phe Asp Pro Ala Phe Arg Thr Gly
305                 310                 315                 320

Ala Lys Leu Ala Val Val Asp Ala Thr Gly Lys Met Leu Thr Thr Gln
                325                 330                 335

Val Ile Tyr Pro Val Lys Pro Ala Ser Ala Arg Gln Ile Glu Glu Ala
            340                 345                 350

Lys Lys Asp Leu Ala Asp Leu Ile Gly Gln Tyr Gly Val Glu Ile Ile
        355                 360                 365

Ala Ile Gly Asn Gly Thr Ala Ser Arg Glu Ser Glu Ala Phe Val Ala
    370                 375                 380

Glu Val Leu Lys Asp Phe Pro Glu Val Ser Tyr Val Ile Val Asn Glu
385                 390                 395                 400

Ser Gly Ala Ser Val Tyr Ser Ala Ser Glu Leu Ala Arg Gln Glu Phe
                405                 410                 415

Pro Asp Leu Thr Val Glu Lys Arg Ser Ala Ile Ser Ile Ala Arg Arg
            420                 425                 430
```

-continued

```
Leu Gln Asp Pro Leu Ala Glu Leu Val Lys Ile Asp Pro Lys Ser Ile
        435                 440                 445

Gly Val Gly Gln Tyr Gln His Asp Val Ser Gln Lys Lys Leu Ser Glu
    450                 455                 460

Ser Leu Asp Phe Val Val Asp Thr Val Val Asn Gln Val Gly Val Asn
465                 470                 475                 480

Val Asn Thr Ala Ser Pro Ala Leu Leu Ser His Val Ala Gly Leu Asn
                485                 490                 495

Lys Thr Ile Ser Glu Asn Ile Val Lys Tyr Arg Glu Glu Glu Gly Lys
            500                 505                 510

Ile Thr Ser Arg Ala Gln Ile Lys Lys Val Pro Arg Leu Gly Ala Lys
        515                 520                 525

Ala Phe Glu Gln Ala Ala Gly Phe Leu Arg Ile Pro Glu Ser Ser Asn
    530                 535                 540

Ile Leu Asp Asn Thr Gly Val His Pro Glu
545                 550


<210> SEQ ID NO 23
<211> LENGTH: 1799
<212> TYPE: DNA
<213> ORGANISM: Streptococcus pneumoniae
<220> FEATURE:
<221> NAME/KEY: CDS
<222> LOCATION: (138)...(1799)

<400> SEQUENCE: 23

atggcttggt taaaaaaagg tggcaatgct ctttaagtgc aagttattgc gctgtagcat      60

ataaatctat ttcctacata ttttttaaac gttctacgag ttaatttgaa acgtttagct     120

tgtggtataa tagattt atg gat aaa aaa tat gaa aaa atc tct cag gat        170
                   Met Asp Lys Lys Tyr Glu Lys Ile Ser Gln Asp
                     1               5                  10

ttg gga gtg acg tta aag caa att gat acc gtt cta agt ttg aca gct       218
Leu Gly Val Thr Leu Lys Gln Ile Asp Thr Val Leu Ser Leu Thr Ala
            15                  20                  25

gaa ggg gcg act att ccc ttt atc gcg cgt tat cgc aag gac atg act       266
Glu Gly Ala Thr Ile Pro Phe Ile Ala Arg Tyr Arg Lys Asp Met Thr
        30                  35                  40

ggt agt ctg gat gag gtg gcg att aag gct att att gat ttg gat aaa       314
Gly Ser Leu Asp Glu Val Ala Ile Lys Ala Ile Ile Asp Leu Asp Lys
     45                  50                  55

agt ctg aca aat ctc aat gac cgt aag gaa gct gtc tta gct aag att       362
Ser Leu Thr Asn Leu Asn Asp Arg Lys Glu Ala Val Leu Ala Lys Ile
 60                  65                  70                  75

caa gaa caa ggt aag ttg acc aag gaa ttg gaa gaa gct atc tta gtt       410
Gln Glu Gln Gly Lys Leu Thr Lys Glu Leu Glu Glu Ala Ile Leu Val
                80                  85                  90

gcc gaa aaa tta gca gac gtt gaa gaa ctc tat ctt cct tat aag gaa       458
Ala Glu Lys Leu Ala Asp Val Glu Glu Leu Tyr Leu Pro Tyr Lys Glu
            95                 100                 105

aag cgt cgt acc aag gca acc att gcc cgt gaa gct gga ctc ttt cct       506
Lys Arg Arg Thr Lys Ala Thr Ile Ala Arg Glu Ala Gly Leu Phe Pro
        110                 115                 120

ctt gct cgt ttg att ttg cag aat ata gtt gac tta gag aaa gaa gct       554
Leu Ala Arg Leu Ile Leu Gln Asn Ile Val Asp Leu Glu Lys Glu Ala
    125                 130                 135

gaa aag ttc gtc tgt gaa gga ttt gcg act ggc aag gaa gcc ttg acc       602
Glu Lys Phe Val Cys Glu Gly Phe Ala Thr Gly Lys Glu Ala Leu Thr
140                 145                 150                 155
```

-continued

```
ggt gca gtt gat att ttg gtc gaa gcc tta tcg gaa gat gtg acc ttg      650
Gly Ala Val Asp Ile Leu Val Glu Ala Leu Ser Glu Asp Val Thr Leu
                160                 165                 170

cgt tct atg act tat cag gaa gtg ctg aga cac tct aaa ctc act tct      698
Arg Ser Met Thr Tyr Gln Glu Val Leu Arg His Ser Lys Leu Thr Ser
            175                 180                 185

caa gcc aag gat gaa agt ctt gat gaa aag cag gtt ttt cag att tat      746
Gln Ala Lys Asp Glu Ser Leu Asp Glu Lys Gln Val Phe Gln Ile Tyr
        190                 195                 200

tat gat ttt tca gag aca gtt gga act atg caa ggc tat cgt acc ttg      794
Tyr Asp Phe Ser Glu Thr Val Gly Thr Met Gln Gly Tyr Arg Thr Leu
    205                 210                 215

gct ctc aat cgt ggg gag aaa ctt ggt gtc ttg aag atc ggt ttt gaa      842
Ala Leu Asn Arg Gly Glu Lys Leu Gly Val Leu Lys Ile Gly Phe Glu
220                 225                 230                 235

cat gcg acg gac cgt att ctt gcc ttc ttt gct act cgt ttc aag gtg      890
His Ala Thr Asp Arg Ile Leu Ala Phe Phe Ala Thr Arg Phe Lys Val
                240                 245                 250

aaa aat gct tat att gat gaa gtt gtt cag caa tcc gtt aag aaa aag      938
Lys Asn Ala Tyr Ile Asp Glu Val Val Gln Gln Ser Val Lys Lys Lys
            255                 260                 265

gtc ttg cct gct att gag cgt cgt att cgg aca gaa tta act gag aaa      986
Val Leu Pro Ala Ile Glu Arg Arg Ile Arg Thr Glu Leu Thr Glu Lys
        270                 275                 280

gct gaa gag gga gct atc caa ctt ttt tct gac aat ctg cgc aat ctc     1034
Ala Glu Glu Gly Ala Ile Gln Leu Phe Ser Asp Asn Leu Arg Asn Leu
    285                 290                 295

ctc ttg gtt gct cca ctg aaa ggg cgc gtg gtt ctt gga ttt gac cca     1082
Leu Leu Val Ala Pro Leu Lys Gly Arg Val Val Leu Gly Phe Asp Pro
300                 305                 310                 315

gcc ttt cgt aca ggt gcc aag tta gct gtc gtg gat gca aca gga aaa     1130
Ala Phe Arg Thr Gly Ala Lys Leu Ala Val Val Asp Ala Thr Gly Lys
                320                 325                 330

atg ctg aca act cag gtt att tat cct gtt aaa cca gca tca gct cgt     1178
Met Leu Thr Thr Gln Val Ile Tyr Pro Val Lys Pro Ala Ser Ala Arg
            335                 340                 345

caa atc gaa gaa gcc aag aaa gat tta gca gat tta att ggt caa tac     1226
Gln Ile Glu Glu Ala Lys Lys Asp Leu Ala Asp Leu Ile Gly Gln Tyr
        350                 355                 360

ggt gta gag att att gcc att gga aat gga acg gcc agt cgt gaa agt     1274
Gly Val Glu Ile Ile Ala Ile Gly Asn Gly Thr Ala Ser Arg Glu Ser
    365                 370                 375

gaa gct ttt gta gcg gaa gtt ctg aaa gat ttc cct gaa gtc agc tat     1322
Glu Ala Phe Val Ala Glu Val Leu Lys Asp Phe Pro Glu Val Ser Tyr
380                 385                 390                 395

gtt atc gtt aat gaa agt ggt gct tct gtc tat tct gcc agc gaa ctt     1370
Val Ile Val Asn Glu Ser Gly Ala Ser Val Tyr Ser Ala Ser Glu Leu
                400                 405                 410

gct cgt cag gag ttt cca gac ttg acc gtt gaa aaa cgc tct gcc att     1418
Ala Arg Gln Glu Phe Pro Asp Leu Thr Val Glu Lys Arg Ser Ala Ile
            415                 420                 425

tct atc gcc cgt cgt ttg caa gat cct ctt gcg gaa ttg gtc aaa atc     1466
Ser Ile Ala Arg Arg Leu Gln Asp Pro Leu Ala Glu Leu Val Lys Ile
        430                 435                 440

gat cct aag tca att ggt gtc ggt caa tac caa cac gat gtc agt cag     1514
Asp Pro Lys Ser Ile Gly Val Gly Gln Tyr Gln His Asp Val Ser Gln
    445                 450                 455

aag aaa cta tct gag agt ctg gac ttt gtt gtc gat aca gtg gtt aac     1562
Lys Lys Leu Ser Glu Ser Leu Asp Phe Val Val Asp Thr Val Val Asn
```

-continued

```
460                 465                 470                 475

caa gtt ggt gtc aat gtc aat aca gct agc cca gct ctt ctt tca cac     1610
Gln Val Gly Val Asn Val Asn Thr Ala Ser Pro Ala Leu Leu Ser His
              480                 485                 490

gta gct gga ctc aac aaa act atc tct gaa aat att gtc aaa tac cgc     1658
Val Ala Gly Leu Asn Lys Thr Ile Ser Glu Asn Ile Val Lys Tyr Arg
            495                 500                 505

gag gaa gaa gga aaa atc act tca cgc gcc caa atc aag aaa gtt cct     1706
Glu Glu Glu Gly Lys Ile Thr Ser Arg Ala Gln Ile Lys Lys Val Pro
        510                 515                 520

cgt ctg gga gcc aag gcc ttt gag cag gct gct ggt ttc ctt cgt atc     1754
Arg Leu Gly Ala Lys Ala Phe Glu Gln Ala Ala Gly Phe Leu Arg Ile
    525                 530                 535

cct gaa agt agc aat atc ctt gat aat aca gga gtt cac cca gag         1799
Pro Glu Ser Ser Asn Ile Leu Asp Asn Thr Gly Val His Pro Glu
540                 545                 550
```

<210> SEQ ID NO 24
<211> LENGTH: 1799
<212> TYPE: DNA
<213> ORGANISM: Streptococcus pneumoniae

<400> SEQUENCE: 24

```
taccgaacca atttttttcc accgttacga gaaattcacg ttcaataacg cgacatcgta     60

tatttagata aaggatgtat aaaaaatttg caagatgctc aattaaactt tgcaaatcga    120

acaccatatt atctaaatac ctatttttta tactttttta gagagtccta aaccctcact    180

gcaatttcgt ttaactatgg caagattcaa actgtcgact tccccgctga taagggaaat    240

agcgcgcaat agcgttcctg tactgaccat cagacctact ccaccgctaa ttccgataat    300

aactaaacct attttcagac tgtttagagt tactggcatt ccttcgacag aatcgattct    360

aagttcttgt tccattcaac tggttcctta accttcttcg atagaatcaa cggcttttta    420

atcgtctgca acttcttgag atagaaggaa tattcctttt cgcagcatgg ttccgttggt    480

aacgggcact tcgacctgag aaaggagaac gagcaaacta aaacgtctta tatcaactga    540

atctctttct tcgacttttc aagcagacac ttcctaaacg ctgaccgttc cttcggaact    600

ggccacgtca actataaaac cagcttcgga atagccttct acactggaac gcaagatact    660

gaatagtcct tcacgactct gtgagatttg agtgaagagt tcggttccta ctttcagaac    720

tacttttcgt ccaaaaagtc taaataatac taaaaagtct ctgtcaacct tgatacgttc    780

cgatagcatg gaaccgagag ttagcacccc tctttgaacc acagaacttc tagccaaaac    840

ttgtacgctg cctggcataa gaacggaaga aacgatgagc aaagttccac tttttacgaa    900

tataactact tcaacaagtc gttaggcaat tctttttcca gaacggacga taactcgcag    960

cataagcctg tcttaattga ctctttcgac ttctccctcg ataggttgaa aaaagactgt   1020

tagacgcgtt agaggagaac caacgaggtg actttcccgc gcaccaagaa cctaaactgg   1080

gtcggaaagc atgtccacgg ttcaatcgac agcacctacg ttgtcctttt tacgactgtt   1140

gagtccaata aataggacaa tttggtcgta gtcgagcagt ttagcttctt cggttctttc   1200

taaatcgtct aaattaacca gttatgccac atctctaata acggtaacct ttaccttgcc   1260

ggtcagcact ttcacttcga aaacatcgcc ttcaagactt tctaaaggga cttcagtcga   1320

tacaatagca attactttca ccacgaagac agataagacg gtcgcttgaa cgagcagtcc   1380

tcaaaggtct gaactggcaa ctttttgcga gacggtaaag atagcgggca gcaaacgttc   1440

taggagaacg ccttaaccag ttttagctag gattcagtta accacagcca gttatggttg   1500
```

-continued

```
tgctacagtc agtcttcttt gatagactct cagacctgaa acaacagcta tgtcaccaat   1560

tggttcaacc acagttacag ttatgtcgat cgggtcgaga agaaagtgtg catcgacctg   1620

agttgttttg atagagactt ttataacagt ttatggcgct ccttcttcct ttttagtgaa   1680

gtgcgcgggt ttagttcttt caaggagcag accctcggtt ccggaaactc gtccgacgac   1740

caaaggaagc atagggactt tcatcgttat aggaactatt atgtcctcaa gtgggtctc    1799
```

<210> SEQ ID NO 25
<211> LENGTH: 174
<212> TYPE: PRT
<213> ORGANISM: Streptococcus pneumoniae
<220> FEATURE:
<221> NAME/KEY: VARIANT
<222> LOCATION: (1)...(174)
<223> OTHER INFORMATION: Xaa = Any Amino Acid

<400> SEQUENCE: 25

```
Thr Gly Ala Arg Val Ser Tyr Pro Val Leu Asn Val Lys Val Phe Leu
  1               5                  10                  15

Glu Asn Gly Glu Val Lys Ile Phe Arg Ala Leu Asn Glu Ala Xaa Ile
             20                  25                  30

Arg Arg Ser Asp Arg Thr Met Val Ala Asp Ile Val Ile Asn Gly Val
         35                  40                  45

Pro Phe Glu Arg Phe Arg Gly Asp Gly Leu Thr Val Ser Thr Pro Thr
     50                  55                  60

Gly Ser Thr Ala Tyr Asn Lys Ser Leu Gly Gly Ala Val Leu His Pro
 65                  70                  75                  80

Thr Ile Glu Ala Leu Gln Leu Thr Glu Ile Ala Ser Leu Asn Asn Arg
                 85                  90                  95

Val Tyr Arg Thr Leu Gly Ser Ser Ile Ile Val Pro Lys Lys Asp Lys
            100                 105                 110

Ile Glu Leu Ile Pro Thr Arg Asn Asp Tyr His Thr Ile Ser Val Asp
        115                 120                 125

Asn Ser Val Tyr Ser Phe Arg Asn Ile Glu Arg Ile Glu Tyr Gln Ile
    130                 135                 140

Asp His His Lys Ile His Phe Val Ala Thr Pro Ser His Thr Ser Phe
145                 150                 155                 160

Trp Asn Arg Val Lys Asp Ala Phe Ile Gly Glu Val Asp Glu
                165                 170
```

<210> SEQ ID NO 26
<211> LENGTH: 578
<212> TYPE: DNA
<213> ORGANISM: Streptococcus pneumoniae
<220> FEATURE:
<221> NAME/KEY: CDS
<222> LOCATION: (2)...(523)
<221> NAME/KEY: misc_feature
<222> LOCATION: (1)...(578)
<223> OTHER INFORMATION: n = A,T,C or G

<400> SEQUENCE: 26

```
t act ggg gca agg gtt tct tac cct gtt ctg aat gtg aag gtc ttt ctt      49
  Thr Gly Ala Arg Val Ser Tyr Pro Val Leu Asn Val Lys Val Phe Leu
    1               5                  10                  15

gaa aat ggt gaa gtt aag att ttc aga gca ctc aac gaa gcc agn atc        97
Glu Asn Gly Glu Val Lys Ile Phe Arg Ala Leu Asn Glu Ala Xaa Ile
             20                  25                  30

cgc agg tct gat cga acc atg gtg gca gat att gta ata aat ggt gtt       145
```

-continued

Arg Arg Ser Asp Arg Thr Met Val Ala Asp Ile Val Ile Asn Gly Val
35 40 45 ccc ttt gaa cgt ttt cgt gga gac ggg cta aca gtt tcg aca ccg act 193
Pro Phe Glu Arg Phe Arg Gly Asp Gly Leu Thr Val Ser Thr Pro Thr
50 55 60 ggt agt act gcc tat aac aag tct ctt ggc ggt gct gtt tta cac cct 241
Gly Ser Thr Ala Tyr Asn Lys Ser Leu Gly Gly Ala Val Leu His Pro
65 70 75 80 acc att gaa gct ttg caa tta acg gag att gcc agc ctt aat aat cgt 289
Thr Ile Glu Ala Leu Gln Leu Thr Glu Ile Ala Ser Leu Asn Asn Arg
85 90 95 gtc tat cga aca ttg ggc tct tcc att att gtg cct aag aag gat aag 337
Val Tyr Arg Thr Leu Gly Ser Ser Ile Ile Val Pro Lys Lys Asp Lys
100 105 110 att gaa ctt att cca aca aga aac gat tat cat act att tcg gtt gac 385
Ile Glu Leu Ile Pro Thr Arg Asn Asp Tyr His Thr Ile Ser Val Asp
115 120 125 aat agc gtt tat tct ttc cgt aat att gag cgt att gag tat caa atc 433
Asn Ser Val Tyr Ser Phe Arg Asn Ile Glu Arg Ile Glu Tyr Gln Ile
130 135 140 gac cat cat aag att cac ttt gtc gcg act cct agc cat acc agt ttc 481
Asp His His Lys Ile His Phe Val Ala Thr Pro Ser His Thr Ser Phe
145 150 155 160 tgg aac cgt gtt aag gat gcc ttt atc ggt gag gtg gat gaa 523
Trp Asn Arg Val Lys Asp Ala Phe Ile Gly Glu Val Asp Glu
165 170 tgaggtttga atttatcgca gatgaacatg tcaaggttaa gaccttttta aaaaa 578

<210> SEQ ID NO 27
<211> LENGTH: 578
<212> TYPE: DNA
<213> ORGANISM: Streptococcus pneumoniae
<220> FEATURE:
<221> NAME/KEY: misc_feature
<222> LOCATION: (1)...(578)
<223> OTHER INFORMATION: n = A,T,C or G

<400> SEQUENCE: 27
atgaccccgt tcccaaagaa tgggacaaga cttacacttc cagaaagaac ttttaccact 60
tcaattctaa aagtctcgtg agttgcttcg gtcntaggcg tccagactag cttggtacca 120
ccgtctataa cattatttac cacaagggaa acttgcaaaa gcacctctgc ccgattgtca 180
aagctgtggc tgaccatcat gacggatatt gttcagagaa ccgccacgac aaaatgtggg 240
atggtaactt cgaaacgtta attgcctcta acggtcggaa ttattagcac agatagcttg 300
taacccgaga aggtaataac acggattctt cctattctaa cttgaataag gttgttcttt 360
gctaatagta tgataaagcc aactgttatc gcaaataaga aaggcattat aactcgcata 420
actcatagtt tagctggtag tattctaagt gaaacagcgc tgaggatcgg tatggtcaaa 480
gaccttggca caattcctac ggaaatagcc actccaccta cttactccaa acttaaatag 540
cgtctacttg tacagttcca attctggaaa aatttttt 578

<210> SEQ ID NO 28
<211> LENGTH: 224
<212> TYPE: PRT
<213> ORGANISM: Streptococcus pneumoniae

<400> SEQUENCE: 28

Met Val Val Gly Trp Gln Tyr Ile Pro Ala Pro His Lys Gly Val Thr
1 5 10 15

-continued

```
Ile Gly Pro Ser Pro Arg Ile Glu Ile Ala Leu Arg Pro Asp Trp Phe
            20                  25                  30

Tyr Phe Gly Gln Asp Gly Val Leu Gln Glu Phe Val Gly Lys Gln Val
        35                  40                  45

Leu Glu Ala Lys Thr Ala Thr Asn Thr Asn Lys His His Gly Glu Glu
    50                  55                  60

Tyr Asp Ser Gln Ala Glu Lys Arg Val Tyr Tyr Phe Glu Asp Gln Arg
 65                 70                  75                  80

Ser Tyr His Thr Leu Lys Thr Gly Trp Ile Tyr Glu Glu Gly Tyr Trp
                85                  90                  95

Tyr Tyr Leu Gln Lys Asp Gly Gly Phe Asp Ser Arg Ile Asn Arg Leu
            100                 105                 110

Thr Val Gly Glu Leu Ala Arg Gly Trp Val Lys Asp Tyr Pro Leu Thr
        115                 120                 125

Tyr Asp Glu Glu Lys Leu Lys Ala Ala Pro Trp Tyr Tyr Leu Asp Pro
    130                 135                 140

Ala Thr Gly Trp Gln Asn Leu Gly Asn Lys Trp Tyr Tyr Leu Arg Ser
145                 150                 155                 160

Ser Gly Ala Met Val Thr Gly Trp Tyr Gln Asp Gly Leu Thr Trp Tyr
                165                 170                 175

Tyr Leu Asn Ala Gly Asn Gly Asp Met Lys Thr Gly Trp Phe Gln Val
            180                 185                 190

Asn Gly Asn Trp Tyr Tyr Ala Tyr Asp Ser Gly Ala Leu Ala Val Asn
        195                 200                 205

Thr Thr Val Gly Gly Tyr Tyr Leu Asn Tyr Asn Gly Glu Trp Val Lys
    210                 215                 220


<210> SEQ ID NO 29
<211> LENGTH: 800
<212> TYPE: DNA
<213> ORGANISM: Streptococcus pneumoniae
<220> FEATURE:
<221> NAME/KEY: CDS
<222> LOCATION: (71)...(742)

<400> SEQUENCE: 29

ggctctaaaa gaaacctact ggagagtgat agatgggaag tactattatt ttgatccttt      60

atccggagag atg gtt gtc ggc tgg caa tat ata cct gct cca cac aag        109
           Met Val Val Gly Trp Gln Tyr Ile Pro Ala Pro His Lys
             1               5                  10

ggg gtt acg att ggt cct tct cca aga ata gag att gct ctt aga cca       157
Gly Val Thr Ile Gly Pro Ser Pro Arg Ile Glu Ile Ala Leu Arg Pro
     15                  20                  25

gat tgg ttt tat ttt ggt caa gat ggt gtc tta caa gaa ttt gtt ggc       205
Asp Trp Phe Tyr Phe Gly Gln Asp Gly Val Leu Gln Glu Phe Val Gly
 30                  35                  40                  45

aag caa gtt tta gaa gca aaa act gct acg aat acc aac aaa cat cat       253
Lys Gln Val Leu Glu Ala Lys Thr Ala Thr Asn Thr Asn Lys His His
                50                  55                  60

ggg gaa gaa tat gat agc caa gca gag aaa cga gtc tat tat ttt gaa       301
Gly Glu Glu Tyr Asp Ser Gln Ala Glu Lys Arg Val Tyr Tyr Phe Glu
            65                  70                  75

gat cag cgt agt tat cat act tta aaa act ggt tgg att tat gaa gag       349
Asp Gln Arg Ser Tyr His Thr Leu Lys Thr Gly Trp Ile Tyr Glu Glu
        80                  85                  90

ggt tat tgg tat tat tta cag aag gat ggt ggc ttt gat tct cgc atc       397
Gly Tyr Trp Tyr Tyr Leu Gln Lys Asp Gly Gly Phe Asp Ser Arg Ile
```

-continued

```
     95                  100                 105

aac aga ttg acg gtt gga gag cta gca cgt ggt tgg gtt aag gat tac      445
Asn Arg Leu Thr Val Gly Glu Leu Ala Arg Gly Trp Val Lys Asp Tyr
110                 115                 120                 125

cct ctt acg tat gat gaa gag aag cta aaa gca gct cca tgg tac tat      493
Pro Leu Thr Tyr Asp Glu Glu Lys Leu Lys Ala Ala Pro Trp Tyr Tyr
                130                 135                 140

cta gat cca gca act ggc tgg caa aac ctt ggg aac aaa tgg tac tac      541
Leu Asp Pro Ala Thr Gly Trp Gln Asn Leu Gly Asn Lys Trp Tyr Tyr
            145                 150                 155

ctc cgt tca tca gga gct atg gta act ggc tgg tat caa gat ggt tta      589
Leu Arg Ser Ser Gly Ala Met Val Thr Gly Trp Tyr Gln Asp Gly Leu
        160                 165                 170

act tgg tac tac cta aat gca ggt aat gga gac atg aag aca ggt tgg      637
Thr Trp Tyr Tyr Leu Asn Ala Gly Asn Gly Asp Met Lys Thr Gly Trp
    175                 180                 185

ttc caa gtc aat ggt aac tgg tac tat gcc tat gat tca ggt gct tta      685
Phe Gln Val Asn Gly Asn Trp Tyr Tyr Ala Tyr Asp Ser Gly Ala Leu
190                 195                 200                 205

gct gtt aat acc aca gta ggt ggt tac tac tta aac tat aat ggt gaa      733
Ala Val Asn Thr Thr Val Gly Gly Tyr Tyr Leu Asn Tyr Asn Gly Glu
                210                 215                 220

tgg gtt aag taatgaaggc taattgtaaa ctgtgatgga tacttaactt               782
Trp Val Lys

tgtataatag gtggataa                                                    800


<210> SEQ ID NO 30
<211> LENGTH: 800
<212> TYPE: DNA
<213> ORGANISM: Streptococcus pneumoniae

<400> SEQUENCE: 30

ccgagatttt ctttggatga cctctcacta tctacccttc atgataataa aactaggaaa      60

taggcctctc taccaacagc cgaccgttat atatggacga ggtgtgttcc cccaatgcta     120

accaggaaga ggttcttatc tctaacgaga atctggtcta accaaaataa aaccagttct     180

accacagaat gttcttaaac aaccgttcgt tcaaaatctt cgtttttgac gatgcttatg     240

gttgtttgta gtaccccttc ttatactatc ggttcgtctc tttgctcaga taataaaact     300

tctagtcgca tcaatagtat gaaatttttg accaacctaa atacttctcc caataaccat     360

aataaatgtc ttcctaccac cgaaactaag agcgtagttg tctaactgcc aacctctcga     420

tcgtgcacca acccaattcc taatgggaga atgcatacta cttctcttcg attttcgtcg     480

aggtaccatg atagatctag gtcgttgacc gaccgttttg gaacccttgt ttaccatgat     540

ggaggcaagt agtcctcgat accattgacc gaccatagtt ctaccaaatt gaaccatgat     600

ggatttacgt ccattacctc tgtacttctg tccaaccaag gttcagttac cattgaccat     660

gatacggata ctaagtccac gaaatcgaca attatggtgt catccaccaa tgatgaattt     720

gatattacca cttacccaat tcattacttc cgattaacat ttgacactac ctatgaattg     780

aaacatatta tccacctatt                                                  800


<210> SEQ ID NO 31
<211> LENGTH: 324
<212> TYPE: PRT
<213> ORGANISM: Streptococcus pneumoniae

<400> SEQUENCE: 31
```

-continued

```
Met Asp Ile Tyr Ile Lys Lys Ala Ile Ile His Gln Phe Ser Pro Asp
  1               5                  10                  15

Asp Thr Glu Leu Phe Leu Ala Asp Lys Phe Leu Asn Ile Thr Pro Lys
            20                  25                  30

Ile Glu Glu Tyr Leu Arg Lys Lys Ile Glu His Val Tyr Ser Asp Glu
        35                  40                  45

Ala Lys Thr Gly Ile Phe Glu Glu Glu Asn Pro Phe Phe Asn His Ile
    50                  55                  60

Thr Asp Asp Leu Leu Glu Thr Ser Val Thr Leu Ala Asn Leu Trp Lys
 65                  70                  75                  80

Glu Glu Phe Ser Ile Ser Glu Asn Leu Lys Thr Asn Asp Leu Ile Phe
                85                  90                  95

Val Gln Phe Ser Lys Glu Gly Val Glu His Phe Ala Phe Leu Arg Ile
            100                 105                 110

Ala Leu Arg Glu Thr Leu Thr His Leu Gly Gly Glu Val Asp Asn Pro
        115                 120                 125

Ile Lys Leu Thr Gln Asn Asn Leu Pro Gly Phe Gly Thr Gly Ala Asp
    130                 135                 140

Glu Ala Leu Val Val Asn Leu Gln Ser Arg Lys Tyr His Leu Ile Glu
145                 150                 155                 160

Lys Arg Ile Lys Tyr Asn Gly Thr Phe Leu Asn Tyr Phe Ser Asp Asn
                165                 170                 175

Leu Leu Ala Val Ala Pro Lys Ile Ser Pro Lys Lys Ser Ile Lys Glu
            180                 185                 190

Leu Glu Lys Thr Ala Gln Arg Ile Ala Glu Ser Phe Asn Thr Asp Asp
        195                 200                 205

Phe Gln Phe Gln Ser Lys Val Lys Ser Ala Ile Phe Asn Asn Leu Glu
    210                 215                 220

Glu Ser Asn Glu Leu Ser Pro Glu Lys Leu Ala Asn Asp Leu Phe Asp
225                 230                 235                 240

Asn Asn Leu Thr Ala Arg Leu Ser Phe Ile Asp Gln Val Arg Glu Ala
                245                 250                 255

Val Pro Glu Pro Val Gln Phe Asp Glu Ile Asp Ala Ser Arg Gln Leu
            260                 265                 270

Lys Lys Phe Glu Asn Gln Lys Leu Ser Leu Ser Asn Gly Ile Glu Leu
        275                 280                 285

Ile Val Pro Asn Asn Val Tyr Gln Asp Ala Glu Ser Val Glu Phe Ile
    290                 295                 300

Gln Asn Glu Asn Gly Thr Tyr Ser Ile Leu Ile Lys Asn Ile Glu Asp
305                 310                 315                 320

Ile Gln Ser Lys
```

```
<210> SEQ ID NO 32
<211> LENGTH: 1100
<212> TYPE: DNA
<213> ORGANISM: Streptococcus pneumoniae
<220> FEATURE:
<221> NAME/KEY: CDS
<222> LOCATION: (5)...(976)

<400> SEQUENCE: 32

tttt atg gat att tat att aag aaa gcc att att cac cag ttc agt ccg      49
     Met Asp Ile Tyr Ile Lys Lys Ala Ile Ile His Gln Phe Ser Pro
       1               5                  10                  15

gat gat acc gag ctg ttc tta gca gat aag ttt ctc aat att act cca       97
Asp Asp Thr Glu Leu Phe Leu Ala Asp Lys Phe Leu Asn Ile Thr Pro
```

-continued

```
                20                  25                  30

aaa atc gaa gaa tac cta cgt aaa aaa att gaa cat gtg tat tca gat      145
Lys Ile Glu Glu Tyr Leu Arg Lys Lys Ile Glu His Val Tyr Ser Asp
            35                  40                  45

gaa gcc aag act ggg att ttc gaa gaa gaa aat ccc ttc ttc aat cat      193
Glu Ala Lys Thr Gly Ile Phe Glu Glu Glu Asn Pro Phe Phe Asn His
        50                  55                  60

att aca gac gat ttg ttg gag aca tca gta acg ctg gct aat ctc tgg      241
Ile Thr Asp Asp Leu Leu Glu Thr Ser Val Thr Leu Ala Asn Leu Trp
    65                  70                  75

aaa gag gag ttt agc att tct gaa aat ctc aag acc aat gac ttg att      289
Lys Glu Glu Phe Ser Ile Ser Glu Asn Leu Lys Thr Asn Asp Leu Ile
 80                  85                  90                  95

ttt gtt caa ttt tct aaa gaa ggt gta gaa cat ttc gct ttc ttg cga      337
Phe Val Gln Phe Ser Lys Glu Gly Val Glu His Phe Ala Phe Leu Arg
                100                 105                 110

att gcc ctg cgg gag acc ttg acc cac ctc gga gga gaa gtt gat aat      385
Ile Ala Leu Arg Glu Thr Leu Thr His Leu Gly Gly Glu Val Asp Asn
            115                 120                 125

cca atc aag ctg act cag aat aac ctg cct gga ttt gga acg ggt gct      433
Pro Ile Lys Leu Thr Gln Asn Asn Leu Pro Gly Phe Gly Thr Gly Ala
        130                 135                 140

gac gag gcc ttg gtg gtc aat ctt cag agt cgc aag tat cac ctg att      481
Asp Glu Ala Leu Val Val Asn Leu Gln Ser Arg Lys Tyr His Leu Ile
    145                 150                 155

gaa aaa cga atc aag tac aac ggg act ttt ttg aac tat ttt tca gat      529
Glu Lys Arg Ile Lys Tyr Asn Gly Thr Phe Leu Asn Tyr Phe Ser Asp
160                 165                 170                 175

aat ctt ctt gct gtc gct cct aag att tct cct aaa aaa tct atc aag      577
Asn Leu Leu Ala Val Ala Pro Lys Ile Ser Pro Lys Lys Ser Ile Lys
                180                 185                 190

gaa ctg gaa aaa aca gcc cag aga att gct gaa tct ttt aac aca gat      625
Glu Leu Glu Lys Thr Ala Gln Arg Ile Ala Glu Ser Phe Asn Thr Asp
            195                 200                 205

gat ttt caa ttt caa tcc aag gtc aaa tca gct att ttc aac aac cta      673
Asp Phe Gln Phe Gln Ser Lys Val Lys Ser Ala Ile Phe Asn Asn Leu
        210                 215                 220

gaa gaa agc aat gaa ttg tca cct gag aaa ttg gct aat gac ctt ttt      721
Glu Glu Ser Asn Glu Leu Ser Pro Glu Lys Leu Ala Asn Asp Leu Phe
    225                 230                 235

gac aac aat ctg acg gct cgt ttg agc ttt att gac caa gtc aga gaa      769
Asp Asn Asn Leu Thr Ala Arg Leu Ser Phe Ile Asp Gln Val Arg Glu
240                 245                 250                 255

gcc gta cca gaa cct gtt caa ttt gat gaa att gat gcc agt cgc caa      817
Ala Val Pro Glu Pro Val Gln Phe Asp Glu Ile Asp Ala Ser Arg Gln
                260                 265                 270

tta aag aaa ttt gaa aac caa aaa ctc tcc tta tca aat gga att gag      865
Leu Lys Lys Phe Glu Asn Gln Lys Leu Ser Leu Ser Asn Gly Ile Glu
            275                 280                 285

ctc atc gtt ccc aat aac gtc tat caa gac gcc gag tct gtt gag ttt      913
Leu Ile Val Pro Asn Asn Val Tyr Gln Asp Ala Glu Ser Val Glu Phe
        290                 295                 300

atc caa aac gaa aat gga acc tac tct atc tta atc aaa aat atc gag      961
Ile Gln Asn Glu Asn Gly Thr Tyr Ser Ile Leu Ile Lys Asn Ile Glu
    305                 310                 315

gat atc caa agt aaa taatgtttaa acgaattcga agagtgcttg tactagcagt     1016
Asp Ile Gln Ser Lys
320

cttccttttt gctggctata aagcttaccg cgttcatcaa gatgtcaaac aagtcatgac   1076
```

-continued

```
ctatcaaccc atggtgcgag aaat                                          1100


<210> SEQ ID NO 33
<211> LENGTH: 1100
<212> TYPE: DNA
<213> ORGANISM: Streptococcus pneumoniae

<400> SEQUENCE: 33

aaaataccta taaatataat tctttcggta ataagtggtc aagtcaggcc tactatggct     60

cgacaagaat cgtctattca aagagttata atgaggtttt tagcttctta tggatgcatt    120

tttttaactt gtacacataa gtctacttcg gttctgaccc taaaagcttc ttcttttagg    180

gaagaagtta gtataatgtc tgctaaacaa cctctgtagt cattgcgacc gattagagac    240

ctttctcctc aaatcgtaaa gacttttaga gttctggtta ctgaactaaa aacaagttaa    300

aagatttctt ccacatcttg taaagcgaaa gaacgcttaa cgggacgccc tctggaactg    360

ggtggagcct cctcttcaac tattaggtta gttcgactga gtcttattgg acggacctaa    420

accttgccca cgactgctcc ggaaccacca gttagaagtc tcagcgttca tagtggacta    480

actttttgct tagttcatgt tgccctgaaa aaacttgata aaaagtctat tagaagaacg    540

acagcgagga ttctaaagag gattttttag atagttcctt gacctttttt gtcgggtctc    600

ttaacgactt agaaaattgt gtctactaaa agttaaagtt aggttccagt ttagtcgata    660

aaagttgttg gatcttcttt cgttacttaa cagtggactc tttaaccgat tactggaaaa    720

actgttgtta gactgccgag caaactcgaa ataactggtt cagtctcttc ggcatggtct    780

tggacaagtt aaactacttt aactacggtc agcggttaat ttctttaaac ttttggtttt    840

tgagaggaat agtttacctt aactcgagta gcaagggtta ttgcagatag ttctgcggct    900

cagacaactc aaataggttt tgcttttacc ttggatgaga tagaattagt ttttatagct    960

cctataggtt tcatttatta caaatttgct taagcttctc acgaacatga tcgtcagaag   1020

gaaaaacgac cgatatttcg aatggcgcaa gtagttctac agtttgttca gtactggata   1080

gttgggtacc acgctcttta                                                1100


<210> SEQ ID NO 34
<211> LENGTH: 299
<212> TYPE: PRT
<213> ORGANISM: Streptococcus pneumoniae

<400> SEQUENCE: 34

Met Ala Ile Phe Phe Met Ile Phe Leu Ile Val Cys Val Leu Leu Leu
  1               5                  10                  15

Val Ile Val Thr Leu Ser Thr Val Tyr Val Val Arg Gln Gln Ser Val
             20                  25                  30

Ala Ile Ile Glu Arg Phe Gly Lys Tyr Gln Lys Val Ala Asn Ser Gly
         35                  40                  45

Ile His Ile Arg Leu Pro Phe Gly Ile Asp Ser Ile Ala Ala Arg Ile
     50                  55                  60

Gln Leu Arg Leu Leu Gln Ser Asp Ile Val Val Glu Thr Lys Thr Lys
 65                  70                  75                  80

Asp Asn Val Phe Val Met Met Asn Val Ala Thr Gln Tyr Arg Val Asn
                 85                  90                  95

Glu Gln Ser Val Thr Asp Ala Tyr Tyr Lys Leu Ile Arg Pro Glu Ser
            100                 105                 110

Gln Ile Lys Ser Tyr Ile Glu Asp Ala Leu Arg Ser Ser Val Pro Lys
```

-continued

```
        115                 120                 125

Leu Thr Leu Asp Glu Leu Phe Glu Lys Lys Asp Glu Ile Ala Leu Glu
    130                 135                 140

Val Gln His Gln Val Ala Glu Glu Met Thr Thr Tyr Gly Tyr Ile Ile
145                 150                 155                 160

Val Lys Thr Leu Ile Thr Lys Val Glu Pro Asp Ala Glu Val Lys Gln
                165                 170                 175

Ser Met Asn Glu Ile Asn Ala Ala Gln Arg Lys Arg Val Ala Ala Gln
            180                 185                 190

Glu Leu Ala Glu Ala Asp Lys Ile Lys Ile Val Thr Ala Ala Glu Ala
        195                 200                 205

Glu Ala Glu Lys Asp Arg Leu His Gly Val Gly Ile Ala Gln Gln Arg
    210                 215                 220

Lys Ala Ile Val Asp Gly Leu Ala Glu Ser Ile Thr Glu Leu Lys Glu
225                 230                 235                 240

Ala Asn Val Gly Met Thr Glu Glu Gln Ile Met Ser Ile Leu Leu Thr
                245                 250                 255

Asn Gln Tyr Leu Asp Thr Leu Asn Thr Phe Ala Ser Lys Gly Asn Gln
            260                 265                 270

Thr Ile Phe Leu Pro Asn Thr Pro Asn Gly Val Asp Asp Ile Arg Thr
        275                 280                 285

Gln Ile Leu Ser Ala Leu Arg Ala Glu Lys Lys
    290                 295


<210> SEQ ID NO 35
<211> LENGTH: 1000
<212> TYPE: DNA
<213> ORGANISM: Streptococcus pneumoniae
<220> FEATURE:
<221> NAME/KEY: CDS
<222> LOCATION: (44)...(940)

<400> SEQUENCE: 35

aaatgtgcta taatactaga aaaatacttg tggaggttcc att atg gca ata ttt       55
                                                Met Ala Ile Phe
                                                  1

ttc atg att ttt ctg att gtt tgt gtg ctc cta ttg gtg ata gtc aca      103
Phe Met Ile Phe Leu Ile Val Cys Val Leu Leu Leu Val Ile Val Thr
  5                  10                  15                  20

ctg agt aca gtt tat gtg gtt cgt cag cag tcg gtg gcg att att gaa      151
Leu Ser Thr Val Tyr Val Val Arg Gln Gln Ser Val Ala Ile Ile Glu
                 25                  30                  35

cgc ttt ggg aaa tac caa aag gtt gct aat agc ggt att cat att cgc      199
Arg Phe Gly Lys Tyr Gln Lys Val Ala Asn Ser Gly Ile His Ile Arg
             40                  45                  50

ttg cct ttt ggg att gac tcg att gca gca cgg att cag ttg cgc ttg      247
Leu Pro Phe Gly Ile Asp Ser Ile Ala Ala Arg Ile Gln Leu Arg Leu
         55                  60                  65

ttg caa agt gat att gtg gtt gag act aag acc aag gac aat gtg ttc      295
Leu Gln Ser Asp Ile Val Val Glu Thr Lys Thr Lys Asp Asn Val Phe
     70                  75                  80

gtt atg atg aat gta gcg act cag tac cgt gtc aac gag cag agc gtg      343
Val Met Met Asn Val Ala Thr Gln Tyr Arg Val Asn Glu Gln Ser Val
 85                  90                  95                 100

aca gat gct tac tat aaa ctc ata cgt cca gaa tct cag att aaa tct      391
Thr Asp Ala Tyr Tyr Lys Leu Ile Arg Pro Glu Ser Gln Ile Lys Ser
                105                 110                 115

tat atc gaa gat gct ctt cgc tct tct gtt cca aaa tta acc ttg gat      439
```

-continued

```
Tyr Ile Glu Asp Ala Leu Arg Ser Ser Val Pro Lys Leu Thr Leu Asp
            120                 125                 130

gaa ttg ttt gag aaa aaa gat gag att gcc ctt gag gtt caa cac caa      487
Glu Leu Phe Glu Lys Lys Asp Glu Ile Ala Leu Glu Val Gln His Gln
        135                 140                 145

gta gca gaa gaa atg acc act tac ggc tac att atc gtg aaa acc ttg      535
Val Ala Glu Glu Met Thr Thr Tyr Gly Tyr Ile Ile Val Lys Thr Leu
    150                 155                 160

att acc aag gtc gaa cca gat gca gaa gtt aag caa tct atg aat gaa      583
Ile Thr Lys Val Glu Pro Asp Ala Glu Val Lys Gln Ser Met Asn Glu
165                 170                 175                 180

atc aat gcg gcg caa cgt aag cgg gtc gca gca caa gaa ttg gcg gaa      631
Ile Asn Ala Ala Gln Arg Lys Arg Val Ala Ala Gln Glu Leu Ala Glu
                185                 190                 195

gct gac aag att aaa att gtc act gca gct gaa gcc gaa gca gaa aaa      679
Ala Asp Lys Ile Lys Ile Val Thr Ala Ala Glu Ala Glu Ala Glu Lys
            200                 205                 210

gac cgc ctt cat ggt gtg ggg att gcc caa caa cgt aag gcg att gtg      727
Asp Arg Leu His Gly Val Gly Ile Ala Gln Gln Arg Lys Ala Ile Val
        215                 220                 225

gat gga ttg gca gag tct atc acc gaa ctc aag gaa gcc aat gtt ggc      775
Asp Gly Leu Ala Glu Ser Ile Thr Glu Leu Lys Glu Ala Asn Val Gly
    230                 235                 240

atg aca gaa gaa caa atc atg tct atc ctc ttg acc aac cag tat ttg      823
Met Thr Glu Glu Gln Ile Met Ser Ile Leu Leu Thr Asn Gln Tyr Leu
245                 250                 255                 260

gat acc ttg aat acc ttt gcc tct aaa gga aat caa acc atc ttt tta      871
Asp Thr Leu Asn Thr Phe Ala Ser Lys Gly Asn Gln Thr Ile Phe Leu
                265                 270                 275

cca aat act cca aat ggt gtg gat gat atc cgt aca caa atc ttg tca      919
Pro Asn Thr Pro Asn Gly Val Asp Asp Ile Arg Thr Gln Ile Leu Ser
            280                 285                 290

gcc ctt cgc gct gag aag aaa taatagacta atactcttcg aaaatctctt         970
Ala Leu Arg Ala Glu Lys Lys
        295

caaactacgt cagcgtcgtc ttgccgtata                                    1000
```

<210> SEQ ID NO 36
<211> LENGTH: 1000
<212> TYPE: DNA
<213> ORGANISM: Streptococcus pneumoniae

<400> SEQUENCE: 36

```
tttacacgat attatgatct ttttatgaac acctccaagg taataccgtt ataaaaagta      60

ctaaaaagac taacaaacac acgaggataa ccactatcag tgtgactcat gtcaaataca     120

ccaagcagtc gtcagccacc gctaataact tgcgaaaccc tttatggttt tccaacgatt     180

atcgccataa gtataagcga acggaaaacc ctaactgagc taacgtcgtg cctaagtcaa     240

cgcgaacaac gtttcactat aacaccaact ctgattctgg ttcctgttac acaagcaata     300

ctacttacat cgctgagtca tggcacagtt gctcgtctcg cactgtctac gaatgatatt     360

tgagtatgca ggtcttagag tctaatttag aatatagctt ctacgagaag cgagaagaca     420

aggttttaat tggaacctac ttaacaaact ctttttttcta ctctaacggg aactccaagt     480

tgtggttcat cgtcttcttt actggtgaat gccgatgtaa tagcactttt ggaactaatg     540

gttccagctt ggtctacgtc ttcaattcgt tagatactta ctttagttac gccgcgttgc     600

attcgcccag cgtcgtgttc ttaaccgcct tcgactgttc taattttaac agtgacgtcg     660
```

-continued

```
acttcggctt cgtctttttc tggcggaagt accacacccc taacgggttg ttgcattccg    720

ctaacaccta cctaaccgtc tcagatagtg gcttgagttc cttcggttac aaccgtactg    780

tcttcttgtt tagtacagat aggagaactg gttggtcata aacctatgga acttatggaa    840

acggagattt cctttagttt ggtagaaaaa tggtttatga ggtttaccac acctactata    900

ggcatgtgtt tagaacagtc gggaagcgcg actcttcttt attatctgat tatgagaagc    960

ttttagagaa gtttgatgca gtcgcagcag aacggcatat                          1000


<210> SEQ ID NO 37
<211> LENGTH: 388
<212> TYPE: PRT
<213> ORGANISM: Streptococcus pneumoniae

<400> SEQUENCE: 37

Leu Lys Ser Ile Gly Phe Ile Glu Lys Leu Lys Gly Leu Ser Ser Lys
  1               5                  10                  15

Glu Leu Ile Leu Leu Gly Ile Ile Leu Ser Ile Phe Leu Pro Phe Tyr
             20                  25                  30

Leu Phe Val Val Val Leu Cys Leu Tyr Ile Ile Ser Leu Ile Phe Thr
         35                  40                  45

Gly Asp Met Lys Ser Ile Leu Gln Lys Met Gly Glu His Pro Met Leu
     50                  55                  60

Leu Leu Phe Leu Ser Tyr Ser Thr Val Ile Ser Ile Leu Ala Gln Asn
 65                  70                  75                  80

Trp Met Gly Leu Val Ala Ser Val Gly Met Phe Leu Phe Thr Ile Phe
                 85                  90                  95

Phe Leu His Tyr Gln Ser Ile Leu Ser His Lys Phe Phe Arg Leu Ile
            100                 105                 110

Leu Gln Phe Val Leu Phe Gly Ser Val Leu Ser Ala Ala Phe Ala Ser
        115                 120                 125

Leu Glu His Phe Gln Ile Val Lys Lys Phe Asn Tyr Ala Phe Leu Ser
    130                 135                 140

Pro Asn Met Gln Val Trp His Gln Asn Arg Ala Glu Val Thr Phe Phe
145                 150                 155                 160

Asn Pro Asn Tyr Tyr Gly Ile Ile Cys Cys Phe Cys Ile Met Ile Ala
                165                 170                 175

Phe Tyr Leu Phe Thr Thr Thr Lys Leu Asn Trp Leu Lys Val Phe Cys
            180                 185                 190

Val Ile Ala Gly Phe Val Asn Leu Phe Gly Leu Asn Phe Thr Gln Asn
        195                 200                 205

Arg Thr Ala Phe Pro Ala Ile Ile Ala Gly Ala Ile Ile Tyr Leu Phe
    210                 215                 220

Thr Thr Ile Lys Asn Trp Lys Ala Phe Trp Leu Ser Ile Gly Val Phe
225                 230                 235                 240

Ala Ile Gly Leu Ser Phe Leu Phe Ser Ser Asp Leu Gly Val Arg Met
                245                 250                 255

Gly Thr Leu Asp Ser Ser Met Glu Glu Arg Ile Ser Ile Trp Asp Ala
            260                 265                 270

Gly Met Ala Leu Phe Lys Gln Asn Pro Phe Trp Gly Glu Gly Pro Leu
        275                 280                 285

Thr Tyr Met His Ser Tyr Pro Arg Ile His Ala Pro Tyr His Glu His
    290                 295                 300

Ala His Ser Leu Tyr Ile Asp Thr Ile Leu Ser Tyr Gly Ile Val Gly
305                 310                 315                 320
```

-continued

```
Thr Ile Leu Leu Val Leu Ser Ser Val Ala Pro Val Arg Leu Met Met
                325                 330                 335

Asp Met Ser Gln Glu Ser Gly Lys Arg Pro Ile Ile Gly Leu Tyr Leu
            340                 345                 350

Ser Phe Leu Thr Val Val Ala Val His Gly Ile Phe Asp Leu Ala Leu
        355                 360                 365

Phe Trp Ile Gln Ser Gly Phe Ile Phe Leu Leu Val Met Cys Ser Ile
    370                 375                 380

Pro Leu Ala Leu
385


<210> SEQ ID NO 38
<211> LENGTH: 1299
<212> TYPE: DNA
<213> ORGANISM: Streptococcus pneumoniae
<220> FEATURE:
<221> NAME/KEY: CDS
<222> LOCATION: (136)...(1299)
<221> NAME/KEY: misc_feature
<222> LOCATION: (1)...(1299)
<223> OTHER INFORMATION: n = A,T,C or G

<400> SEQUENCE: 38

ccttgatatg gtggataaaa tagggttttn attttggaaa acgtttcctt tgtnttcaaa      60

ttgctaaaaa antggtacaa tanaggaaag cttactatta tctgaatcag cagatttgga     120

gagaaaggat tcatt ttg aaa tca ata ggc ttt att gaa aag ctg aag ggg      171
                 Leu Lys Ser Ile Gly Phe Ile Glu Lys Leu Lys Gly
                   1               5                  10

ttg tct agt aaa gag ctg att tta ttg gga att atc cta agt atc ttt      219
Leu Ser Ser Lys Glu Leu Ile Leu Leu Gly Ile Ile Leu Ser Ile Phe
         15                  20                  25

tta ccc ttt tat ctt ttt gta gtt gta ctc tgt tta tat att atc agt      267
Leu Pro Phe Tyr Leu Phe Val Val Val Leu Cys Leu Tyr Ile Ile Ser
     30                  35                  40

ttg att ttt aca gga gac atg aaa agt att ctt cag aaa atg ggg gag      315
Leu Ile Phe Thr Gly Asp Met Lys Ser Ile Leu Gln Lys Met Gly Glu
 45                  50                  55                  60

cat ccg atg ctg ctt ctt ttt ctt agc tat agt act gtt ata tcc att      363
His Pro Met Leu Leu Leu Phe Leu Ser Tyr Ser Thr Val Ile Ser Ile
                 65                  70                  75

ctt gca caa aat tgg atg ggt ctt gtg gct tca gta gga atg ttt cta      411
Leu Ala Gln Asn Trp Met Gly Leu Val Ala Ser Val Gly Met Phe Leu
             80                  85                  90

ttt act att ttc ttt ttg cac tat cag tcg att tta tcc cat aaa ttc      459
Phe Thr Ile Phe Phe Leu His Tyr Gln Ser Ile Leu Ser His Lys Phe
         95                 100                 105

ttt cga ttg att ttg cag ttc gtc ttg ttt ggt agt gtc ttg tca gct      507
Phe Arg Leu Ile Leu Gln Phe Val Leu Phe Gly Ser Val Leu Ser Ala
    110                 115                 120

gct ttt gcc agt tta gaa cat ttc caa att gtg aag aaa ttt aac tat      555
Ala Phe Ala Ser Leu Glu His Phe Gln Ile Val Lys Lys Phe Asn Tyr
125                 130                 135                 140

gct ttt ctt tca ccc aat atg cag gtg tgg cat cag aac cgg gca gaa      603
Ala Phe Leu Ser Pro Asn Met Gln Val Trp His Gln Asn Arg Ala Glu
                145                 150                 155

gtg acc ttc ttt aat cct aat tat tat gga att att tgt tgt ttc tgt      651
Val Thr Phe Phe Asn Pro Asn Tyr Tyr Gly Ile Ile Cys Cys Phe Cys
            160                 165                 170

att atg att gct ttc tat ctg ttt aca acg acc aag ttg aat tgg ttg      699
```

-continued

```
Ile Met Ile Ala Phe Tyr Leu Phe Thr Thr Thr Lys Leu Asn Trp Leu
        175                 180                 185

aaa gta ttc tgt gtg att gca ggc ttt gtt aat ctc ttt ggt ttg aac      747
Lys Val Phe Cys Val Ile Ala Gly Phe Val Asn Leu Phe Gly Leu Asn
    190                 195                 200

ttt act caa aat cga act gcc ttt cct gct att atc gct gga gca att      795
Phe Thr Gln Asn Arg Thr Ala Phe Pro Ala Ile Ile Ala Gly Ala Ile
205                 210                 215                 220

atc tat ctc ttt acg act att aaa aac tgg aag gcc ttt tgg ctt agt      843
Ile Tyr Leu Phe Thr Thr Ile Lys Asn Trp Lys Ala Phe Trp Leu Ser
                225                 230                 235

att ggg gtc ttc gcg att ggt ttg agt ttc ctc ttt tct agt gat ttg      891
Ile Gly Val Phe Ala Ile Gly Leu Ser Phe Leu Phe Ser Ser Asp Leu
            240                 245                 250

gga gtt cga atg ggt act tta gac tct tct atg gaa gaa cgc att tct      939
Gly Val Arg Met Gly Thr Leu Asp Ser Ser Met Glu Glu Arg Ile Ser
        255                 260                 265

atc tgg gat gct ggg atg gcc ttg ttt aag caa aat cct ttt tgg ggt      987
Ile Trp Asp Ala Gly Met Ala Leu Phe Lys Gln Asn Pro Phe Trp Gly
    270                 275                 280

gaa ggg cca ttg acc tat atg cac tct tat cct cgg ata cat gct cct     1035
Glu Gly Pro Leu Thr Tyr Met His Ser Tyr Pro Arg Ile His Ala Pro
285                 290                 295                 300

tat cat gaa cat gcc cac agt ctt tat att gat acg att ctg agt tac     1083
Tyr His Glu His Ala His Ser Leu Tyr Ile Asp Thr Ile Leu Ser Tyr
                305                 310                 315

gga att gtg ggt acc att tta tta gtt ttg tct tct gtt gct cct gtt     1131
Gly Ile Val Gly Thr Ile Leu Leu Val Leu Ser Ser Val Ala Pro Val
            320                 325                 330

cgc ttg atg atg gat atg agt cag gag tcg ggg aaa cgt ccg att atc     1179
Arg Leu Met Met Asp Met Ser Gln Glu Ser Gly Lys Arg Pro Ile Ile
        335                 340                 345

ggc ctt tat cta tct ttc ctt aca gtg gtt gct gtg cac gga att ttt     1227
Gly Leu Tyr Leu Ser Phe Leu Thr Val Val Ala Val His Gly Ile Phe
    350                 355                 360

gac ttg gct ctc ttc tgg att cag tca ggc ttt att ttc ttg cta gtt     1275
Asp Leu Ala Leu Phe Trp Ile Gln Ser Gly Phe Ile Phe Leu Leu Val
365                 370                 375                 380

atg tgc agt att cca ttg gct tta                                     1299
Met Cys Ser Ile Pro Leu Ala Leu
                385
```

<210> SEQ ID NO 39
<211> LENGTH: 1299
<212> TYPE: DNA
<213> ORGANISM: Streptococcus pneumoniae
<220> FEATURE:
<221> NAME/KEY: misc_feature
<222> LOCATION: (1)...(1299)
<223> OTHER INFORMATION: n = A,T,C or G

<400> SEQUENCE: 39

```
ggaactatac cacctatttt atcccaaaan taaaaccttt tgcaaaggaa acanaagttt     60

aacgattttt tnaccatgtt atntcctttc gaatgataat agacttagtc gtctaaacct    120

ctctttccta agtaaaactt tagttatccg aaataacttt tcgacttccc caacagatca    180

tttctcgact aaaataaccc ttaataggat tcatagaaaa atgggaaaat agaaaaacat    240

caacatgaga caaatatata atagtcaaac taaaaatgtc ctctgtactt ttcataagaa    300

gtcttttacc ccctcgtagg ctacgacgaa gaaaaagaat cgatatcatg acaatatagg    360
```

-continued

```
taagaacgtg ttttaaccta cccagaacac cgaagtcatc cttacaaaga taaatgataa    420

aagaaaaacg tgatagtcag ctaaaatagg gtatttaaga aagctaacta aaacgtcaag    480

cagaacaaac catcacagaa cagtcgacga aaacggtcaa atcttgtaaa ggtttaacac    540

ttctttaaat tgatacgaaa agaaagtggg ttatacgtcc acaccgtagt cttggcccgt    600

cttcactgga agaaattagg attaataata ccttaataaa caacaaagac ataatactaa    660

cgaaagatag acaaatgttg ctggttcaac ttaaccaact ttcataagac acactaacgt    720

ccgaaacaat tagagaaacc aaacttgaaa tgagttttag cttgacggaa aggacgataa    780

tagcgacctc gttaatagat agagaaatgc tgataatttt tgaccttccg gaaaaccgaa    840

tcataacccc agaagcgcta accaaactca aaggagaaaa gatcactaaa ccctcaagct    900

tacccatgaa atctgagaag ataccttctt gcgtaaagat agaccctacg accctaccgg    960

aacaaattcg ttttaggaaa aaccccactt cccggtaact ggatatacgt gagaatagga   1020

gcctatgtac gaggaatagt acttgtacgg gtgtcagaaa tataactatg ctaagactca   1080

atgccttaac acccatggta aaataatcaa aacagaagac aacgaggaca agcgaactac   1140

tacctatact cagtcctcag ccccttgca ggctaatagc cggaaataga tagaaaggaa   1200

tgtcaccaac gacacgtgcc ttaaaaactg aaccgagaga agacctaagt cagtccgaaa   1260

taaaagaacg atcaatacac gtcataaggt aaccgaaat                          1299
```

<210> SEQ ID NO 40
<211> LENGTH: 200
<212> TYPE: PRT
<213> ORGANISM: Streptococcus pneumoniae

<400> SEQUENCE: 40

```
Met Asn Val Lys Glu Asn Thr Glu Leu Val Phe Arg Glu Val Ala Glu
  1               5                  10                  15

Ala Ser Leu Ser Ala His Arg Glu Ser Gly Ser Val Ser Val Ile Ala
             20                  25                  30

Val Ile Lys Tyr Val Asp Val Pro Thr Ala Glu Ala Leu Leu Pro Leu
         35                  40                  45

Gly Val His His Ile Gly Glu Asn Arg Val Asp Lys Phe Leu Glu Lys
     50                  55                  60

Tyr Glu Ala Leu Lys Asp Arg Asp Val Thr Trp His Leu Ile Gly Thr
 65                  70                  75                  80

Leu Gln Arg Arg Lys Val Lys Asp Val Ile Gln Tyr Val Asp Tyr Phe
                 85                  90                  95

His Ala Leu Asp Ser Val Lys Leu Ala Gly Glu Ile Gln Lys Arg Ser
            100                 105                 110

Asp Arg Val Ile Lys Cys Phe Leu Gln Val Asn Ile Ser Lys Glu Glu
        115                 120                 125

Ser Lys His Gly Phe Ser Arg Glu Glu Leu Leu Glu Ile Leu Pro Glu
    130                 135                 140

Leu Ala Arg Leu Asp Lys Ile Glu Tyr Val Gly Leu Met Thr Met Ala
145                 150                 155                 160

Pro Phe Glu Ala Ser Ser Glu Gln Leu Lys Glu Ile Phe Lys Ala Ala
                165                 170                 175

Gln Asp Leu Gln Arg Glu Ile Gln Glu Lys Gln Ile Pro Asn Met Pro
            180                 185                 190

Leu Glu His Thr Gly Gly Arg Tyr
        195                 200
```

-continued

<210> SEQ ID NO 41
<211> LENGTH: 999
<212> TYPE: DNA
<213> ORGANISM: Streptococcus pneumoniae
<220> FEATURE:
<221> NAME/KEY: CDS
<222> LOCATION: (400)...(999)

<400> SEQUENCE: 41

```
aaggagtgaa catctggctc ggtacttcaa ttgatgaaag tatgcgtgat gaaattcgtg      60

taacagttgt cgcaacgggt gttcgtcaag accgcgtaga aaaggttgtg gctccacaag     120

ctagatctgc tactaactac cgtgagacag tgaaaccagc tcattcacat ggctttgatc     180

gtcattttga tatggcagaa acagttgaat tgccaaaaca aaatccacgt cgtttggaac     240

caactcaggc atctgctttt ggtgattggg atcttcgccg tgaatcgatt gttcgtacaa     300

cagattcagt cgtttctcca gtcgagcgct ttgaagcccc aatttcacaa gatgaagatg     360

aattggatac acctccattt ttcaaaaatc gttaagtaa atg aat gta aaa gaa       414
                                           Met Asn Val Lys Glu
                                            1               5

aat aca gaa ctt gtt ttt cga gaa gtt gca gag gct agt ctg agt gct      462
Asn Thr Glu Leu Val Phe Arg Glu Val Ala Glu Ala Ser Leu Ser Ala
                10                  15                  20

cat cga gag agt ggt tcg gtc tct gtc att gca gtt atc aag tat gta      510
His Arg Glu Ser Gly Ser Val Ser Val Ile Ala Val Ile Lys Tyr Val
            25                  30                  35

gat gta ccg aca gcg gaa gcc ttg ctt ccg cta ggt gtt cat cat atc      558
Asp Val Pro Thr Ala Glu Ala Leu Leu Pro Leu Gly Val His His Ile
        40                  45                  50

ggt gaa aat cgt gta gat aag ttt ctg gaa aaa tat gaa gct tta aaa      606
Gly Glu Asn Arg Val Asp Lys Phe Leu Glu Lys Tyr Glu Ala Leu Lys
    55                  60                  65

gat cga gat gtg act tgg cat ttg att ggt acc ttg caa aga cgt aag      654
Asp Arg Asp Val Thr Trp His Leu Ile Gly Thr Leu Gln Arg Arg Lys
 70                  75                  80                  85

gtg aaa gat gtc att caa tac gtt gat tat ttc cat gca ttg gac tca      702
Val Lys Asp Val Ile Gln Tyr Val Asp Tyr Phe His Ala Leu Asp Ser
                90                  95                  100

gta aag cta gca ggg gaa att caa aaa aga agt gac cga gtc atc aag      750
Val Lys Leu Ala Gly Glu Ile Gln Lys Arg Ser Asp Arg Val Ile Lys
            105                 110                 115

tgt ttc ctt caa gta aat att tct aaa gaa gaa agc aaa cac ggt ttt      798
Cys Phe Leu Gln Val Asn Ile Ser Lys Glu Glu Ser Lys His Gly Phe
        120                 125                 130

tcg aga gag gaa ctg ctg gaa atc ttg cca gag tta gcc aga cta gat      846
Ser Arg Glu Glu Leu Leu Glu Ile Leu Pro Glu Leu Ala Arg Leu Asp
    135                 140                 145

aag att gaa tat gtt ggt tta atg acg atg gca cct ttt gag gct agc      894
Lys Ile Glu Tyr Val Gly Leu Met Thr Met Ala Pro Phe Glu Ala Ser
150                 155                 160                 165

agt gag cag ttg aaa gag att ttc aag gcg gcc caa gat tta caa aga      942
Ser Glu Gln Leu Lys Glu Ile Phe Lys Ala Ala Gln Asp Leu Gln Arg
                170                 175                 180

gaa att caa gag aaa caa att cca aat atg cct tta gag cac act ggc      990
Glu Ile Gln Glu Lys Gln Ile Pro Asn Met Pro Leu Glu His Thr Gly
            185                 190                 195

ggc cgt tac                                                          999
Gly Arg Tyr
        200
```

-continued

<210> SEQ ID NO 42
<211> LENGTH: 999
<212> TYPE: DNA
<213> ORGANISM: Streptococcus pneumoniae

<400> SEQUENCE: 42

```
ttcctcactt gtagaccgag ccatgaagtt aactactttc atacgcacta ctttaagcac     60

attgtcaaca gcgttgccca caagcagttc tggcgcatct tttccaacac cgaggtgttc    120

gatctagacg atgattgatg gcactctgtc actttggtcg agtaagtgta ccgaaactag    180

cagtaaaact ataccgtctt tgtcaactta acggttttgt tttaggtgca gcaaaccttg    240

gttgagtccg tagacgaaaa ccactaaccc tagaagcggc acttagctaa caagcatgtt    300

gtctaagtca gcaaagaggt cagctcgcga aacttcgggg ttaaagtgtt ctacttctac    360

ttaacctatg tggaggtaaa aagtttttag caattcattt acttacattt tcttttatgt    420

cttgaacaaa aagctcttca acgtctccga tcagactcac gagtagctct ctcaccaagc    480

cagagacagt aacgtcaata gttcatacat ctacatggct gtcgccttcg gaacgaaggc    540

gatccacaag tagtatagcc acttttagca catctattca aagacctttt tatacttcga    600

aattttctag ctctacactg aaccgtaaac taaccatgga acgtttctgc attccacttt    660

ctacagtaag ttatgcaact aataaaggta cgtaacctga gtcatttcga tcgtcccctt    720

taagtttttt cttcactggc tcagtagttc acaaaggaag ttcatttata aagatttctt    780

ctttcgtttg tgccaaaaag ctctctcctt gacgaccttt agaacggtct caatcggtct    840

gatctattct aacttataca accaaattac tgctaccgtg gaaaactccg atcgtcactc    900

gtcaactttc tctaaaagtt ccgccgggtt ctaaatgttt ctctttaagt tctctttgtt    960

taaggtttat acggaaatct cgtgtgaccg ccggcaatg                           999
```

<210> SEQ ID NO 43
<211> LENGTH: 163
<212> TYPE: PRT
<213> ORGANISM: Streptococcus pneumoniae

<400> SEQUENCE: 43

```
Thr Pro Ser Pro Leu Leu Ala Val Ser Leu Leu Phe Thr Phe Asn Gln
  1               5                  10                  15

Pro Gln Phe Leu Val Leu Asn Gln Ile Leu Val Gly Ser Leu Val Ile
             20                  25                  30

Leu Leu Ile Ala Tyr Ile Val Val Lys Ile Pro Phe Ser Tyr Arg Met
         35                  40                  45

Val Arg Ala Ile Leu Phe Ser Val Asp Asp Glu Met Glu Asp Ala Ala
     50                  55                  60

Arg Ser Met Gly Ala Ser Pro Phe Tyr Thr Met Met Lys Val Ile Ile
 65                  70                  75                  80

Pro Phe Ile Leu Pro Val Val Leu Ser Val Ile Ala Leu Asn Phe Asn
                 85                  90                  95

Ser Leu Leu Thr Asp Phe Asp Leu Ser Val Phe Leu Tyr His Pro Leu
            100                 105                 110

Ala Gln Pro Leu Gly Ile Thr Ile Arg Ser Ala Gly Asp Glu Thr Ala
        115                 120                 125

Thr Ser Asn Ala Gln Ala Leu Val Phe Val Tyr Thr Ile Val Leu Met
    130                 135                 140

Ile Ile Ser Gly Thr Val Leu Tyr Phe Thr Gln Arg Pro Gly Arg Lys
145                 150                 155                 160
```

-continued

```
Val Arg Lys


<210> SEQ ID NO 44
<211> LENGTH: 978
<212> TYPE: DNA
<213> ORGANISM: Streptococcus pneumoniae
<220> FEATURE:
<221> NAME/KEY: CDS
<222> LOCATION: (3)...(491)

<400> SEQUENCE: 44

gt act ccc agt cca ctt tta gca gta agt tta tta ttt act ttt aat        47
   Thr Pro Ser Pro Leu Leu Ala Val Ser Leu Leu Phe Thr Phe Asn
     1               5                  10                  15

cag cca caa ttt ctt gtc ttg aat cag att ttg gta ggt agt ttg gta       95
Gln Pro Gln Phe Leu Val Leu Asn Gln Ile Leu Val Gly Ser Leu Val
                 20                  25                  30

att cta ctt att gca tat ata gtt gta aaa atc cca ttt tct tat aga      143
Ile Leu Leu Ile Ala Tyr Ile Val Val Lys Ile Pro Phe Ser Tyr Arg
             35                  40                  45

atg gta cgt gct att tta ttt agt gtt gat gat gag atg gaa gat gca      191
Met Val Arg Ala Ile Leu Phe Ser Val Asp Asp Glu Met Glu Asp Ala
         50                  55                  60

gca aga agt atg ggt gct tca cct ttt tat act atg atg aag gtt atc      239
Ala Arg Ser Met Gly Ala Ser Pro Phe Tyr Thr Met Met Lys Val Ile
     65                  70                  75

att cca ttt att tta ccg gtt gtt ctc tct gtt att gct tta aac ttt      287
Ile Pro Phe Ile Leu Pro Val Val Leu Ser Val Ile Ala Leu Asn Phe
 80                  85                  90                  95

aac tct tta tta act gac ttc gac tta tct gta ttc ctt tac cat ccc      335
Asn Ser Leu Leu Thr Asp Phe Asp Leu Ser Val Phe Leu Tyr His Pro
                100                 105                 110

cta gct caa cca tta ggt att acg att cga tct gca ggt gat gaa aca      383
Leu Ala Gln Pro Leu Gly Ile Thr Ile Arg Ser Ala Gly Asp Glu Thr
            115                 120                 125

gca aca tct aat gca caa gct ctg gta ttt gtt tat aca att gtt ctg      431
Ala Thr Ser Asn Ala Gln Ala Leu Val Phe Val Tyr Thr Ile Val Leu
        130                 135                 140

atg att att tct gga acg gta tta tac ttc aca caa aga ccg ggg cgt      479
Met Ile Ile Ser Gly Thr Val Leu Tyr Phe Thr Gln Arg Pro Gly Arg
    145                 150                 155

aaa gta agg aaa taatcatgac agccactagt cttgggttat caaatattga          531
Lys Val Arg Lys
160

aatagttgtc aggattgttt tatcagtagt cattggtagt ataattggtt tagagagagg    591

gagcaaatcc cagcctgcag gcatccgaac ttatagtatt gtttgtctag ctgcatgttt    651

gattatgatg acgaatgaat acgtatctta taaatttggg acaggagatc ctacacgatt    711

aggagctcaa gttatatcag gtgtgggttt tctaggcgct ggaacgattc ttattacaga    771

taaaaagaaa attacaggtc tgacaactgc agcaggcatt tgggcttcgg caggaattgg    831

attagctatt ggagtaggtt tttatgaggg agctctttta gtagccattt ctgtttgggg    891

tgtgatatcc atgttccaac cactaaaaaa atatctgcaa aatcgttcta aaatgattga    951

attgtatata gtagttaaat cctttag                                        978


<210> SEQ ID NO 45
<211> LENGTH: 978
<212> TYPE: DNA
<213> ORGANISM: Streptococcus pneumoniae
```

-continued

<400> SEQUENCE: 45

```
catgagggtc aggtgaaaat cgtcattcaa ataataaatg aaaattagtc ggtgttaaag     60
aacagaactt agtctaaaac catccatcaa accattaaga tgaataacgt atatatcaac    120
atttttaggg taaaagaata tcttaccatg cacgataaaa taaatcacaa ctactactct    180
accttctacg tcgttcttca tacccacgaa gtggaaaaat atgatactac ttccaatagt    240
aaggtaaata aaatggccaa caagagagac aataacgaaa tttgaaattg agaaataatt    300
gactgaagct gaatagacat aaggaaatgg taggggatcg agttggtaat ccataatgct    360
aagctagacg tccactactt tgtcgttgta gattacgtgt tcgagaccat aaacaaatat    420
gttaacaaga ctactaataa agaccttgcc ataatatgaa gtgtgtttct ggccccgcat    480
ttcattcctt tattagtact gtcggtgatc agaacccaat agtttataac tttatcaaca    540
gtcctaacaa aatagtcatc agtaaccatc atattaacca aatctctctc cctcgtttag    600
ggtcggacgt ccgtaggctt gaatatcata acaaacagat cgacgtacaa actaatacta    660
ctgcttactt atgcatagaa tatttaaacc ctgtcctcta ggatgtgcta atcctcgagt    720
tcaatatagt ccacacccaa aagatccgcg accttgctaa gaataatgtc tatttttctt    780
ttaatgtcca gactgttgac gtcgtccgta aacccgaagc cgtccttaac ctaatcgata    840
acctcatcca aaaatactcc ctcgagaaaa tcatcggtaa agacaaaccc cacactatag    900
gtacaaggtt ggtgattttt ttatagacgt tttagcaaga ttttactaac ttaacatata    960
tcatcaattt aggaaatc                                                  978
```

<210> SEQ ID NO 46
<211> LENGTH: 344
<212> TYPE: PRT
<213> ORGANISM: Streptococcus pneumoniae

<400> SEQUENCE: 46

```
Met Met Asp Arg Ile Arg Gln Glu Leu Glu Lys Gly Gly Ala Val Val
  1               5                  10                  15

Leu Pro Thr Glu Thr Val Tyr Gly Leu Phe Ser Lys Ala Leu Asp Glu
             20                  25                  30

Lys Ala Val Asp His Val Tyr Gln Leu Lys Arg Arg Pro Arg Asp Lys
         35                  40                  45

Ala Leu Asn Leu Asn Ile Ala Ser Phe Glu Asp Ile Leu His Phe Ser
     50                  55                  60

Lys Asn Gln Pro Ala Tyr Leu Gln Lys Leu Val Glu Thr Phe Leu Pro
 65                  70                  75                  80

Gly Pro Leu Thr Ile Ile Leu Glu Ala Asn Asp Arg Val Pro Tyr Trp
                 85                  90                  95

Val Asn Ser Asp Leu Ala Thr Ile Gly Phe Arg Met Pro Ser His Pro
            100                 105                 110

Ile Thr Leu Asp Leu Ile Arg Glu Thr Gly Pro Leu Ile Gly Pro Ser
        115                 120                 125

Ala Asn Ile Ser Gly Gln Ala Ser Gly Val Thr Phe Glu Gln Ile Leu
    130                 135                 140

Lys Asp Phe Asp Gln Glu Val Leu Gly Leu Glu Asp Asp Ala Phe Leu
145                 150                 155                 160

Thr Gly Gln Asp Ser Thr Ile Val Asp Leu Ser Gly Asp Lys Val Lys
                165                 170                 175

Ile Leu Pro Lys Ala Gln Leu Asn Glu Lys Ile Phe Leu Leu Gly Cys
```

-continued

```
            180                 185                 190

Gln Arg Phe Leu Leu Arg Arg Leu Glu Met Leu Arg Asp Leu Gln Glu
        195                 200                 205

Thr Asp Val Lys Ala Ile Cys Asp Ile Asn Gln Glu Ala Leu Gly Tyr
    210                 215                 220

Thr Phe Ser Pro Glu Glu Thr Ala Ser Gln Leu Ala Arg Leu Ser Gln
225                 230                 235                 240

Asp Ser His His Phe Leu Leu Gly Tyr Glu Asp Ala Ala Asn His Val
                245                 250                 255

Leu Leu Gly Tyr Val His Ala Glu Val Tyr Glu Ser Leu Tyr Ser Lys
            260                 265                 270

Ala Gly Phe Asn Ile Leu Ala Leu Ala Val Ser Pro Gln Ala Gln Gly
        275                 280                 285

Gln Gly Ile Gly Lys Ser Leu Leu Gln Gly Leu Glu Gln Glu Ala Lys
    290                 295                 300

Arg Cys Gly Tyr Gly Phe Ile Arg Leu Asn Ser Ala Asn His Arg Leu
305                 310                 315                 320

Gly Ala His Ala Phe Tyr Glu Lys Val Gly Tyr Thr Cys Asp Lys Met
                325                 330                 335

Gln Lys Arg Phe Ile Arg Ile Phe
            340


<210> SEQ ID NO 47
<211> LENGTH: 1200
<212> TYPE: DNA
<213> ORGANISM: Streptococcus pneumoniae
<220> FEATURE:
<221> NAME/KEY: CDS
<222> LOCATION: (95)...(1126)

<400> SEQUENCE: 47

caatgtgttc ccgaactttt tagaaaacat cttcctgaaa aaagagttcg aacactcaaa      60

gaccaatttg gtcaaaatag gatggttgtg gttg atg atg gac agg att aga caa     115
                                      Met Met Asp Arg Ile Arg Gln
                                        1               5

gag ttg gaa aag ggt gga gct gtc gtt cta cct aca gag act gtt tat       163
Glu Leu Glu Lys Gly Gly Ala Val Val Leu Pro Thr Glu Thr Val Tyr
         10                  15                  20

ggt ctt ttt tcc aag gcc tta gat gaa aaa gca gtt gac cat gtt tac       211
Gly Leu Phe Ser Lys Ala Leu Asp Glu Lys Ala Val Asp His Val Tyr
     25                  30                  35

caa ctc aaa cgt cgt cct aga gat aag gca ctc aat ctc aat atc gcc       259
Gln Leu Lys Arg Arg Pro Arg Asp Lys Ala Leu Asn Leu Asn Ile Ala
 40                  45                  50                  55

tct ttc gag gac atc ttg cac ttt tca aag aat cag cca gct tat cta       307
Ser Phe Glu Asp Ile Leu His Phe Ser Lys Asn Gln Pro Ala Tyr Leu
                 60                  65                  70

caa aaa ctt gta gag acc ttt ttg cca ggt ccc ttg acc att att ctc       355
Gln Lys Leu Val Glu Thr Phe Leu Pro Gly Pro Leu Thr Ile Ile Leu
             75                  80                  85

gaa gcc aat gac cga gtt ccc tat tgg gta aat tct gac ctt gca act       403
Glu Ala Asn Asp Arg Val Pro Tyr Trp Val Asn Ser Asp Leu Ala Thr
         90                  95                 100

att gga ttt cgg atg ccc agt cac cct atc aca ctg gat tta att cga       451
Ile Gly Phe Arg Met Pro Ser His Pro Ile Thr Leu Asp Leu Ile Arg
    105                 110                 115

gag aca ggt ccc ttg att ggg ccg tct gcc aat atc tca ggt cag gca       499
Glu Thr Gly Pro Leu Ile Gly Pro Ser Ala Asn Ile Ser Gly Gln Ala
```

-continued

```
120                 125                 130                 135

agt ggt gta acc ttt gaa caa att ctg aag gat ttt gac caa gag gtt      547
Ser Gly Val Thr Phe Glu Gln Ile Leu Lys Asp Phe Asp Gln Glu Val
                140                 145                 150

ctg ggt ctg gaa gac gat gct ttt cta act gga cag gat tca act att      595
Leu Gly Leu Glu Asp Asp Ala Phe Leu Thr Gly Gln Asp Ser Thr Ile
            155                 160                 165

gtg gat ttg tct gga gac aag gtg aaa atc tta ccc aag gcg caa tta      643
Val Asp Leu Ser Gly Asp Lys Val Lys Ile Leu Pro Lys Ala Gln Leu
        170                 175                 180

aac gag aag ata ttc ttg ctc ggt tgc cag aga ttt ctt ttg agg agg      691
Asn Glu Lys Ile Phe Leu Leu Gly Cys Gln Arg Phe Leu Leu Arg Arg
    185                 190                 195

ctt gaa atg cta aga gat ttg caa gaa aca gat gtg aaa gcg ata tgt      739
Leu Glu Met Leu Arg Asp Leu Gln Glu Thr Asp Val Lys Ala Ile Cys
200                 205                 210                 215

gac atc aac caa gag gct ttg ggt tat act ttt agt cca gag gaa acg      787
Asp Ile Asn Gln Glu Ala Leu Gly Tyr Thr Phe Ser Pro Glu Glu Thr
                220                 225                 230

gct agc caa cta gct aga ctg tct cag gat tcc cat cat ttc cta ctt      835
Ala Ser Gln Leu Ala Arg Leu Ser Gln Asp Ser His His Phe Leu Leu
            235                 240                 245

ggc tat gag gat gca gct aat cat gtc tta ctt gga tat gtc cac gct      883
Gly Tyr Glu Asp Ala Ala Asn His Val Leu Leu Gly Tyr Val His Ala
        250                 255                 260

gaa gtt tac gaa tca ctc tat tcc aaa gca gga ttt aat atc tta gct      931
Glu Val Tyr Glu Ser Leu Tyr Ser Lys Ala Gly Phe Asn Ile Leu Ala
    265                 270                 275

tta gca gtt tca cct caa gcg caa ggt caa ggt atc ggt aaa agt tta      979
Leu Ala Val Ser Pro Gln Ala Gln Gly Gln Gly Ile Gly Lys Ser Leu
280                 285                 290                 295

cta caa ggg ttg gaa caa gaa gcc aaa aga tgt ggt tat ggg ttt atc     1027
Leu Gln Gly Leu Glu Gln Glu Ala Lys Arg Cys Gly Tyr Gly Phe Ile
                300                 305                 310

cgc tta aat tct gcc aat cat cgt ctg ggt gct cat gca ttt tat gaa     1075
Arg Leu Asn Ser Ala Asn His Arg Leu Gly Ala His Ala Phe Tyr Glu
            315                 320                 325

aaa gtt ggc tat act tgt gat aaa atg cag aaa cgg ttt att cgc atc     1123
Lys Val Gly Tyr Thr Cys Asp Lys Met Gln Lys Arg Phe Ile Arg Ile
        330                 335                 340

ttt tagtttgatt ttcttattgt aaaatcaaac taatggacta gtcacacaat          1176
Phe

aaaggagaag acctatgatt tttg                                          1200


<210> SEQ ID NO 48
<211> LENGTH: 1200
<212> TYPE: DNA
<213> ORGANISM: Streptococcus pneumoniae

<400> SEQUENCE: 48

gttacacaag ggcttgaaaa atcttttgta gaaggacttt tttctcaagc ttgtgagttt     60

ctggttaaac cagttttatc ctaccaacac caactactac ctgtcctaat ctgttctcaa    120

ccttttccca cctcgacagc aagatggatg tctctgacaa ataccagaaa aaaggttccg    180

gaatctactt tttcgtcaac tggtacaaat ggttgagttt gcagcaggat ctctattccg    240

tgagttagag ttatagcgga gaaagctcct gtagaacgtg aaaagtttct tagtcggtcg    300

aatagatgtt tttgaacatc tctggaaaaa cggtccaggg aactggtaat aagagcttcg    360
```

-continued

```
gttactggct caagggataa cccatttaag actggaacgt tgataaccta aagcctacgg    420

gtcagtggga tagtgtgacc taaattaagc tctctgtcca gggaactaac ccggcagacg    480

gttatagagt ccagtccgtt caccacattg gaaacttgtt taagacttcc taaaactggt    540

tctccaagac ccagaccttc tgctacgaaa agattgacct gtcctaagtt gataacacct    600

aaacagacct ctgttccact tttagaatgg gttccgcgtt aatttgctct tctataagaa    660

cgagccaacg gtctctaaag aaaactcctc cgaactttac gattctctaa acgttctttg    720

tctacacttt cgctatacac tgtagttggt tctccgaaac ccaatatgaa aatcaggtct    780

cctttgccga tcggttgatc gatctgacag agtcctaagg gtagtaaagg atgaaccgat    840

actcctacgt cgattagtac agaatgaacc tatacaggtg cgacttcaaa tgcttagtga    900

gataaggttt cgtcctaaat tatagaatcg aaatcgtcaa agtggagttc gcgttccagt    960

tccatagcca ttttcaaatg atgttcccaa ccttgttctt cggttttcta caccaatacc   1020

caaataggcg aatttaagac ggttagtagc agacccacga gtacgtaaaa tactttttca   1080

accgatatga acactatttt acgtctttgc caaataagcg tagaaaatca aactaaaaga   1140

ataacatttt agtttgatta cctgatcagt gtgttatttc ctcttctgga tactaaaaac   1200
```

```
<210> SEQ ID NO 49
<211> LENGTH: 399
<212> TYPE: PRT
<213> ORGANISM: Streptococcus pneumoniae

<400> SEQUENCE: 49

Met Phe Leu Asp Thr Ala Lys Ile Lys Val Lys Ala Gly Asn Gly Gly
  1               5                  10                  15

Asp Gly Met Val Ala Phe Arg Arg Glu Lys Tyr Val Pro Asn Gly Gly
             20                  25                  30

Pro Trp Gly Gly Asp Gly Gly Arg Gly Gly Asn Val Val Phe Val Val
         35                  40                  45

Asp Glu Gly Leu Arg Thr Leu Met Asp Phe Arg Tyr Asn Arg His Phe
     50                  55                  60

Lys Ala Asp Ser Gly Glu Lys Gly Met Thr Lys Gly Met His Gly Arg
 65                  70                  75                  80

Gly Ala Glu Asp Leu Arg Val Arg Val Pro Gln Gly Thr Thr Val Arg
                 85                  90                  95

Asp Ala Glu Thr Gly Lys Val Leu Thr Asp Leu Ile Glu His Gly Gln
            100                 105                 110

Glu Phe Ile Val Ala His Gly Gly Arg Gly Gly Arg Gly Asn Ile Arg
        115                 120                 125

Phe Ala Thr Pro Lys Asn Pro Ala Pro Glu Ile Ser Glu Asn Gly Glu
    130                 135                 140

Pro Gly Gln Glu Arg Glu Leu Gln Leu Glu Leu Lys Ile Leu Ala Asp
145                 150                 155                 160

Val Gly Leu Val Gly Phe Pro Ser Val Gly Lys Ser Thr Leu Leu Ser
                165                 170                 175

Val Ile Thr Ser Ala Lys Pro Lys Ile Gly Ala Tyr His Phe Thr Thr
            180                 185                 190

Ile Val Pro Asn Leu Gly Met Val Arg Thr Gln Ser Gly Glu Ser Phe
        195                 200                 205

Ala Val Ala Asp Leu Pro Gly Leu Ile Glu Gly Ala Ser Gln Gly Val
    210                 215                 220

Gly Leu Gly Thr Gln Phe Leu Arg His Ile Glu Arg Thr Arg Val Ile
```

-continued

```
225                 230                 235                 240

Leu His Ile Ile Asp Met Ser Ala Ser Glu Gly Arg Asp Pro Tyr Glu
                245                 250                 255

Asp Tyr Leu Ala Ile Asn Lys Glu Leu Glu Ser Tyr Asn Leu Arg Leu
            260                 265                 270

Met Glu Arg Pro Gln Ile Ile Val Thr Asn Lys Met Asp Met Pro Glu
        275                 280                 285

Ser Gln Glu Asn Leu Glu Glu Phe Lys Lys Lys Leu Ala Glu Asn Tyr
    290                 295                 300

Asp Glu Phe Glu Glu Leu Pro Ala Ile Phe Pro Ile Ser Gly Leu Thr
305                 310                 315                 320

Lys Gln Gly Leu Ala Thr Leu Leu Asp Ala Thr Ala Glu Leu Leu Asp
                325                 330                 335

Lys Thr Pro Glu Phe Leu Leu Tyr Asp Glu Ser Asp Met Glu Glu Glu
            340                 345                 350

Val Tyr Tyr Gly Phe Asp Glu Glu Glu Lys Ala Phe Glu Ile Ser Arg
        355                 360                 365

Asp Asp Asp Ala Thr Trp Val Leu Ser Gly Glu Lys Leu Met Lys Leu
    370                 375                 380

Phe Asn Met Thr Asn Phe Asp Arg Asp Glu Ser Val Met Lys Leu
385                 390                 395


<210> SEQ ID NO 50
<211> LENGTH: 1441
<212> TYPE: DNA
<213> ORGANISM: Streptococcus pneumoniae
<220> FEATURE:
<221> NAME/KEY: CDS
<222> LOCATION: (243)...(1439)

<400> SEQUENCE: 50

aagataatag aaaatagaat gtaacgaatg agagaaaaat ggcatttgga gataatggaa      60

atcgtaaaaa aactatgttt gagaaaataa ccttgtttat cgtgattatc atgctagtag     120

caagtttatt gggaattttt gcaactgcaa ttggtgcctt cagtaatcta taaaattgat     180

tcaagaaaat ttagtgactg ggatttccca gccctttttt aaagtgagaa gaaataatga     240

gt atg ttt tta gat aca gct aag att aag gtc aag gct ggt aat ggt        287
   Met Phe Leu Asp Thr Ala Lys Ile Lys Val Lys Ala Gly Asn Gly
     1               5                  10                  15

ggc gat ggt atg gtt gcc ttt cgt cgt gaa aaa tat gtc cct aat gga       335
Gly Asp Gly Met Val Ala Phe Arg Arg Glu Lys Tyr Val Pro Asn Gly
                 20                  25                  30

ggc cct tgg ggt ggt gat ggt ggt cgt gga ggc aat gtg gtc ttc gtt       383
Gly Pro Trp Gly Gly Asp Gly Gly Arg Gly Gly Asn Val Val Phe Val
             35                  40                  45

gta gac gaa gga cta cgt acc ttg atg gat ttc cgc tac aat cgt cat       431
Val Asp Glu Gly Leu Arg Thr Leu Met Asp Phe Arg Tyr Asn Arg His
         50                  55                  60

ttc aag gct gat tct ggt gaa aaa ggg atg acc aaa ggg atg cat ggt       479
Phe Lys Ala Asp Ser Gly Glu Lys Gly Met Thr Lys Gly Met His Gly
     65                  70                  75

cgt ggt gct gag gac ctt aga gtt cga gta cca caa ggt acg act gtt       527
Arg Gly Ala Glu Asp Leu Arg Val Arg Val Pro Gln Gly Thr Thr Val
 80                  85                  90                  95

cgt gat gcg gag act ggc aag gtt tta aca gat ttg att gaa cat ggg       575
Arg Asp Ala Glu Thr Gly Lys Val Leu Thr Asp Leu Ile Glu His Gly
                100                 105                 110
```

-continued

```
caa gaa ttt atc gtt gcc cac ggt ggt cgt ggt gga cgt gga aat att      623
Gln Glu Phe Ile Val Ala His Gly Gly Arg Gly Gly Arg Gly Asn Ile
            115                 120                 125

cgt ttc gcg aca cca aaa aat cct gca ccg gaa atc tct gaa aat gga      671
Arg Phe Ala Thr Pro Lys Asn Pro Ala Pro Glu Ile Ser Glu Asn Gly
        130                 135                 140

gaa cca ggt cag gaa cgt gag tta caa ttg gaa cta aaa atc ttg gca      719
Glu Pro Gly Gln Glu Arg Glu Leu Gln Leu Glu Leu Lys Ile Leu Ala
    145                 150                 155

gat gtc ggt tta gta gga ttc cca tct gta ggg aag tca aca ctt tta      767
Asp Val Gly Leu Val Gly Phe Pro Ser Val Gly Lys Ser Thr Leu Leu
160                 165                 170                 175

agt gtt att acc tca gct aag cct aaa att ggt gcc tac cac ttt acc      815
Ser Val Ile Thr Ser Ala Lys Pro Lys Ile Gly Ala Tyr His Phe Thr
                180                 185                 190

act att gta cca aat tta ggt atg gtt cgc acc caa tca ggt gaa tcc      863
Thr Ile Val Pro Asn Leu Gly Met Val Arg Thr Gln Ser Gly Glu Ser
            195                 200                 205

ttt gca gta gcc gac ttg cca ggt ttg att gaa ggg gct agt caa ggt      911
Phe Ala Val Ala Asp Leu Pro Gly Leu Ile Glu Gly Ala Ser Gln Gly
        210                 215                 220

gtt ggt ttg gga act cag ttc ctc cgt cac atc gag cgt aca cgt gtt      959
Val Gly Leu Gly Thr Gln Phe Leu Arg His Ile Glu Arg Thr Arg Val
    225                 230                 235

atc ctt cac atc att gat atg tca gct agc gaa ggc cgt gat cca tat     1007
Ile Leu His Ile Ile Asp Met Ser Ala Ser Glu Gly Arg Asp Pro Tyr
240                 245                 250                 255

gag gat tac cta gct atc aat aaa gag ctg gag tct tac aat ctt cgc     1055
Glu Asp Tyr Leu Ala Ile Asn Lys Glu Leu Glu Ser Tyr Asn Leu Arg
                260                 265                 270

ctc atg gag cgt cca cag att att gta act aat aag atg gac atg cct     1103
Leu Met Glu Arg Pro Gln Ile Ile Val Thr Asn Lys Met Asp Met Pro
            275                 280                 285

gag agt cag gaa aat ctt gaa gaa ttt aag aaa aaa ttg gct gaa aat     1151
Glu Ser Gln Glu Asn Leu Glu Glu Phe Lys Lys Lys Leu Ala Glu Asn
        290                 295                 300

tat gat gaa ttt gaa gag tta cca gct atc ttc cca att tct gga ttg     1199
Tyr Asp Glu Phe Glu Glu Leu Pro Ala Ile Phe Pro Ile Ser Gly Leu
    305                 310                 315

acc aag caa ggt ctg gca aca ctt tta gat gct aca gct gaa ttg tta     1247
Thr Lys Gln Gly Leu Ala Thr Leu Leu Asp Ala Thr Ala Glu Leu Leu
320                 325                 330                 335

gac aag aca cca gaa ttt ttg ctc tac gac gag tcc gat atg gaa gaa     1295
Asp Lys Thr Pro Glu Phe Leu Leu Tyr Asp Glu Ser Asp Met Glu Glu
                340                 345                 350

gaa gtt tac tat gga ttt gac gaa gaa gaa aaa gcc ttt gaa att agt     1343
Glu Val Tyr Tyr Gly Phe Asp Glu Glu Glu Lys Ala Phe Glu Ile Ser
            355                 360                 365

cgt gat gac gat gcg aca tgg gta ctt tct ggt gaa aaa ctc atg aaa     1391
Arg Asp Asp Asp Ala Thr Trp Val Leu Ser Gly Glu Lys Leu Met Lys
        370                 375                 380

ctc ttt aat atg acc aac ttt gat cgt gat gaa tct gtc atg aaa ctt     1439
Leu Phe Asn Met Thr Asn Phe Asp Arg Asp Glu Ser Val Met Lys Leu
    385                 390                 395

ta                                                                  1441
```

<210> SEQ ID NO 51
<211> LENGTH: 1441
<212> TYPE: DNA
<213> ORGANISM: Streptococcus pneumoniae -continued

<400> SEQUENCE: 51
ttctattatc ttttatctta cattgcttac tctcttttta ccgtaaacct ctattacctt 60
tagcattttt ttgatacaaa ctcttttatt ggaacaaata gcactaatag tacgatcatc 120
gttcaaataa cccttaaaaa cgttgacgtt aaccacggaa gtcattagat attttaacta 180
agttctttta aatcactgac cctaaagggt cgggaaaaaa tttcactctt ctttattact 240
catacaaaaa tctatgtcga ttctaattcc agttccgacc attaccaccg ctaccatacc 300
aacggaaagc agcacttttt atacagggat tacctccggg aaccccacca ctaccaccag 360
cacctccgtt acaccagaag caacatctgc ttcctgatgc atggaactac ctaaaggcga 420
tgttagcagt aaagttccga ctaagaccac tttttcccta ctggtttccc tacgtaccag 480
caccacgact cctggaatct caagctcatg gtgttccatg ctgacaagca ctacgcctct 540
gaccgttcca aaattgtcta aactaacttg tacccgttct taaatagcaa cgggtgccac 600
cagcaccacc tgcaccttta taagcaaagc gctgtggttt tttaggacgt ggcctttaga 660
gacttttacc tcttggtcca gtccttgcac tcaatgttaa ccttgatttt tagaaccgtc 720
tacagccaaa tcatcctaag ggtagacatc ccttcagttg tgaaaattca caataatgga 780
gtcgattcgg attttaacca cggatggtga aatggtgata acatggttta aatccatacc 840
aagcgtgggt tagtccactt aggaaacgtc atcggctgaa cggtccaaac taacttcccc 900
gatcagttcc acaaccaaac ccttgagtca aggaggcagt gtagctcgca tgtgcacaat 960
aggaagtgta gtaactatac agtcgatcgc ttccggcact aggtatactc ctaatggatc 1020
gatagttatt tctcgacctc agaatgttag aagcggagta cctcgcaggt gtctaataac 1080
attgattatt ctacctgtac ggactctcag tccttttaga acttcttaaa ttctttttta 1140
accgactttt aatactactt aaacttctca atggtcgata gaagggttaa agacctaact 1200
ggttcgttcc agaccgttgt gaaaatctac gatgtcgact taacaatctg ttctgtggtc 1260
ttaaaaacga gatgctgctc aggctatacc ttcttcttca aatgatacct aaactgcttc 1320
ttctttttcg gaaactttaa tcagcactac tgctacgctg tacccatgaa agaccacttt 1380
ttgagtactt tgagaaatta tactggttga aactagcact acttagacag tactttgaaa 1440
t 1441

<210> SEQ ID NO 52
<211> LENGTH: 388
<212> TYPE: PRT
<213> ORGANISM: Streptococcus pneumoniae

<400> SEQUENCE: 52

Met Ala Glu Glu Arg Val Glu Pro Lys Pro Ile Asp Leu Gly Glu Tyr
1 5 10 15

Lys Phe Gly Phe His Asp Asp Val Glu Pro Val Leu Ser Thr Gly Lys
20 25 30

Gly Leu Asn Glu Gly Val Ile Arg Glu Leu Ser Ala Ala Lys Gly Glu
35 40 45

Pro Glu Trp Met Leu Glu Phe Arg Leu Lys Ser Tyr Glu Thr Phe Lys
50 55 60

Lys Met Pro Met Gln Thr Trp Gly Ala Asp Leu Ser Glu Ile Asp Phe
65 70 75 80

Asp Asp Leu Ile Tyr Tyr Gln Lys Pro Ser Asp Lys Pro Ala Arg Ser
85 90 95

-continued

```
Trp Asp Asp Val Pro Glu Lys Ile Lys Glu Thr Phe Glu Arg Ile Gly
            100                 105                 110

Ile Pro Glu Ala Glu Arg Ala Tyr Leu Ala Gly Ala Ser Ala Gln Tyr
        115                 120                 125

Glu Ser Glu Val Val Tyr His Asn Met Lys Glu Glu Phe Gln Lys Leu
    130                 135                 140

Gly Ile Ile Phe Thr Asp Thr Asp Ser Ala Leu Lys Glu Tyr Pro Asp
145                 150                 155                 160

Leu Phe Lys Gln Tyr Phe Ala Lys Leu Val Pro Pro Thr Asp Asn Lys
                165                 170                 175

Leu Ala Ala Leu Asn Ser Ala Val Trp Ser Gly Gly Thr Phe Ile Tyr
            180                 185                 190

Val Pro Lys Gly Val Lys Val Asp Ile Pro Leu Gln Thr Tyr Phe Arg
        195                 200                 205

Ile Asn Asn Glu Asn Ile Gly Gln Phe Glu Arg Thr Leu Ile Ile Val
    210                 215                 220

Asp Glu Gly Ala Ser Val His Tyr Val Glu Gly Cys Thr Ala Pro Thr
225                 230                 235                 240

Tyr Ser Ser Asn Ser Leu His Ala Ala Ile Val Glu Ile Phe Ala Leu
                245                 250                 255

Asp Gly Ala Tyr Met Arg Tyr Thr Thr Ile Gln Asn Trp Ser Asp Asn
            260                 265                 270

Val Tyr Asn Leu Val Thr Lys Arg Ala Lys Ala Gln Lys Asp Ala Thr
        275                 280                 285

Val Glu Trp Ile Asp Gly Asn Leu Gly Ala Lys Thr Thr Met Lys Tyr
    290                 295                 300

Pro Ser Val Tyr Leu Asp Gly Glu Gly Ala Arg Gly Thr Met Leu Ser
305                 310                 315                 320

Ile Ala Phe Ala Asn Ala Gly Gln His Gln Asp Thr Gly Ala Lys Met
                325                 330                 335

Ile His Asn Ala Pro His Thr Ser Ser Ser Ile Val Ser Lys Ser Ile
            340                 345                 350

Ala Lys Gly Gly Gly Lys Val Asp Tyr Arg Gly Gln Val Thr Phe Asn
        355                 360                 365

Lys Asn Ser Lys Lys Ser Val Ser His Ile Glu Cys Asp Thr Ile Ile
    370                 375                 380

Met Asp Asp Leu
385


<210> SEQ ID NO 53
<211> LENGTH: 1263
<212> TYPE: DNA
<213> ORGANISM: Streptococcus pneumoniae
<220> FEATURE:
<221> NAME/KEY: CDS
<222> LOCATION: (99)...(1262)

<400> SEQUENCE: 53

tggaatgccc ttaagaaaac aattgaaaat caagaaaaac agtaagacaa gtttcttttg      60

tcttatgaat tattagaaat gaagaaagaa aggatatt atg gct gaa gaa aga gta     116
                                          Met Ala Glu Glu Arg Val
                                            1               5

gaa cca aaa cca att gac ctt ggt gaa tat aaa ttt ggt ttc cat gac      164
Glu Pro Lys Pro Ile Asp Leu Gly Glu Tyr Lys Phe Gly Phe His Asp
            10                  15                  20

gat gta gag cct gtc tta tcg aca gga aaa gga ctc aac gaa ggt gtt      212
```

-continued

```
Asp Val Glu Pro Val Leu Ser Thr Gly Lys Gly Leu Asn Glu Gly Val
        25                  30                  35

att cgt gaa tta tct gct gct aag ggt gag cct gag tgg atg ttg gag      260
Ile Arg Glu Leu Ser Ala Ala Lys Gly Glu Pro Glu Trp Met Leu Glu
    40                  45                  50

ttc cgt ttg aag tct tat gaa acc ttc aaa aaa atg ccc atg caa act      308
Phe Arg Leu Lys Ser Tyr Glu Thr Phe Lys Lys Met Pro Met Gln Thr
 55                  60                  65                  70

tgg gga gca gac ttg tca gag att gac ttt gat gac tta atc tac tac      356
Trp Gly Ala Asp Leu Ser Glu Ile Asp Phe Asp Asp Leu Ile Tyr Tyr
                 75                  80                  85

caa aaa cca tct gac aaa cca gcc cgt tct tgg gat gat gta cct gaa      404
Gln Lys Pro Ser Asp Lys Pro Ala Arg Ser Trp Asp Asp Val Pro Glu
             90                  95                 100

aag att aaa gaa acc ttt gaa cgt atc ggg att cca gaa gct gaa cgt      452
Lys Ile Lys Glu Thr Phe Glu Arg Ile Gly Ile Pro Glu Ala Glu Arg
        105                 110                 115

gct tat tta gca ggg gct tct gcc cag tac gag tca gaa gtg gtt tac      500
Ala Tyr Leu Ala Gly Ala Ser Ala Gln Tyr Glu Ser Glu Val Val Tyr
    120                 125                 130

cac aac atg aag gaa gag ttc caa aaa tta ggt att atc ttt aca gat      548
His Asn Met Lys Glu Glu Phe Gln Lys Leu Gly Ile Ile Phe Thr Asp
135                 140                 145                 150

aca gat tcc gca ctc aag gaa tac cca gac tta ttt aaa caa tac ttt      596
Thr Asp Ser Ala Leu Lys Glu Tyr Pro Asp Leu Phe Lys Gln Tyr Phe
                155                 160                 165

gcg aag ttg gta ccg ccg aca gat aac aag ttg gca gcc ctc aac tca      644
Ala Lys Leu Val Pro Pro Thr Asp Asn Lys Leu Ala Ala Leu Asn Ser
            170                 175                 180

gca gta tgg tcg ggt gga act ttt atc tac gtg cca aaa ggt gtc aag      692
Ala Val Trp Ser Gly Gly Thr Phe Ile Tyr Val Pro Lys Gly Val Lys
        185                 190                 195

gta gat att cca ctt caa act tat ttc cgt atc aat aac gaa aat ata      740
Val Asp Ile Pro Leu Gln Thr Tyr Phe Arg Ile Asn Asn Glu Asn Ile
    200                 205                 210

ggt cag ttc gaa cgt acc ttg att atc gtt gat gag gga gca agc gtc      788
Gly Gln Phe Glu Arg Thr Leu Ile Ile Val Asp Glu Gly Ala Ser Val
215                 220                 225                 230

cac tac gta gaa gga tgt aca gca cca aca tat tca agc aat agc tta      836
His Tyr Val Glu Gly Cys Thr Ala Pro Thr Tyr Ser Ser Asn Ser Leu
                235                 240                 245

cac gct gcc att gta gaa att ttt gct ttg gac gga gct tat atg cgt      884
His Ala Ala Ile Val Glu Ile Phe Ala Leu Asp Gly Ala Tyr Met Arg
            250                 255                 260

tat aca act atc caa aac tgg tct gat aac gtc tat aac ttg gta aca      932
Tyr Thr Thr Ile Gln Asn Trp Ser Asp Asn Val Tyr Asn Leu Val Thr
        265                 270                 275

aag cgt gct aag gct caa aag gat gcc act gtt gag tgg att gat gga      980
Lys Arg Ala Lys Ala Gln Lys Asp Ala Thr Val Glu Trp Ile Asp Gly
    280                 285                 290

aac ttg ggt gcc aaa acg act atg aaa tat cca tct gtt tac ctt gat     1028
Asn Leu Gly Ala Lys Thr Thr Met Lys Tyr Pro Ser Val Tyr Leu Asp
295                 300                 305                 310

gga gaa gga gcg cgt ggt acc atg ctc tct atc gcc ttt gct aat gca     1076
Gly Glu Gly Ala Arg Gly Thr Met Leu Ser Ile Ala Phe Ala Asn Ala
                315                 320                 325

ggg caa cac caa gac acg ggt gct aag atg att cac aat gct cca cat     1124
Gly Gln His Gln Asp Thr Gly Ala Lys Met Ile His Asn Ala Pro His
            330                 335                 340
```

-continued

```
acc agc tcg tct att gtg tct aaa tcc atc gct aaa ggt gga gga aag      1172
Thr Ser Ser Ser Ile Val Ser Lys Ser Ile Ala Lys Gly Gly Gly Lys
        345                 350                 355

gtt gac tac cgt gga caa gtc acc ttt aac aag aac tct aag aaa tct      1220
Val Asp Tyr Arg Gly Gln Val Thr Phe Asn Lys Asn Ser Lys Lys Ser
    360                 365                 370

gtt tcc cac att gaa tgt gat acc att atc atg gat gac ctt              1262
Val Ser His Ile Glu Cys Asp Thr Ile Ile Met Asp Asp Leu
375                 380                 385

t                                                                    1263
```

<210> SEQ ID NO 54
<211> LENGTH: 1263
<212> TYPE: DNA
<213> ORGANISM: Streptococcus pneumoniae

<400> SEQUENCE: 54

```
accttacggg aattcttttg ttaactttta gttctttttg tcattctgtt caaagaaaac     60

agaatactta ataatcttta cttctttctt tcctataata ccgacttctt tctcatcttg    120

gttttggtta actggaacca cttatattta aaccaaaggt actgctacat ctcggacaga    180

atagctgtcc ttttcctgag ttgcttccac aataagcact taatagacga cgattcccac    240

tcggactcac ctacaacctc aaggcaaact tcagaatact ttggaagttt ttttacgggt    300

acgtttgaac ccctcgtctg aacagtctct aactgaaact actgaattag atgatggttt    360

ttggtagact gtttggtcgg gcaagaaccc tactacatgg acttttctaa tttctttgga    420

aacttgcata gccctaaggt cttcgacttg cacgaataaa tcgtccccga agacgggtca    480

tgctcagtct tcaccaaatg gtgttgtact tccttctcaa ggtttttaat ccataataga    540

aatgtctatg tctaaggcgt gagttcctta tgggtctgaa taaatttgtt atgaaacgct    600

tcaaccatgg cggctgtcta ttgttcaacc gtcgggagtt gagtcgtcat accagcccac    660

cttgaaaata gatgcacggt tttccacagt tccatctata aggtgaagtt tgaataaagg    720

catagttatt gcttttatat ccagtcaagc ttgcatggaa ctaatagcaa ctactccctc    780

gttcgcaggt gatgcatctt cctacatgtc gtggttgtat aagttcgtta tcgaatgtgc    840

gacggtaaca tctttaaaaa cgaaacctgc ctcgaatata cgcaatatgt tgataggttt    900

tgaccagact attgcagata ttgaaccatt gtttcgcacg attccgagtt ttcctacggt    960

gacaactcac ctaactacct ttgaacccac ggttttgctg atactttata ggtagacaaa   1020

tggaactacc tcttcctcgc gcaccatggt acgagagata gcggaaacga ttacgtcccg   1080

ttgtggttct gtgcccacga ttctactaag tgttacgagg tgtatggtcg agcagataac   1140

acagatttag gtagcgattt ccacctcctt tccaactgat ggcacctgtt cagtggaaat   1200

tgttcttgag attctttaga caaagggtgt aacttacact atggtaatag tacctactgg   1260

aaa                                                                 1263
```

<210> SEQ ID NO 55
<211> LENGTH: 136
<212> TYPE: PRT
<213> ORGANISM: Streptococcus pneumoniae

<400> SEQUENCE: 55

```
Ala Gly Ile Tyr Glu Gln Val Ser Tyr Leu Lys Glu Gly Arg Ser Val
  1               5                  10                  15

Tyr Leu Thr Arg Tyr Asn Glu Val Gln Thr Glu Thr Ala Thr Leu Ile
             20                  25                  30
```

-continued

```
Leu Gly Ala Ile Val Gly Ile Ala Ser Ser Leu Leu Leu Phe Tyr Ser
        35                  40                  45

Val Asn Leu Leu Tyr Phe Glu Gln Phe Arg Arg Asp Ile Leu Ile Lys
     50                  55                  60

Arg Ile Ser Gly Leu Arg Phe Phe Glu Thr His Ala Gln Tyr Met Val
 65                  70                  75                  80

Ser Gln Phe Ala Ser Phe Val Phe Gly Ala Ser Leu Phe Ile Leu Ser
                 85                  90                  95

Ser Arg Asp Leu Val Ile Gly Leu Leu Thr Leu Leu Val Phe Leu Ala
            100                 105                 110

Ser Ala Val Leu Thr Leu Tyr Arg Gln Ala Gln Lys Glu Ser Arg Val
        115                 120                 125

Ser Met Thr Ile Met Lys Gly Lys
    130                 135


<210> SEQ ID NO 56
<211> LENGTH: 481
<212> TYPE: DNA
<213> ORGANISM: Streptococcus pneumoniae
<220> FEATURE:
<221> NAME/KEY: CDS
<222> LOCATION: (2)...(409)

<400> SEQUENCE: 56

a gct gga att tat gag caa gta tcc tat ctt aaa gaa gga aga agt gtt      49
  Ala Gly Ile Tyr Glu Gln Val Ser Tyr Leu Lys Glu Gly Arg Ser Val
    1               5                  10                  15

tat cta act cgt tat aat gaa gtt caa act gaa aca gca act tta atc        97
Tyr Leu Thr Arg Tyr Asn Glu Val Gln Thr Glu Thr Ala Thr Leu Ile
            20                  25                  30

tta gga gct att gtg ggg ata gct agt tcc ttg tta ctc ttt tat tct       145
Leu Gly Ala Ile Val Gly Ile Ala Ser Ser Leu Leu Leu Phe Tyr Ser
        35                  40                  45

gtc aat ctt cta tat ttc gag caa ttc cgc cga gat atc ttg att aaa       193
Val Asn Leu Leu Tyr Phe Glu Gln Phe Arg Arg Asp Ile Leu Ile Lys
     50                  55                  60

cga att tca ggt tta cga ttt ttt gaa aca cat gct cag tat atg gtt       241
Arg Ile Ser Gly Leu Arg Phe Phe Glu Thr His Ala Gln Tyr Met Val
 65                  70                  75                  80

agt caa ttt gcc agt ttt gta ttt ggt gct agt ctc ttt att tta agc       289
Ser Gln Phe Ala Ser Phe Val Phe Gly Ala Ser Leu Phe Ile Leu Ser
                 85                  90                  95

agt cga gac ttg gtg att ggc ttg ctc act tta tta gtc ttt cta gct       337
Ser Arg Asp Leu Val Ile Gly Leu Leu Thr Leu Leu Val Phe Leu Ala
            100                 105                 110

agt gca gtt ttg acg ctt tac cgt caa gcg cag aaa gaa tct cgt gtt       385
Ser Ala Val Leu Thr Leu Tyr Arg Gln Ala Gln Lys Glu Ser Arg Val
        115                 120                 125

tct atg aca att atg aaa gga aaa taggatgatt gaactaaaga atatatctaa      439
Ser Met Thr Ile Met Lys Gly Lys
    130                 135

aaaatttgga agccgtcagc tattttcaga tacgaatctt ta                        481


<210> SEQ ID NO 57
<211> LENGTH: 481
<212> TYPE: DNA
<213> ORGANISM: Streptococcus pneumoniae

<400> SEQUENCE: 57
```

-continued

```
tcgaccttaa atactcgttc ataggataga atttcttcct tcttcacaaa tagattgagc     60

aatattactt caagtttgac tttgtcgttg aaattagaat cctcgataac acccctatcg    120

atcaaggaac aatgagaaaa taagacagtt agaagatata aagctcgtta aggcggctct    180

atagaactaa tttgcttaaa gtccaaatgc taaaaaactt tgtgtacgag tcatatacca    240

atcagttaaa cggtcaaaac ataaaccacg atcagagaaa taaaattcgt cagctctgaa    300

ccactaaccg aacgagtgaa ataatcagaa agatcgatca cgtcaaaact gcgaaatggc    360

agttcgcgtc tttcttagag cacaaagata ctgttaatac tttcctttta tcctactaac    420

ttgatttctt atatagattt tttaaacctt cggcagtcga taaaagtcta tgcttagaaa    480

t                                                                    481
```

<210> SEQ ID NO 58
<211> LENGTH: 195
<212> TYPE: PRT
<213> ORGANISM: Streptococcus pneumoniae

<400> SEQUENCE: 58

```
Met Thr Thr Gly Val Tyr Cys Phe Pro Phe Thr Tyr Ile Leu Phe Phe
  1               5                  10                  15

Phe Tyr Leu Met Asn Asn Tyr Phe Asn Arg Leu Glu Cys Arg Ile Arg
             20                  25                  30

Leu Lys Ser Ile Lys His Phe Thr Ser Phe Ser Phe Lys Leu Ala Ala
         35                  40                  45

Leu Ser Thr Gly Ile Trp Thr Ala Thr Leu Phe Leu Leu Ile Phe Leu
     50                  55                  60

Ile Ala Phe Ser Asn Gly Phe Ser Phe Ser Leu Glu Ile Lys Glu Val
 65                  70                  75                  80

Asp Phe Leu Arg Glu Phe Tyr Gly Ile Ser Ile Ala Asn Asn Ala Ser
                 85                  90                  95

Phe Phe Ile Gly Phe Phe Phe Ser Tyr Ile Ala Tyr Tyr Phe Phe Leu
            100                 105                 110

Ser Leu Leu Thr Ile Ser Ser Phe Ser Trp Phe Lys Lys Ser Asn Met
        115                 120                 125

Ser Leu Val Phe Leu Phe Thr Phe Leu Phe Val Glu Ser Leu Phe Trp
    130                 135                 140

Ile Tyr Gln Leu Asp Asn Gly Ile Ile Gly Leu Leu Pro Ile Phe Gln
145                 150                 155                 160

Tyr Met Val Asn Ser Asn Pro Tyr Ala Leu Ile Tyr Trp Leu Thr Leu
                165                 170                 175

Leu Ser Ile Ile Ile Pro Leu Thr Val Phe Ser Val His Arg Asn Trp
            180                 185                 190

Arg Arg Val
        195
```

<210> SEQ ID NO 59
<211> LENGTH: 700
<212> TYPE: DNA
<213> ORGANISM: Streptococcus pneumoniae
<220> FEATURE:
<221> NAME/KEY: CDS
<222> LOCATION: (90)...(675)

<400> SEQUENCE: 59

```
ttttatctag tacagtatat ttattgcgct gtcgccaata ttcaatccat ccaaatgtat     60

tagaatggat cttagtttta cttcaagat atg acg act gga gta tat tgc ttt      113
```

-continued

```
                               Met Thr Thr Gly Val Tyr Cys Phe
                                 1               5

ccg ttc aca tat ata ttg ttc ttt ttt tat ttg atg aat aac tat ttt      161
Pro Phe Thr Tyr Ile Leu Phe Phe Phe Tyr Leu Met Asn Asn Tyr Phe
     10                  15                  20

aat agg ttg gag tgt cgc att cgt ctg aaa tca att aag cac ttt acc      209
Asn Arg Leu Glu Cys Arg Ile Arg Leu Lys Ser Ile Lys His Phe Thr
 25                  30                  35                  40

agt ttt agt ttc aaa tta gca gct ctt agt acg ggg att tgg acg gcg      257
Ser Phe Ser Phe Lys Leu Ala Ala Leu Ser Thr Gly Ile Trp Thr Ala
                 45                  50                  55

act tta ttt tta ttg att ttt cta att gca ttt agt aat ggt ttt agc      305
Thr Leu Phe Leu Leu Ile Phe Leu Ile Ala Phe Ser Asn Gly Phe Ser
             60                  65                  70

ttc tct ttg gag ata aag gag gtt gat ttt tta aga gaa ttt tat ggt      353
Phe Ser Leu Glu Ile Lys Glu Val Asp Phe Leu Arg Glu Phe Tyr Gly
         75                  80                  85

ata agt att gca aac aat gct agt ttc ttt ata gga ttt ttt ttc tct      401
Ile Ser Ile Ala Asn Asn Ala Ser Phe Phe Ile Gly Phe Phe Phe Ser
     90                  95                 100

tat ata gca tac tat ttc ttt tta tcc tta ctt act att agc agt ttt      449
Tyr Ile Ala Tyr Tyr Phe Phe Leu Ser Leu Leu Thr Ile Ser Ser Phe
105                 110                 115                 120

tct tgg ttt aaa aaa tca aac atg agc tta gta ttt ctg ttt act ttt      497
Ser Trp Phe Lys Lys Ser Asn Met Ser Leu Val Phe Leu Phe Thr Phe
                125                 130                 135

tta ttt gta gaa tcc tta ttc tgg att tat cag ttg gac aat ggg ata      545
Leu Phe Val Glu Ser Leu Phe Trp Ile Tyr Gln Leu Asp Asn Gly Ile
            140                 145                 150

att gga tta ttg cca att ttt cag tat atg gta aat tcc aat ccg tat      593
Ile Gly Leu Leu Pro Ile Phe Gln Tyr Met Val Asn Ser Asn Pro Tyr
        155                 160                 165

gca ttg att tat tgg ctt aca tta cta tct atc ata att cca ttg act      641
Ala Leu Ile Tyr Trp Leu Thr Leu Leu Ser Ile Ile Ile Pro Leu Thr
    170                 175                 180

gta ttt tct gtt cat aga aac tgg agg aga gtg t aaaagttgga             685
Val Phe Ser Val His Arg Asn Trp Arg Arg Val
185                 190                 195

aatgggaaag ttaag                                                     700


<210> SEQ ID NO 60
<211> LENGTH: 700
<212> TYPE: DNA
<213> ORGANISM: Streptococcus pneumoniae

<400> SEQUENCE: 60

aaaatagatc atgtcatata aataacgcga cagcggttat aagttaggta ggtttacata     60

atcttaccta gaatcaaaat gaagttctat actgctgacc tcatataacg aaaggcaagt    120

gtatatataa caagaaaaaa ataaactact tattgataaa attatccaac ctcacagcgt    180

aagcagactt tagttaattc gtgaaatggt caaaatcaaa gtttaatcgt cgagaatcat    240

gcccctaaac ctgccgctga aataaaaata actaaaaaga ttaacgtaaa tcattaccaa    300

aatcgaagag aaacctctat ttcctccaac taaaaaattc tcttaaaata ccatattcat    360

aacgtttgtt acgatcaaag aaatatccta aaaaaaagag aatatatcgt atgataaaga    420

aaaataggaa tgaatgataa tcgtcaaaaa gaaccaaatt ttttagtttg tactcgaatc    480

ataaagacaa atgaaaaaat aaacatctta ggaataagac ctaaatagtc aacctgttac    540
```

-continued

```
cctattaacc taataacggt taaaaagtca tataccattt aaggttaggc atacgtaact    600

aaataaccga atgtaatgat agatagtatt aaggtaactg acataaaaga caagtatctt    660

tgacctcctc tcacattttc aacctttacc ctttcaattc                          700


<210> SEQ ID NO 61
<211> LENGTH: 416
<212> TYPE: PRT
<213> ORGANISM: Streptococcus pneumoniae

<400> SEQUENCE: 61

Met Glu Leu Val His Gly Ile Ser Thr His Phe Ile Gln Ser Lys Lys
  1               5                  10                  15

Phe Lys Thr Asn Lys Ile Thr Val Arg Phe Thr Ala Pro Leu Ser Leu
             20                  25                  30

Asp Thr Ile Ala Gly His Met Leu Ser Ala Ser Met Leu Glu Thr Ala
         35                  40                  45

Asn Gln Met Tyr Pro Thr Ser Gln Asp Leu Arg Arg His Leu Ala Ser
     50                  55                  60

Leu Tyr Gly Thr Asp Met Ser Thr Asn Cys Phe Arg Arg Gly Gln Ser
 65                  70                  75                  80

His Ile Ile Glu Leu Thr Phe Thr Tyr Val Arg Asp Glu Phe Leu Ser
                 85                  90                  95

Arg Lys Asn Val Leu Thr Ser Gln Ile Leu Glu Leu Val Lys Glu Thr
            100                 105                 110

Leu Phe Ser Pro Ala Val Val Asp Asn Gly Phe Asp Pro Ala Leu Phe
        115                 120                 125

Glu Ile Glu Lys Lys Gln Leu Leu Ala Ser Leu Ala Ala Asp Met Asp
    130                 135                 140

Asp Ser Phe Tyr Phe Ala His Lys Glu Leu Asp Lys Leu Phe Phe His
145                 150                 155                 160

Asp Glu Arg Leu Gln Leu Glu Tyr Ser Asp Leu Arg Asn Arg Ile Leu
                165                 170                 175

Ala Glu Thr Pro Gln Ser Ser Tyr Ser Cys Phe Gln Glu Phe Leu Ala
            180                 185                 190

Asn Asp Arg Ile Asp Phe Phe Phe Leu Gly Asp Phe Asn Glu Val Glu
        195                 200                 205

Ile Gln Asn Val Leu Glu Ser Phe Gly Phe Lys Gly Arg Lys Gly Asp
    210                 215                 220

Val Lys Val Gln Tyr Cys Gln Pro Tyr Ser Asn Ile Leu Gln Glu Gly
225                 230                 235                 240

Met Val Arg Lys Asn Val Gly Gln Ser Ile Leu Glu Leu Gly Tyr His
                245                 250                 255

Tyr Arg Ser Lys Tyr Gly Asp Glu Gln His Leu Pro Met Ile Val Met
            260                 265                 270

Asn Gly Leu Leu Gly Gly Phe Ala His Ser Lys Leu Phe Thr Asn Val
        275                 280                 285

Arg Glu Asn Ala Gly Leu Ala Tyr Thr Ile Ser Ser Glu Leu Asp Leu
    290                 295                 300

Phe Ser Gly Phe Leu Arg Met Tyr Ala Gly Ile Asn Arg Glu Asn Arg
305                 310                 315                 320

Asn Gln Ala Arg Lys Met Met Asn Asn Gln Leu Leu Asp Leu Lys Lys
                325                 330                 335

Gly Tyr Phe Thr Glu Phe Glu Leu Asn Gln Thr Lys Glu Met Ile Arg
            340                 345                 350
```

-continued

```
Trp Ser Leu Leu Leu Ser Gln Asp Asn Gln Ser Ser Leu Ile Glu Arg
        355                 360                 365

Ala Tyr Gln Asn Ala Leu Phe Gly Lys Ser Ser Ala Asp Phe Lys Ser
    370                 375                 380

Trp Ile Ala Lys Leu Glu Gln Ile Asp Lys Asp Ala Ile Cys Arg Val
385                 390                 395                 400

Ala Asn Asn Val Lys Leu Gln Ala Ile Tyr Phe Met Glu Gly Ile Glu
                405                 410                 415


<210> SEQ ID NO 62
<211> LENGTH: 1400
<212> TYPE: DNA
<213> ORGANISM: Streptococcus pneumoniae
<220> FEATURE:
<221> NAME/KEY: CDS
<222> LOCATION: (64)...(1311)

<400> SEQUENCE: 62

agggaacaag aaaatttcag gttttcgtga tataatagaa gtctgtatat aaggaggtaa      60

atc atg gag tta gtg cat gga att tca aca cat ttt atc caa tca aaa       108
    Met Glu Leu Val His Gly Ile Ser Thr His Phe Ile Gln Ser Lys
      1               5                  10                  15

aag ttt aaa aca aac aaa att acc gtg cgt ttt acc gct cca tta tcc       156
Lys Phe Lys Thr Asn Lys Ile Thr Val Arg Phe Thr Ala Pro Leu Ser
                 20                  25                  30

ctt gat acg att gca ggt cac atg ttg agt gca agt atg cta gag act       204
Leu Asp Thr Ile Ala Gly His Met Leu Ser Ala Ser Met Leu Glu Thr
             35                  40                  45

gct aat cag atg tac ccc act tct caa gat ttg agg aga cac ttg gcc       252
Ala Asn Gln Met Tyr Pro Thr Ser Gln Asp Leu Arg Arg His Leu Ala
         50                  55                  60

agt cta tac ggt aca gat atg tca acc aat tgt ttc aga aga ggg caa       300
Ser Leu Tyr Gly Thr Asp Met Ser Thr Asn Cys Phe Arg Arg Gly Gln
     65                  70                  75

agc cac att ata gaa ttg aca ttt acc tat gtt cgt gat gag ttt tta       348
Ser His Ile Ile Glu Leu Thr Phe Thr Tyr Val Arg Asp Glu Phe Leu
 80                  85                  90                  95

agt agg aaa aac gtg cta acc tct cag att ttg gaa ctt gta aaa gaa       396
Ser Arg Lys Asn Val Leu Thr Ser Gln Ile Leu Glu Leu Val Lys Glu
                100                 105                 110

act ctt ttt tca ccc gca gta gtt gat aat ggg ttt gat ccg gcc tta       444
Thr Leu Phe Ser Pro Ala Val Val Asp Asn Gly Phe Asp Pro Ala Leu
            115                 120                 125

ttt gaa att gag aaa aaa caa ttg cta gca agt tta gca gct gat atg       492
Phe Glu Ile Glu Lys Lys Gln Leu Leu Ala Ser Leu Ala Ala Asp Met
        130                 135                 140

gat gat tct ttt tat ttt gca cat aaa gaa ttg gat aaa ttg ttt ttt       540
Asp Asp Ser Phe Tyr Phe Ala His Lys Glu Leu Asp Lys Leu Phe Phe
    145                 150                 155

cat gat gaa cgt ctt caa ttg gaa tat agt gat tta cga aat cgt att       588
His Asp Glu Arg Leu Gln Leu Glu Tyr Ser Asp Leu Arg Asn Arg Ile
160                 165                 170                 175

tta gct gaa act cca caa agt tct tat tct tgt ttc caa gaa ttt tta       636
Leu Ala Glu Thr Pro Gln Ser Ser Tyr Ser Cys Phe Gln Glu Phe Leu
                180                 185                 190

gcc aat gat cga ata gat ttc ttt ttc cta ggt gat ttt aat gag gtt       684
Ala Asn Asp Arg Ile Asp Phe Phe Phe Leu Gly Asp Phe Asn Glu Val
            195                 200                 205

gaa att caa aat gta tta gaa tca ttt ggc ttt aaa ggt cga aaa gga       732
```

-continued

```
Glu Ile Gln Asn Val Leu Glu Ser Phe Gly Phe Lys Gly Arg Lys Gly
        210                 215                 220

gat gtg aag gtt cag tat tgt caa cct tat tct aat atc ctt cag gaa      780
Asp Val Lys Val Gln Tyr Cys Gln Pro Tyr Ser Asn Ile Leu Gln Glu
    225                 230                 235

ggt atg gtt cgg aaa aat gtg gga caa tcc att ttg gaa tta ggt tat      828
Gly Met Val Arg Lys Asn Val Gly Gln Ser Ile Leu Glu Leu Gly Tyr
240                 245                 250                 255

cat tac cgt tct aaa tat ggt gat gag caa cat tta ccc atg att gta      876
His Tyr Arg Ser Lys Tyr Gly Asp Glu Gln His Leu Pro Met Ile Val
                260                 265                 270

atg aat ggt tta ctt ggt gga ttt gct cac tct aag ctc ttt aca aat      924
Met Asn Gly Leu Leu Gly Gly Phe Ala His Ser Lys Leu Phe Thr Asn
            275                 280                 285

gtc cgt gaa aat gct gga tta gct tat acc att tca agt gag ctt gat      972
Val Arg Glu Asn Ala Gly Leu Ala Tyr Thr Ile Ser Ser Glu Leu Asp
        290                 295                 300

tta ttt agt gga ttc ttg agg atg tat gct ggt atc aat cga gaa aat     1020
Leu Phe Ser Gly Phe Leu Arg Met Tyr Ala Gly Ile Asn Arg Glu Asn
    305                 310                 315

cgt aac cag gct cgt aaa atg atg aat aat caa ctg ctt gat tta aaa     1068
Arg Asn Gln Ala Arg Lys Met Met Asn Asn Gln Leu Leu Asp Leu Lys
320                 325                 330                 335

aaa ggt tat ttt aca gag ttt gag tta aat cag acc aag gaa atg att     1116
Lys Gly Tyr Phe Thr Glu Phe Glu Leu Asn Gln Thr Lys Glu Met Ile
                340                 345                 350

cgt tgg tcg ttg tta ctt tct caa gat aat caa tct tca ttg att gaa     1164
Arg Trp Ser Leu Leu Leu Ser Gln Asp Asn Gln Ser Ser Leu Ile Glu
            355                 360                 365

cgt gct tat caa aat gcc tta ttt gga aaa tct tca gca gac ttt aaa     1212
Arg Ala Tyr Gln Asn Ala Leu Phe Gly Lys Ser Ser Ala Asp Phe Lys
        370                 375                 380

agt tgg att gca aag ctt gaa caa att gac aaa gat gct att tgt aga     1260
Ser Trp Ile Ala Lys Leu Glu Gln Ile Asp Lys Asp Ala Ile Cys Arg
    385                 390                 395

gta gct aat aat gtg aaa cta caa gcg att tac ttt atg gaa gga ata     1308
Val Ala Asn Asn Val Lys Leu Gln Ala Ile Tyr Phe Met Glu Gly Ile
400                 405                 410                 415

gaa tgacaaaggt tgtttttgaa gaaaaatact atccagctgt aaaagaaaag          1361
Glu

gtttatcgaa ctcgtttggc caacggattg acagttgct                          1400


<210> SEQ ID NO 63
<211> LENGTH: 1400
<212> TYPE: DNA
<213> ORGANISM: Streptococcus pneumoniae

<400> SEQUENCE: 63

tcccttgttc ttttaaagtc caaaagcact atattatctt cagacatata ttcctccatt     60

tagtacctca atcacgtacc ttaaagttgt gtaaaatagg ttagtttttt caaattttgt    120

ttgttttaat ggcacgcaaa atggcgaggt aatagggaac tatgctaacg tccagtgtac    180

aactcacgtt catacgatct ctgacgatta gtctacatgg ggtgaagagt tctaaactcc    240

tctgtgaacc ggtcagatat gccatgtcta tacagttggt taacaaagtc ttctcccgtt    300

tcggtgtaat atcttaactg taaatggata caagcactac tcaaaaattc atcctttttg    360

cacgattgga gagtctaaaa ccttgaacat tttctttgag aaaaaagtgg gcgtcatcaa    420

ctattaccca aactaggccg gaataaactt taactctttt ttgttaacga tcgttcaaat    480
```

-continued

```
cgtcgactat acctactaag aaaaataaaa cgtgtatttc ttaacctatt taacaaaaaa    540

gtactacttg cagaagttaa ccttatatca ctaaatgctt tagcataaaa tcgactttga    600

ggtgtttcaa gaataagaac aaaggttctt aaaaatcggt tactagctta tctaaagaaa    660

aaggatccac taaaattact ccaactttaa gttttacata atcttagtaa accgaaattt    720

ccagcttttc ctctacactt ccaagtcata acagttggaa taagattata ggaagtcctt    780

ccataccaag cctttttaca ccctgttagg taaaacctta atccaatagt aatggcaaga    840

tttataccac tactcgttgt aaatgggtac taacattact taccaaatga accacctaaa    900

cgagtgagat tcgagaaatg tttacaggca cttttacgac ctaatcgaat atggtaaagt    960

tcactcgaac taaataaatc acctaagaac tcctacatac gaccatagtt agctctttta   1020

gcattggtcc gagcatttta ctacttatta gttgacgaac taaatttttt tccaataaaa   1080

tgtctcaaac tcaatttagt ctggttcctt tactaagcaa ccagcaacaa tgaaagagtt   1140

ctattagtta gaagtaacta acttgcacga atagttttac ggaataaacc ttttagaagt   1200

cgtctgaaat tttcaaccta acgtttcgaa cttgtttaac tgtttctacg ataaacatct   1260

catcgattat tacactttga tgttcgctaa atgaaatacc ttccttatct tactgtttcc   1320

aacaaaaact tctttttatg ataggtcgac attttctttt ccaaatagct tgagcaaacc   1380

ggttgcctaa ctgtcaacga                                                 1400
```

```
<210> SEQ ID NO 64
<211> LENGTH: 370
<212> TYPE: PRT
<213> ORGANISM: Streptococcus pneumoniae

<400> SEQUENCE: 64

Met Val Tyr Gly Glu Val Pro Val Tyr Ala Asn Glu Asp Leu Val Val
  1               5                  10                  15

Glu Ser Gly Lys Leu Thr Pro Lys Thr Ser Phe Gln Ile Thr Glu Trp
             20                  25                  30

Arg Leu Asn Lys Gln Gly Ile Pro Val Phe Lys Leu Ser Asn His Gln
         35                  40                  45

Phe Ile Ala Ala Asp Lys Arg Phe Leu Tyr Asp Gln Ser Glu Val Thr
     50                  55                  60

Pro Thr Ile Lys Lys Val Trp Leu Glu Ser Asp Phe Lys Leu Tyr Asn
 65                  70                  75                  80

Ser Pro Tyr Asp Leu Lys Glu Val Lys Ser Ser Leu Ser Ala Tyr Ser
                 85                  90                  95

Gln Val Ser Ile Asp Lys Thr Met Phe Val Glu Gly Arg Glu Phe Leu
            100                 105                 110

His Ile Asp Gln Ala Gly Trp Val Ala Lys Glu Ser Thr Ser Glu Glu
        115                 120                 125

Asp Asn Arg Met Ser Lys Val Gln Glu Met Leu Ser Glu Lys Tyr Gln
    130                 135                 140

Lys Asp Ser Phe Ser Ile Tyr Val Lys Gln Leu Thr Thr Gly Lys Glu
145                 150                 155                 160

Ala Gly Ile Asn Gln Asp Glu Lys Met Tyr Ala Ala Ser Val Leu Lys
                165                 170                 175

Leu Ser Tyr Leu Tyr Tyr Thr Gln Glu Lys Ile Asn Glu Gly Leu Tyr
            180                 185                 190

Gln Leu Asp Thr Thr Val Lys Tyr Val Ser Ala Val Asn Asp Phe Pro
        195                 200                 205
```

-continued

```
Gly Ser Tyr Lys Pro Glu Gly Ser Gly Ser Leu Pro Lys Lys Glu Asp
    210                 215                 220

Asn Lys Glu Tyr Ser Leu Lys Asp Leu Ile Thr Lys Val Ser Lys Glu
225                 230                 235                 240

Ser Asp Asn Val Ala His Asn Leu Leu Gly Tyr Tyr Ile Ser Asn Gln
                245                 250                 255

Ser Asp Ala Thr Phe Lys Ser Lys Met Ser Ala Ile Met Gly Asp Asp
            260                 265                 270

Trp Asp Pro Lys Glu Lys Leu Ile Ser Ser Lys Met Ala Gly Lys Phe
        275                 280                 285

Met Glu Ala Ile Tyr Asn Gln Asn Gly Phe Val Leu Glu Ser Leu Thr
    290                 295                 300

Lys Thr Asp Phe Asp Ser Gln Arg Ile Ala Lys Gly Val Ser Val Lys
305                 310                 315                 320

Val Ala His Lys Ile Gly Asp Ala Asp Glu Phe Lys His Asp Thr Gly
                325                 330                 335

Val Val Tyr Ala Asp Ser Pro Phe Ile Leu Ser Ile Phe Thr Lys Asn
            340                 345                 350

Ser Asp Tyr Asp Thr Ile Ser Lys Ile Ala Lys Asp Val Tyr Glu Val
        355                 360                 365

Leu Lys
    370


<210> SEQ ID NO 65
<211> LENGTH: 1300
<212> TYPE: DNA
<213> ORGANISM: Streptococcus pneumoniae
<220> FEATURE:
<221> NAME/KEY: CDS
<222> LOCATION: (123)...(1232)

<400> SEQUENCE: 65

gttttttgac catttcaaaa gtcgttagca cagaaaaaga agtcgtctat acttcgaaag      60

aaatttatta cctttcacaa tctgactttg gtatttattt tagagaaaaa ttaagttctc     120

cc atg gtt tat gga gag gtt cct gtt tat gcg aat gaa gat tta gta       167
   Met Val Tyr Gly Glu Val Pro Val Tyr Ala Asn Glu Asp Leu Val
     1               5                  10                  15

gtg gaa tct ggg aaa ttg act ccc aaa aca agt ttt caa ata acc gag      215
Val Glu Ser Gly Lys Leu Thr Pro Lys Thr Ser Phe Gln Ile Thr Glu
                20                  25                  30

tgg cgc tta aat aaa caa gga att cca gta ttt aag cta tca aat cat      263
Trp Arg Leu Asn Lys Gln Gly Ile Pro Val Phe Lys Leu Ser Asn His
            35                  40                  45

caa ttt ata gct gcg gac aaa cga ttt tta tat gat caa tca gag gta      311
Gln Phe Ile Ala Ala Asp Lys Arg Phe Leu Tyr Asp Gln Ser Glu Val
        50                  55                  60

act cca aca ata aaa aaa gta tgg tta gaa tct gac ttt aaa ctg tac      359
Thr Pro Thr Ile Lys Lys Val Trp Leu Glu Ser Asp Phe Lys Leu Tyr
     65                  70                  75

aat agt cct tat gat tta aaa gaa gtg aaa tca tcc tta tca gct tat      407
Asn Ser Pro Tyr Asp Leu Lys Glu Val Lys Ser Ser Leu Ser Ala Tyr
 80                  85                  90                  95

tcg caa gta tca atc gac aag acc atg ttt gta gaa gga aga gaa ttt      455
Ser Gln Val Ser Ile Asp Lys Thr Met Phe Val Glu Gly Arg Glu Phe
                100                 105                 110

cta cat att gat cag gct gga tgg gta gct aaa gaa tca act tct gaa      503
Leu His Ile Asp Gln Ala Gly Trp Val Ala Lys Glu Ser Thr Ser Glu
```

-continued

```
            115                 120                 125

gaa gat aat cgg atg agt aaa gtt caa gaa atg tta tct gaa aaa tat      551
Glu Asp Asn Arg Met Ser Lys Val Gln Glu Met Leu Ser Glu Lys Tyr
        130                 135                 140

cag aaa gat tct ttc tct att tat gtt aag caa ctg act act gga aaa      599
Gln Lys Asp Ser Phe Ser Ile Tyr Val Lys Gln Leu Thr Thr Gly Lys
    145                 150                 155

gaa gct ggt atc aat caa gat gaa aag atg tat gca gcc agc gtt ttg      647
Glu Ala Gly Ile Asn Gln Asp Glu Lys Met Tyr Ala Ala Ser Val Leu
160                 165                 170                 175

aaa ctc tct tat ctc tat tat acg caa gaa aaa ata aat gag ggt ctt      695
Lys Leu Ser Tyr Leu Tyr Tyr Thr Gln Glu Lys Ile Asn Glu Gly Leu
                180                 185                 190

tat cag tta gat acg act gta aaa tac gta tct gca gtc aat gat ttt      743
Tyr Gln Leu Asp Thr Thr Val Lys Tyr Val Ser Ala Val Asn Asp Phe
            195                 200                 205

cca ggt tct tat aaa cca gag gga agt ggt agt ctt cct aaa aaa gaa      791
Pro Gly Ser Tyr Lys Pro Glu Gly Ser Gly Ser Leu Pro Lys Lys Glu
        210                 215                 220

gat aat aaa gaa tat tct tta aag gat tta att acg aaa gta tca aaa      839
Asp Asn Lys Glu Tyr Ser Leu Lys Asp Leu Ile Thr Lys Val Ser Lys
    225                 230                 235

gaa tct gat aat gta gct cat aat cta ttg gga tat tac att tca aac      887
Glu Ser Asp Asn Val Ala His Asn Leu Leu Gly Tyr Tyr Ile Ser Asn
240                 245                 250                 255

caa tct gat gcc aca ttc aaa tcc aag atg tct gcc att atg gga gat      935
Gln Ser Asp Ala Thr Phe Lys Ser Lys Met Ser Ala Ile Met Gly Asp
                260                 265                 270

gat tgg gat cca aaa gaa aaa ttg att tct tct aag atg gcc ggg aag      983
Asp Trp Asp Pro Lys Glu Lys Leu Ile Ser Ser Lys Met Ala Gly Lys
            275                 280                 285

ttt atg gaa gct att tat aat caa aat gga ttt gtg cta gag tct ttg     1031
Phe Met Glu Ala Ile Tyr Asn Gln Asn Gly Phe Val Leu Glu Ser Leu
        290                 295                 300

act aaa aca gat ttt gat agt cag cga att gcc aaa ggt gtt tct gtt     1079
Thr Lys Thr Asp Phe Asp Ser Gln Arg Ile Ala Lys Gly Val Ser Val
    305                 310                 315

aaa gta gct cat aaa att gga gat gcg gat gaa ttt aag cat gat acg     1127
Lys Val Ala His Lys Ile Gly Asp Ala Asp Glu Phe Lys His Asp Thr
320                 325                 330                 335

ggt gtt gtc tat gca gat tct cca ttt att ctt tct att ttc act aag     1175
Gly Val Val Tyr Ala Asp Ser Pro Phe Ile Leu Ser Ile Phe Thr Lys
                340                 345                 350

aat tct gat tat gat acg att tct aag ata gcc aag gat gtt tat gag     1223
Asn Ser Asp Tyr Asp Thr Ile Ser Lys Ile Ala Lys Asp Val Tyr Glu
            355                 360                 365

gtt cta aaa tgagggaacc agatttttta aatcattttc tcaagaaggg             1272
Val Leu Lys
        370

atatttcaaa aagcatgcta aggcggtt                                      1300


<210> SEQ ID NO 66
<211> LENGTH: 1300
<212> TYPE: DNA
<213> ORGANISM: Streptococcus pneumoniae

<400> SEQUENCE: 66

caaaaaactg gtaaagtttt cagcaatcgt gtctttttct tcagcagata tgaagctttc     60

tttaaataat ggaaagtgtt agactgaaac cataaataaa atctcttttt aattcaagag    120
```

-continued

```
ggtaccaaat acctctccaa ggacaaatac gcttacttct aaatcatcac cttagaccct    180

ttaactgagg gttttgttca aaagtttatt ggctcaccgc gaatttattt gttccttaag    240

gtcataaatt cgatagttta gtagttaaat atcgacgcct gtttgctaaa aatatactag    300

ttagtctcca ttgaggttgt tattttttc ataccaatct tagactgaaa tttgacatgt    360

tatcaggaat actaaatttt cttcacttta gtaggaatag tcgaataagc gttcatagtt    420

agctgttctg gtacaaacat cttccttctc ttaaagatgt ataactagtc cgacctaccc    480

atcgatttct tagttgaaga cttcttctat tagcctactc atttcaagtt ctttacaata    540

gactttttat agtctttcta agaaagagat aaatacaatt cgttgactga tgacctttc    600

ttcgaccata gttagttcta cttttctaca tacgtcggtc gcaaaacttt gagagaatag    660

agataatatg cgttcttttt tatttactcc cagaaatagt caatctatgc tgacatttta    720

tgcatagacg tcagttacta aaaggtccaa gaatatttgg tctcccttca ccatcagaag    780

gatttttct tctattattt cttataagaa atttcctaaa ttaatgcttt catagttttc    840

ttagactatt acatcgagta ttagataacc ctataatgta aagtttggtt agactacggt    900

gtaagtttag gttctacaga cggtaatacc ctctactaac cctaggtttt ctttttaact    960

aaagaagatt ctaccggccc ttcaaatacc ttcgataaat attagtttta cctaaacacg   1020

atctcagaaa ctgattttgt ctaaaactat cagtcgctta acggtttcca caaagacaat   1080

ttcatcgagt attttaacct ctacgcctac ttaaattcgt actatgccca caacagatac   1140

gtctaagagg taaataagaa agataaaagt gattcttaag actaatacta tgctaaagat   1200

tctatcggtt cctacaaata ctccaagatt ttactccctt ggtctaaaaa atttagtaaa   1260

agagttcttc cctataaagt ttttcgtacg attccgccaa                          1300
```

<210> SEQ ID NO 67
<211> LENGTH: 210
<212> TYPE: PRT
<213> ORGANISM: Streptococcus pneumoniae

<400> SEQUENCE: 67

```
Met Lys Lys Lys Ile Leu Ala Ser Leu Leu Leu Ser Thr Val Met Val
  1               5                  10                  15

Ser Gln Val Ala Val Leu Thr Thr Ala His Ala Glu Thr Thr Asp Asp
             20                  25                  30

Lys Ile Ala Ala Gln Asp Asn Lys Ile Ser Asn Leu Thr Ala Gln Gln
         35                  40                  45

Gln Glu Ala Gln Lys Gln Val Asp Gln Ile Gln Glu Gln Val Ser Ala
     50                  55                  60

Ile Gln Ala Glu Gln Ser Asn Leu Gln Ala Glu Asn Asp Arg Leu Gln
 65                  70                  75                  80

Ala Glu Ser Lys Lys Leu Glu Gly Glu Ile Thr Glu Leu Ser Lys Asn
                 85                  90                  95

Ile Val Ser Arg Asn Gln Ser Leu Glu Lys Gln Ala Arg Ser Ala Gln
            100                 105                 110

Thr Asn Gly Ala Val Thr Ser Tyr Ile Asn Thr Ile Val Asn Ser Lys
        115                 120                 125

Ser Ile Thr Glu Ala Ile Ser Arg Val Ala Ala Met Ser Glu Ile Val
    130                 135                 140

Ser Ala Asn Asn Lys Met Leu Glu Gln Gln Lys Ala Asp Lys Lys Ala
145                 150                 155                 160
```

-continued

```
Ile Ser Glu Lys Gln Val Ala Asn Asn Asp Ala Ile Asn Thr Val Ile
                165                 170                 175

Ala Asn Gln Gln Lys Leu Ala Asp Asp Ala Gln Ala Leu Thr Thr Lys
            180                 185                 190

Gln Ala Glu Leu Lys Ala Ala Glu Leu Ser Leu Ala Ala Glu Lys Ala
        195                 200                 205

Thr Ser
    210


<210> SEQ ID NO 68
<211> LENGTH: 800
<212> TYPE: DNA
<213> ORGANISM: Streptococcus pneumoniae
<220> FEATURE:
<221> NAME/KEY: CDS
<222> LOCATION: (114)...(743)

<400> SEQUENCE: 68

ttgaaaaata ttatctataa gaacgacata taaatgtaac aaaggcgtaa tatttattag      60

gccttttttt ggtatactag tattgtcttt aaaagaagga gtatctacgt aat atg        116
                                                           Met
                                                             1

aag aaa aaa atc tta gcg tca ctt tta tta agt aca gta atg gtt tct       164
Lys Lys Lys Ile Leu Ala Ser Leu Leu Leu Ser Thr Val Met Val Ser
            5                  10                  15

caa gta gct gtt tta aca act gcg cat gca gaa acg act gat gac aaa       212
Gln Val Ala Val Leu Thr Thr Ala His Ala Glu Thr Thr Asp Asp Lys
        20                  25                  30

att gct gct caa gat aat aaa att agt aac tta aca gca caa caa caa       260
Ile Ala Ala Gln Asp Asn Lys Ile Ser Asn Leu Thr Ala Gln Gln Gln
    35                  40                  45

gaa gcc caa aaa caa gtt gac caa att cag gag caa gta tca gct att       308
Glu Ala Gln Lys Gln Val Asp Gln Ile Gln Glu Gln Val Ser Ala Ile
 50                  55                  60                  65

caa gct gag cag tct aac ttg caa gct gaa aat gat aga tta caa gca       356
Gln Ala Glu Gln Ser Asn Leu Gln Ala Glu Asn Asp Arg Leu Gln Ala
                 70                  75                  80

gaa tct aag aaa ctc gag ggt gag att aca gaa ctt tct aaa aac att       404
Glu Ser Lys Lys Leu Glu Gly Glu Ile Thr Glu Leu Ser Lys Asn Ile
            85                  90                  95

gtt tct cgt aac caa tcg ttg gaa aaa caa gct cgt agt gct caa aca       452
Val Ser Arg Asn Gln Ser Leu Glu Lys Gln Ala Arg Ser Ala Gln Thr
        100                 105                 110

aat gga gcc gta act agc tat atc aat acc att gta aac tca aaa tca       500
Asn Gly Ala Val Thr Ser Tyr Ile Asn Thr Ile Val Asn Ser Lys Ser
    115                 120                 125

att aca gaa gct att tca cgt gtt gct gca atg agt gaa atc gta tct       548
Ile Thr Glu Ala Ile Ser Arg Val Ala Ala Met Ser Glu Ile Val Ser
130                 135                 140                 145

gca aac aac aaa atg tta gaa caa caa aag gca gat aaa aaa gct att       596
Ala Asn Asn Lys Met Leu Glu Gln Gln Lys Ala Asp Lys Lys Ala Ile
                150                 155                 160

tct gaa aaa caa gta gca aat aat gat gct atc aat act gta att gct       644
Ser Glu Lys Gln Val Ala Asn Asn Asp Ala Ile Asn Thr Val Ile Ala
            165                 170                 175

aat caa caa aaa ttg gct gat gat gct caa gca ttg act acg aaa cag       692
Asn Gln Gln Lys Leu Ala Asp Asp Ala Gln Ala Leu Thr Thr Lys Gln
        180                 185                 190

gca gaa cta aaa gct gct gaa tta agt ctt gct gct gag aaa gcg act       740
Ala Glu Leu Lys Ala Ala Glu Leu Ser Leu Ala Ala Glu Lys Ala Thr
```

-continued

```
    195                 200                 205

agc tgaaggggaa aaagcaaggc tattagagca agaagcagca gctgaggcag           793
Ser
210

aggctcg                                                              800


<210> SEQ ID NO 69
<211> LENGTH: 800
<212> TYPE: DNA
<213> ORGANISM: Streptococcus pneumoniae

<400> SEQUENCE: 69

aactttttat aatagatatt cttgctgtat atttacattg tttccgcatt ataaataatc     60

cggaaaaaaa ccatatgatc ataacagaaa ttttcttcct catagatgca ttatacttct    120

ttttttagaa tcgcagtgaa aataattcat gtcattacca aagagttcat cgacaaaatt    180

gttgacgcgt acgtctttgc tgactactgt tttaacgacg agttctatta ttttaatcat    240

tgaattgtcg tgttgttgtt cttcgggttt ttgttcaact ggtttaagtc ctcgttcata    300

gtcgataagt tcgactcgtc agattgaacg ttcgactttt actatctaat gttcgtctta    360

gattctttga gctcccactc taatgtcttg aaagattttt gtaacaaaga gcattggtta    420

gcaacctttt tgttcgagca tcacgagttt gtttacctcg gcattgatcg atatagttat    480

ggtaacattt gagttttagt taatgtcttc gataaagtgc acaacgacgt tactcacttt    540

agcatagacg tttgttgttt tacaatcttg ttgttttccg tctatttttt cgataaagac    600

tttttgttca tcgtttatta ctacgatagt tatgacatta acgattagtt gtttttaacc    660

gactactacg agttcgtaac tgatgctttg tccgtcttga ttttcgacga cttaattcag    720

aacgacgact ctttcgctga tcgacttccc ctttttcgtt ccgataatct cgttcttcgt    780

cgtcgactcc gtctccgagc                                                800


<210> SEQ ID NO 70
<211> LENGTH: 193
<212> TYPE: PRT
<213> ORGANISM: Streptococcus pneumoniae

<400> SEQUENCE: 70

Met Leu Ile Ala Leu Leu Ile Ile Leu Ala Tyr Leu Ile Gly Ser Ile
  1               5                  10                  15

Pro Ser Gly Leu Ile Val Gly Lys Leu Ala Lys Gly Ile Asp Ile Arg
             20                  25                  30

Glu His Gly Ser Gly Asn Leu Gly Ala Thr Asn Ala Phe Arg Thr Leu
         35                  40                  45

Gly Val Lys Ala Gly Ser Val Val Ile Ala Gly Asp Ile Leu Lys Gly
     50                  55                  60

Thr Leu Ala Thr Ala Leu Pro Phe Leu Met His Val Asp Ile His Pro
 65                  70                  75                  80

Leu Leu Ala Gly Val Phe Ala Val Leu Gly His Val Phe Pro Ile Phe
                 85                  90                  95

Ala Lys Phe Lys Gly Gly Lys Ala Val Ala Thr Ser Gly Gly Val Leu
            100                 105                 110

Leu Phe Tyr Ala Pro Leu Leu Phe Ile Thr Met Val Ala Val Phe Phe
        115                 120                 125

Ile Phe Leu Tyr Leu Thr Lys Phe Val Ser Leu Ser Ser Met Leu Thr
    130                 135                 140
```

-continued

```
Gly Ile Tyr Thr Val Ile Tyr Ser Phe Phe Val His Asp Thr Tyr Leu
145                 150                 155                 160

Leu Ile Val Val Thr Leu Leu Thr Ile Phe Val Ile Tyr Arg His Arg
                165                 170                 175

Ala Asn Ile Lys Arg Ile Ile Asn Lys Thr Glu Pro Lys Val Lys Trp
            180                 185                 190

Leu


<210> SEQ ID NO 71
<211> LENGTH: 582
<212> TYPE: DNA
<213> ORGANISM: Streptococcus pneumoniae
<220> FEATURE:
<221> NAME/KEY: CDS
<222> LOCATION: (1)...(579)

<400> SEQUENCE: 71

atg tta att gct tta ttg att att ttg gcc tac ttg ata ggc agc att        48
Met Leu Ile Ala Leu Leu Ile Ile Leu Ala Tyr Leu Ile Gly Ser Ile
  1               5                  10                  15

cca tct ggc tta att gtg ggc aag ctt gcc aaa gga att gat att cgg        96
Pro Ser Gly Leu Ile Val Gly Lys Leu Ala Lys Gly Ile Asp Ile Arg
             20                  25                  30

gag cac gga agc ggc aac tta ggc gct acc aat gca ttc cgt aca ttg       144
Glu His Gly Ser Gly Asn Leu Gly Ala Thr Asn Ala Phe Arg Thr Leu
         35                  40                  45

ggt gta aaa gct ggt tcg gtc gtc ata gcc gga gat att ttg aaa ggg       192
Gly Val Lys Ala Gly Ser Val Val Ile Ala Gly Asp Ile Leu Lys Gly
     50                  55                  60

aca ctg gca act gca ttg cct ttt ctc atg cat gtt gat att cac ccg       240
Thr Leu Ala Thr Ala Leu Pro Phe Leu Met His Val Asp Ile His Pro
 65                  70                  75                  80

ctt ctt gca gga gtc ttt gcg gtt tta ggc cac gtg ttt ccc atc ttc       288
Leu Leu Ala Gly Val Phe Ala Val Leu Gly His Val Phe Pro Ile Phe
                 85                  90                  95

gcc aaa ttt aaa ggc ggt aaa gcc gtg gcg aca tca gga ggc gtt ttg       336
Ala Lys Phe Lys Gly Gly Lys Ala Val Ala Thr Ser Gly Gly Val Leu
            100                 105                 110

cta ttt tac gca ccc ctg tta ttt atc acg atg gtt gcg gta ttc ttc       384
Leu Phe Tyr Ala Pro Leu Leu Phe Ile Thr Met Val Ala Val Phe Phe
        115                 120                 125

atc ttt tta tac ttg act aaa ttt gtt tct ctc tca tcg atg tta aca       432
Ile Phe Leu Tyr Leu Thr Lys Phe Val Ser Leu Ser Ser Met Leu Thr
    130                 135                 140

ggg atc tat act gtt ata tat agt ttc ttt gtc cat gat acg tat tta       480
Gly Ile Tyr Thr Val Ile Tyr Ser Phe Phe Val His Asp Thr Tyr Leu
145                 150                 155                 160

ttg att gtc gtt acc ctg ctc act att ttt gtg ata tac aga cac cga       528
Leu Ile Val Val Thr Leu Leu Thr Ile Phe Val Ile Tyr Arg His Arg
                165                 170                 175

gcg aac att aaa cga att atc aat aaa aca gaa cct aaa gta aaa tgg       576
Ala Asn Ile Lys Arg Ile Ile Asn Lys Thr Glu Pro Lys Val Lys Trp
            180                 185                 190

tta taa                                                                582
Leu


<210> SEQ ID NO 72
<211> LENGTH: 582
<212> TYPE: DNA
<213> ORGANISM: Streptococcus pneumoniae
```

-continued

<400> SEQUENCE: 72
tacaattaac gaaataacta ataaaaccgg atgaactatc cgtcgtaagg tagaccgaat 60
taacacccgt tcgaacggtt tccttaacta taagccctcg tgccttcgcc gttgaatccg 120
cgatggttac gtaaggcatg taacccacat tttcgaccaa gccagcagta tcggcctcta 180
taaaactttc cctgtgaccg ttgacgtaac ggaaaagagt acgtacaact ataagtgggc 240
gaagaacgtc ctcagaaacg ccaaaatccg gtgcacaaag ggtagaagcg gtttaaattt 300
ccgccatttc ggcaccgctg tagtcctccg caaaacgata aaatgcgtgg ggacaataaa 360
tagtgctacc aacgccataa gaagtagaaa aatatgaact gatttaaaca aagagagagt 420
agctacaatt gtccctagat atgacaatat atatcaaaga aacaggtact atgcataaat 480
aactaacagc aatgggacga gtgataaaaa cactatatgt ctgtggctcg cttgtaattt 540
gcttaatagt tattttgtct tggatttcat tttaccaata tt 582

<210> SEQ ID NO 73
<211> LENGTH: 23
<212> TYPE: DNA
<213> ORGANISM: Streptococcus pneumoniae

<400> SEQUENCE: 73
gcagcccggt tttccagaac agg 23

<210> SEQ ID NO 74
<211> LENGTH: 23
<212> TYPE: DNA
<213> ORGANISM: Streptococcus pneumoniae

<400> SEQUENCE: 74
gatttagccc agtcggccgc acg 23

<210> SEQ ID NO 75
<211> LENGTH: 21
<212> TYPE: DNA
<213> ORGANISM: Streptococcus pneumoniae

<400> SEQUENCE: 75
ccgccattct ttgctgtttc g 21

<210> SEQ ID NO 76
<211> LENGTH: 22
<212> TYPE: DNA
<213> ORGANISM: Streptococcus pneumoniae

<400> SEQUENCE: 76
ttacacgtta ctaaagggaa tg 22

<210> SEQ ID NO 77
<211> LENGTH: 21
<212> TYPE: DNA
<213> ORGANISM: Bacillus subtilis

<400> SEQUENCE: 77
gtgttcgtgc tgacttgcac c 21

<210> SEQ ID NO 78
<211> LENGTH: 21
<212> TYPE: DNA
<213> ORGANISM: Bacillus subtilis

<400> SEQUENCE: 78

-continued gaattatttc ctcccgttaa a 21

<210> SEQ ID NO 79
<211> LENGTH: 20
<212> TYPE: DNA
<213> ORGANISM: Streptococcus pneumoniae

<400> SEQUENCE: 79
ctccgtgaag tccacctgat 20

<210> SEQ ID NO 80
<211> LENGTH: 41
<212> TYPE: DNA
<213> ORGANISM: Streptococcus pneumoniae

<400> SEQUENCE: 80
ggtgcaagtc agcacgaaca ctgctcgcgt agattgattt g 41

<210> SEQ ID NO 81
<211> LENGTH: 41
<212> TYPE: DNA
<213> ORGANISM: Streptococcus pneumoniae

<400> SEQUENCE: 81
tttaacggga ggaaataatt cggggattga acctaaccca t 41

<210> SEQ ID NO 82
<211> LENGTH: 20
<212> TYPE: DNA
<213> ORGANISM: Streptococcus pneumoniae

<400> SEQUENCE: 82
ttggcaagaa ggcagagaat 20

<210> SEQ ID NO 83
<211> LENGTH: 20
<212> TYPE: DNA
<213> ORGANISM: Streptococcus pneumoniae

<400> SEQUENCE: 83
gcatgagaaa cccagtctcc 20

<210> SEQ ID NO 84
<211> LENGTH: 43
<212> TYPE: DNA
<213> ORGANISM: Streptococcus pneumoniae

<400> SEQUENCE: 84
ggtgcaagtc agcacgaaca cgcgacatag gttccagtta ggg 43

<210> SEQ ID NO 85
<211> LENGTH: 41
<212> TYPE: DNA
<213> ORGANISM: Streptococcus pneumoniae

<400> SEQUENCE: 85
tttaacggga ggaaataatt cccatatcgt ggctcctgaa t 41

<210> SEQ ID NO 86
<211> LENGTH: 20
<212> TYPE: DNA
<213> ORGANISM: Streptococcus pneumoniae -continued

<400> SEQUENCE: 86
taaagccctc atgtcgaacc 20

<210> SEQ ID NO 87
<211> LENGTH: 22
<212> TYPE: DNA
<213> ORGANISM: Streptococcus pneumoniae

<400> SEQUENCE: 87
cagtgacgat acagatgaag aa 22

<210> SEQ ID NO 88
<211> LENGTH: 41
<212> TYPE: DNA
<213> ORGANISM: Streptococcus pneumoniae

<400> SEQUENCE: 88
ggtgcaagtc agcacgaaca cgatgctggc ttcgttgagt g 41

<210> SEQ ID NO 89
<211> LENGTH: 41
<212> TYPE: DNA
<213> ORGANISM: Streptococcus pneumoniae

<400> SEQUENCE: 89
tttaacggga ggaaataatt cgtcgcgact cctagccata c 41

<210> SEQ ID NO 90
<211> LENGTH: 20
<212> TYPE: DNA
<213> ORGANISM: Streptococcus pneumoniae

<400> SEQUENCE: 90
ccagcaaagg aaaaccgata 20

<210> SEQ ID NO 91
<211> LENGTH: 20
<212> TYPE: DNA
<213> ORGANISM: Streptococcus pneumoniae

<400> SEQUENCE: 91
ggtcagtgac agcagcagat 20

<210> SEQ ID NO 92
<211> LENGTH: 41
<212> TYPE: DNA
<213> ORGANISM: Streptococcus pneumoniae

<400> SEQUENCE: 92
ggtgcaagtc agcacgaaca cggccttgga aaaaagacca t 41

<210> SEQ ID NO 93
<211> LENGTH: 41
<212> TYPE: DNA
<213> ORGANISM: Streptococcus pneumoniae

<400> SEQUENCE: 93
tttaacggga ggaaataatt cccgcttaaa ttctgccaat c 41

<210> SEQ ID NO 94
<211> LENGTH: 20
<212> TYPE: DNA
<213> ORGANISM: Streptococcus pneumoniae -continued

<400> SEQUENCE: 94
cccataaccg tatcacctgg 20

<210> SEQ ID NO 95
<211> LENGTH: 20
<212> TYPE: DNA
<213> ORGANISM: Streptococcus pneumoniae

<400> SEQUENCE: 95
cggaacggct atgaaaaaaa 20

<210> SEQ ID NO 96
<211> LENGTH: 41
<212> TYPE: DNA
<213> ORGANISM: Streptococcus pneumoniae

<400> SEQUENCE: 96
ggtgcaagtc agcacgaaca cacgacgaaa ggcaaccata c 41

<210> SEQ ID NO 97
<211> LENGTH: 41
<212> TYPE: DNA
<213> ORGANISM: Streptococcus pneumoniae

<400> SEQUENCE: 97
tttaacggga ggaaataatt ctggtatggg ggttgatgaa g 41

<210> SEQ ID NO 98
<211> LENGTH: 20
<212> TYPE: DNA
<213> ORGANISM: Bacillus subtilis

<400> SEQUENCE: 98
tcgccctact tttcgtatgc 20

<210> SEQ ID NO 99
<211> LENGTH: 20
<212> TYPE: DNA
<213> ORGANISM: Bacillus subtilis

<400> SEQUENCE: 99
agcgatatta gtgcgggaga 20

<210> SEQ ID NO 100
<211> LENGTH: 42
<212> TYPE: DNA
<213> ORGANISM: Bacillus subtilis

<400> SEQUENCE: 100
ggtgcaagtc agcacgaaca ccagcaattt tgtcatcagt cg 42

<210> SEQ ID NO 101
<211> LENGTH: 41
<212> TYPE: DNA
<213> ORGANISM: Bacillus subtilis

<400> SEQUENCE: 101
tttaacggga ggaaataatt cctggggtaa tggagcacag t 41

<210> SEQ ID NO 102
<211> LENGTH: 20
<212> TYPE: DNA

-continued

<213> ORGANISM: Bacillus subtilis

<400> SEQUENCE: 102
gggattgtca cggtaaaacc 20